US008710089B2

(12) United States Patent
Perrissoud et al.

(10) Patent No.: US 8,710,089 B2
(45) Date of Patent: Apr. 29, 2014

(54) TRIAZOLE DERIVATIVES AS GHRELIN ANALOGUE LIGANDS OF GROWTH HORMONE SECRETAGOGUE RECEPTORS

(75) Inventors: Daniel Perrissoud, Bad Homburg (DE); Jean Martinez, Caux (FR); Aline Moulin, Portes-les-Valence (FR); Jean-Alain Fehrentz, St. Nazaire de Pezan (FR); Damien Boeglin, Eguisheim (FR); Luc Demange, Orsay (FR)

(73) Assignees: Zentaris GmbH, Frankfurt (DE); Le Centre National de la Recherche Scientifique, Paris (FR); University of Montpellier I, Montpellier (FR); University of Montpellier II, Montpellier (FR)

( * ) Notice: Subject to any disclaimer, the term of this patent is extended or adjusted under 35 U.S.C. 154(b) by 366 days.

(21) Appl. No.: 12/880,774

(22) Filed: Sep. 13, 2010

(65) Prior Publication Data

US 2010/0331343 A1 Dec. 30, 2010

Related U.S. Application Data

(62) Division of application No. 11/502,473, filed on Aug. 11, 2006, now Pat. No. 7,829,724.

(60) Provisional application No. 60/707,941, filed on Aug. 15, 2005, provisional application No. 60/787,543, filed on Mar. 31, 2006.

(30) Foreign Application Priority Data

Aug. 16, 2005 (EP) ..................................... 05017732

(51) Int. Cl.
*A01N 43/64* (2006.01)
*A61K 31/41* (2006.01)
*C07D 249/08* (2006.01)

(52) U.S. Cl.
USPC ........................................ 514/383; 548/262.2

(58) Field of Classification Search
USPC ........................................ 514/383; 548/262.2
See application file for complete search history.

(56) References Cited

U.S. PATENT DOCUMENTS

| | | | |
|---|---|---|---|
| 4,411,890 A | 10/1983 | Momany |
| 5,612,359 A | 3/1997 | Murugesan |
| 5,624,941 A | 4/1997 | Barth et al. |
| 5,703,092 A | 12/1997 | Xue et al. |
| 5,977,178 A | 11/1999 | Hansen et al. |
| 6,043,265 A | 3/2000 | Murugesan et al. |
| 6,071,926 A | 6/2000 | Van Cauter et al. |
| 6,127,391 A | 10/2000 | Hansen et al. |
| 6,184,231 B1 | 2/2001 | Hewawasam et al. |
| 6,194,578 B1 | 2/2001 | Griffith et al. |
| 6,251,902 B1 | 6/2001 | Carpino et al. |
| 6,329,342 B1 | 12/2001 | Kauffman et al. |
| 6,506,782 B1 | 1/2003 | Thorsett et al. |
| 6,518,292 B1 | 2/2003 | Robl et al. |
| 6,525,203 B1 | 2/2003 | Tino |
| 6,548,529 B1 | 4/2003 | Robl et al. |
| 6,555,570 B2 | 4/2003 | Hansen et al. |
| 6,660,760 B1 | 12/2003 | Robl et al. |
| 6,849,650 B2 | 2/2005 | Thorsett et al. |
| 2001/0020012 A1 | 9/2001 | Andersen et al. |
| 2001/0041673 A1 | 11/2001 | Fossa |
| 2002/0002137 A1 | 1/2002 | Busch et al. |
| 2002/0013320 A1 | 1/2002 | Busch et al. |
| 2003/0130188 A1 | 7/2003 | Thorsett et al. |
| 2006/0293370 A1* | 12/2006 | Saunders et al. ............... 514/362 |

FOREIGN PATENT DOCUMENTS

| | | |
|---|---|---|
| CN | 1344160 | 4/2002 |
| WO | WO 89/07110 | 8/1989 |
| WO | WO 89/07111 | 8/1989 |
| WO | WO 93/09095 | 5/1993 |
| WO | WO 95/14666 | 6/1995 |
| WO | WO 96/15148 | 5/1996 |
| WO | WO 96/33176 | 10/1996 |
| WO | WO 97/23508 | 7/1997 |
| WO | WO 98/38177 | 9/1998 |
| WO | WO 00/01389 | 1/2000 |
| WO | 00/54729 | 9/2000 |
| WO | WO 00/54729 | 9/2000 |
| WO | WO 00/76970 A2 | 12/2000 |
| WO | WO 00/76971 A2 | 12/2000 |

(Continued)

OTHER PUBLICATIONS

Nagaya et al. "Treatment of Cachexia With Ghrelin in Patients with COPD" Chest, 2005, vol. 128, pp. 1187-1193.*

(Continued)

*Primary Examiner* — Kendra D Carter
(74) *Attorney, Agent, or Firm* — Oblon, Spivak, McClelland, Maier & Neustadt, L.L.P.

(57) ABSTRACT

The present invention provides novel triazole derivatives as ghrelin analogue ligands of growth hormone secretagogue receptors according to formula (I) that are useful in the treatment or prophylaxis of physiological and/or pathophysiological conditions in mammals, preferably humans, that are mediated by GHS receptors. The present invention further provides GHS receptor antagonists and agonists that can be used for modulation of these receptors and are useful for treating above conditions, in particular growth retardation, cachexia, short-, medium- and/or long term regulation of energy balance; short-, medium- and/or long term regulation (stimulation and/or inhibition) of food intake; adipogenesis, adiposity and/or obesity; body weight gain and/or reduction; diabetes, diabetes type I, diabetes type II, tumor cell proliferation; inflammation, inflammatory effects, gastric postoperative ileus, postoperative ileus and/or gastrectomy (ghrelin replacement therapy).

20 Claims, 23 Drawing Sheets

(56) References Cited

FOREIGN PATENT DOCUMENTS

| WO | 01/36395 | 5/2001 |
|---|---|---|
| WO | WO 01/36395 A1 | 5/2001 |
| WO | WO 01/94317 A2 | 12/2001 |
| WO | WO 01/94318 A2 | 12/2001 |
| WO | WO 01/96300 A1 | 12/2001 |
| WO | WO 02/00651 A2 | 1/2002 |
| WO | WO 03/011210 A2 | 2/2003 |
| WO | WO 03/011831 A1 | 2/2003 |
| WO | WO 03/051389 A2 | 6/2003 |
| WO | WO 2004/021984 A2 | 3/2004 |
| WO | WO 2004/052280 A2 | 6/2004 |
| WO | WO 2004/096795 A2 | 11/2004 |
| WO | WO 2004/103270 A2 | 12/2004 |
| WO | WO 2004/111015 A1 | 12/2004 |

OTHER PUBLICATIONS

Berryman et al. "Effect of Growth Hormone on Susceptibility to Diet-Induced Obesity", Endocrinology,2006, vol. 147, No. 6, p. 2801-2808.*
Halford, J.C.G. "Clinical Pharmacotherapy for Obesity: Current Drugs and Those in Advanced Development" Current Drug Targets, 2004, vol. 5, pp. 637-646.*
Kopchick et al. "Growth Hormone Receptor Antagonists: Discovery, Development, and Use i nPatients with Acromegaly" Endocrine Reviews, 2002, vol. 23, pp. 623-646).*
Utz, Andrea L. "The Effect of Obesity on Growth Hormone Secretion", Neuroendocrine Bulletin, Fall/Winter 2006, vol. 12, issue 1, pp. 1-3.*
Wikipedia "Anorexia nervosa" May 8, 2013, http://en.wikipedia.org/wiki/Anorexia_nervosa, pp. 1-37.*
Israel Examination Report dated Jan. 6, 2011 as received in Patent Application No. 189459.
New Zealand Examination Report dated Nov. 30, 2009 as received in Application No. 565740.
Australian Examination Report dated Mar. 9, 2011 as receied in Application No. 2006281594.
European Examination Report dated Dec. 30, 2008 as received in Application 06 776 764.0-2107.
Russian Examination Report dated Aug. 11, 2006 as received in Application 2008109929/04(010728).
Chinese Examination Report dated Dec. 5, 2010 as received in Application No. 200680035287.5.
Korean Examination Report dated Sep. 1, 2010 as received in Application No. 10-2008-7003755.
Singapore Examination Report dated Jul. 7, 2009 as received in Application No. 200800911-0.
Emanuela Arvat, et al., "Endocrine Activities of Ghrelin, a Natural Growth Hormone Secretagogue (GHS), in Humans: Comparison and Interactions With Hexarelin, a Nonnatural Peptidyl GHS, and GH-Releasing Hormone", The Journal of Clinical Endocrinology & Metabolism, vol. 86, No. 3, 2001, pp. 1169-1174.
A. Asakawa, et al., "Antagonism of Ghrelin Receptor Reduces Food Intake and Body Weight Gain in Mice", Gut Online gut.bmjjournals.com, vol. 52, 2003, pp. 947-952.
Michela Bagnasco, et al., "Endogenous Ghrelin is an Orexigenic Peptide Acting in the Arcuate Nucleus in Response to Fasting", Regulatory Peptides, vol. 111, 2003, pp. 161-167.
Marie-Thérèse Bluet-Pajot, et al., "Growth Hormone Secretagogues and Hypothalamic Networks", Endocrine, vol. 14, No. 1, 2001, pp. 1-8.
V. Bodart, et al., "Identification and Characterization of a New Growth Hormone-Releasing Peptide Receptor in the Heart", Circulation Research, Journal of the American Heart Association, vol. 85, 1999, pp. 796-802.
V. Bodart, et al., "CD36 Mediates the Cardiovascular Action of Growth Hormone-Releasing Peptides in the Heart", Circulation Research, Journal of the American Heart Association, vol. 90, 2002, pp. 844-849.

Design of Prodrugs (editor: Hans Bundgaard), 1985, pp. 1-360.
A Textbook of Drug Design and Development (editors: P. Krogsgaard-Larson, et al.) 1991, Chapter 5 pp. 113-191.
Franco Camanni, et al., "Growth Hormone-Releasing Peptides and Their Analogs", Frontiers in Neuroendocrinology, vol. 19, 1998, pp. 47-72.
Felipe F. Casanueva, et al., "Growth Hormone Secretagogues: Physiological Role and Clinical Utility", Trends Endocrinol. Metab., vol. 10, No. 1, 1999, pp. 30-38.
P. Cassoni, et al., "Specific Binding Sites for Synthetic Growth Hormone Secretagogues in Non-Tumoral and Neoplastic Human Thyroid Tissue" Journal of Endocrinology, vol. 165, 2000, pp. 139-146.
Paola Cassoni, et al., "Identification, Characterization, and Biological Activity of Specific Receptors for Natural (Ghrelin) and Synthetic Growth Hormone Secretagogues and Analogs in Human Breast Carcinomas and Cell Lines" The Journal of Clinical Endocrinology & Metabolism, vol. 86, No. 4, 2001, pp. 1738-1745.
B. Castro, et al., "Reactifs de Couplage Peptidique IV (1)—L'Hexafluorophosphate de Benzotriazolyl N-Oxytrisdimethylamino Phosphonium (B.O.P.)", Tetrahedron Letters, No. 14, 1975, pp. 1219-1222.
Kichoon Choi, et al., "The Role of Ghrelin and Growth Hormone Secretagogues Receptor on Rat Adipogenesis", Endocrinology, vol. 144, 2003, pp. 754-759.
Michael A. Cowley, et al., "The Distribution and Mechanism of Action of Ghrelin in the CNS Demonstrates a Novel Hypothalamic Circuit Regulating Energy Homeostasis", Neuron, vol. 37, 2003, pp. 649-661.
H. V. Czetsch-Lindenwald, "Hilfsstoffe Für Pharmazie and Angrenzende Gebiete", Pharmazeutische Technologie, 1961, pp. 72-74.
C. Dornonville de la Cour, et al., "Ghrelin Treatment Reverses the Reduction in Weight Gain and Body Fat in Gastrectomised Mice", Gut Online gut.bmjjournals.com, vol. 54, 2005, pp. 907-913.
James P. Edwards, et al., "Nonsteroidal Androgen Receptor Agonists Based on 4-(Trifluoromethyl)-2$H$-Pyrano[3,2-G]Quinolin-2-One" Bioorganic & Medicinal Chemistry Letters 9, 1999, pp. 1003-1008.
Scott D. Feighner, et al., "Receptor for Motilin Identified in the Human Gastrointestinal System", Science, vol. 284, 1999, pp. 2184-2188.
H. P. Fiedler, "Lexikon Der Hilfsstoffe für Pharmazie, Kosmetik Und Angrenzende Gebiete", Cantor KG, Aulendorf in Württembert, 1971, pp. 65-68.
Corrado Ghé, et al., "The Antiproliferative Effect of Synthetic Peptidyl GH Secretagogues in Human Calu-1 Lung Carcinoma Cells", Endocrinology, vol. 143, pp. 484-491 (2002).
Sharmilee Gnanapavan, et al., "The Tissue Distribution of the MRNA of Ghrelin and Subtypes of Its Receptor, GHS-R, in Humans", The Journal of Clinical Endocrinology & Metabolism, vol. 87, 2002, pp. 2988-2991.
Miriam Granado, et al., "Anti-Inflammatory Effect of the Ghrelin Agonist Growth Hormone-Releasing Peptide-2 (GHRP-2) in Arthritic Rats" American Journal of Physiology—Endocrinology and Metabolism, vol. 288, 2005, pp. 486-492.
Xiao-Ming Guan, et al., "Distribution of MRNA Encoding the Growth Hormone Secretagogue Receptor in Brain and Peripheral Tissues", Molecular Brain Research, vol. 48, 1997, pp. 23-29.
Vincent Guerlavais, et al., "New Active Series of Growth Hormone Secretagogues", Journal of Medicinal Chemistry, vol. 46, No. 7, 2003, pp. 1191-1203.
Lawrence G. Hamann, et al., "Discovery of a Potent, Orally Active, Nonsteroidal Androgen Receptor Agonist: 4-Ethyl-1,2,3,4-Tetrahydro-6-(Trifluoromethyl)-8-Pyridono[5,6-$G$]-Quinoline (LG121071)", Journal of Medicinal Chemistry, vol. 42, No. 2, 1999, pp. 210-212.
Naoki Hattori, et al., "GH, GH Receptor, GH Secretagogue Receptor, and Ghrelin Expression in Human T Cells, B Cells, and Neutrophils", The Journal of Clinical Endocrinology & Metabolism, vol. 86, 2001, pp. 4284-4291.
Yukio Hitotsuyanagi, et al., "A $CIS$ Amide Bond Surrogate Incorporating 1,2,4-Triazole", J. Org. Chem., vol. 67, No. 10, 2002, pp. 3266-3271.

(56) References Cited

OTHER PUBLICATIONS

Tamas L. Horvath, et al., "Ghrelin as a Potential Anti-Obesity Target" Current Pharmaceutical Design, vol. 9, No. 17, 2003, pp. 1383-1395.
Andrew D. Howard, et al., "A Receptor in Pituitary and Hypothalamus That Functions in Growth Hormone Release", Science, vol. 273, 1996, pp. 974-977.
I. Ibañez de Cáceres, et al., "IGF-I and IGF-I-Binding Proteins in Rats With Adjuvant-Induced Arthritis Given Recombinant Human Growth Hormone", Journal of Endocrinology, vol. 165, 2000, pp. 537-544.
P. L. Jeffery, et al., "Rapid Communication, Expression of Action of the Growth Hormone Releasing Peptides Ghrelin and Its Receptor in Prostate Cancer Cell Lines." Journal of Endocrinology, vol. 172, 2002, pp. 7-11.
Penny L. Jeffery, et al., "The Potential Autocrine/Paracrine Roles of Ghrelin and Its Receptor in Hormone-Dependent Cancer", Cytokine & Growth Factor Reviews, vol. 14, pp. 113-122, (2003).
Masayasu Kojima, et al., "Ghrelin is a Growth-Hormone-Releasing Acylated Peptide From Stomach", Nature, vol. 402, 1999, pp. 656-660.
Masayasu Kojima, et al., "Ghrelin, an Orexigenic Signaling Molecule From the Gastrointestinal Tract", Current Opinion in Pharmacology, vol. 2, 2002, pp. 665-668.
Márta Korbonits, et al., "Expression of the Growth Hormone Secretagogue Receptor in Pituitary Adenomas and Other Neuroendocrine Tumors" Journal of Clinical Endocrinology and Metabolism, vol. 83, No. 10, 1998, pp. 3624-3630.
S. Lazareno, et al., "Estimation of Antagonist $K_B$ From Inhibition Curves in Functional Experiments: Alternatives to the Cheng-Prusoff Equation" Trends Pharmacol. Sci., vol. 14, 1993, pp. 237-239.
Dung Le Nguyen, et al., "Bop Reagent: Rising a "Major" for Peptide Coupling.", Peptide Chemistry, 1987.
Karen Kulju McKee, et al., "Cloning and Characterization of Two Human G Protein-Coupled Receptor Genes (GPR38 and GPR39) Related to the Growth Hormone Secretagogue and Neurotensin Receptors" Genomics, vol. 46, 1997, pp. 426-434.
Karen Kulju McKee, et al., "Molecular Analysis of Rat Pituitary and Hypothalamic Growth Hormone Secretagogue Receptors", Molecular Endocrinology, vol. 11, 1997, pp. 415-423.
G. Muccioli, et al., "Specific Receptors for Synthetic GH Secretagogues in the Human Brain and Pituitary Gland", Journal of Endocrinology, vol. 157, 1998, pp. 99-106.
G. Muccioli, et al., "Growth Hormone-Releasing Peptides and the Cardiovascular System", Annales D'Endocrinologie, vol. 61, No. 1, 2000, pp. 27-31.
Giampiero Muccioli, et al., "Neuroendocrine and Peripheral Activities of Ghrelin: Implications in Metabolism and Obesity" European Journal of Pharmacology, vol. 440, 2002, pp. 235-254.
Giampiero Muccioli, et al., "Ghrelin and Des-Acyl Ghrelin Both Inhibit Isoproterenol-Induced Lipolysis in Rat Adipocytes Via a Non-Type 1A Growth Hormone Secretagogue Receptor" European Journal of Pharmacology, vol. 498, 2004, pp. 27-35.
N. Murakami, et al., "Role for Central Ghrelin in Food Intake and Secretion Profile of Stomach Ghrelin in Rats", Journal of Endocrinology, vol. 174, 2002, pp. 283-288.
Noritoshi Nagaya, et al., "Hemodynamic and Hormonal Effects of Human Ghrelin in Healthy Volunteers", Am J Physiol Regulatory Integrative Comp Physiol, vol. 280, 2001, pp. 1483-1487.
Maxine A. Papadakis, et al., "Growth Hormone Replacement in Healthy Older Men Improves Body Composition But Not Functional Ability" Annals of Internal Medicine, vol. 124, No. 8, 1996, pp. 708-716.
Mauro Papotti, et al., "Growth Hormone Secretagogue Binding Sites in Peripheral Human Tissues", The Journal of Clinical Endocrinology & Metabolism, vol. 85, No. 10, 2000, pp. 3803-3807.
S. Petersenn, "Structure and Regulation of the Growth Hormone Secretagogue Receptor" Minerva Endocrinologica, vol. 27, No. 4, 2002, pp. 243-256.
Jean-François Pons, et al., "Thiazole Formation Via Traceless Cleavage of Rink Resin" Tetrahedron Letters 41, 2000, pp. 4965-4968.
Ronenn Roubenoff, et al., "Rheumatoid Cachexia: Cytokine-Driven Hypermetabolism Accompanying Reduced Body Cell Mass in Chronic Inflammation" The Journal of Clinical Investigation, vol. 93, 1994, pp. 2379-2386.
Ronenn Roubenoff, et al., "Adjuvant Arthritis as a Model of Inflammatory Cachexia", Arthritis & Rheumatism, vol. 40, No. 3, 1997, pp. 534-539.
Daniel Rudman, et al., "Effects of Human Growth Hormone in Men Over 60 Years Old", The New England Journal of Medicine, vol. 323, No. 1, 1990, pp. 1-6.
Roy G. Smith, et al., "Peptidomimetic Regulation of Growth Hormone Secretion", Endocrine Reviews, vol. 18, No. 5, 1997, pp. 621-645.
Roy G. Smith, et al., "Growth Hormone Releasing Substances: Types and Their Receptors", Hormone Research, vol. 51 (suppl. 3), 1999, pp. 1-8.
Roy G. Smith, et al., "Growth Hormone Secretagogue Receptor Family Members and Ligands", Endocrine, vol. 14, No. 1, 2001, pp. 9-14.
A. J. Spiegel, et al., "Use of Nonaqueous Solvents in Parenteral Products", Journal of Pharmaceutical Sciences, vol. 52, No. 10, 1963, pp. 917-927.
Jeannine S. Strobl, et al., "Human Growth Hormone", Pharmacological Reviews, vol. 46, No. 1, 1994, pp. 1-34.
Yuxiang Sun, et al., "Ablation of *Ghrelin* Improves the Diabetic But Not Obese Phenotype of *OB/OB* Mice", Cell Metabolism, vol. 3, 2006, pp. 379-386.
Kazuhiko Takaya, et al., "Ghrelin Strongly Stimulates Growth Hormone (GH) Release in Humans", The Journal of Clinical Endocrinology & Metabolism, vol. 85, No. 12, 2000, pp. 4908-4911.
Carina P. Tan, et al., "Cloning and Characterization of a Human and Murine T-Cell Orphan G-Protein-Coupled Receptor Similar to the Growth Hormone Secretagogue and Neurotensin Receptors", Genomics, vol. 52, 1998, pp. 223-229.
Nichola M. Thompson, et al., "Ghrelin and Des-Octanoyl Ghrelin Promote Adipogenesis Directly in Vivo by a Mechanism Independent of the Type 1A Growth Hormone Secretagogue Receptor", Endocrinology, vol. 145, No. 1, 2004, pp. 234-242.
Michael H. Torosian, "Growth Hormone and Prostate Cancer Growth and Metastasis in Tumor-Bearing Animals", Journal of Pediatric Endocrinology, vol. 6, No. 1, 1993, pp. 93-97.
Antonio Torsello, et al., "Novel Hexarelin Analogs Stimulate Feeding in the Rat Through a Mechanism Not Involving Growth Hormone Release", European Journal of Pharmacology, vol. 360, 1998, pp. 123-129.
Antonio Torsello, et al., "Differential Orexigenic Effects of Hexarelin and Its Analogs in the Rat Hypothalamus: Indication for Multiple Growth Hormone Secretagogue Receptor Subtypes" Neuroendocrinology, vol. 72, 2000, pp. 327-332.
L. Trudel, et al., "Ghrelin/Motilin-Related Peptide is a Potent Prokinetic to Reverse Gastric Postoperative Ileus in Rat", Am J Physiol Gastrointest Liver Physiol, vol. 282, 2002, pp. 948-952.
Matthias Tschöp, et al., "Ghrelin Induces Adiposity in Rodents", Nature, vol. 407, 2000, pp. 908-913.
Matthias Tschöp, et al., "Circulating Ghrelin Levels Are Decreased in Human Obesity", Diabetes, vol. 50, 2001, pp. 707-709.
"Pharmaceutical Dosage Forms", Ullmann's Encyclopedia of Technical Chemistry, vol. 4, 1953, pp. 1-33.
Aart J. Van Der Lely, et al., "Biological, Physiological, Pathophysiological, and Pharmacological Aspects of Ghrelin", Endocrine Reviews, vol. 25, 2004, pp. 426-457.
Stephen Welle, et al., "Growth Hormone Increases Muscle Mass and Strength But Does Not Rejuvenate Myofibrillar Protein Synthesis in Healthy Subjects Over 60 Years Old", Journal of Clinical Endocrinology and Metabolism, vol. 81, No. 9, 1996, pp. 3239-3243.
Camille G. Wermuth, et al., "Designing Prodrugs and Bioprecursors I: Carrier Prodrugs", The Practice of Medicinal Chemistry, Chapter 31, 1996.
Mette Georgi Willesen, et al., "Co-Localization of Growth Hormone Secretagogue Receptor and NPY MRNA in the Arcuate Nucleus of the Rat", Neuroendocrinology, vol. 70, 1999, pp. 306-316.
Alison M. Wren, et al., "Ghrelin Causes Hyperphagia and Obesity in Rats", Diabetes, vol. 50, 2001, pp. 2540-2547.

(56) References Cited

OTHER PUBLICATIONS

A. M. Wren, et al., "Ghrelin Enhances Appetite and Increases Food Intake in Humans", The Journal of Clinical Endocrinology & Metabolism, vol. 86, 2001, pp. 5992-5995.

Damien Boeglin, et al., "Solution and Solid-Supported Synthesis of 3,4,5-Trisubstituted 1,2,4-Triazole-Based Peptidomimetics", 2003, vol. 5, No. 23, pp. 4465-4468.

International Search Report issued Feb. 3, 2007 in PCT/EP2006/007945.

Office Action issued Jan. 6, 2011, in Israel Patent Application No. 189459.

Office Action issued Nov. 30, 2009, in New Zealand Patent Application No. 565740.

Office Action issued Aug. 11, 2006, in Taiwan Patent Application No. 095129659.

Office Action issued Mar. 9, 2011, in Australian Patent Application No. 2006281594.

Office Action issued Jun. 30, 2008, in European Patent Application No. 06 776 764.0-2107.

Office Action issued Aug. 11, 2006, in Russian Patent Application No. 2008109929/04(010728).

Office Action issued Nov. 25, 2009, in U.S. Appl. No. 11/502,473, filed Aug. 11, 2006.

Office Action issued May 12, 2010, in Chinese Patent Application No. 200680035287.5.

Office Action issued Sep. 1, 2010, in Korean Patent Application No. 10-2008-7003755.

Office Action issued Jul. 7, 2012, in Singapore Patent Application No. 200800911-0.

* cited by examiner

Figure 1 (compound 9)
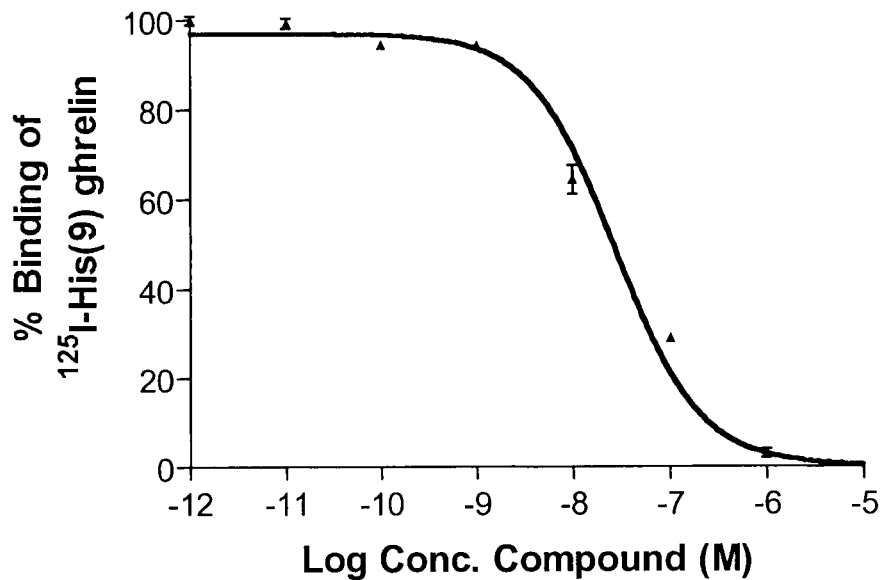
Figure 2 (compound 31)
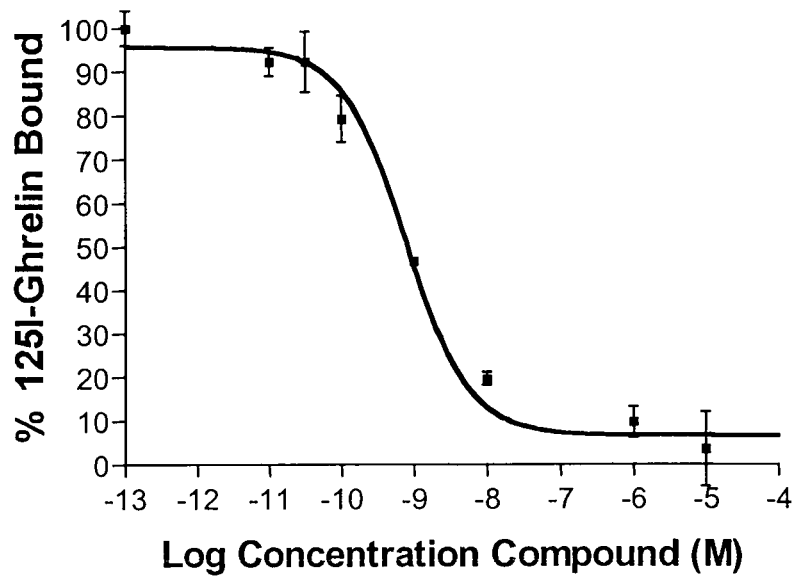

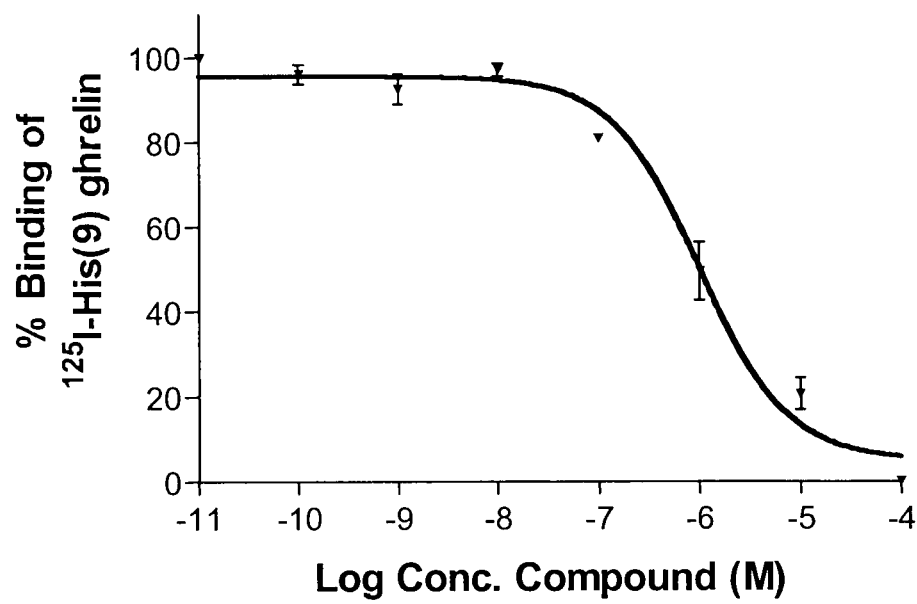
Figure 3 (compound 39)
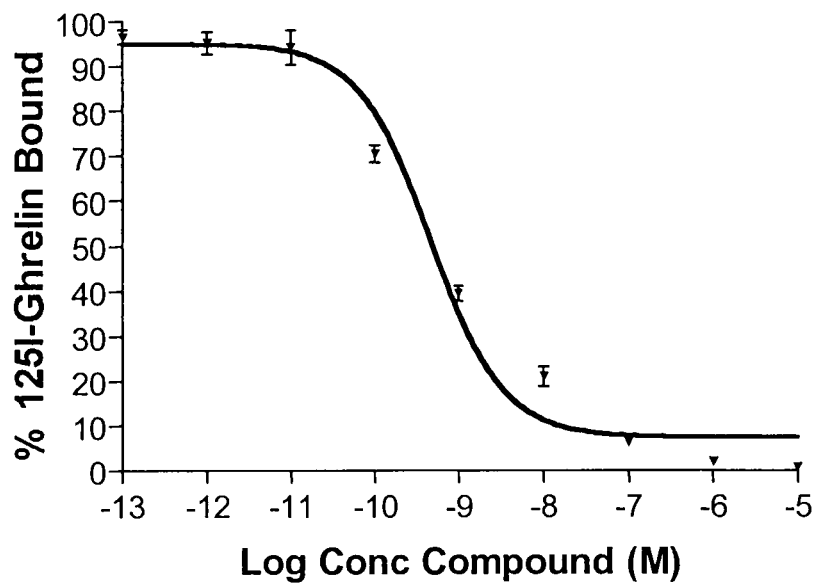
Figure 4 (compound 45)

Figure 5 (compound 50)
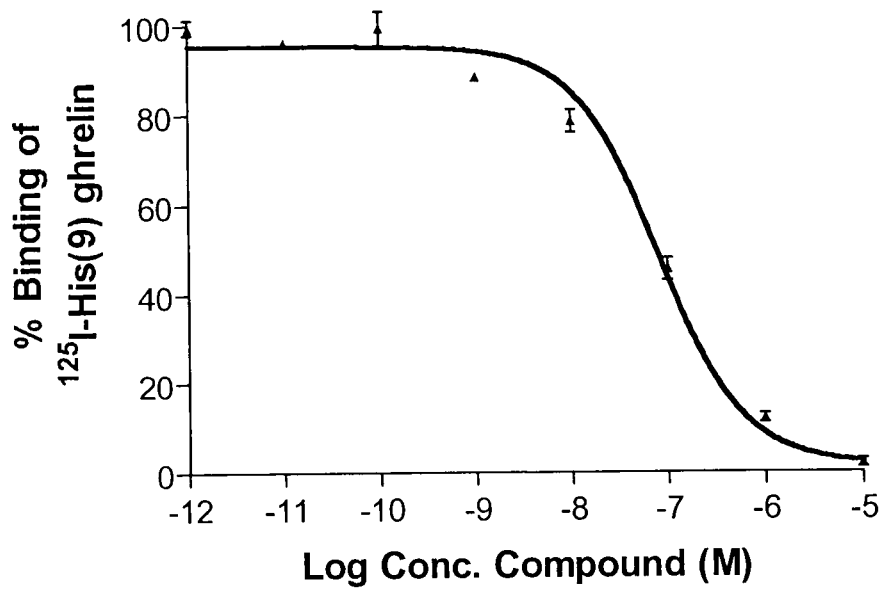
Figure 6 (compound 62)
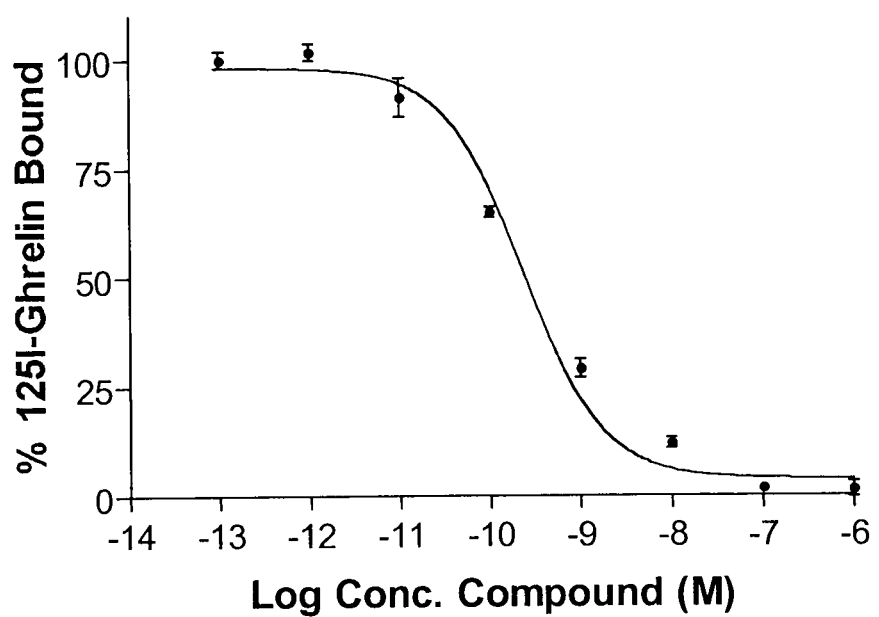

Figure 7 (compound 64)
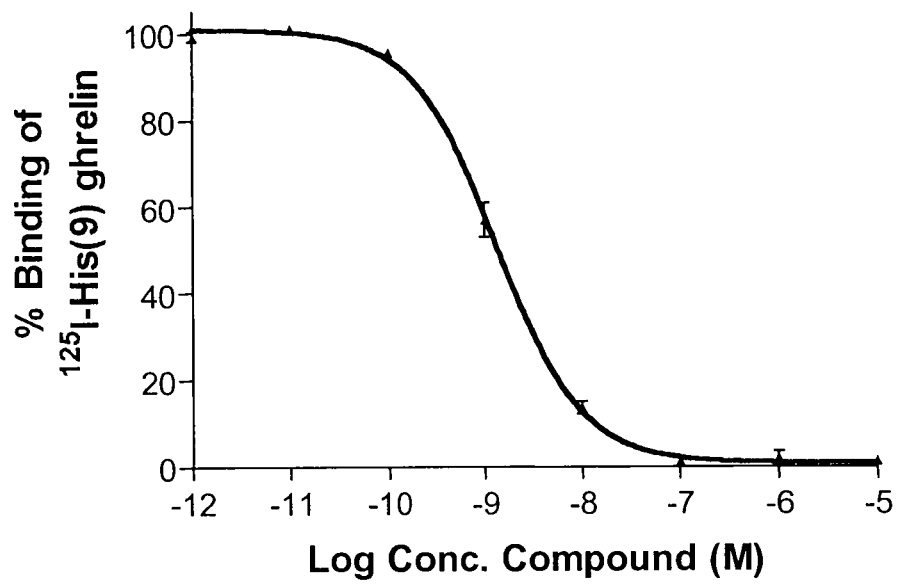
Figure 8 (compound 71)
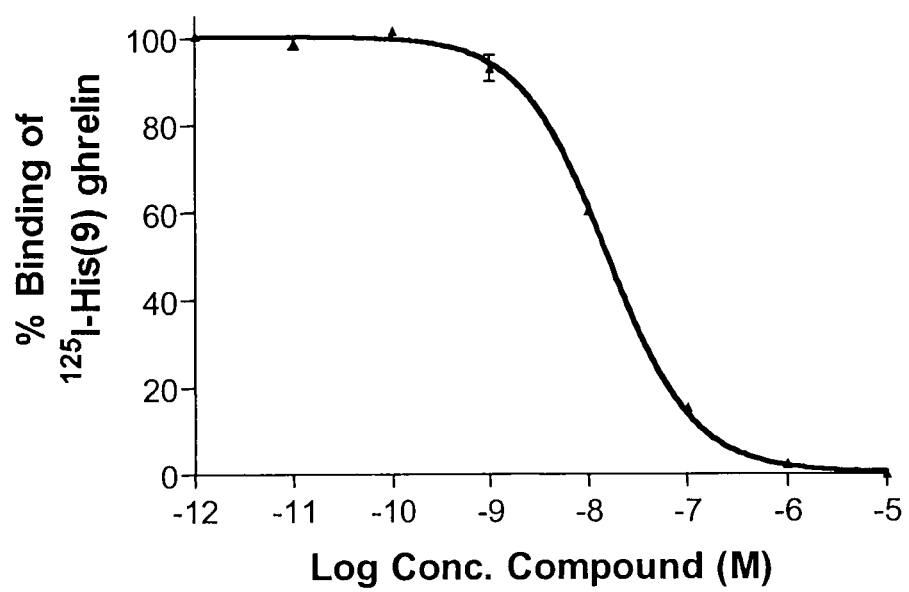

Figure 9 (compound 73)
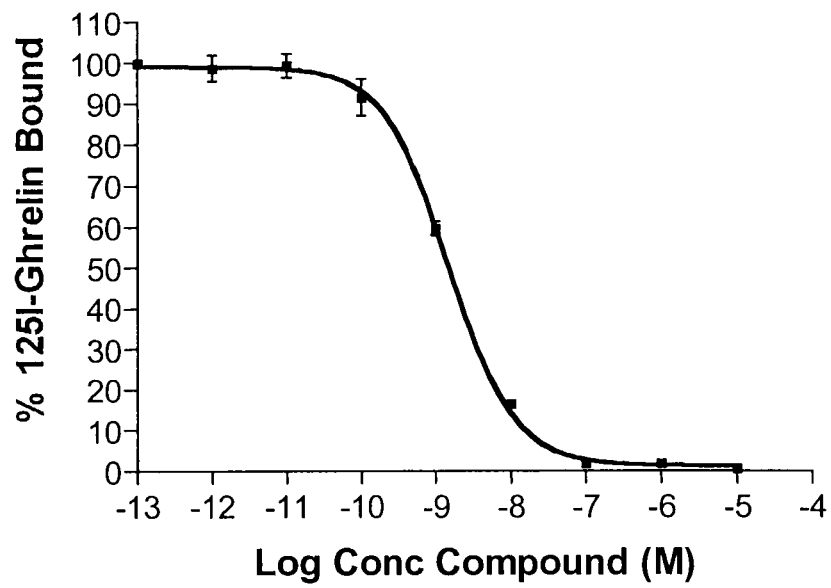
Figure 10 (compound 74)
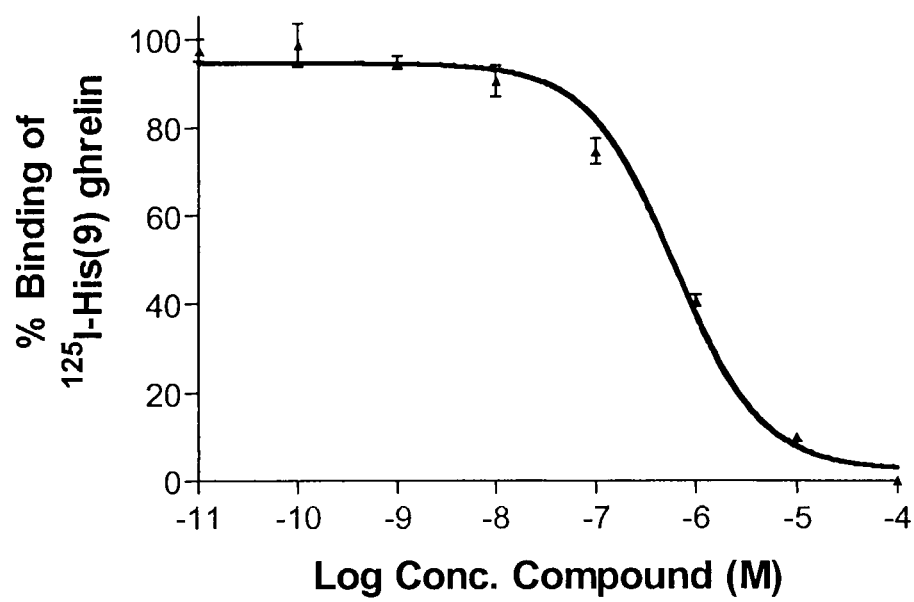

Figure 11 (compound 79)
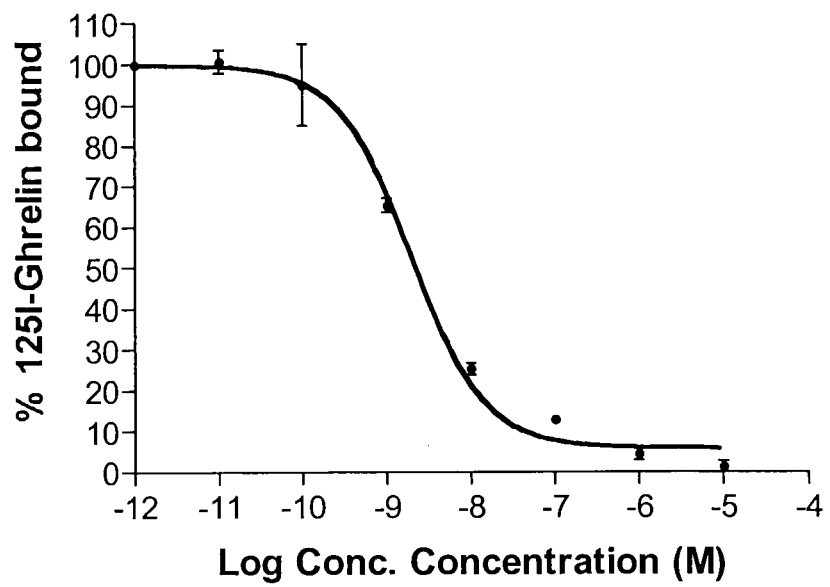
Figure 12 (compound 81)
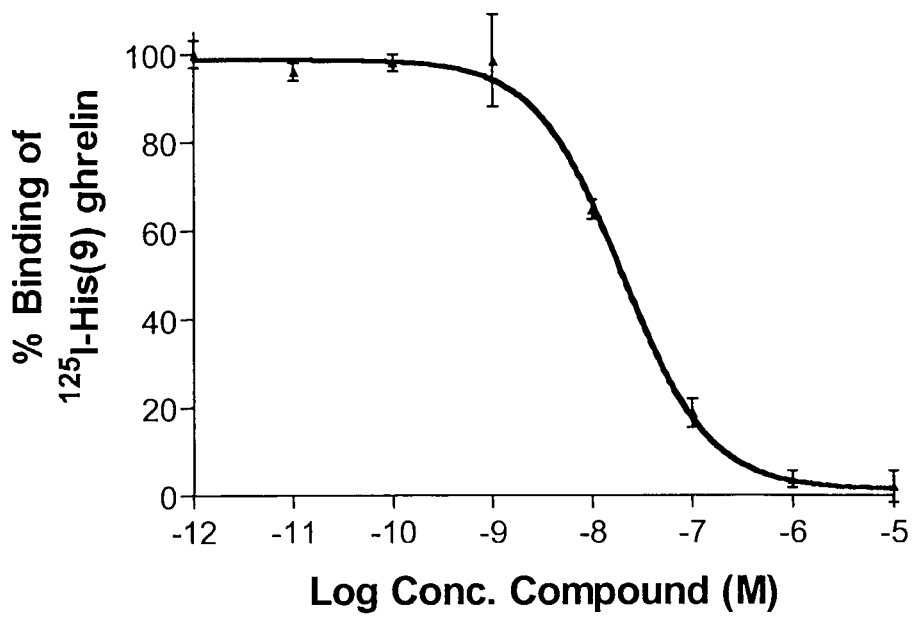

Figure 13 (compound 90)
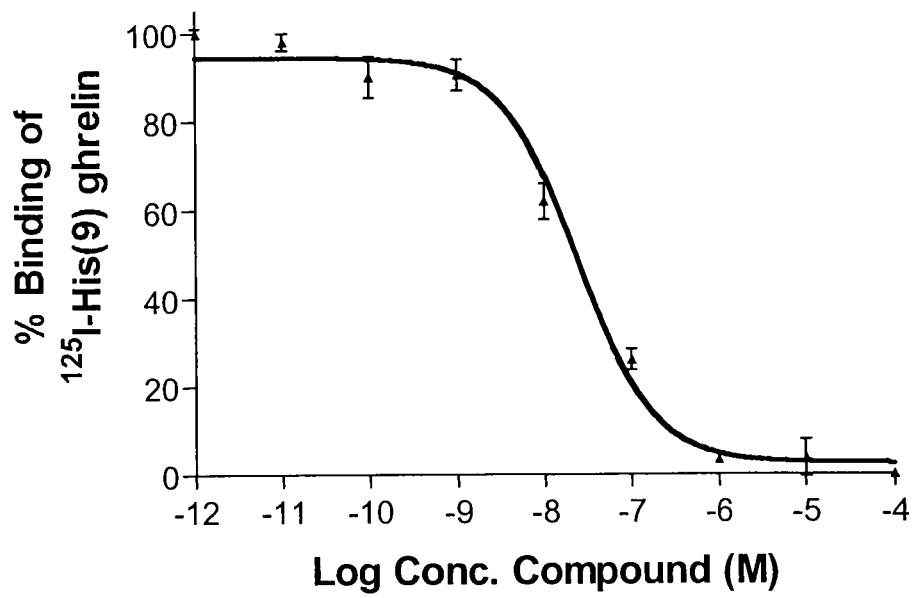
Figure 14 (compound 1)
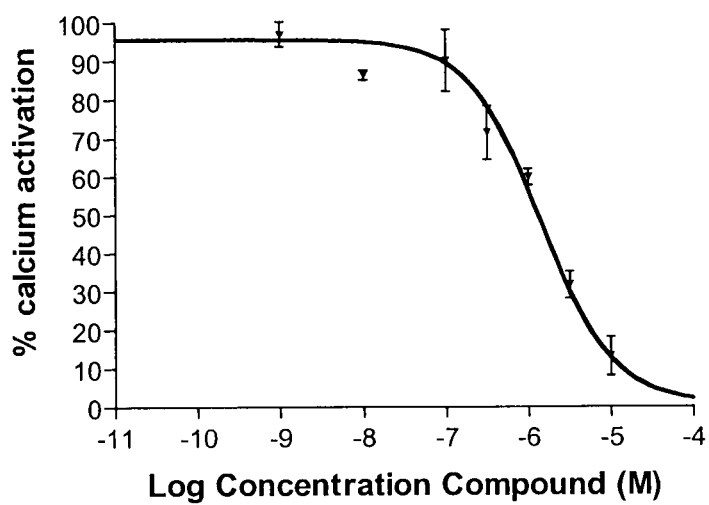
IC50=1,42e-6
Kb = 1,23e-8M Figure 15 (compound 9)
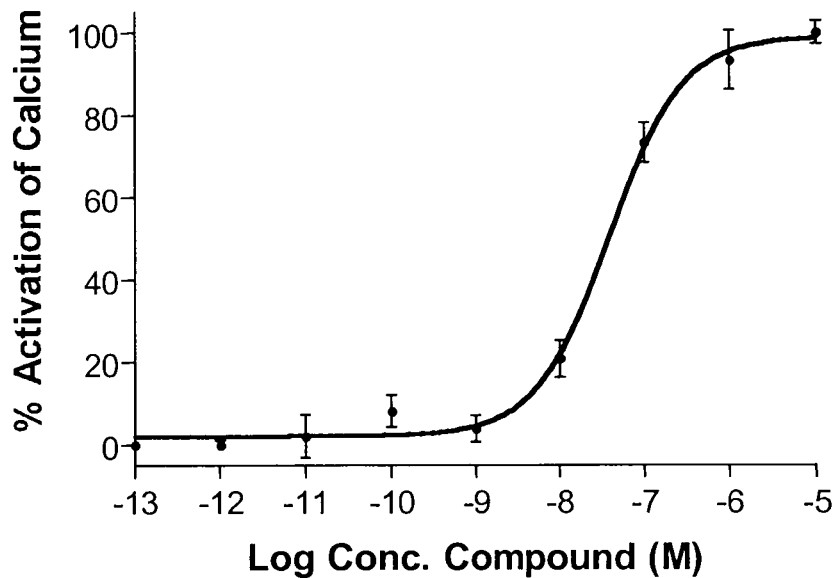
EC50: 3,89e-08
Figure 16 (compound 12)
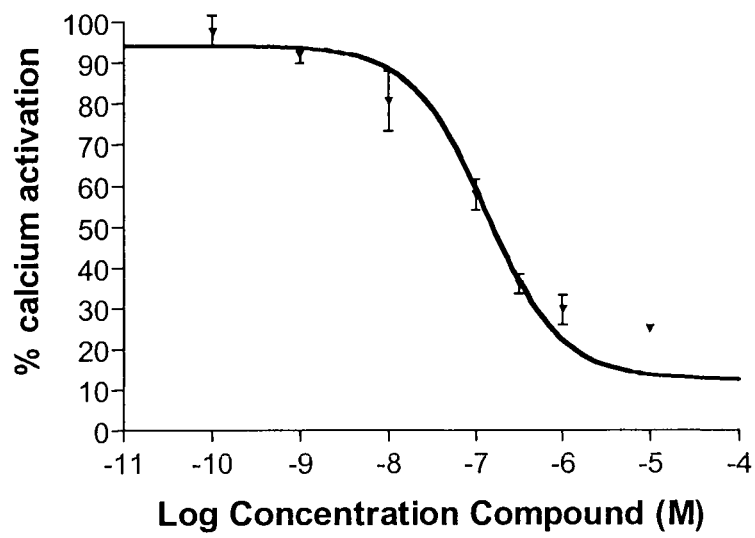
IC50 = 1.34e-7
Kb = 2,4e-9M Figure 17 (compound 20)
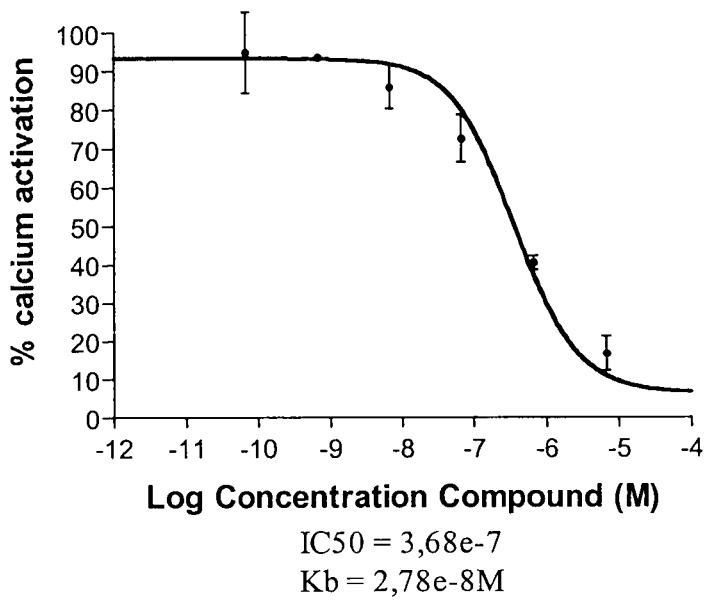
IC50 = 3,68e-7
Kb = 2,78e-8M
Figure 18 (compound 22)
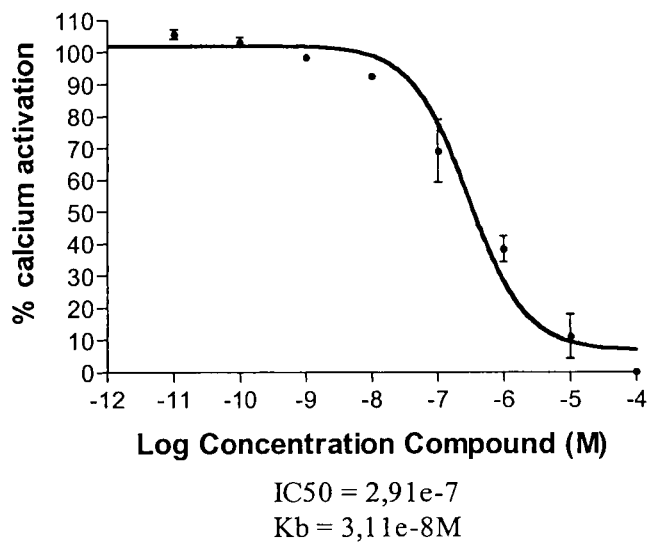
IC50 = 2,91e-7
Kb = 3,11e-8M Figure 19 (compound 31)
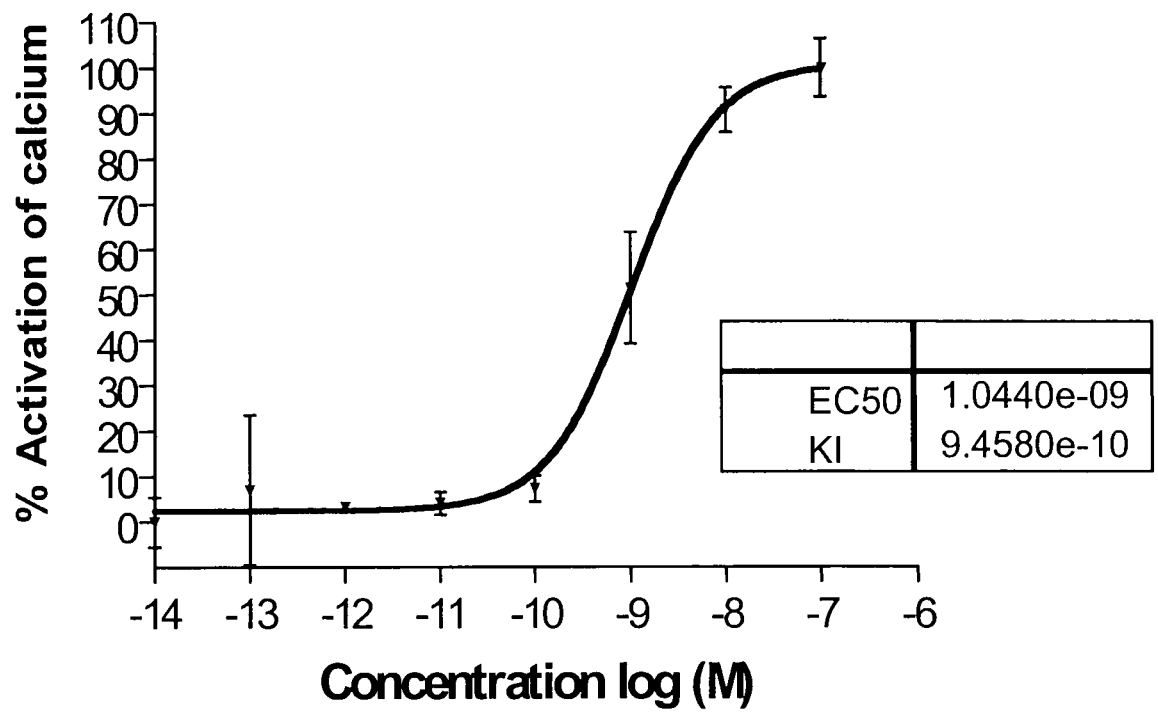
Figure 20 (compound 39)
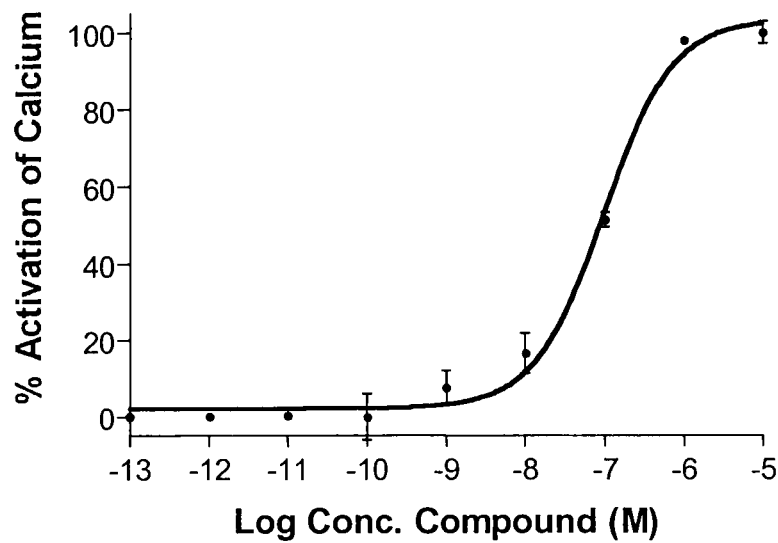

Figure 21 (compound 41)
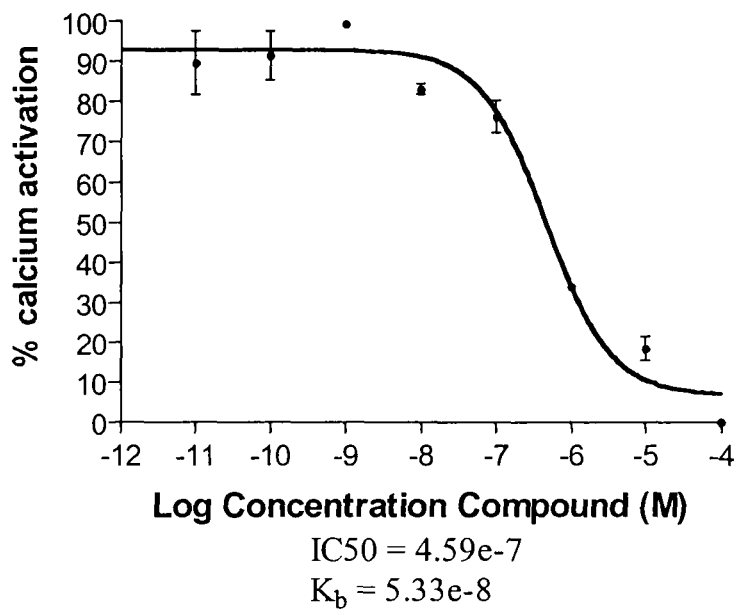
IC50 = 4.59e-7
$K_b$ = 5.33e-8
Figure 22 (compound 42)
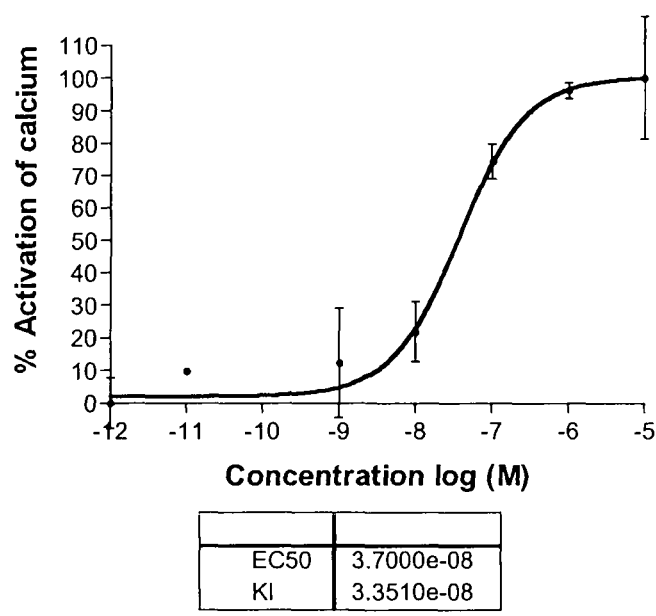
| EC50 | 3.7000e-08 |
|---|---|
| KI | 3.3510e-08 |

Figure 23 (compound 45)
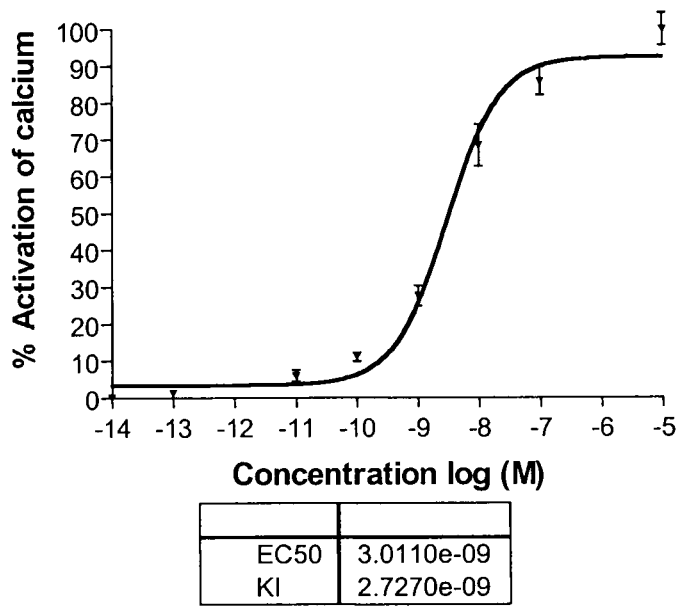
Figure 24 (compound 46)
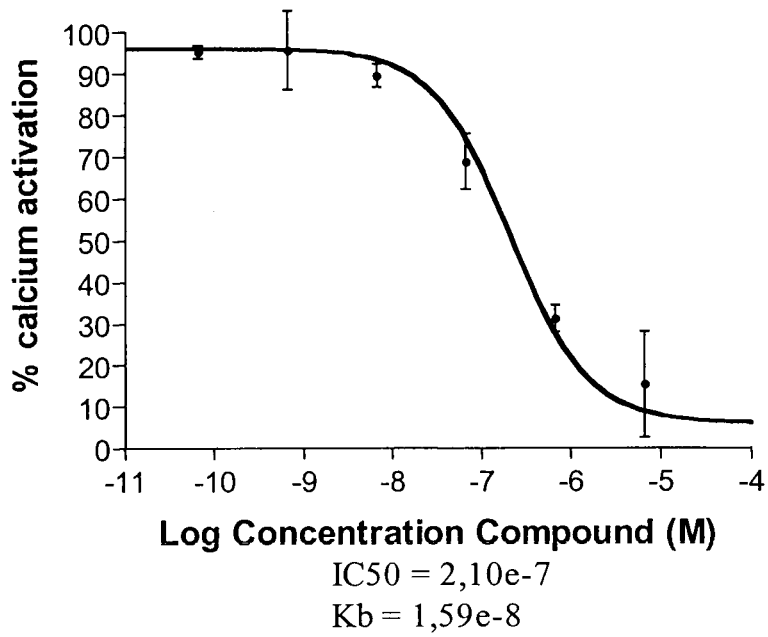
IC50 = 2,10e-7
Kb = 1,59e-8

Figure 25 (compound 47)
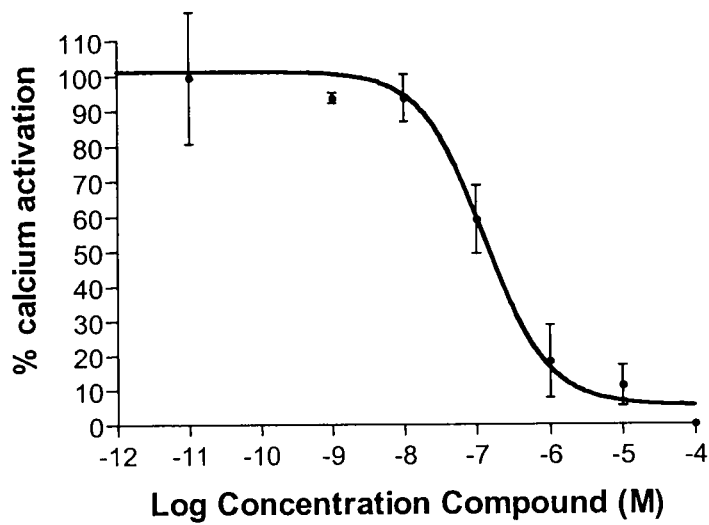
IC50 = 1,30e-7
$K_b$ = 5,37e-9
Figure 26 (compound 48)
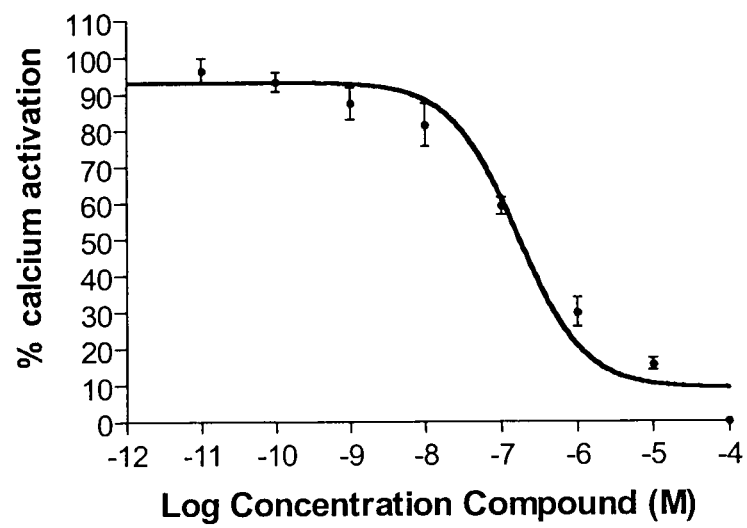
IC50 = 1,627e-7
$K_b$ = 1,74e-8M Figure 27 (compound 49)
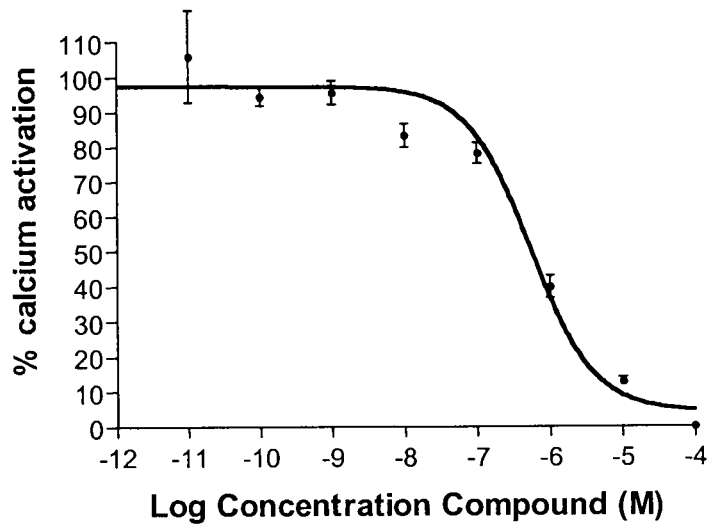
IC50 = 5,37e-7
$K_b$ = 5,84e-8
Figure 28 (compound 50)
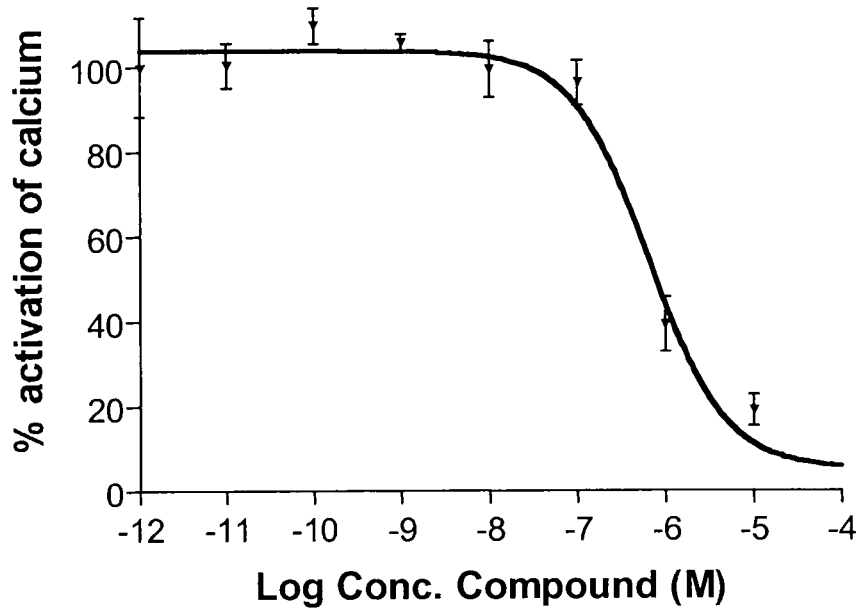
| IC50: | 6,23e-07 |
|---|---|
| Kb: | 1,46e-08 |

Figure 29 (compound 51)
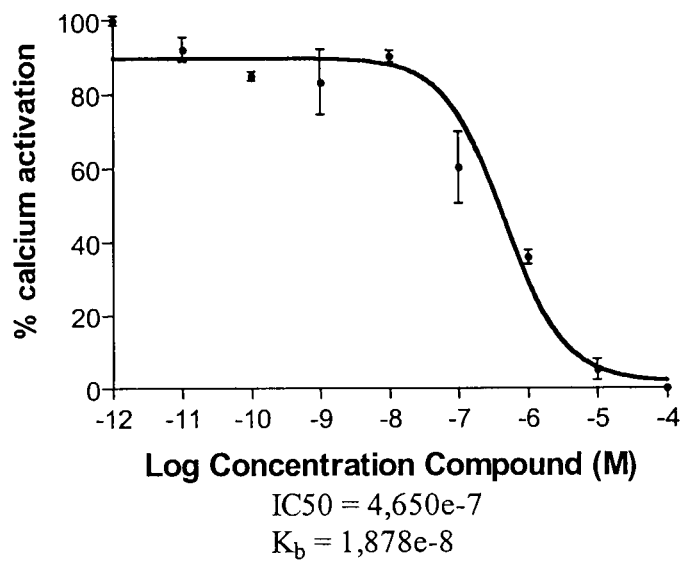
IC50 = 4,650e-7
$K_b$ = 1,878e-8
Figure 30 (compound 55)
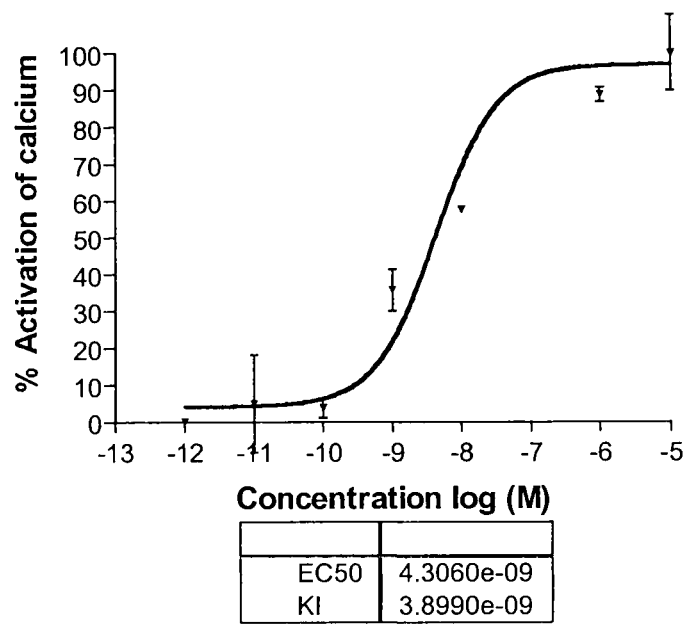
| EC50 | 4.3060e-09 |
|---|---|
| KI | 3.8990e-09 |

Figure 31 (compound 62)
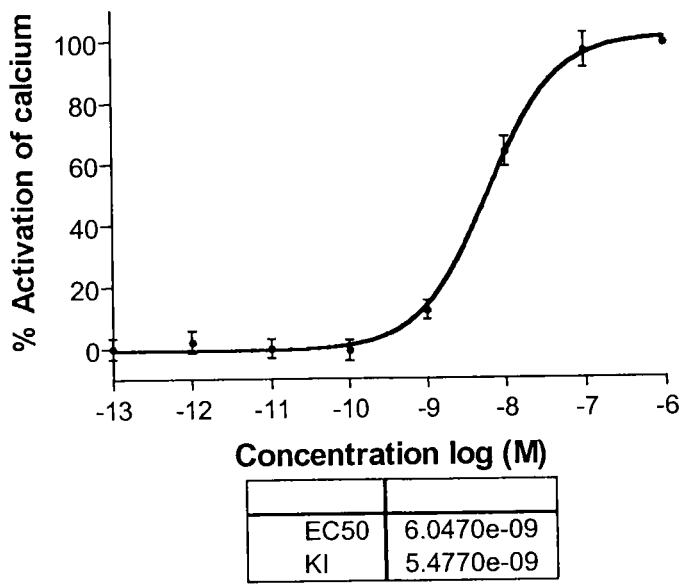
Figure 32 (compound 64)
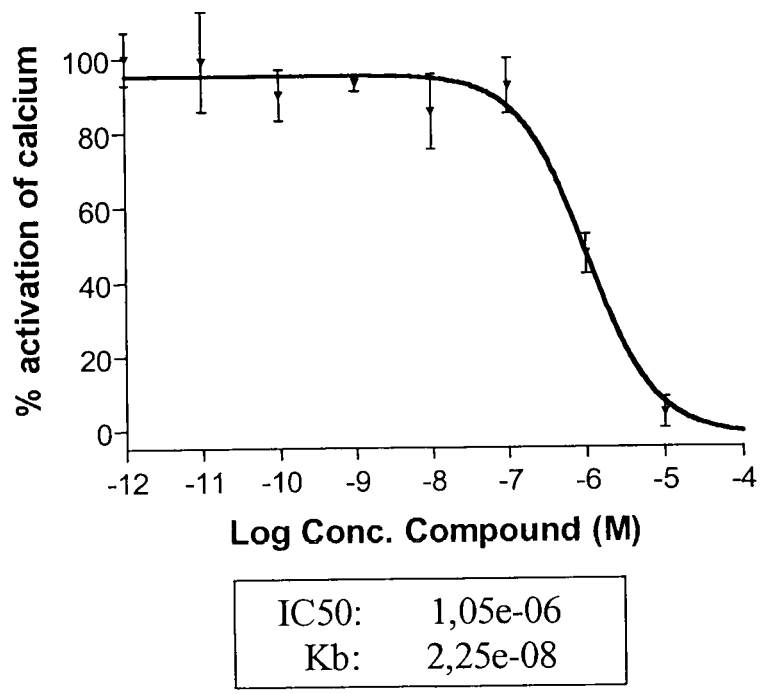

Figure 33 (compound 67)
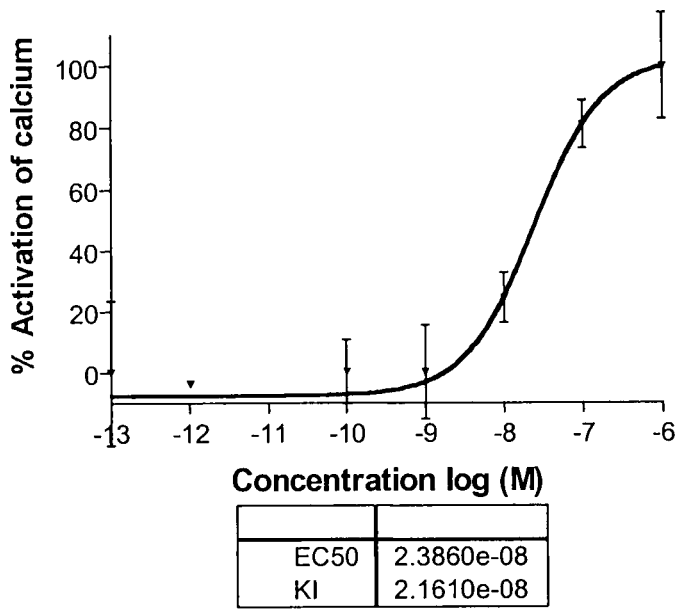
Figure 34 (compound 71)
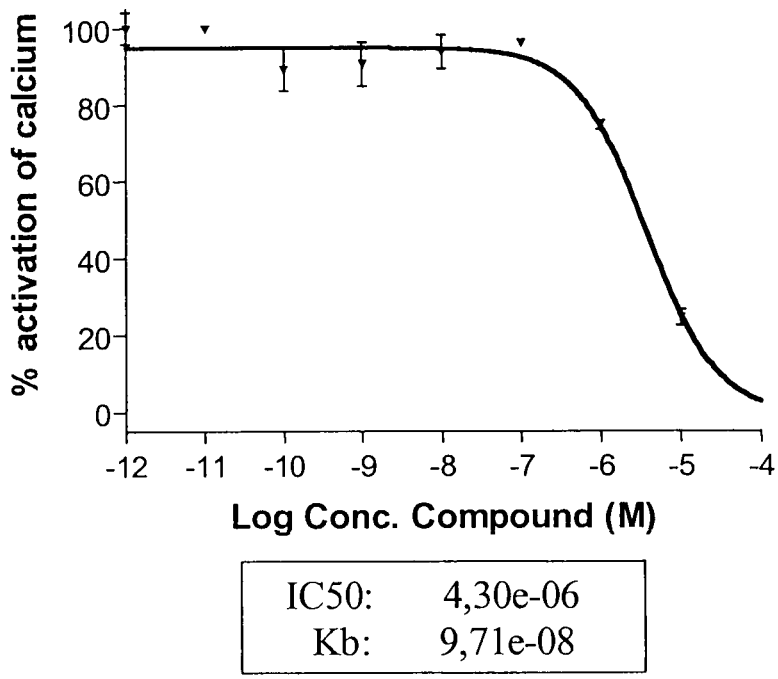

Figure 35 (compound 73)
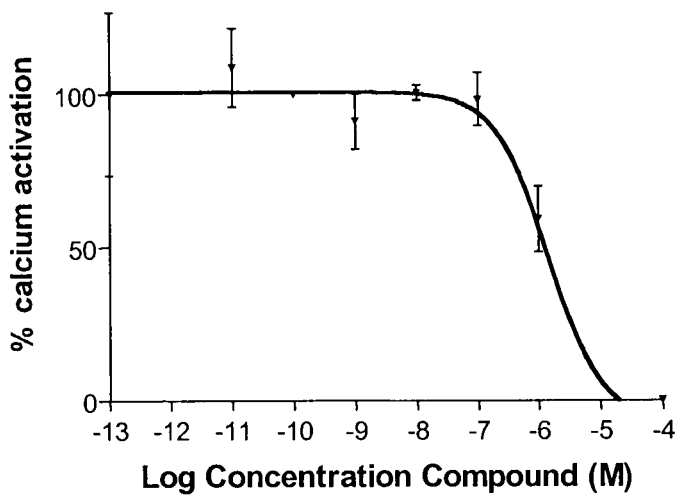
IC50 = 1,44e-6
$K_b$ = 1,66e-8M
Figure 36 (compound 74)
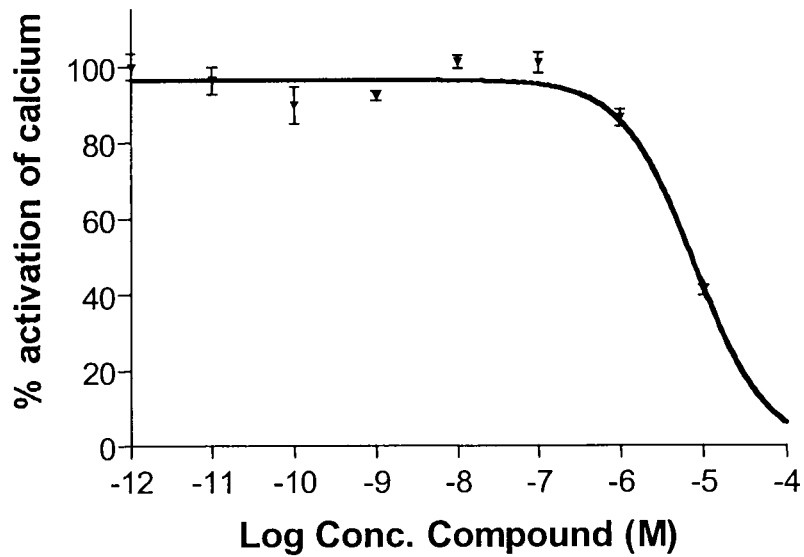
| IC50: | 7,82e-06 |
|---|---|
| $K_b$: | 1,68e-07 |

Figure 37 (compound 79)
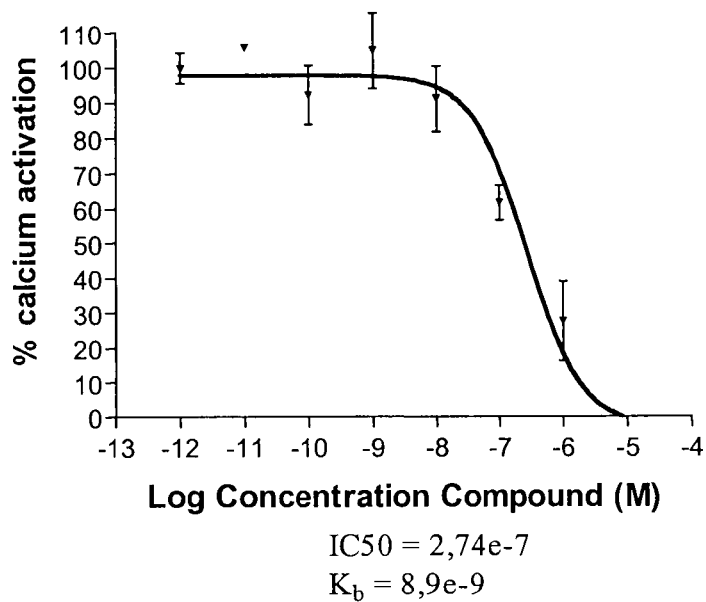
IC50 = 2,74e-7
$K_b$ = 8,9e-9
Figure 38 (compound 81)
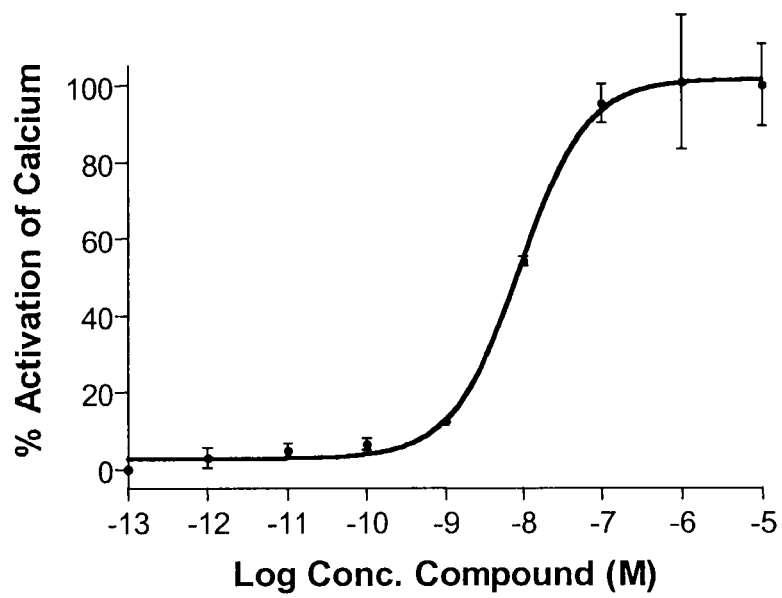
EC50:   9,64e-09

Figure 39 (compound 90)
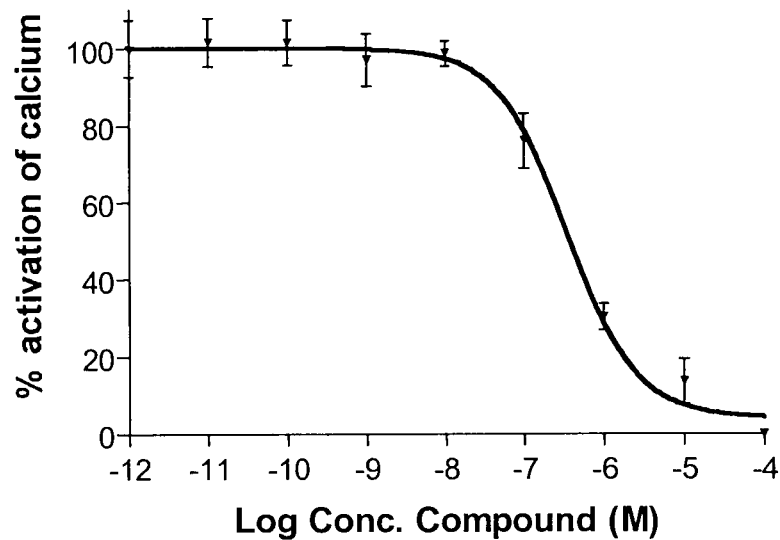
Figure 40 (ghrelin)
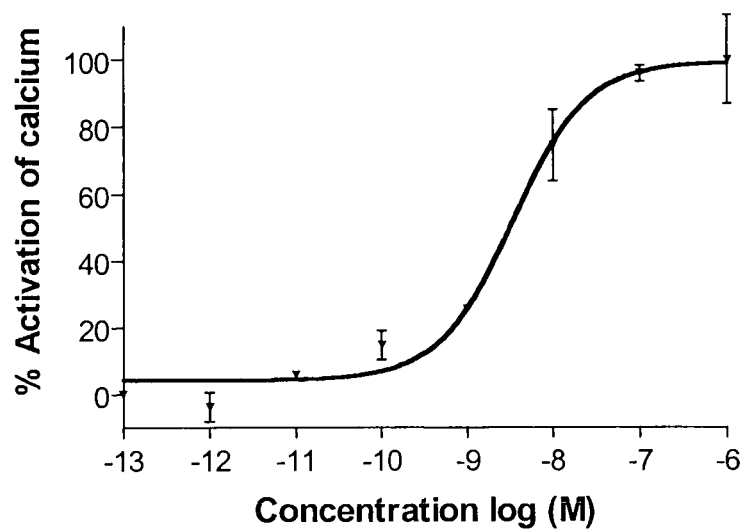

Figure 41 (compound 9)
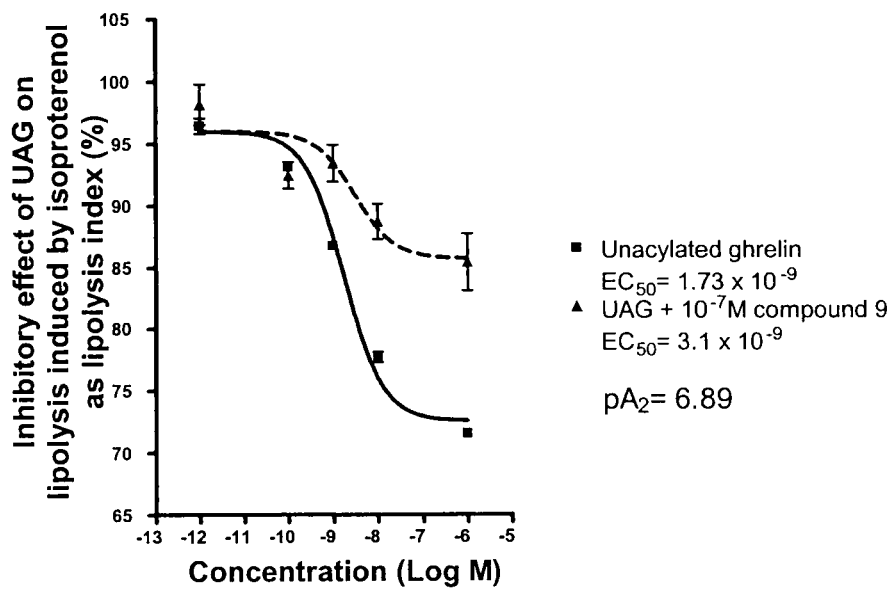
Figure 42 (compound 38)
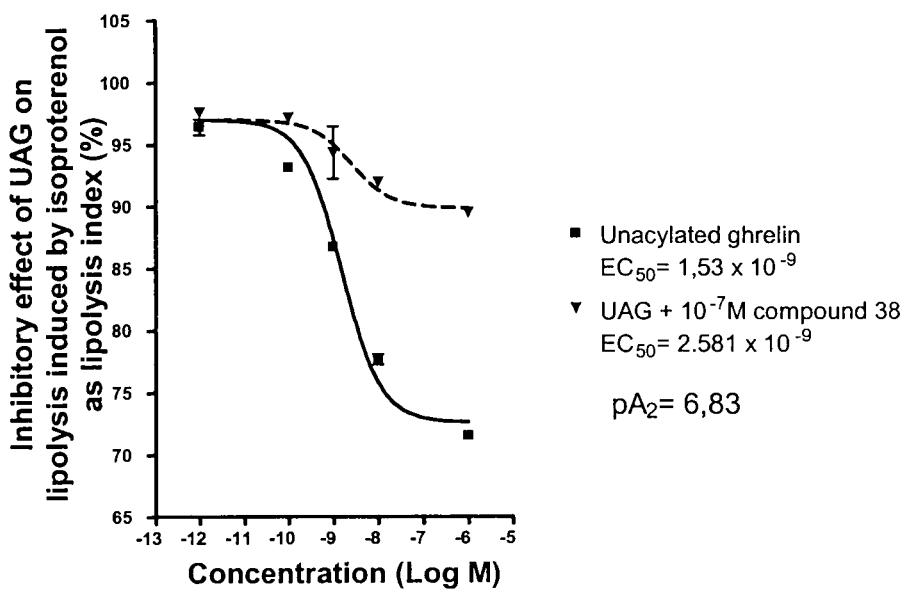

Figure 43 (compound 50)
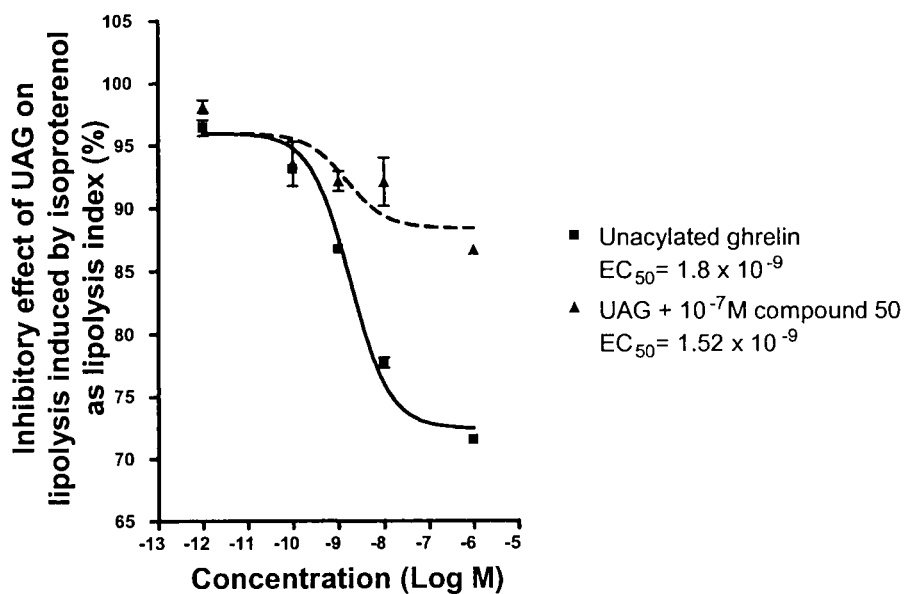
Figure 44 (compound 64)
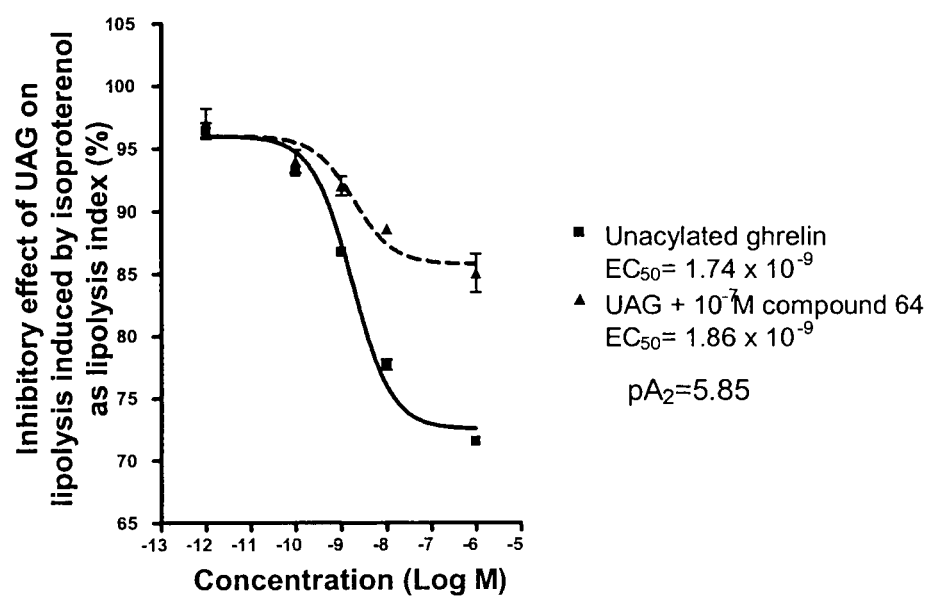

Figure 45 (compound 74)
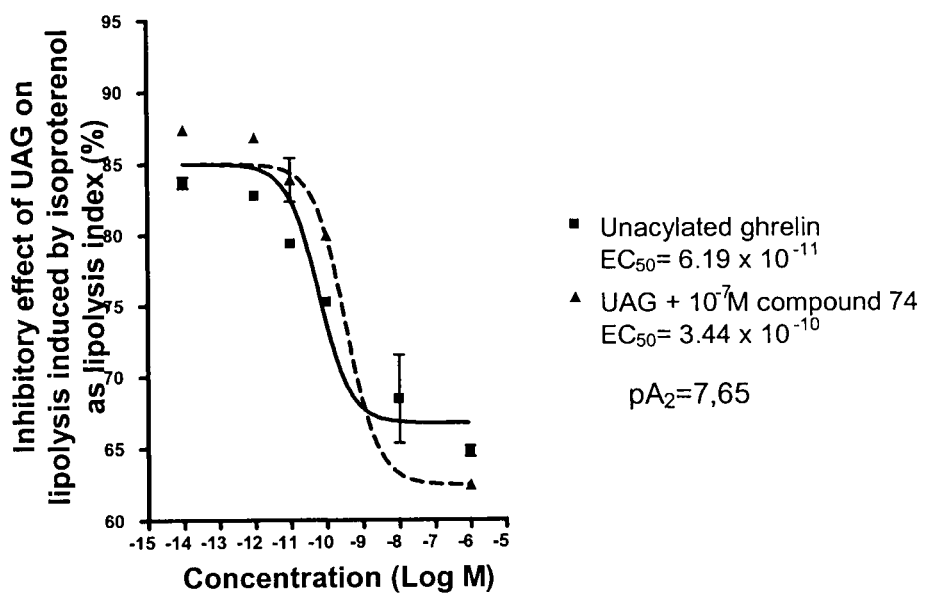
- Unacylated ghrelin
  $EC_{50}= 6.19 \times 10^{-11}$
- UAG + $10^{-7}$M compound 74
  $EC_{50}= 3.44 \times 10^{-10}$
$pA_2=7,65$
Figure 46 (compound 81)
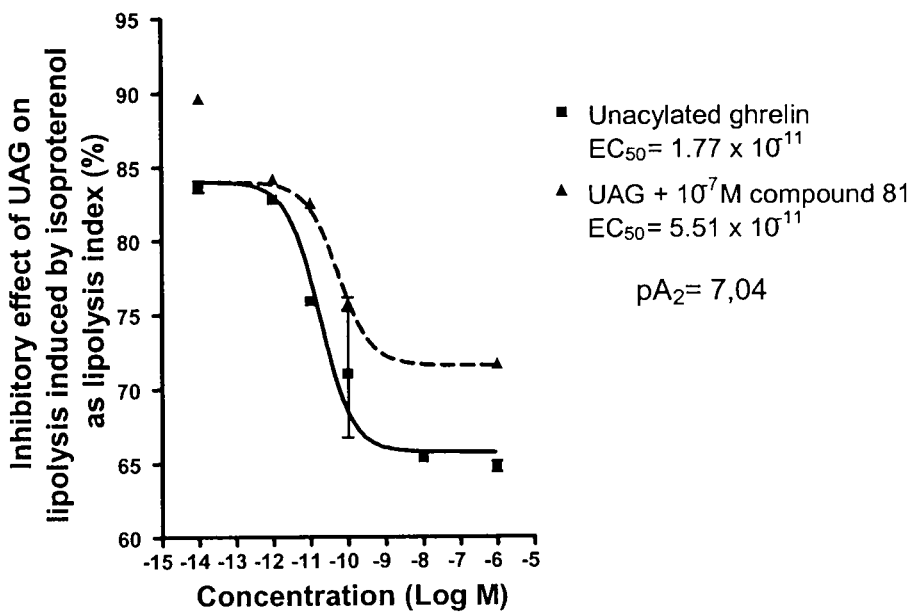
- Unacylated ghrelin
  $EC_{50}= 1.77 \times 10^{-11}$
- UAG + $10^{-7}$M compound 81
  $EC_{50}= 5.51 \times 10^{-11}$
$pA_2= 7,04$

TRIAZOLE DERIVATIVES AS GHRELIN ANALOGUE LIGANDS OF GROWTH HORMONE SECRETAGOGUE RECEPTORS

REFERENCE TO RELATED APPLICATIONS

This application is a Divisional under 35 U.S.C. §120 to U.S. utility application Ser. No. 11/502,473, filed Aug. 11, 2006, now U.S. Pat. No. 7,829,724 which claims priority 35 U.S.C. §119(e) to U.S. provisional application 60/707,941 filed Aug. 15, 2005, and to U.S. provisional application 60/787,543 filed Mar. 31, 2006; a claim is also made for priority under 35 U.S.C. §119 to European application 05017732.8 filed Aug. 16, 2005, all of which are incorporated herein by reference.

TECHNICAL FIELD

The invention relates to novel triazole derivatives that act as ghrelin analogue ligands of growth hormone secretagogue receptors. These compounds are useful in modulating growth hormone plasma levels in mammals as well as in the treatment and/or regulation of various physiological and pathophysiological conditions, such as growth retardation, obesity, food intake, energy balance, tumor cell proliferation, wound/burn healing, metabolic disorders and inflammation.

BACKGROUND OF THE INVENTION

Ghrelin, a 28 amino acid peptide with a unique octanoyl modification on Ser-3 (Kojima M et al., Nature 1999, 402: 656-660), was identified as an endogenous ligand for the growth hormone secretagogue receptor type 1a (GHS-R 1a), a G-protein coupled receptor (Howard A D et al., Science 1996, 273: 974-977). Ghrelin is essentially produced in the upper intestinal tract/stomach but lower amounts were also detected in bowel, pancreas, kidney, the immune system, placenta, testes, pituitary, lung and in the hypothalamus (van der Lely A J et al., Endocrine Rev. 2004, 25: 426-457; Cowley M et al., Neuron 2003, 37: 649-661).

In humans, ghrelin stimulates growth hormone (GH) via a pathway independent from GHRH receptor and in synergy with GHRH on GH secretion (Arvat E et al., J. Clin. Endocrinol. Metab. 2001, 86: 1169-1174). Besides, it also stimulates ACTH, prolactin, cortisol, aldosterone and epinephrine secretion (Arvat E et al., J. Clin. Endocrinol. Metab. 2001, 86: 1169-1174; Nagaya N et al., Am. J. Physiol. Regul. Integr. Comp. Physiol. 2001, 280: R1483-1487; Takaya K et al., J. Clin. Endocrinol. Metab. 2000, 85: 4908-4911).

Ghrelin is thought to participate in metabolism regulation and energy expenditure, so ghrelin expression and secretion into the general circulation from the stomach is expected to be influenced by metabolic hormones. In obese humans, plasma ghrelin levels are reduced, suggesting that the elevated insulin or leptin levels of obese subjects lower ghrelin secretion (Tschop M et al, Diabetes 2001, 50: 707-709).

The release of growth hormone in humans and animals is believed to treat physiological or pathophysiological conditions characterized by a deficiency in growth hormone secretion as well as to treat those conditions which are improved by the anabolic effects of growth hormone.

Initially, clinical applications with GH were limited to treatment of GH-deficient children, but the commercialization of recombinant human growth hormone (rhGH) allowed many studies which showed other potential clinical uses of GH (Strobl J S et al., Pharmacol. Rev. 1994, 46: 1-34; Torosian M H, J. Pediatr. Endocrinol. 1993, 6: 93-97). rhGH has shown promise in the treatment of patients with burns, wounds, bone fractures and more recently in reversing the catabolic effects of glucocorticoids, chemotherapy and AIDS as well as in modifying body composition (Rudman D et al., N. Engl. J. Med. 1990, 323: 1-6; Papadakis M A et al., Ann. Intern. Med. 1996, 124: 708-716; Welle S et al., J. Clin. Endocrinol. Metab. 1996, 81: 3239-3243).

GH, synthesized and stored in the pituitary gland, is released under the control of two known hypothalamic hormones: growth hormone releasing hormone (GHRH) and the inhibitory hormone somatostatin (SRIF). In most cases, GH deficiency is related to a hypothalamic defect and not to a pituitary deficiency in GH. Therefore, as an alternative treatment to rhGH, GH-deficient patients could also be treated with any compound that releases endogenous GH from the pituitary gland. This can either be performed with GHRH which stimulates GH release but also with synthetic growth hormone secretagogues (GHS).

Many synthetic, peptidyl and non-peptidyl GHS, such as GHRPs 1, 2 and 6, Hexarelin, MK-0677, EP-01572, were shown to specifically bind to the then orphan receptor GHS receptor—several of them long before ghrelin and ghrelin/GHS receptor were discovered (see Camanni F et al., Front Neuroendocrinol. 1998, 19: 47-72; Casanueva F F et al., Trends Endocrinol. Metab. 1999, 10: 30-38; van der Lely A J et al., Endocrine Rev. 2004, 25: 426-457 for further references). GHS also show potent GH releasing action and have the same biological activities as mentioned above for ghrelin.

GHS were also disclosed in the following patents or patent applications (not exhaustive list): U.S. Pat. No. 6,071,926, U.S. Pat. No. 6,329,342, U.S. Pat. No. 6,194,578, US 2001/0041673, U.S. Pat. No. 6,251,902, US 2001/0020012, US 2002/0013320, US 2002/0002137, WO 95/14666, WO 96/15148, WO 01/96300.

While the ghrelin/GHS induced GH secretion is mediated by the activation of the ghrelin/GHS receptor type 1a (GHS-R 1a), there is evidence so far that at least some of the other effects of ghrelin and GHS are also mediated by different receptors of the GHS receptor family or even different binding sites on a given GHS receptor.

GHS receptors are concentrated in the hypothalamus-pituitary area but appear also to be distributed in other central and peripheral tissues (Hattori N et al., J. Clin. Endocrinol. Metab. 2001, 86: 4284-4291; Gnanapavan S et al., J. Clin. Endocrinol. Metab. 2002, 87: 2988-2991; Muccioli G et al., J. Endocrinol. 2000, 157: 99-106; Muccioli G et al., Ann. Endocrinol. 2000, 61: 27-31; Muccioli G et al., Eur. J. Pharmacol. 2002, 440: 235-254; Papotti M et al., J. Clin. Endocrinol. Metab. 2000, 85: 3803-3807; Cassoni P et al., J. Clin. Endocrinol. Metab. 2001, 86: 1738-1745; Guan X M et al., Brain Res. Mol. Brain. Res. 1997, 48: 23-29; Bluet-Pajot M T et al., Endocrine 2001, 14: 1-8; Korbonits M et al., J. Clin. Endocrinol. Metab. 1998, 83: 3624-3630).

Two GHS type 1 receptors have been identified, GHS-R 1a and GHS-R 1b, that in human are presumably expressed by a single gene and alternatively spliced (van der Lely A J et al., Endocrine Rev. 2004, 25: 426-457; Howard A D et al., Science 1996, 273: 974-977; Smith R G et al., Endocr. Rev. 1997, 18: 621-645; Smith R G et al., Endocrine 2001, 14: 9-14; McKee K K et al., Mol. Endocrinol. 1997, 11: 415-423; Petersenn S, Minerva Endocrinol. 2002; 27: 243-256). Among mammalian species a high degree of sequence identity has been reported for GHS-R 1a (Petersenn S, Minerva Endocrinol. 2002; 27: 243-256: between 91.8% and 95.6%).

Motilin receptor, was discovered as a member of the GHS receptor family, having 52% identity (Smith R G et al., Endocrine 2001, 14: 9-14; McKee K K et al., Genomics 1997, 46:

426-434). Gastrointestinal motilin receptor 1a and GHS-R 1a show a high similarity (Smith R G et al., Endocrine 2001, 14: 9-14; Feighner S D et al., Science 1999, 284: 2184-2188).

Other GHS receptor family members appear to be neurotensin receptor, TRH receptor, GPR38 (FM1), GPR39 (FM2) and FM3 (Smith R G et al., Endocr. Rev. 1997, 18: 621-645; Smith R G et al., Horm. Res. 1999, 51 (Suppl. 3): 1-8; Tan C P et al., Genomics 1998, 52: 223-229; Howard A D et al., Science 1996, 273: 974-977). Further GHS receptor subtypes appear to exist in a wide variety of central and peripheral tissues (van der Lely A J et al., Endocrine Rev. 2004, 25: 426-457). For instance, a cardiac GHS-R has been reported (Bodart V et al., Circ. Res. 1999, 85: 796-802) with a predicted sequence similar to that of CD36, a multifunctional receptor known as glycoprotein IV (Bodart V et al., Circ. Res. 2002, 90: 844-849). Cassoni et al. (J. Clin. Endocrinol. Metab. 2001, 86: 1738-1745) report the existence of GHS-R subtypes in neoplastic mammary cells that are activated by ligands binding to specific binding sites different from the classical GHS-R type 1. Furthermore, data gathered by these authors support the hypothesis that even different binding site subtypes do exist for GHS-R in peripheral organs, which are possibly due to their endocrine or non-endocrine, but also on their normal or neoplastic nature.

The ubiquity of GHS binding sites explains that independently from their strong growth hormone secretagogue properties, ghrelin as well as synthetic GHS are implicated in several important physiological and pathophysiological conditions.

Accordingly, potential clinical applications include among others a) Short-, medium- and long term regulation of energy balance and/or food intake (Tschop M et al., Nature 2000, 407: 908-913; Asakawa A et al., Gut 2003, 52: 947-952; US 2001/0020012; Kojima M et al., Curr. Opin. Pharmacol. 2002, 2: 665-668; Horvath T L et al., Curr. Pharm. Des. 2003, 9: 1383-1395; Wren A M et al., J. Clin. Endocrinol. Metab. 2001, 86: 5992-5995)

Expression of GHS-R1a has been shown on neurons of hypothalamus paraventricular nucleus. These neurons send efferents onto key hypothalamic circuits for the control of food intake, like the arcuate nucleus which produces the mediator NPY. It is thought that the stimulation of food intake by ghrelin and/or GHS is mediated by an increase of NPY in the arcuate nucleus (Willesen M G et al., Neuroendocrin. 1999, 70: 306-316). Single administration (icy or ip) of antighrelin IgG suppressed acute feeding in lean rats (Bagnasco M et al., Regul. Pept. 2003, 111: 161-167). Chronic twice-daily icy administration of anti-ghrelin IgG reduced body weight over a five-day period (Murakami N et al., J. Endocrinol. 2002, 174: 283-288).

A recent study using a peptidic GHS-R 1a antagonist, [D-Lys-3]-GHRP-6, showed a reduction of food intake and body weight gain in diet induced obese mice (Asakawa A et al., Gut, 2003, 52: 947-952). The fact that peptidyl compounds, initially characterized as growth hormone secretagogues, are able to stimulate selectively food intake in rats without inducing growth hormone secretion, suggests the existence of a GHS-R subtype different from GHS-R 1a in the hypothalamus (Torsello A et al., Neuroendocrin. 2000, 72: 327-332; Torsello A et al., Eur. J. Pharmacol. 1998, 360: 123-129).

b) Treatment of adipogenesis, adiposity and/or obesity and reduction of body weight (Tschop M et al., Nature 2000, 407: 908-913; Asakawa A et al., Gut 2003, 52: 947-952)

Chronic administration of ghrelin and/or GHS in freely feeding mice and rats results in increased body weight and decreased fat utilization (Tschop M et al., Nature 2000, 407: 908-913). Furthermore, it has been reported that ghrelin and des-octanoyl ghrelin promote adipogenesis in vivo (Thompson N M et al., Endocrinol. 2004, 145: 234-242) and inhibit isoproterenol-induced lipolysis in rat adipocytes via a nontype GHS-R 1a (Muccioli G et al., Eur. J. Pharmacol. 2004, 498: 27-35). On the other hand, there is also a report describing that the expression of the GHS-R1a in rat adipocytes increases with age and during adipogenesis (Choi K et al., Endocrinol. 2003, 144, 754-759).

c) Treatment of tumor cell proliferation

As in the case for other members of the hypothalamus-pituitary axis which regulates the secretion of growth hormone, evidence is emerging to indicate that ghrelin and GHS-receptors may play an important autocrine/paracrine role in some cancers (Jeffery P L et al., Cytokine Growth Factor Rev. 2003, 14: 113-122). Specific binding sites for ghrelin, peptidyl- and non-peptidyl GHS are present in tumoral tissues, like prostate cancer cell line PC3 (Jeffery P L et al., J. Endocrinology 2002, 172: R7-R11), thyroid tissue (Cassoni P et al., J. Endocrinol. 2000, 165: 139-146), lung carcinoma cells CALU-1 (Ghè C et al., Endocrinol. 2002, 143: 484-491) and breast carcinomas (Cassoni P et al., J. Clin. Endocrinol. Metab. 2001, 86: 1738-1745).

In the case of breast, the specific binding sites for GHS were found in tumoral tissue while the normal mammary parenchyma did not reveal such receptors. Synthetic GHS have been reported to inhibit the proliferation of lung carcinoma cells CALU-1 (Ghè C et al., Endocrinol. 2002, 143: 484-491) and that of breast carcinoma cell lines (Cassoni P et al., J. Clin. Endocrinol. Metab. 2001, 86: 1738-1745).

Both ghrelin and non-acylated ghrelin bind to tumoral tissues. Because non-acylated ghrelin is unable to bind the GHS-R 1a, it is likely that the binding site of GHS to tumoral tissues is different from the GHS-R 1a. From these data, one can anticipate that the binding site in tumoral tissues recognizes ligands of the GHS-R 1a and in addition other not yet characterized chemical structures. Synthetic ligands of GHS-R 1a may have therefore the potential to inhibit the proliferation of tumor cells expressing subtypes of GHS receptors.

d) Treatment of inflammation/anti-inflammatory effects

The anti-inflammatory effect of the ghrelin agonist growth hormone-releasing peptide-2 (GHRP-2) in chronic arthritis with clinical manifestations of hypermetabolism and cachexia was demonstrated (Granado M et al., Am. J. Physiol. Endocrinol. Metab. 2005, 288: E486-492). These data suggest that the anti-inflammatory action of GHRP-2 is mediated by activation of ghrelin receptors expressed by immune competent cells.

e) Treatment of cachexia

The anti-cachetic effect of administered recombinant growth hormone in an animal model of chachexia (Roubenoff R et al., Arthritis Rheum. 1997, 40(3): 534-539) could be demonstrated (Ibanez de Caceres I et al., J. Endocrin. 2000, 165(3): 537-544). The findings are also in line with data of patients with rheumatoid arthritis (Roubenoff R et al., J Clin Invest. 1994, 93(6): 2379-2386).

f) Treatment of gastrectomy (ghrelin replacement therapy)

The gastric hormone ghrelin was given to mice subjected to gastrectomy or sham operation (Dornonville de la Cour C et al., Gut 2005, 54(7): 907-913). The results presented show that ghrelin replacement therapy at least partially reverse gastrectomy induced reduction in body weight and body fat.

g) Treatment of (gastric) postoperative ileus

The effect of ghrelin on the motor function of the gastrointestinal tract in rat was evaluated. It could be shown that ghrelin reverses the delayed gastric evacuation and is a strong prokinetic agent useful for the treatment/reversion of post-operative gastric ileus (Trudel L et al., Am J Physiol Gastrointest Liver Physiol 2002, 282(6): G948-G952).

h) Treatment of diabetes (diabetes type I and type II)

The effect of ablation of ghrelin in leptin-deficient mice was studied (Sun et al., Cell Metabolism 2006, 3: 379-386). The results show that deletion of ghrelin augments insulin secretion in response to glucose challenge indicating that inhibition of ghrelin or counteracting its activity may be a possible way for the treatment of diabetes including its subtypes I and II (see also WO 03/051389).

Further fields of application comprise acceleration of recovery of patients having undergone major surgery (e.g. U.S. Pat. No. 6,194,578); accelerating the recovery of burn patients (e.g. U.S. Pat. No. 6,194,578); attenuating protein catabolic response after a major operation (e.g. U.S. Pat. No. 6,194,578); reducing cachexia and protein loss due to acute or chronic illness (e.g. U.S. Pat. No. 6,194,578); treating central nervous system disorders of patients undergoing a medical procedure in combination with antidepressants (e.g. US 2002/0002137 A1); acceleration of bone fracture repair and cartilage growth (e.g. U.S. Pat. No. 6,194,578); treatment or prevention of osteoporosis; stimulation of the immune system; accelerating wound healing (e.g. U.S. Pat. No. 6,194, 578); treatment of growth retardation associated with the Prader-Willi syndrome, Turner's syndrome and obesity; treatment of intrauterine growth retardation, skeletal dysplasia, hypercortisolism and Cushing's syndrome; treatment of osteochondrodysplasias, Noonan's syndrome, schizophrenia, depressions and Alzheimer's disease; treatment of pulmonary dysfunction and ventilator dependency; treatment of hyperinsulinemia including nesidioblastosis; adjuvant treatment for ovulation induction; prevention of the age-related decline of thymic function; improvement in muscle strength and mobility (e.g. U.S. Pat. No. 6,194,578); maintenance of skin thickness (e.g. U.S. Pat. No. 6,194,578); improvement of sleep quality (e.g. U.S. Pat. No. 6,071,926); prevention of congestive heart failure alone (e.g. U.S. Pat. No. 6,329,342; U.S. Pat. No. 6,194,578) and in combination with corticotropin releasing factor antagonists (e.g. US 2001/0041673); metabolic homeostasis or renal homeostasis (e.g. in the frail elderly)(e.g. U.S. Pat. No. 6,194,578); improving glycemic control (e.g. U.S. Pat. No. 6,251,902); treatment of systemic lupus erythematosus and inflammatory bowel disease (e.g. US 2002/0013320); treating or preventing frailty associated with aging or obesity (e.g. U.S. Pat. No. 6,194,578); as well as stimulation of osteoblasts.

Animals were not forgotten in potential applications such as stimulation of food intake (Wren A M et al., Diabetes 2001, 50: 2540-2547), stimulation of the immune system in companion animals and treatment of disorder of aging, growth promotion in livestock and stimulation of wool growth in sheep.

Compounds containing triazole moieties have been widely recognized in the medicinal chemistry due to their various biological activities. The following patent families are all directed to heterocyclic compounds that are said to show certain biological action for use in different medicinal indications. Triazole moieties are implicitly or explicitly contained. However, neither of these patent families mentions ghrelin analogue ligands of the GHS receptor family nor modulation of these receptors nor GH secretagogue properties or the like.

WO 2004/111015 discloses modulators of the glucocorticoid receptor. WO 2004/052280 describes anti-agiogenic compounds as inhibitors of tyrosine kinase activity of VEGF receptors and their use in cancer. WO 2004/096795 also discloses tyrosine kinase inhibitors, preferably C-FMS inhibitors. WO 03/011831 and WO 03/011210 both describe heteroarylheteroalkylamine derivatives as inhibitors of nitric oxide synthase. WO 02/00651 is directed to Factor XA inhibitors for use in thromboembolic disorders. WO 01/94318 and WO 01/94317 both describe chemical libraries of substituted azole derivatives and methods of their synthesis for use in drug discovery high-throughput screening. However, they fail to provide any biological activity or any medicinal use nor do they name specific compounds. WO 00/76971 and WO 00/76970 both claim serine protease inhibitors useful as antithrombotic agents. WO 01/36395 discloses triazole derivatives as farnesyl transferase inhibitors. WO 96/33176 and U.S. Pat. No. 5,703,092 are directed to hydroxamic acid compounds as metalloprotease and TNF inhibitors. WO 93/09095 describes 2-heterocyclicethylamine derivatives and their use in neurological and neurodegenerative disorders. WO 2004/103270 claims compounds for the treatment of thrombosis, in particular Factor XIa inhibitors. WO 98/38177, U.S. Pat. No. 6,506,782, U.S. Pat. No. 6,849,650 and US 2003/0130188 all describe heterocyclic compounds as inhibitors of beta-amyloid peptide release or its synthesis for use in Alzheimer's disease.

Heterocyclic compounds that may be useful as GHS have also been described in the literature.

WO 00/54729, for instance, discloses heterocyclic aromatic compounds as GH secretagogues which are said to stimulate endogenous production and/or release of GH and can also contain triazole moieties. In addition, a method for increasing levels of endogenous GH or increasing the endogenous production or release of GH administering such GHS is described. Furthermore, a method is provided for preventing or treating osteoporosis (improving bone density and/or strength), or treating obesity, or increasing muscle mass and/or muscle strength and function in elderly humans, or reversal or prevention of frailty in elderly humans administering such GHS.

However, although claiming in vivo GH release WO 00/54729 fails to actually prove such effect. Neither in vitro nor in vivo data are contained that demonstrate any stimulation of or increase in endogenous production and/or release of GH.

Besides, WO 00/54729 fails to describe and show action of those claimed compounds on any biological target, i.e. claimed compounds are not shown/described to be ligands of one or more specific receptors, for instance of a receptor family, that bind to them and modulate their activity.

Furthermore, WO 00/54729 fails to describe and demonstrate inhibitory and/or antagonistic activity of claimed compounds. As a matter of fact, such compounds are not shown to decrease levels of endogenous GH and/or inhibit or decrease endogenous production and/or release of GH. Nor is an inhibitory action on any receptor mentioned nor made obvious.

U.S. Pat. No. 6,525,203, U.S. Pat. No. 6,518,292 U.S. Pat. No. 6,660,760 are members of the same patent family as WO 00/54729 that, however, do not comprise triazole moieties as claimed subject matter any more. With regard to biological activity, the above stated facts as for WO 00/54729 apply.

WO 2004/021984 describes heterocyclic aromatic compounds GH secretagogues which are said to be useful in stimulating endogenous production or release of GH. However, claimed compounds consists of bi- to tetracylic aromatic rings and do not contain triazoles.

Analogous to WO 00/54729 in vivo GH release is claimed, but neither in vitro nor in vivo data are contained that demonstrate any stimulation of or increase in endogenous production and/or release of GH. With regard to biological activity, the same stated facts as for WO 00/54729 apply.

WO 97/23508 claims compounds of peptide mimetic nature as GHS and are said to act directly on pituitary cells in vitro to release GH therefrom and show improved properties, such as improved resistance to proteolytic degradation and improved bioavailability. In addition, claimed compounds could also be administered in vivo to increase GH release. The compounds are peptide derivatives and do not explicitly contain triazole moieties.

However, once again and in analogy to above WO 00/54729 and WO 2004/021984, WO 97/23508 fails to exhibit any in vitro or in vivo data that demonstrate the claimed effects such as direct action on pituitary cells, GH release therefrom and improved properties. Furthermore, with regard to biological targets and inhibitory/antagonistic activity, the above stated facts as for WO 00/54729 apply.

U.S. Pat. No. 6,127,391, U.S. Pat. No. 5,977,178 and U.S. Pat. No. 6,555,570 are members of the same patent family as WO 97/23508. The facts as stated for WO 97/23508 do apply.

BRIEF DESCRIPTION OF THE INVENTION

The present invention has as one object to provide novel compounds which can be employed for the treatment of physiological and/or pathophysiological conditions in mammals, in particular humans, that are mediated by GHS receptors. It is another object of the underlying invention to provide compounds for the above treatment where the treatment is achieved by modulation of GHS receptors. A further object of the present invention is to provide antagonists of GHS receptors for those treatments. It is yet another object of the underlying invention to provide agonists of GHS receptors for those treatments.

The object of the invention has been surprisingly solved in one aspect by providing compounds according to formula (I)

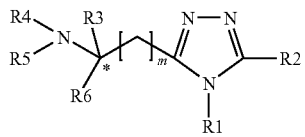

(I)

wherein:
R1 and R2 are independently of one another selected from the group consisting of hydrogen atom, alkyl, alkenyl, alkynyl, cycloalkyl, cycloalkylalkyl, aryl, heteroaryl, arylalkyl, heteroarylalkyl, heterocyclyl, heterocyclylalkyl, alkylsulfonyl, arylsulfonyl, arylalkylsulfonyl which are optionally substituted in the alkyl, cycloalkyl, cycloalkylalkyl, aryl, heteroaryl, arylalkyl, heteroarylalkyl, heterocyclyl and/or heterocyclylalkyl group by up to 3 substituents independently selected from the group consisting of halogen, —F, —Cl, —Br, —I, —N₃, —CN, —NR7R8, —OH, —NO₂, alkyl, aryl, arylalkyl, —O-alkyl, —O-aryl, —O-arylalkyl; and preferably are selected from the group consisting of alkyl, aryl, heteroaryl, arylalkyl, heteroarylalkyl optionally being substituted by up to 3 substituents independently selected from the group consisting of halogen, —F, —Cl, —Br, —I, —N₃, —CN, —NR7R8, —OH, —NO₂, alkyl, aryl, arylalkyl, —O-alkyl, —O-aryl, —O-arylalkyl;

one of radicals R3 and R4 is a hydrogen atom, whereas the other radical is selected from the group consisting of hydrogen atom, alkyl, aryl, heteroaryl, arylalkyl, heteroarylalkyl, heterocyclyl, heterocyclylalkyl, -alkyl-O-aryl, -alkyl-O-arylalkyl, -alkyl-O-heteroaryl, -alkyl-O-heteroarylalkyl, -alkyl-O-heterocyclyl, alkyl-O-heterocyclylalkyl, -alkyl-CO-aryl, -alkyl-CO-arylalkyl, -alkyl-CO-heteroaryl, -alkyl-CO-heteroarylalkyl, -alkyl-CO-heterocyclyl, -alkyl-CO-heterocyclylalkyl, -alkyl-C(O)O-aryl, -alkyl-C(O)O-arylalkyl, -alkyl-C(O)O-heteroaryl, -alkyl-C(O)O-heteroarylalkyl, -alkyl-C(O)O-heterocyclyl, -alkyl-C(O)O-heterocyclylalkyl, -alkyl-CO—NH₂, -alkyl-CO—OH, -alkyl-NH₂, -alkyl-NH—C(NH)—NH₂, alkylsulfonyl, arylsulfonyl, arylalkylsulfonyl, alkyl-5-alkyl, alkyl-S—H which are optionally substituted in the aryl, heteroaryl, arylalkyl, heteroarylalkyl, heterocyclyl and/or heterocyclylalkyl group by up to 3 substituents independently selected from the group consisting of halogen, —F, —Cl, —Br, —I, —N₃, —CN, —NR7R8, —OH, —NO₂, alkyl, aryl, arylalkyl, —O-alkyl, —O-aryl, —O-arylalkyl; and preferably are selected from the group consisting of arylalkyl, heteroarylalkyl, heterocyclylalkyl, -alkyl-O-aryl, -alkyl-O-arylalkyl, -alkyl-O-heteroaryl, -alkyl-O-heteroarylalkyl, -alkyl-O-heterocyclyl, alkyl-O-heterocyclylalkyl, -alkyl-CO-aryl, -alkyl-CO-arylalkyl, -alkyl-CO-heteroaryl, -alkyl-CO-heteroarylalkyl, -alkyl-CO-heterocyclyl, alkyl-CO-heterocyclylalkyl, -alkyl-C(O)O-aryl, -alkyl-C(O)O-arylalkyl, -alkyl-C(O)O-heteroaryl, -alkyl-C(O)O-heteroarylalkyl, -alkyl-C(O)O-heterocyclyl, -alkyl-C(O)O-heterocyclylalkyl, -alkyl-CO—NH₂, -alkyl-CO—OH, -alkyl-NH₂, -alkyl-NH—C(NH)—NH₂, optionally being substituted in the aryl, heteroaryl, arylalkyl, heteroarylalkyl, heterocyclyl and/or heterocyclylalkyl group by up to 3 substituents independently selected from the group consisting of halogen, —F, —Cl, —Br, —I, —N₃, —CN, —NR7R8, —OH, —NO₂, alkyl, aryl, arylalkyl, —O-alkyl, —O-aryl, —O-arylalkyl;

R5 is selected from the group consisting of hydrogen atom, alkyl, cycloalkyl, cycloalkylalkyl, aryl, heteroaryl, arylalkyl, heteroarylalkyl, heterocyclyl, heterocyclylalkyl, —CO-alkyl, —CO-cycloalkyl, —CO-cycloalkylalkyl, —CO-aryl, —CO-arylalkyl, —CO-heteroaryl, —CO-heteroarylalkyl, —CO-heterocyclyl, —CO-heterocyclylalkyl, —CO—C*(R9R10)-NH₂, —CO—CH₂—C*(R9R10)-NH₂, —CO—C*(R9R10)-CH₂—NH₂, alkylsulfonyl, arylsulfonyl, arylalkylsulfonyl which are optionally substituted by up to 3 substituents independently selected from the group consisting of halogen, —F, —Cl, —Br, —I, —N₃, —CN, —NR7R8, —OH, —NO₂, alkyl, aryl, arylalkyl, —O-alkyl, —O-aryl, —O-arylalkyl; and preferably is selected from the group consisting of hydrogen atom, —CO-alkyl, —CO-cycloalkyl, —CO-aryl, —CO-heteroaryl, —CO-arylalkyl, —CO-heteroarylalkyl, —CO-heterocyclyl, —CO—C*(R9R10)-NH$_2$, —CO—CH$_2$—C*(R9R10)-NH$_2$, —CO—C*(R9R10)-CH$_2$—NH$_2$, optionally being substituted by up to 3 substituents independently selected from the group consisting of halogen, —F, —Cl, —Br, —I, —N$_3$, —CN, —NR7R8, —OH, —NO$_2$, alkyl, aryl, arylalkyl, —O-alkyl, —O-aryl, —O-arylalkyl;

R6 is selected from the group consisting of hydrogen atom, alkyl, cycloalkyl, cycloalkylalkyl and preferably is a hydrogen atom;

R7 and R8 are independently of one another selected from the group consisting of hydrogen atom, alkyl, cycloalkyl, cycloalkylalkyl and preferably are a hydrogen atom;

R9 and R10 are independently of one another selected from the group consisting of hydrogen atom, alkyl, natural alpha-amino acid side chain, unnatural alpha-amino acid side chain and preferably are selected from the group consisting of hydrogen atom, alkyl;

m is 0, 1 or 2 and preferably is 0; and

* means a carbon atom of R or S configuration when chiral;

that can be used for the manufacture of a medicament for the treatment or prophylaxis of physiological and/or pathophysiological conditions in mammals that are mediated by GHS receptors.

BRIEF DESCRIPTION OF THE DRAWINGS

FIGS. 1-13 show the measured competition plots of the GHS-R 1a receptor-ligand binding assay with $^{125}$I-His$^9$-ghrelin and selected compounds 9, 31, 39, 45, 50, 62, 64, 71, 73, 74, 79, 81 and 90 as described in II) of the example section.

FIGS. 14-40 show the calculated dose-response plots of the in vitro intracellular Calcium release assay with human GHS-R 1a transfected CHO cells of the selected compounds 1, 9, 12, 20, 22, 31, 39, 41, 42, 45, 46, 47, 48, 49, 50, 51, 55, 62, 64, 67, 71, 73, 74, 79, 81, 90 and ghrelin as described in III) of the example section as well as EC$_{50}$ and KI values for GHS receptor agonists and IC$_{50}$ and Kb values for GHS receptor antagonists.

FIGS. 41-46 show the effects of selected compounds 9, 38, 50, 64, 74, 81 on the isoprorerenol-induced lipolysis inhibition curve of unacylated ghrelin (UAG) in primary adipocytes from mice under diet-induced obesity as described in VIII) of the example section.

DESCRIPTION OF THE PREFERRED EMBODIMENTS

In a preferred embodiment compounds according to above formula (I) are provided, where R3 is selected from the group consisting of -alkyl-CO-aryl, -alkyl-CO-arylalkyl, -alkyl-CO-heteroaryl, -alkyl-CO-heteroarylalkyl, -alkyl-CO-heterocyclyl, alkyl-CO-heterocyclylalkyl, -alkyl-C(O)O-aryl, -alkyl-C(O)O-arylalkyl, -alkyl-C(O)O -heteroaryl, -alkyl-C(O)O-heteroarylalkyl, -alkyl-C(O)O-heterocyclyl, -alkyl-C(O)O-heterocyclylalkyl, -alkyl-CO—NH$_2$, -alkyl-CO—OH, -alkyl-NH—C(NH)—NH$_2$, alkyl-5-alkyl, alkyl-S—H, and preferably is selected from the group consisting of -alkyl-CO-arylalkyl, -alkyl-C(O)O-arylalkyl, -alkyl-CO—NH$_2$, -alkyl-CO—OH; that can be used for the manufacture of a medicament for the treatment or prophylaxis of physiological and/or pathophysiological conditions in mammals that are mediated by GHS receptors.

In another preferred embodiment compounds according to above formula (I) are provided, where R4 is a hydrogen atom;

R5 is selected from the group consisting of hydrogen atom, alkyl, cycloalkyl, cycloalkylalkyl, aryl, heteroaryl, arylalkyl, heteroarylalkyl, heterocyclyl, heterocyclylalkyl, alkylsulfonyl, arylsulfonyl, arylalkylsulfonyl, —CO-cycloalkyl, —CO-cycloalkyl-alkyl, —CO-aryl, —CO-arylalkyl, —CO-heteroaryl, —CO-heteroarylalkyl, —CO-heterocyclyl, —CO-heterocyclylalkyl;

with the proviso that if R5 is —CO-heteroarylalkyl, heteroaryl is not imidazole; and with the proviso that if R5 is —CO-heterocyclyl and heterocyclyl contains only nitrogen atoms as heteroatoms, that at least two nitrogen atoms are contained in heterocyclyl; and with the proviso that if R5 is —CO-heterocyclylalkyl and heterocyclyl contains only nitrogen atoms as heteroatoms that in the case that one or two nitrogen atoms are contained in heterocyclyl no nitrogen atom is positioned at position 1 of heterocyclyl that is the atom directly linking heterocyclyl to the carbonyl group —CO—;

where alkyl, cycloalkyl, cycloalkylalkyl, aryl, heteroaryl, arylalkyl, heteroarylalkyl, heterocyclyl, heterocyclylalkyl, alkylsulfonyl, arylsulfonyl, arylalkylsulfonyl, —CO-cycloalkyl, —CO-cycloalkylalkyl, —CO-aryl, —CO-arylalkyl, —CO-heteroaryl, —CO-heteroarylalkyl, —CO-heterocyclyl, and/or —CO-heterocyclylalkyl are optionally substituted by up to 3 substituents independently selected from the group consisting of halogen, —F, —Cl, —Br, —I, —N$_3$, —CN, —NR7R8, —OH, —NO$_2$, alkyl, aryl, arylalkyl, —O-alkyl, —O-aryl, —O-arylalkyl;

with the proviso that if R5 is —CO-cycloalkyl or —CO-cycloalkylalkyl, R5 is not substituted with NR7R8 at position 1 of cycloalkyl, that is the C atom directly linking cycloalkyl to the carbonyl group —CO— in case of R5=—CO-cycloalkyl or to the alkyl in case R5=—CO-cycloalkylalkyl; and with the proviso that if R5 is —CO-aryl or —CO-arylalkyl and aryl is phenyl/benzene and is only substituted with one substituent, this one substituent is not —NR7R8;

R6 is a hydrogen atom;

R7 and R8 are independently of one another selected from the group consisting of hydrogen atom, alkyl, cycloalkyl, cycloalkylalkyl and preferably are a hydrogen atom; and m is 0, 1 or 2, and more preferably is 0;

that can be used for the manufacture of a medicament for the treatment or prophylaxis of physiological and/or pathophysiological conditions in mammals that are mediated by GHS receptors.

In a further aspect, the object of the invention has surprisingly been achieved by providing compounds according to formula (I), where R1 is selected from the group consisting of hydrogen, methyl, (2-methoxyphenyl)-methyl, (3-methoxyphenyl)-methyl, (4-methoxyphenyl)-methyl, (3-methoxyphenyl)-ethyl, (4-methoxyphenyl)-ethyl, phenyl, phenyl-methyl, phenyl-ethyl, (4-ethylphenyl)-methyl, (4-methylphenyl)-methyl, (4-fluorophenyl)-methyl, (4-bromophenyl)-methyl, (2,4-dimethoxyphenyl)-methyl, (3,5-dimethoxyphenyl)-methyl, 2,2-diphenylethyl, naphthaline-1-yl-methyl, 1H-indole-3-yl-methyl, 2-(1H-indole-3-yl)-ethyl, 3-(1H-indole-3-yl)-propyl, 4-methyl-phenyl, 4-ethyl-phenyl, n-hexyl, (3,4-dichlorophenyl)-methyl, (4-nitro-phenyl)-methyl, (pyridine- 2-yl)-methyl, (pyridine-3-yl)-methyl, (pyridine-4-yl)-methyl, (thiophene-2-yl)-methyl, (thiophene-3-yl)-methyl, (furan-2-yl)-methyl, (furan-3-yl)-methyl;

R2 is selected from the group consisting of methyl, 1H-indole-3-yl-methyl, 2-(1H-indole-3-yl)-ethyl, 3-(1H-indole-3-yl)-propyl, 2-phenyl-ethyl, 3-phenyl-propyl, 4-phenyl-butyl, 2-methoxy-phenylmethyl, 3-methoxy-phenylmethyl, 4-methoxy-phenylmethyl, 2-methoxy-phenylethyl, 3-methoxy-phenylethyl, 4-methoxy-phenylethyl;

R3 is selected from the group consisting of hydrogen atom, methyl, propan-2-yl, 2-methyl-propan-1-yl, butan-2-yl, butan-1-yl, —CH$_2$—SH, —(CH$_2$)$_2$—S—CH$_3$, 1H-indole-3-yl-methyl, phenyl-methyl, 2-phenyl-ethyl, —CH$_2$—O—CH$_2$-phenyl, —CH$_2$—CO—CH$_2$-phenyl, —(CH$_2$)$_2$—CO—CH$_2$-phenyl, —CH$_2$—C(O)O-phenyl, —(CH$_2$)$_2$—C(O)O-phenyl, hydroxy-methyl, 1-hydroxy-ethan-1-yl, —CH$_2$—CO—NH$_2$, —(CH$_2$)$_2$—CO—NH$_2$, (1-hydroxy-benzene-4-yl)-methyl, —CH$_2$—CO—OH, —(CH$_2$)$_2$—CO—OH, —(CH$_2$)$_4$—NH$_2$, (1H-imidazol-5-yl)-methyl, —(CH$_2$)$_3$—NH—C(NH)—NH$_2$, —(CH$_2$)$_3$—NH$_2$, —(CH$_2$)$_3$—NH—CO—NH$_2$, and preferably is selected from the group consisting of 1H-indole-3-yl-methyl, —CH$_2$—CO—CH$_2$-phenyl, —(CH$_2$)$_2$—CO—CH$_2$-phenyl, —CH$_2$—C(O)O-phenyl, —(CH$_2$)$_2$—C(O)O-phenyl;

R4 is a hydrogen atom;

R5 is selected from the group consisting of hydrogen atom, —CO—CH$_2$—NH$_2$ (Gly residue), —CO—CH$_2$—CH$_2$—NH$_2$ (beta-Ala residue), —CO—CHCH$_3$—NH$_2$ (D- and/or L-alpha-Ala residue), —CO-(pyrrolidine-2-yl) (D- and/or L-Pro residue), 2-amino-2-carbonyl-propane (2-amino-isobutyric acid/Aib residue), 4-carbonyl-1H-piperidine, 3-carbonyl-1H-piperidine, R-(3-carbonyl-1H-piperidine), S-(3-carbonyl-1H-piperidine), 2-carbonyl-1H-piperidine, R-(2-carbonyl-1H-piperidine), S-(2-carbonyl-1H-piperidine), 1-amino-2-carbonyl-benzene, carbonyl-cyclohexane, 2-acetyl-pyridine, 3-acetyl-pyridine, 4-acetyl-pyridine, 2-propionyl-pyridine, 3-propionyl-pyridine, 4-propionyl-pyridine, (R-1-amino)-2-carbonyl-cyclohexane, (S-1-amino)-2-carbonyl-cyclohexane, 2-carbonyl-1H-imidazole, 2-carbonyl-pyridine, 3-carbonyl-pyridine, 4-carbonyl-pyridine, 2-amino-3-carbonyl-pyridine, 2-carbonyl-pyrazine, 2-carbonyl-4-hydroxy-1H-pyrrolidine, 4-carbonyl-1H,3H-diazacyclohexane, methylsulfonyl, phenylsulfonyl, 1-carbonyl-1-amino-2-phenylethane, phenylmethyl, 1-carbonyl-4-azide-benzene, 2-carbonyl-2,5-dihydro-1H-pyrrole, 2-carbonyl-piperazine, 2-carbonyl-1H-pyrrolidine, 2-aminoethane, carbonyl-benzene, 2-carbonyl-pyrazine, 3-carbonyl-pyrazine, 4-carbonyl-oxacyclohexane, 4-methyl-phenylsulfonyl, phenylmethyl-sulfonyl;

R6 is a hydrogen atom; and m is 0;

that can be used for the manufacture of a medicament for the treatment or prophylaxis of physiological and/or pathophysiological conditions in mammals that are mediated by GHS receptors.

In a preferred embodiment compounds according to above formula (I) are provided, where R3 is selected from the group consisting of —CH$_2$—CO—CH$_2$-phenyl, —(CH$_2$)$_2$—CO—CH$_2$-phenyl, —CH$_2$—CO—NH$_2$, —(CH$_2$)$_2$—CO—NH$_2$, —CH$_2$—CO—OH, —(CH$_2$)$_2$—CO—OH, —(CH$_2$)$_3$—NH—C(NH)—NH$_2$, —CH$_2$—SH, —(CH$_2$)$_2$—S—CH$_3$;

that can be used for the manufacture of a medicament for the treatment or prophylaxis of physiological and/or pathophysiological conditions in mammals that are mediated by GHS receptors.

In another preferred embodiment compounds according to above formula (I) are provided, where R5 is selected from the group consisting of hydrogen atom, methylsulfonyl, phenylsulfonyl, carbonyl-cyclohexane, (R-1-amino)-2-carbonyl-cyclohexane, (S-1-amino)-2-carbonyl-cyclohexane, 2-carbonyl-pyridine, 3-carbonyl-pyridine, 4-carbonyl-pyridine, 2-acetyl-pyridine, 3-acetyl-pyridine, 4-acetyl-pyridine, 2-propionyl-pyridine, 3-propionyl-pyridine, 4-propionyl-pyridine, 2-amino-3-carbonyl-pyridine, 2-carbonyl-1H-imidazole, 2-carbonyl-pyrazine, 4-carbonyl-1H,3H-diazacyclohexane;

that can be used for the manufacture of a medicament for the treatment or prophylaxis of physiological and/or pathophysiological conditions in mammals that are mediated by GHS receptors.

In a further aspect, the object of the invention has surprisingly been achieved by providing novel triazole compounds selected from the group consisting of:

compound 1 (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-amino-2-methylpropanamide,

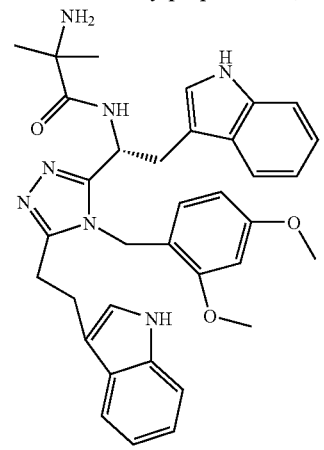

compound 2 (R)—N-(1-(5-(2-(1H-indol-3-yl)ethyl)-4-phenethyl-4H-1,2,4-triazol-3-yl)-2-(1H-indol-3-yl)ethyl)-2-amino-2-methylpropanamide,

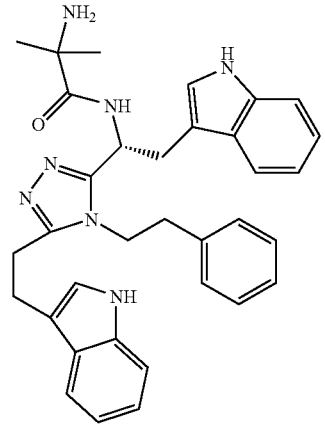 [SMILES: CC(C)(N)C(=O)N[C@H](Cc1c[nH]c2ccccc12)c1nnc(CCc2c[nH]c3ccccc23)n1CCc1ccccc1]

compound 3 (R)—N-(1-(5-(3-(1H-indol-3-yl)propyl)-4-phenethyl-4H-1,2,4-triazol-3-yl)-2-(1H-indol-3-yl)ethyl)-2-amino-2-methylpropanamide,

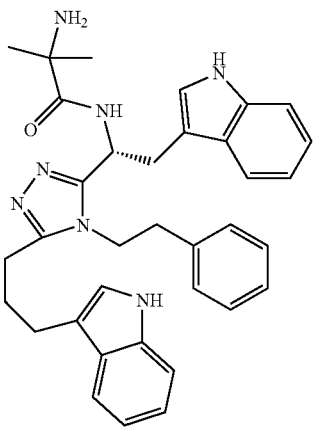 [SMILES: CC(C)(N)C(=O)N[C@H](Cc1c[nH]c2ccccc12)c1nnc(CCCc2c[nH]c3ccccc23)n1CCc1ccccc1]

compound 4 (R)—N-(1-(5-benzyl-4-(naphthalen-1-ylmethyl)-4H-1,2,4-triazol-3-yl)-2-(1H-indol-3-yl)ethyl)-2-amino-2-methylpropanamide,

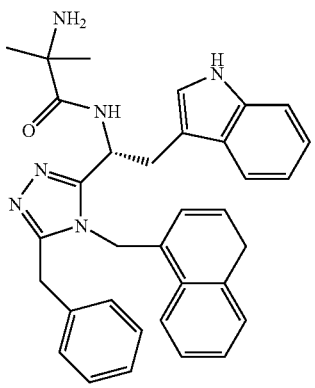

compound 5 (R)—N-(1-(5-(2-(1H-indol-3-yl)ethyl)-4-(naphthalen-1-ylmethyl)-4H-1,2,4-triazol-3-yl)-2-(1H-indol-3-yl)ethyl)-2-amino-2-methylpropanamide,

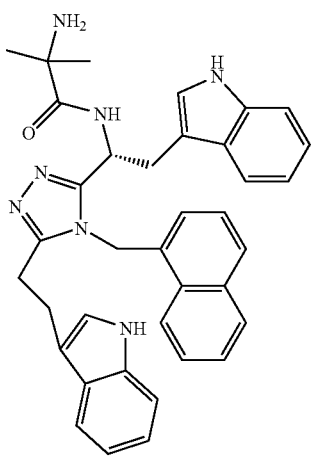 [SMILES: CC(C)(N)C(=O)N[C@H](Cc1c[nH]c2ccccc12)c1nnc(CCc2c[nH]c3ccccc23)n1Cc1cccc2ccccc12]

compound 6 (R)—N-(1-(5-(2-(1H-indol-3-yl)ethyl)-4-(3-methoxybenzyl)-4H-1,2,4-triazol-3-yl)-2-(1H-indol-3-yl)ethyl)-2-amino-2-methylpropanamide,

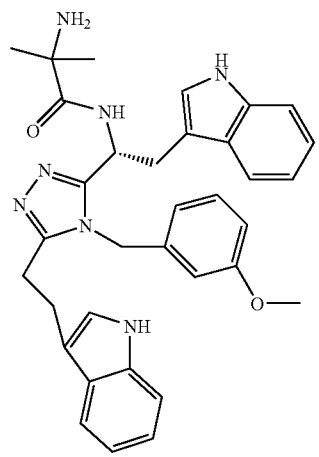 [SMILES: COc1cccc(Cn2c(CCc3c[nH]c4ccccc34)nnc2[C@@H](Cc2c[nH]c3ccccc23)NC(=O)C(C)(C)N)c1]

compound 7 (R)—N-(1-(4-(3-methoxybenzyl)-5-benzyl-4H-1,2,4-triazol-3-yl)-2-(1H-indol-3-yl)ethyl)-2-amino-2-methylpropanamide,

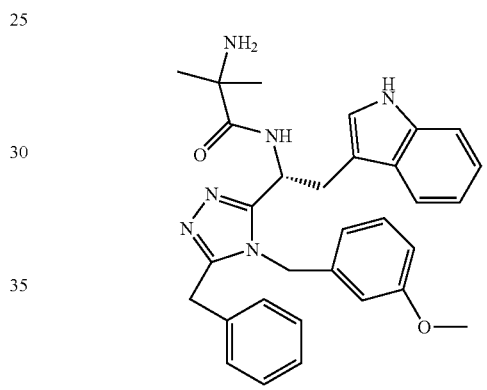

compound 8 (R)—N-(1-(5-(2-(1H-indol-3-yl)ethyl)-4-benzyl-4H-1,2,4-triazol-3-yl)-2-(1H-indol-3-yl)ethyl)-2-amino-2-methylpropanamide,

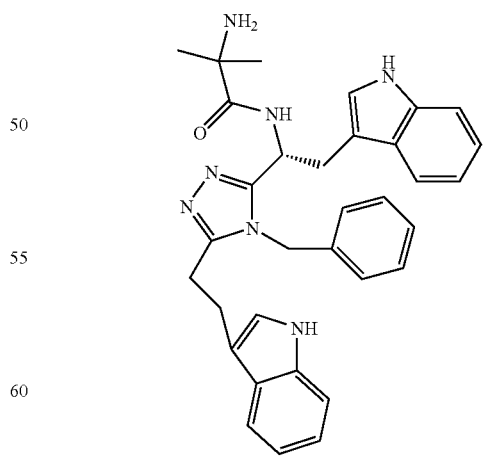

compound 9 (R)—N-(1-(5-(3-(1H-indol-3-yl)propyl)-4-benzyl-4H-1,2,4-triazol-3-yl)-2-(1H-indol-3-yl)ethyl)-2-amino-2-methylpropanamide,

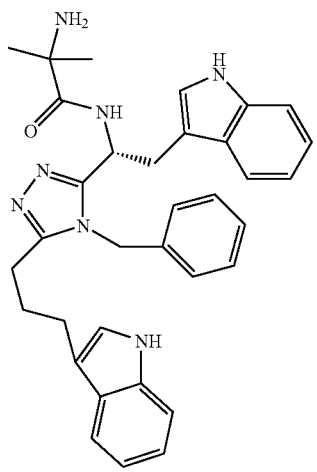 [SMILES: CC(C)(N)C(=O)N[C@H](Cc1c[nH]c2ccccc12)c1nnc(CCCc2c[nH]c3ccccc23)n1Cc1ccccc1]

compound 10 (R)—N-(1-(5-(3-(1H-indol-3-yl)propyl)-4-(3-methoxybenzyl)-4H-1,2,4-triazol-3-yl)-2-(1H-indol-3-yl)ethyl)-2-amino-2-methylpropanamide,

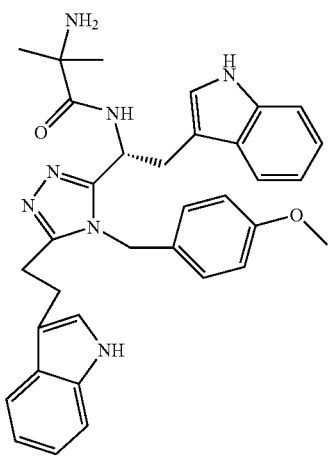 [SMILES: COc1ccc(Cn2c(CCc3c[nH]c4ccccc34)nnc2[C@@H](Cc2c[nH]c3ccccc23)NC(=O)C(C)(C)N)cc1]

compound 13 (R)—N-(1-(4-(4-methoxybenzyl)-5-benzyl-4H-1,2,4-triazol-3-yl)-2-(1H-indol-3-yl)ethyl)-2-amino-2-methylpropanamide,

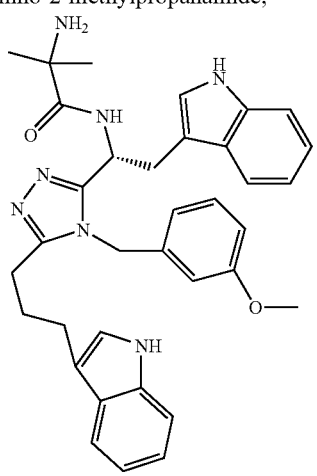

compound 11 (R)—N-(1-(5-(3-(1H-indol-3-yl)propyl)-4-(naphthalen-1-ylmethyl)-4H-1,2,4-triazol-3-yl)-2-(1H-indol-3-yl)ethyl)-2-amino-2-methylpropanamide,

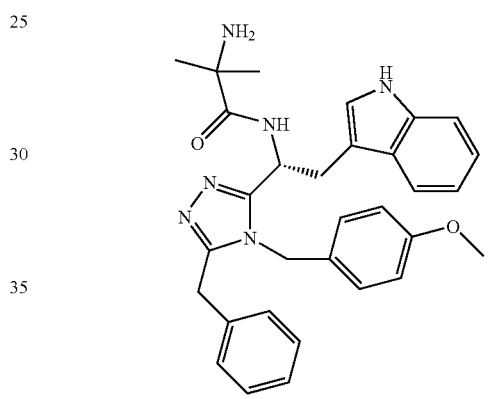

compound 14 (R)—N-(1-(5-(3-(1H-indol-3-yl)propyl)-4-(4-bromobenzyl)-4H-1,2,4-triazol-3-yl)-2-(1H-indol-3-yl)ethyl)-2-amino-2-methylpropanamide,

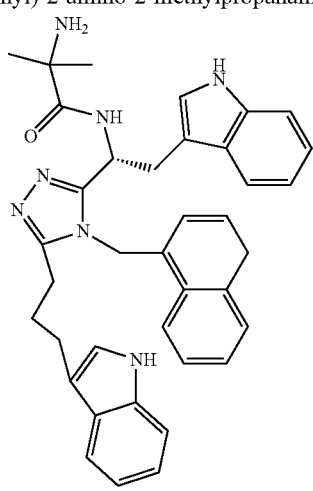

compound 12 (R)—N-(1-(5-(2-(1H-indol-3-yl)ethyl)-4-(4-methoxybenzyl)-4H-1,2,4-triazol-3-yl)-2-(1H-indol-3-yl)ethyl)-2-amino-2-methylpropanamide,

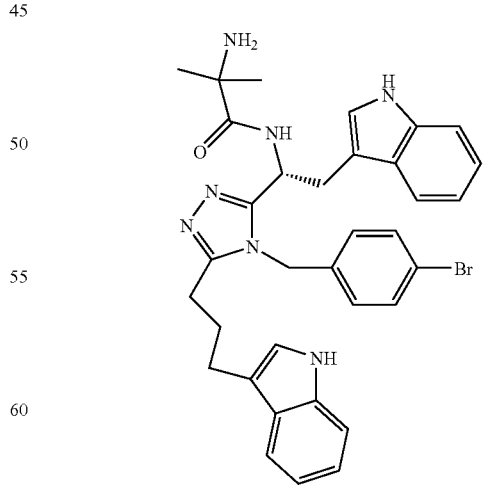

compound 15 (R)—N-(1-(5-(2-(1H-indol-3-yl)ethyl)-4-hexyl-4H-1,2,4-triazol-3-yl)-2-(1H-indol-3-yl)ethyl)-2-amino-2-methylpropanamide,

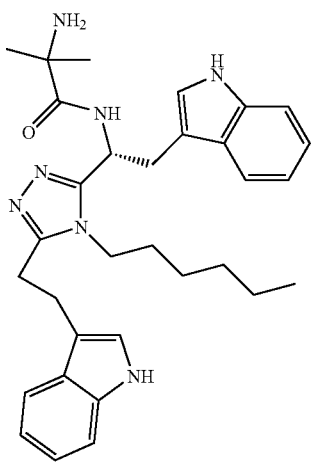 [SMILES: CCCCCCn1c(CCc2c[nH]c3ccccc23)nnc1[C@@H](Cc1c[nH]c2ccccc12)NC(=O)C(C)(C)N]

compound 16 (R)—N-(1-(5-(3-(1H-indol-3-yl)propyl)-4-hexyl-4H-1,2,4-triazol-3-yl)-2-(1H-indol-3-yl)ethyl)-2-amino-2-methylpropanamide,

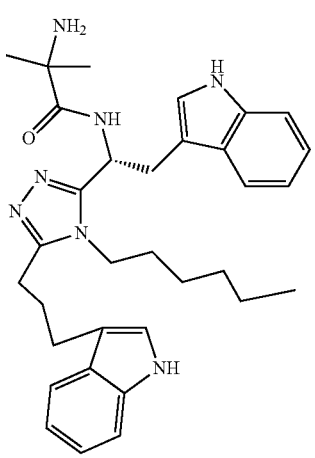 [SMILES: CCCCCCn1c(CCCc2c[nH]c3ccccc23)nnc1[C@@H](Cc1c[nH]c2ccccc12)NC(=O)C(C)(C)N]

compound 17 (R)—N-(1-(4,5-bis(2-(1H-indol-3-yl)ethyl)-4H-1,2,4-triazol-3-yl)-2-(1H-indol-3-yl)ethyl)-2-amino-2-methylpropanamide,

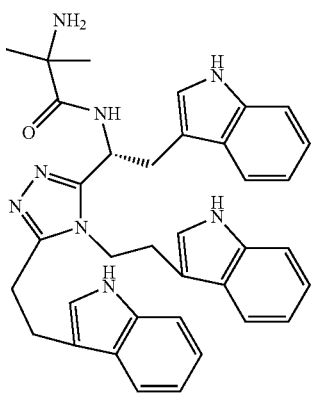 [SMILES: CC(C)(N)C(=O)N[C@H](Cc1c[nH]c2ccccc12)c1nnc(CCc2c[nH]c3ccccc23)n1CCc1c[nH]c2ccccc12]

compound 18 (S)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-amino-2-methylpropanamide,

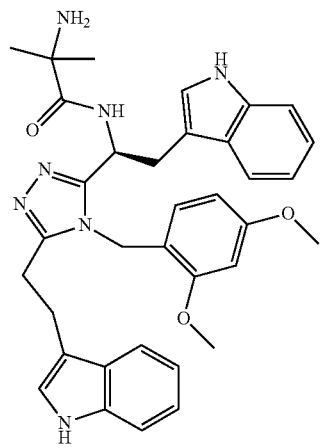 [SMILES: COc1ccc(Cn2c(CCc3c[nH]c4ccccc34)nnc2[C@H](Cc2c[nH]c3ccccc23)NC(=O)C(C)(C)N)c(OC)c1]

compound 19 (R)—N-(1-(4-(3-methoxybenzyl)-5-phenethyl-4H-1,2,4-triazol-3-yl)-2-(1H-indol-3-yl)ethyl)-2-amino-2-methylpropanamide,

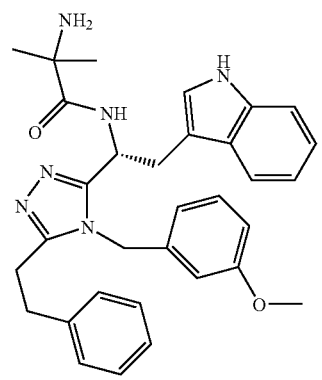 [SMILES: COc1cccc(Cn2c(CCc3ccccc3)nnc2[C@@H](Cc2c[nH]c3ccccc23)NC(=O)C(C)(C)N)c1]

compound 20 (R)—N-(1-(4-(4-methoxybenzyl)-5-phenethyl-4H-1,2,4-triazol-3-yl)-2-(1H-indol-3-yl)ethyl)-2-amino-2-methylpropanamide,

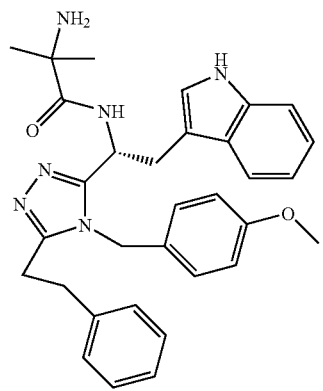 [SMILES: COc1ccc(Cn2c(CCc3ccccc3)nnc2[C@@H](Cc2c[nH]c3ccccc23)NC(=O)C(C)(C)N)cc1]

compound 21 (R)—N-(1-(5-(2-(1H-indol-3-yl)ethyl)-4-(3,5-dimethoxybenzyl)-4H-1,2,4-triazol-3-yl)-2-(1H-indol-3-yl)ethyl)-2-amino-2-methylpropanamide,

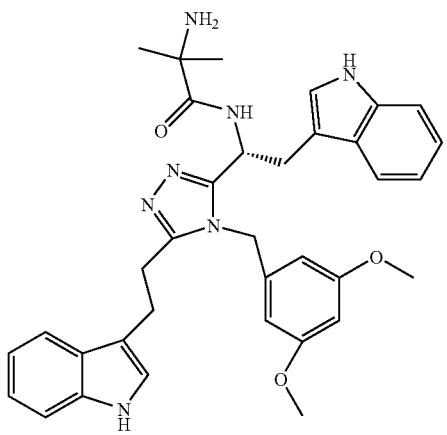 [SMILES: COc1cc(Cn2c(CCc3c[nH]c4ccccc34)nnc2[C@@H](Cc2c[nH]c3ccccc23)NC(=O)C(C)(C)N)cc(OC)c1]

compound 22 (R)—N-(1-(4-(4-methoxybenzyl)-5-(3-phenylpropyl)-4H-1,2,4-triazol-3-yl)-2-(1H-indol-3-yl)ethyl)-2-amino-2-methylpropanamide,

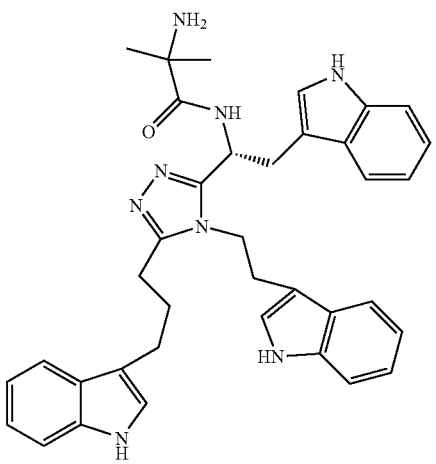 [SMILES: CC(C)(N)C(=O)N[C@H](Cc1c[nH]c2ccccc12)c1nnc(CCCc2c[nH]c3ccccc23)n1CCc1c[nH]c2ccccc12]

compound 25 (R)—N-(1-(5-(2-(1H-indol-3-yl)ethyl)-4-(2-methoxy)benzyl)-4H-1,2,4-triazol-3-yl)-2-(1H-indol-3-yl)ethyl)-2-amino-2-methylpropanamide, compound 23 (R)—N-(1-(5-(3-(1H-indol-3-yl)propyl)-4-(4-methoxybenzyl)-4H-1,2,4-triazol-3-yl)-2-(1H-indol-3-yl)ethyl)-2-amino-2-methylpropanamide, compound 26 (R)—N-(1-(4-(2-methoxybenzyl)-5-phenethyl-4H-1,2,4-triazol-3-yl)-2-(1H-indol-3-yl)ethyl)-2-amino-2-methylpropanamide, compound 24 (R)—N-(1-(4-(2-(1H-indol-3-yl)ethyl)-5-(3-(1H-indol-3-yl)propyl)-4H-1,2,4-triazol-3-yl)-2-(1H-indol-3-yl)ethyl)-2-amino-2-methylpropanamide, compound 27 (R)—N-(2-(1H-indol-3-yl)-1-(4-(naphthalen-1-ylmethyl)-5-phenethyl-4H-1,2,4-triazol-3-yl)ethyl)-2-amino-2-methylpropanamide,

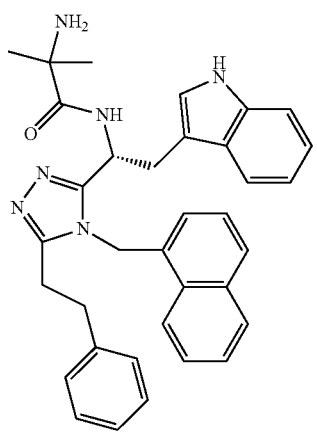 [SMILES: CC(C)(N)C(=O)N[C@H](Cc1c[nH]c2ccccc12)c1nnc(CCc2ccccc2)n1Cc1cccc2ccccc12]

compound 28 (R)—N-(1-(5-(2-(1H-indol-3-yl)ethyl)-4-(3,4-dichlorobenzyl)-4H-1,2,4-triazol-3-yl)-2-(1H-indol-3-yl)ethyl)-2-amino-2-methylpropanamide,

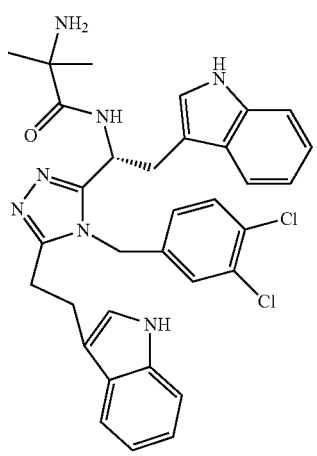 [SMILES: CC(C)(N)C(=O)N[C@H](Cc1c[nH]c2ccccc12)c1nnc(CCc2c[nH]c3ccccc23)n1Cc1ccc(Cl)c(Cl)c1]

compound 29 (R)—N-(1-(5-(2-(1H-indol-3-yl)ethyl)-4-(4-fluorobenzyl)-4H-1,2,4-triazol-3-yl)-2-(1H-indol-3-yl)ethyl)-2-amino-2-methylpropanamide,

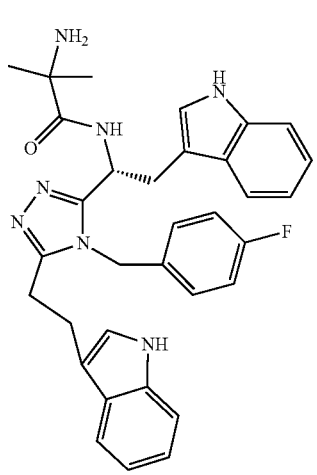 [SMILES: CC(C)(N)C(=O)N[C@H](Cc1c[nH]c2ccccc12)c1nnc(CCc2c[nH]c3ccccc23)n1Cc1ccc(F)cc1]

compound 30 (R)—N-(1-(4-(4-fluorobenzyl)-5-benzyl-4H-1,2,4-triazol-3-yl)-2-(1H-indol-3-yl)ethyl)-2-amino-2-methylpropanamide,

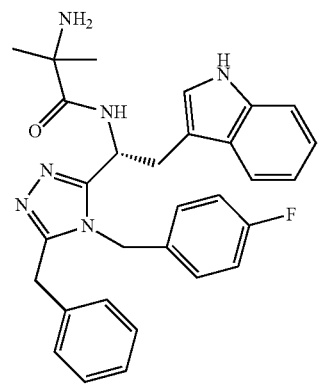 [SMILES: CC(C)(N)C(=O)N[C@H](Cc1c[nH]c2ccccc12)c1nnc(Cc2ccccc2)n1Cc1ccc(F)cc1]

compound 31 (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)piperidine-4-carboxamide,

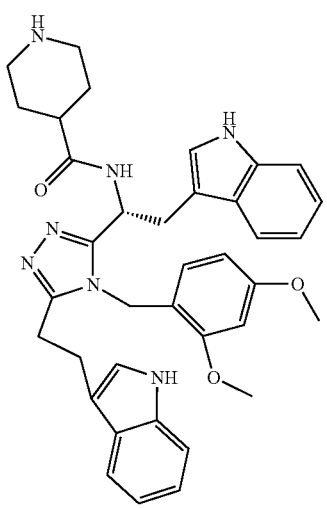 [SMILES: COc1ccc(Cn2c(CCc3c[nH]c4ccccc34)nnc2[C@@H](Cc2c[nH]c3ccccc23)NC(=O)C2CCNCC2)c(OC)c1]

compound 32 (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)piperidine-3-carboxamide,

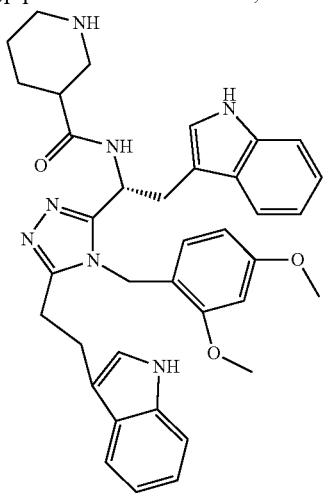

compound 33 (R)—N-(1-(4-(4-methylbenzyl)-5-(3-phenyl-propyl)-4H-1,2,4-triazol-3-yl)-2-(1H-indol-3-yl)ethyl)-2-amino-2-methylpropanamide,

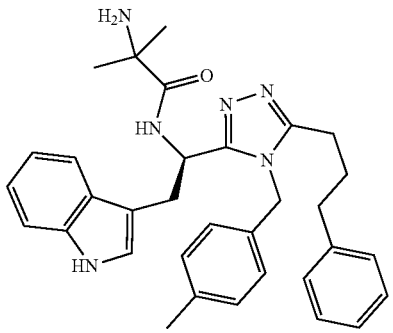 [SMILES: Cc1ccc(Cn2c(CCCc3ccccc3)nnc2[C@@H](Cc2c[nH]c3ccccc23)NC(=O)C(C)(C)N)cc1]

compound 34 (R)-N-(1-(5-(2-(1H-indol-3-yl)ethyl)-4-(4-methylbenzyl)-4H-1,2,4-triazol-3-yl)-2-(1H-indol-3-yl)ethyl)-2-amino-2-methylpropanamide,

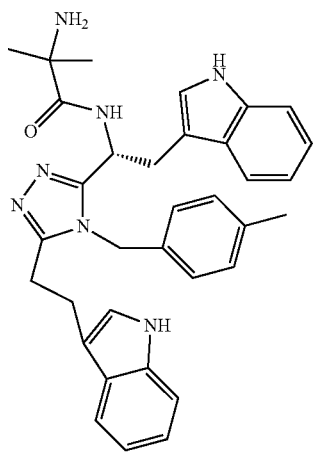 [SMILES: Cc1ccc(Cn2c(CCc3c[nH]c4ccccc34)nnc2[C@@H](Cc2c[nH]c3ccccc23)NC(=O)C(C)(C)N)cc1]

compound 36 (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)piperidine-2-carboxamide,

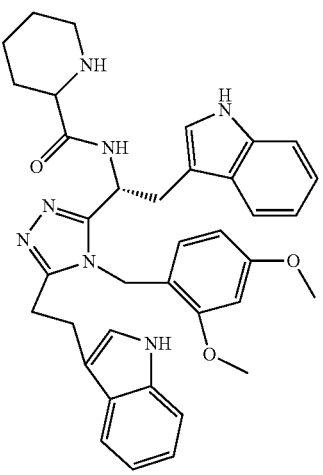 [SMILES: COc1ccc(Cn2c(CCc3c[nH]c4ccccc34)nnc2[C@@H](Cc2c[nH]c3ccccc23)NC(=O)C2CCCCN2)c(OC)c1]

compound 37 (R)—N-(1-(4-(4-methylbenzyl)-5-phenethyl-4H-1,2,4-triazol-3-0)-2-(1H-indol-3-yl)ethyl)-2-amino-2-methylpropanamide,

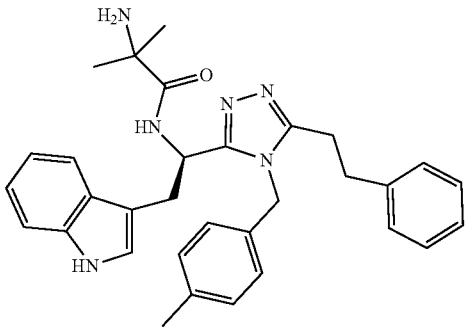 [SMILES: Cc1ccc(Cn2c(CCc3ccccc3)nnc2[C@@H](Cc2c[nH]c3ccccc23)NC(=O)C(C)(C)N)cc1]

compound 38 (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-aminobenzamide,

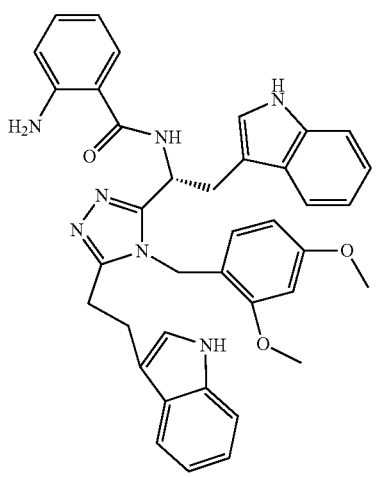 [SMILES: COc1ccc(Cn2c(CCc3c[nH]c4ccccc34)nnc2[C@@H](Cc2c[nH]c3ccccc23)NC(=O)c2ccccc2N)c(OC)c1]

compound 39 (R)—N-(1-(5-benzyl-4-(pyridin-2-ylmethyl)-4H-1,2,4-triazol-3-yl)-2-(1H-indol-3-yl)ethyl)-2-amino-2-methylpropanamide,

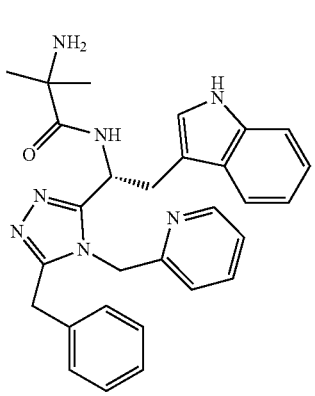 [SMILES: CC(C)(N)C(=O)N[C@H](Cc1c[nH]c2ccccc12)c1nnc(Cc2ccccc2)n1Cc1ccccn1]

compound 40 (2S,4R)—N—((R)-1-(4-(4-methoxybenzyl)-5-phenethyl-4H-1,2,4-triazol-3-yl)-2-(1H-indol-3-yl)ethyl)-4-hydroxypyrrolidine-2-carboxamide,

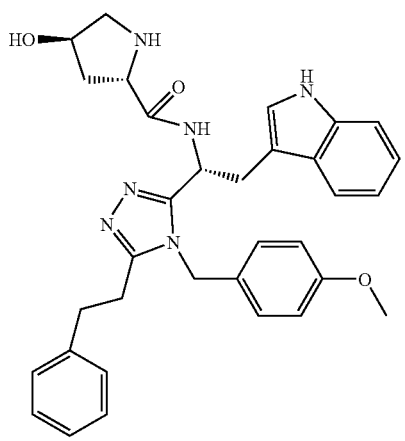 [SMILES: COc1ccc(Cn2c(CCc3ccccc3)nnc2[C@@H](Cc2c[nH]c3ccccc23)NC(=O)[C@@H]2C[C@@H](O)CN2)cc1]

compound 41 (S)—N—((R)-1-(4-(4-methoxybenzyl)-5-phenethyl-4H-1,2,4-triazol-3-yl)-2-(1H-indol-3-yl)ethyl)piperidine-3-carboxamide,

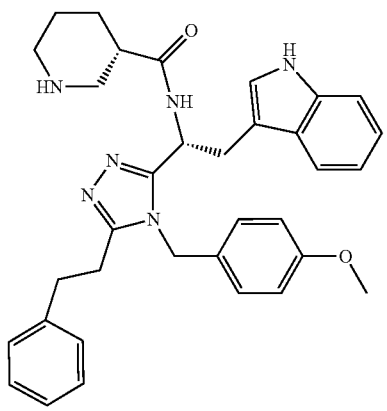 [SMILES: COc1ccc(Cn2c(CCc3ccccc3)nnc2[C@@H](Cc2c[nH]c3ccccc23)NC(=O)[C@H]2CCCNC2)cc1]

compound 42 (R)—N—((R)-1-(4-(4-methoxybenzyl)-5-phenethyl-4H-1,2,4-triazol-3-yl)-2-(1H-indol-3-yl)ethyl)piperidine-3-carboxamide,

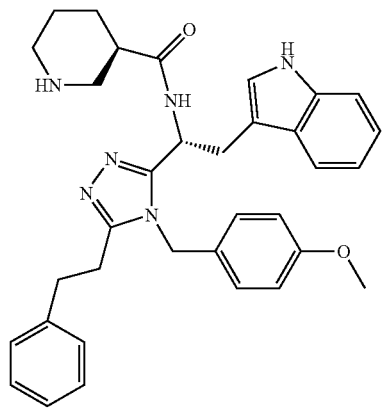 [SMILES: COc1ccc(Cn2c(CCc3ccccc3)nnc2[C@@H](Cc2c[nH]c3ccccc23)NC(=O)[C@@H]2CCCNC2)cc1]

compound 43 (R)—N-(1-(4-(4-ethylbenzyl)-5-phenethyl-4H-1,2,4-triazol-3-yl)-2-(1H-indol-3-yl)ethyl)-2-amino-2-methylpropanamide,

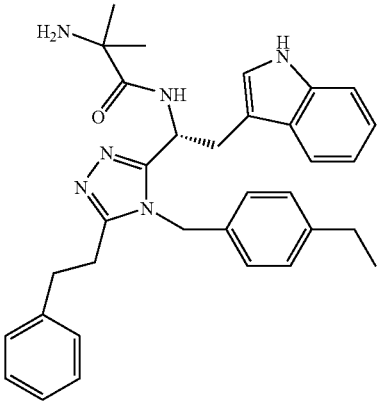 [SMILES: CCc1ccc(Cn2c(CCc3ccccc3)nnc2[C@@H](Cc2c[nH]c3ccccc23)NC(=O)C(C)(C)N)cc1]

compound 44 (R)—N-(1-(4-(4-methoxybenzyl)-5-phenethyl-4H-1,2,4-triazol-3-yl)-2-(1H-indol-3-yl)ethyl)piperidine-4-carboxamide,

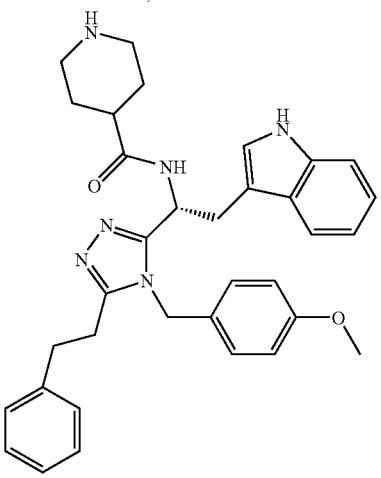

compound 45 (R)—N-(1-(5-(2-(1H-indol-3-yl)ethyl)-4-(4-methoxybenzyl)-4H-1,2,4-triazol-3-yl)-2-(1H-indol-3-yl)ethyl)piperidine-4-carboxamide,

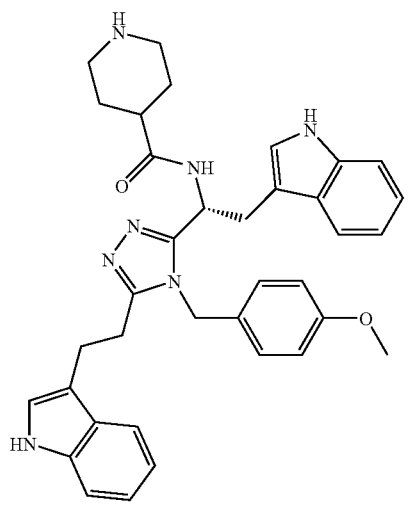 [SMILES: COc1ccc(Cn2c(CCc3c[nH]c4ccccc34)nnc2[C@@H](Cc2c[nH]c3ccccc23)NC(=O)C2CCNCC2)cc1]

compound 46 (S)—N—((R)-1-(4-(4-methoxybenzyl)-5-phenethyl-4H-1,2,4-triazol-3-yl)-2-(1H-indol-3-yl)ethyl)pyrrolidine-2-carboxamide,

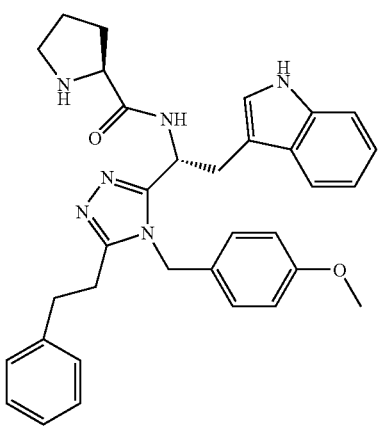 [SMILES: COc1ccc(Cn2c(CCc3ccccc3)nnc2[C@@H](Cc2c[nH]c3ccccc23)NC(=O)[C@@H]2CCCN2)cc1]

compound 47 (R)—N—((R)-1-(4-(4-methoxybenzyl)-5-phenethyl-4H-1,2,4-triazol-3-yl)-2-(1H-indol-3-yl)ethyl)pyrrolidine-2-carboxamide,

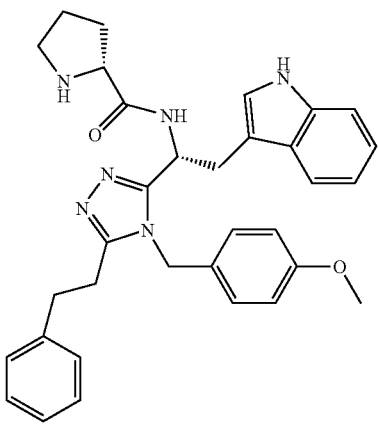 [SMILES: COc1ccc(Cn2c(CCc3ccccc3)nnc2[C@@H](Cc2c[nH]c3ccccc23)NC(=O)[C@H]2CCCN2)cc1]

compound 48 (S)—N—((R)-1-(4-(4-methoxybenzyl)-5-phenethyl-4H-1,2,4-triazol-3-yl)-2-(1H-indol-3-yl)ethyl)piperidine-2-carboxamide,

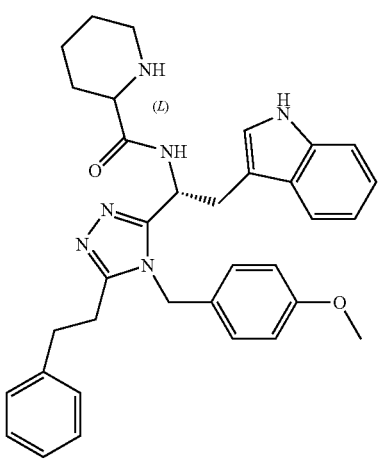 [SMILES: COc1ccc(Cn2c(CCc3ccccc3)nnc2[C@@H](Cc2c[nH]c3ccccc23)NC(=O)C2CCCCN2)cc1]

compound 49 (R)—N—((R)-1-(4-(4-methoxybenzyl)-5-phenethyl-4H-1,2,4-triazol-3-yl)-2-(1H-indol-3-yl)ethyl)piperidine-2-carboxamide,

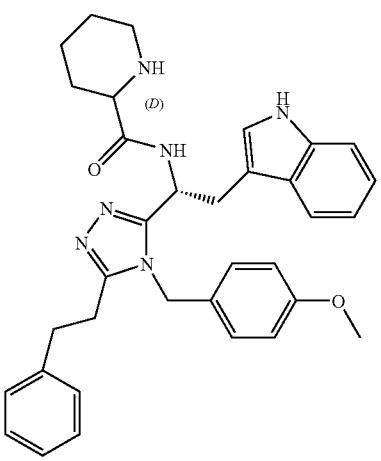

compound 50 (R)—N-(1-(4-(4-methoxybenzyl)-5-phenethyl-4H-1,2,4-triazol-3-yl)-2-(1H-indol-3-yl)ethyl)-2-aminoacetamide,

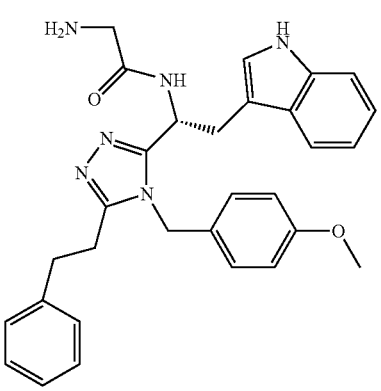 [SMILES: COc1ccc(Cn2c(CCc3ccccc3)nnc2[C@@H](Cc2c[nH]c3ccccc23)NC(=O)CN)cc1]

compound 51 (R)—N-(1-(4-(4-methoxybenzyl)-5-phenethyl-4H-1,2,4-triazol-3-yl)-2-(1H-indol-3-yl)ethyl)-2-(pyridin-2-aminoacetamide,

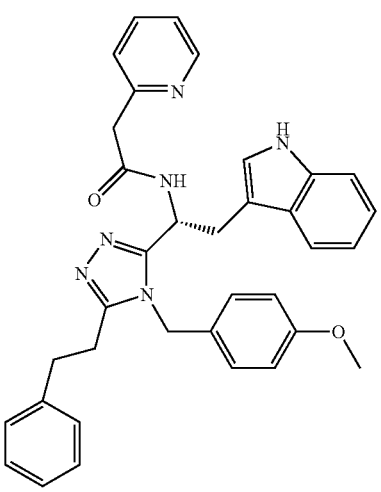 [SMILES: COc1ccc(Cn2c(CCc3ccccc3)nnc2[C@@H](Cc2c[nH]c3ccccc23)NC(=O)Cc2ccccn2)cc1]

compound 52 (R)—N-(1-(4-(4-methoxybenzyl)-5-phenethyl-4H-1,2,4-triazol-3-yl)-2(1H-indol-3-yl)ethyl)-2-(pyridin-4-yl)acetamide,

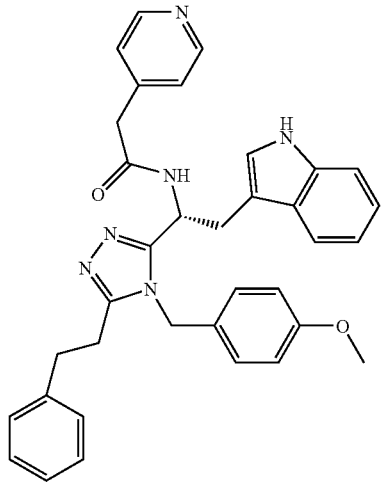 [SMILES: COc1ccc(Cn2c(CCc3ccccc3)nnc2[C@@H](Cc2c[nH]c3ccccc23)NC(=O)Cc2ccncc2)cc1]

compound 53 (R)—N-(1-(4-(4-methoxybenzyl)-5-phenethyl-4H-1,2,4-triazol-3-yl)-2(1H-indol-3-yl)ethyl)cyclohexanecarboxamide,

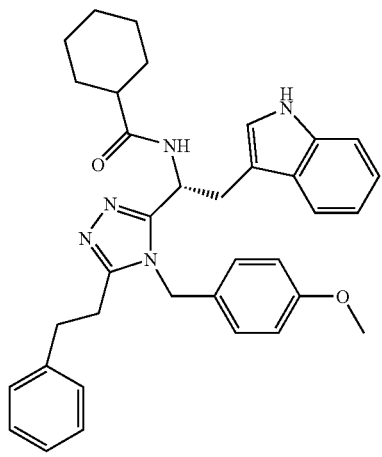 [SMILES: COc1ccc(Cn2c(CCc3ccccc3)nnc2[C@@H](Cc2c[nH]c3ccccc23)NC(=O)C2CCCCC2)cc1]

compound 54 (R)—N-(1-(5-(2-(1H-indol-3-yl)ethyl)-4-benzyl-4H-1,2,4-triazol-3-yl)-2-(1H-indol-3-yl)ethyl)piperidine-4-carboxamide,

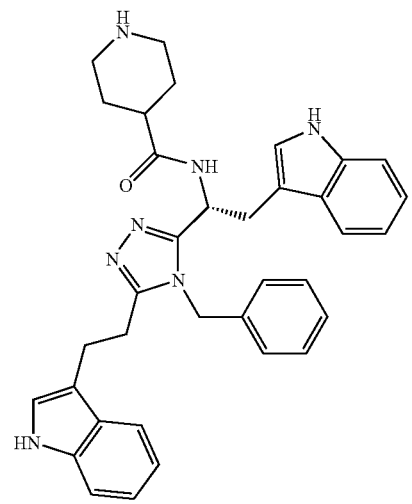 [SMILES: O=C(N[C@H](Cc1c[nH]c2ccccc12)c1nnc(CCc2c[nH]c3ccccc23)n1Cc1ccccc1)C1CCNCC1]

compound 55 (R)—N-(1-(5-(2-(1H-indol-3-yl)ethyl)-4-benzyl-4H-1,2,4-triazol-3-yl)-2-(1H-indol-3-yl)ethyl)piperidine-3-carboxamide,

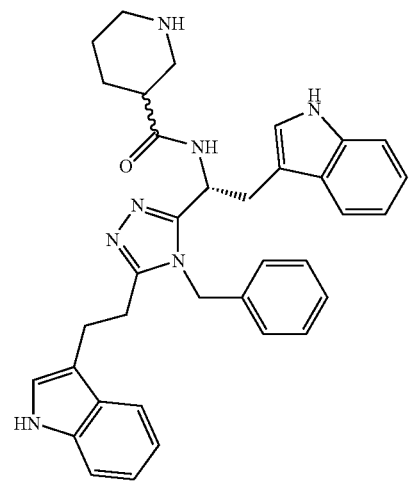 [SMILES: O=C(N[C@H](Cc1c[nH]c2ccccc12)c1nnc(CCc2c[nH]c3ccccc23)n1Cc1ccccc1)C1CCCNC1]

compound 56 (R)—N-(1-(4-(4-methoxybenzyl)-5-phenethyl-4H-1,2,4-triazol-3-yl)-2-(1H-indol-3-yl)ethyl)-3-aminopropanamide,

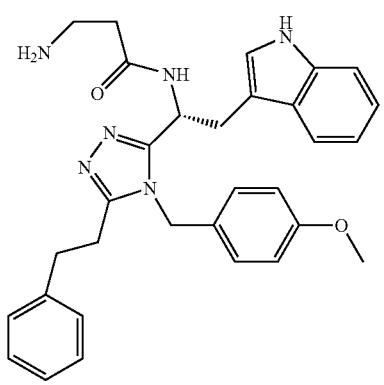 [SMILES: COc1ccc(Cn2c(CCc3ccccc3)nnc2[C@@H](Cc2c[nH]c3ccccc23)NC(=O)CCN)cc1]

compound 57 (S)—N—((R)-1-(4-(4-methoxybenzyl)-5-phenethyl-4H-1,2,4-triazol-3-yl)-2-(1H-indol-3-yl)ethyl)-2-aminopropanamide,

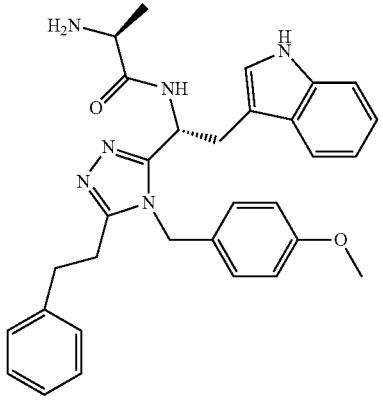 [SMILES: COc1ccc(Cn2c(CCc3ccccc3)nnc2[C@@H](Cc2c[nH]c3ccccc23)NC(=O)[C@H](C)N)cc1]

compound 58 (R)—N-(1-(4-(4-methoxybenzyl)-5-phenethyl-4H-1,2,4-triazol-3-yl)-2-(1H-indol-3-yl)ethyl)-2-(pyridin-3-yl)acetamide,

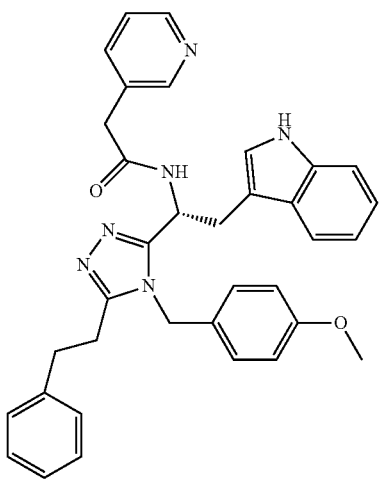

compound 59 (R)—N-(1-(4-(4-methoxybenzyl)-5-phenethyl-4H-1,2,4-triazol-3-yl)-2-(1H-indol-3-yl)ethyl)-3-(pyridin-3-yl)propanamide,

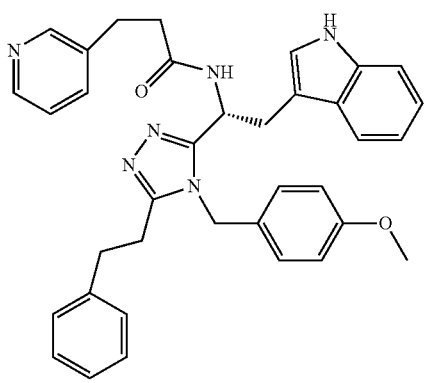 [SMILES: COc1ccc(Cn2c(CCc3ccccc3)nnc2[C@@H](Cc2c[nH]c3ccccc23)NC(=O)CCc2cccnc2)cc1]

compound 60 (R)—N-(1-(5-(2-(1H-indol-3-yl)ethyl)-4-benzyl-4H-1,2,4-triazol-3-yl)-2-(1H-indol-3-yl)ethyl)-2-(pyridin-2-yl)acetamide,

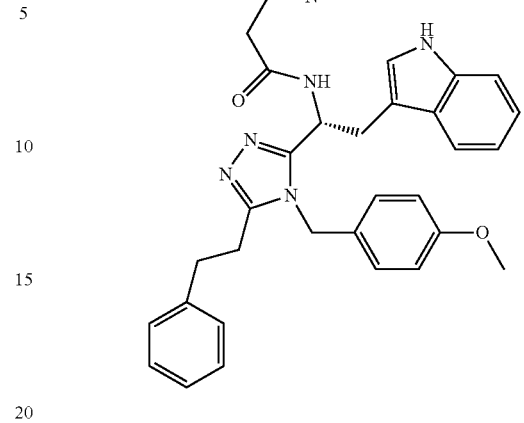

compound 61 (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-(pyridin-2-yl)acetamide, compound 62 (R)—N-(1-(4-(2,4-dimethoxybenzyl)-5-phenethyl-4H-1,2,4-triazol-3-yl)-2-(1H-indol-3-yl)ethyl)piperidine-4-carboxamide,

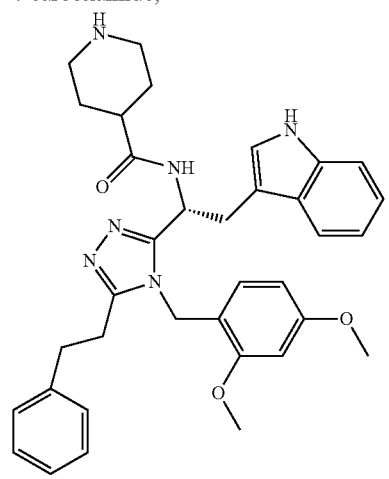

compound 63 (R)—N—((R)-1-(4-(2,4-dimethoxybenzyl)-5-phenethyl-4H-1,2,4-triazol-3-yl)-2-(1H-indol-3-yl)ethyl)piperidine-2-carboxamide,

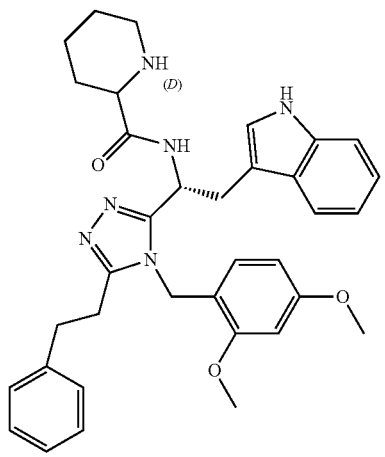

compound 64 (R)—N-(1-(4-(2,4-dimethoxybenzyl)-5-phenethyl-4H-1,2,4-triazol-3-yl)-2-(1H-indol-3-yl)ethyl)picolinamide,

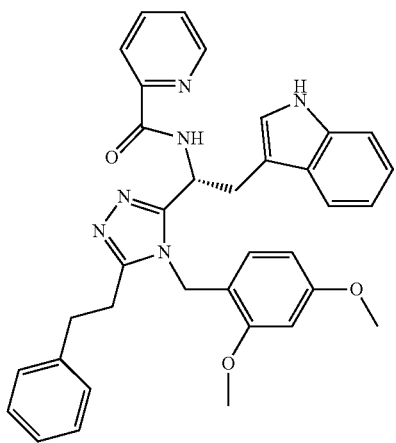 [SMILES: COc1ccc(Cn2c(CCc3ccccc3)nnc2[C@@H](Cc2c[nH]c3ccccc23)NC(=O)c2ccccn2)c(OC)c1]

compound 65 (R)—N-(1-(4-(2,4-dimethoxybenzyl)-5-phenethyl-4H-1,2,4-triazol-3-yl)-2-(1H-indol-3-yl)ethyl)isonicotinamide,

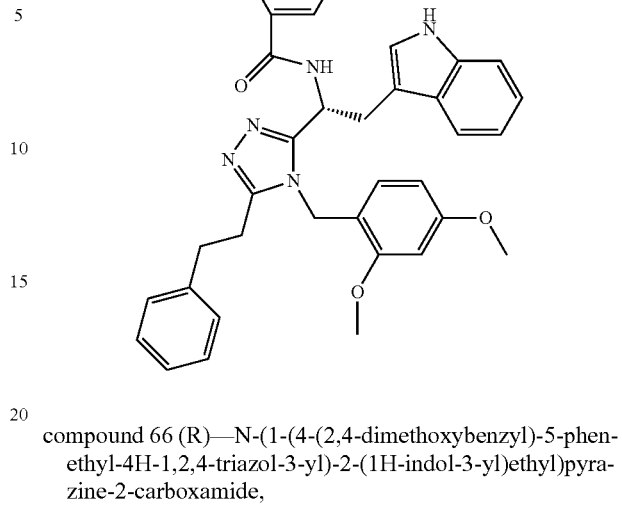

compound 66 (R)—N-(1-(4-(2,4-dimethoxybenzyl)-5-phenethyl-4H-1,2,4-triazol-3-yl)-2-(1H-indol-3-yl)ethyl)pyrazine-2-carboxamide,

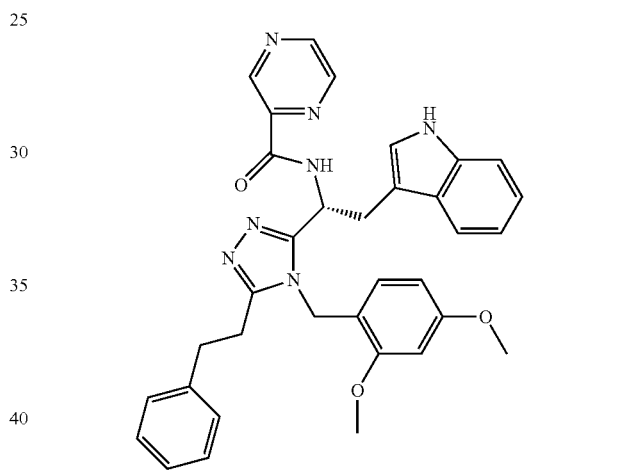

compound 67 (R)—N-1-(4-(2,4-dimethoxybenzyl)-5-phenethyl-4H-1,2,4-triazol-3-yl)-2-(1H-indol-3-yl)ethyl)piperazine-2-carboxamide,

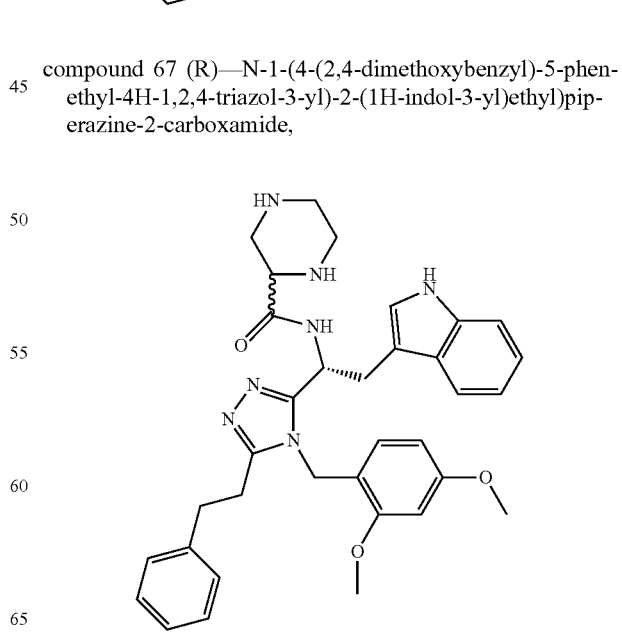

compound 68 (S)—N—((R)-1-(4-(2,4-dimethoxybenzyl)-5-phenethyl-4H-1,2,4-triazol-3-yl)-2-(1H-indol-3-yl)ethyl)pyrrolidine-2-carboxamide,

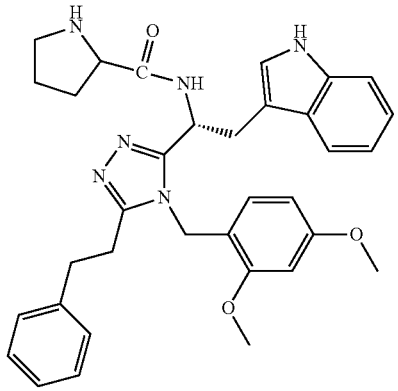 [SMILES: COc1ccc(Cn2c(CCc3ccccc3)nnc2[C@@H](Cc2c[nH]c3ccccc23)NC(=O)C2CCCN2)c(OC)c1]

compound 69 (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-aminoacetamide,

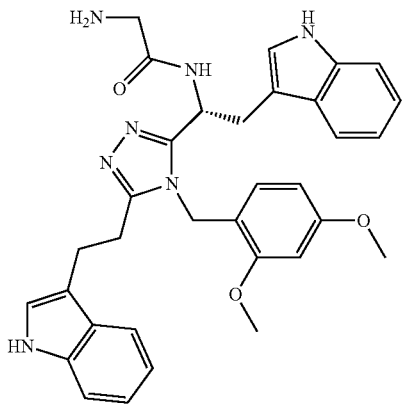 [SMILES: COc1ccc(Cn2c(CCc3c[nH]c4ccccc34)nnc2[C@@H](Cc2c[nH]c3ccccc23)NC(=O)CN)c(OC)c1]

compound 70 (S)—N—((R)-1-(5-(2-(1H-indol-3-yl)ethyl)-4-(2,4-dimethoxybenzyl)-4H-1,2,4-triazol-3-yl)-2-(1H-indol-3-yl)ethyl)pyrrolidine-2-carboxamide,

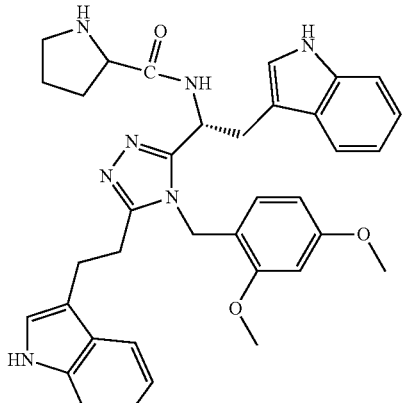

compound 71 (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)pyrazine-2-carboxamide,

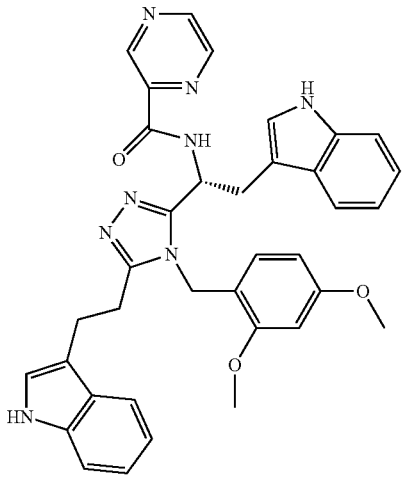 [SMILES: COc1ccc(Cn2c(CCc3c[nH]c4ccccc34)nnc2[C@@H](Cc2c[nH]c3ccccc23)NC(=O)c2cnccn2)c(OC)c1]

compound 72 (R)—N-1-(5-(2-(1H-indol-3-yl)ethyl)-4-(2,4-dimethoxybenzyl)-4H-1,2,4-triazol-3-yl)-2-(1H-indol-3-yl)ethyl)piperazine-2-carboxamide,

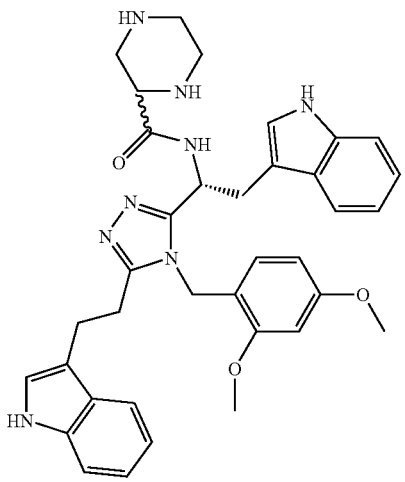 [SMILES: COc1ccc(Cn2c(CCc3c[nH]c4ccccc34)nnc2[C@@H](Cc2c[nH]c3ccccc23)NC(=O)C2CNCCN2)c(OC)c1]

compound 73 (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)picolinamide,

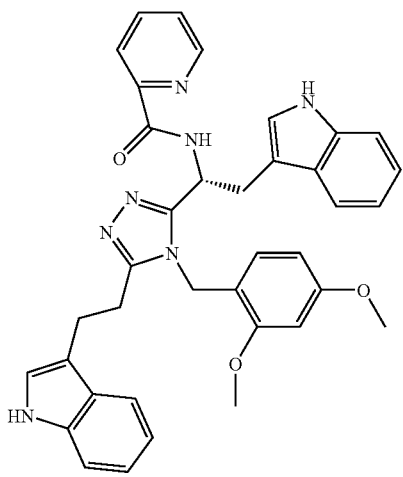 [SMILES: COc1ccc(Cn2c(CCc3c[nH]c4ccccc34)nnc2[C@@H](Cc2c[nH]c3ccccc23)NC(=O)c2ccccn2)c(OC)c1]

compound 74 (R)-1-(5-(2-(1H-indol-3-yl)ethyl)-4-(2,4-dimethoxybenzyl)-4H-1,2,4-triazol-3-yl)-2-(1H-indol-3-yl)ethanamine,

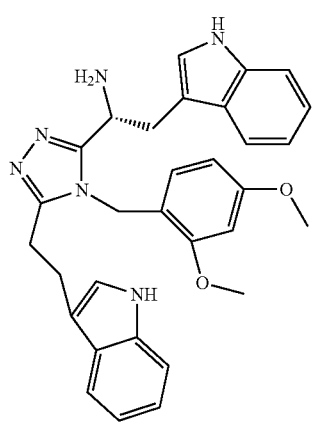 [SMILES: COc1ccc(Cn2c(CCc3c[nH]c4ccccc34)nnc2[C@H](N)Cc2c[nH]c3ccccc23)c(OC)c1]

compound 75 (R)—N-(1-(4-(2,4-dimethoxybenzyl)-5-phenethyl-4H-1,2,4-triazol-3-yl)-2-(1H-indol-3-yl)ethyl)-2-aminoacetamide,

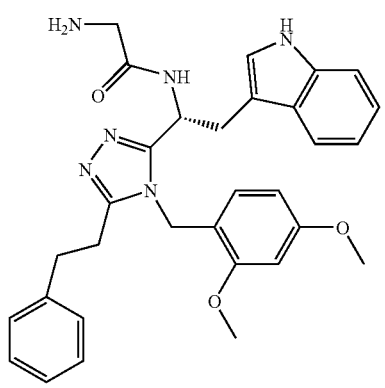 [SMILES: COc1ccc(Cn2c(CCc3ccccc3)nnc2[C@@H](Cc2c[nH]c3ccccc23)NC(=O)CN)c(OC)c1]

compound 76 (R)—N-(1-(4-(4-methoxybenzyl)-5-phenethyl-4H-1,2,4-triazol-3-yl)-2-(1H-indol-3-yl)ethyl)pyrazine-2-carboxamide,

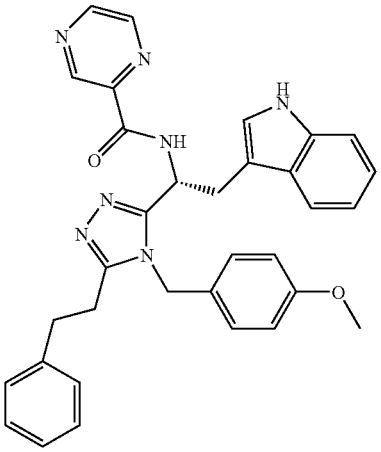 [SMILES: COc1ccc(Cn2c(CCc3ccccc3)nnc2[C@@H](Cc2c[nH]c3ccccc23)NC(=O)c2cnccn2)cc1]

compound 77 (R)—N-(1-(4-(4-methoxybenzyl)-5-phenethyl-4H-1,2,4-triazol-3-yl)-2-(1H-indol-3-yl)ethyl) isonicotinamide,

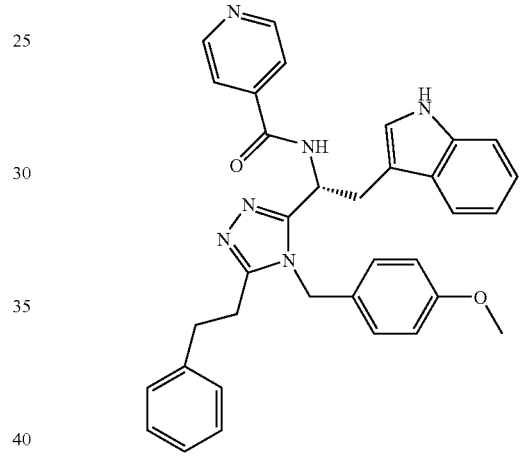

compound 78 (R)—N-1-(4-(4-methoxybenzyl)-5-phenethyl-4H-1,2,4-triazol-3-yl)-2-(1H-indol-3-yl)ethyl)piperazine-2-carboxamide,

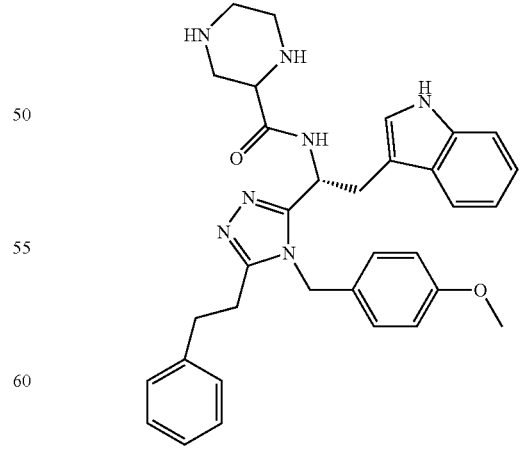

compound 79 (R)—N-(1-(4-(4-methoxybenzyl)-5-phenethyl-4H-1,2,4-triazol-3-yl)-2-(1H-indol-3-yl)ethyl)picolinamide,

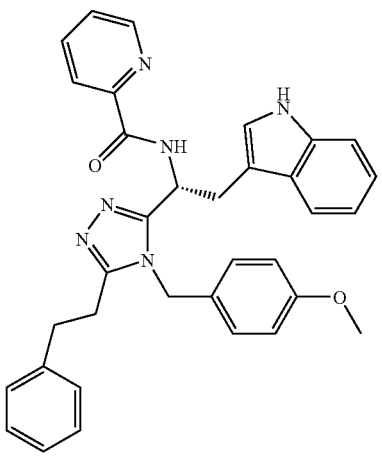 [SMILES: COc1ccc(Cn2c(CCc3ccccc3)nnc2[C@@H](Cc2c[nH]c3ccccc23)NC(=O)c2ccccn2)cc1]

compound 80 (R)—N-(1-(5-(2-(1H-indol-3-yl)ethyl)-4-(4-methoxybenzyl)-4H-1,2,4-triazol-3-yl)-2-(1H-indol-3-yl)ethyl)picolinamide,

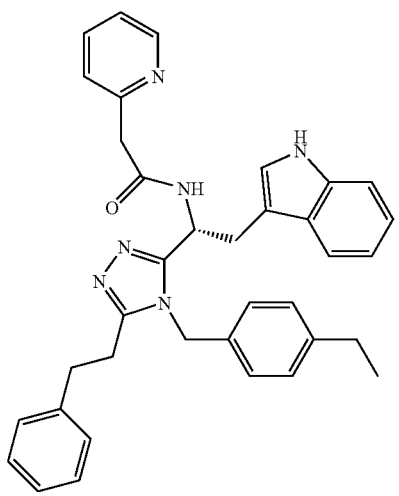

compound 83 (R)—N-(1-(4-(4-ethylbenzyl)-5-phenethyl-4H-1,2,4-triazol-3-yl)-2-(1H-indol-3-yl)ethyl)piperidine-4-carboxamide,

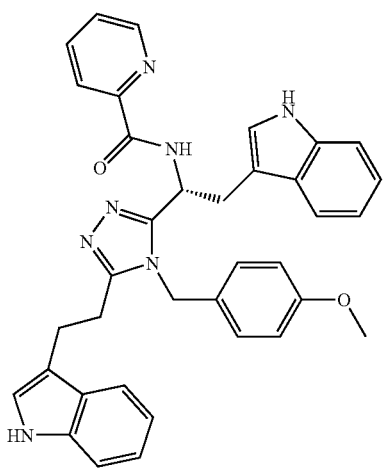 [SMILES: COc1ccc(Cn2c(CCc3c[nH]c4ccccc34)nnc2[C@@H](Cc2c[nH]c3ccccc23)NC(=O)c2ccccn2)cc1]

compound 81 (R)—N-1-(5-(2-(1H-indol-3-yl)ethyl)-4-(4-methoxybenzyl)-4H-1,2,4-triazol-3-yl)-2-(1H-indol-3-yl)ethyl)piperazine-2-carboxamide,

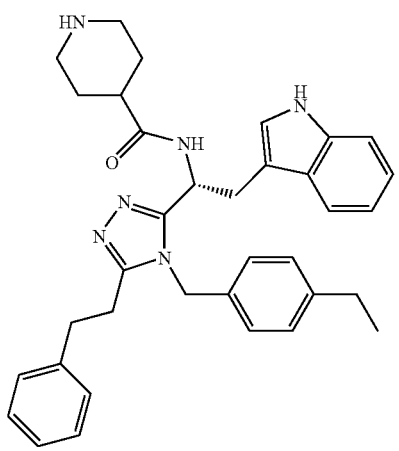

compound 84 (R)—N-1-(4-(4-ethylbenzyl)-5-phenethyl-4H-1,2,4-triazol-3-yl)-2-(1H-indol-3-yl)ethyl)piperazine-2-carboxamide,

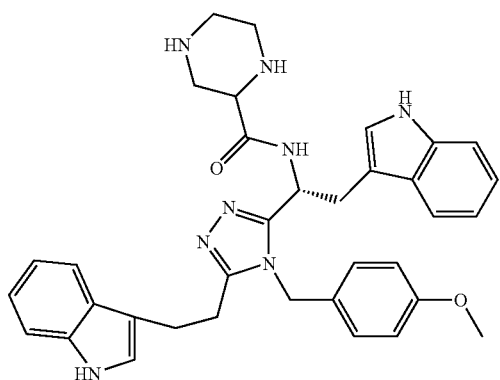 [SMILES: COc1ccc(Cn2c(CCc3c[nH]c4ccccc34)nnc2[C@@H](Cc2c[nH]c3ccccc23)NC(=O)C2CNCCN2)cc1]

compound 82 (R)—N-(1-(4-(4-ethylbenzyl)-5-phenethyl-4H-1,2,4-triazol-3-yl)-2-(1H-indol-3-yl)ethyl)-2-(pyridin-2-yl)acetamide,

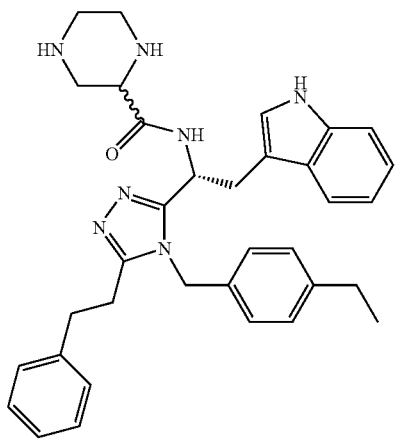 [SMILES: CCc1ccc(Cn2c(CCc3ccccc3)nnc2[C@@H](Cc2c[nH]c3ccccc23)NC(=O)C2CNCCN2)cc1]

compound 85 (R)—N-(1-(4-(4-ethylbenzyl)-5-phenethyl-4H-1,2,4-triazol-3-yl)-2-(1H-indol-3-yl)ethyl)pyrazine-2-carboxamide,

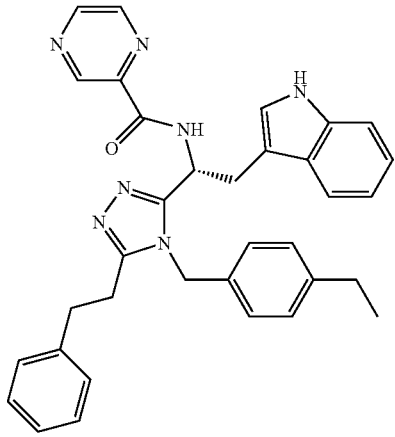 [SMILES: CCc1ccc(Cn2c(CCc3ccccc3)nnc2[C@@H](Cc2c[nH]c3ccccc23)NC(=O)c2cnccn2)cc1]

compound 86 (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-cis-aminocyclohexanecarboxamide,

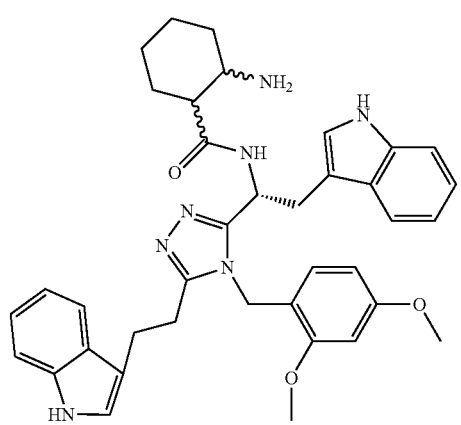 [SMILES: COc1ccc(Cn2c(CCc3c[nH]c4ccccc34)nnc2[C@@H](Cc2c[nH]c3ccccc23)NC(=O)C2CCCCC2N)c(OC)c1]

compound 87 (S)—N—((R)-1-(5-(2-(1H-indol-3-yl)ethyl)-4-(4-methoxybenzyl)-4H-1,2,4-triazol-3-yl)-2-(1H-indol-3-yl)ethyl)piperidine-3-carboxamide,

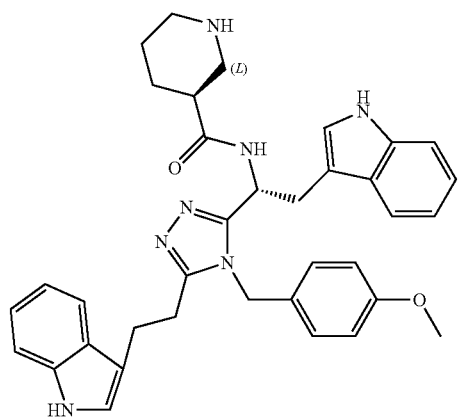

compound 88 (R)—N—((R)-1-(5-(2-(1H-indol-3-yl)ethyl)-4-(4-methoxybenzyl)-4H-1,2,4-triazol-3-yl)-2-(1H-indol-3-yl)ethyl)piperidine-2-carboxamide,

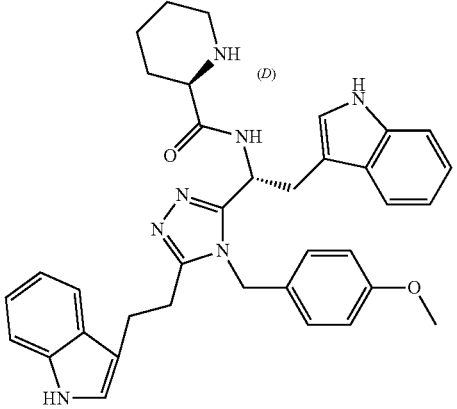

compound 89 (S)—N—((R)-1-(5-(2-(1H-indol-3-yl)ethyl)-4-(4-methoxybenzyl)-4H-1,2,4-triazol-3-yl)-2-(1H-indol-3-yl)ethyl)pyrrolidine-2-carboxamide,

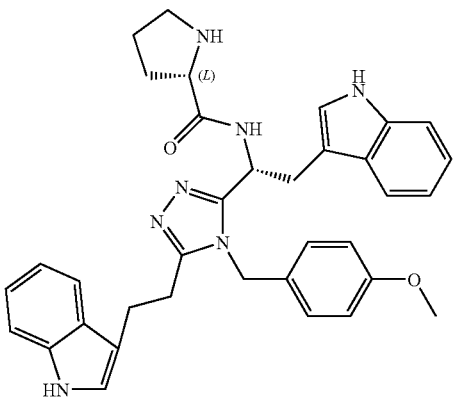

compound 90 (R)—N—((R)-1-(5-(2-(1H-indol-3-yl)ethyl)-4-(4-methoxybenzyl)-4H-1,2,4-triazol-3-yl)-2-(1H-indol-3-yl)ethyl)pyrrolidine-2-carboxamide,

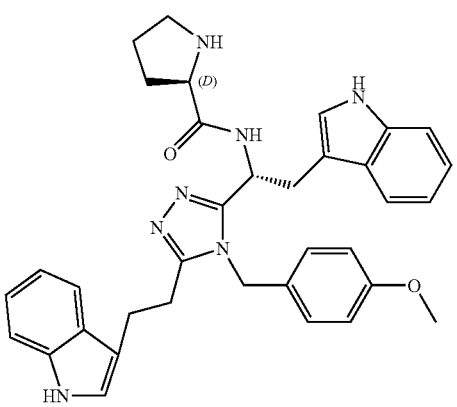

compound 91 (R)—N-(1-(5-(2-(1H-indol-3-yl)ethyl)-4-(4-methoxybenzyl)-4H-1,2,4-triazol-3-yl)-2-(1H-indol-3-yl)ethyl)-2-(pyridin-2-yl)acetamide,

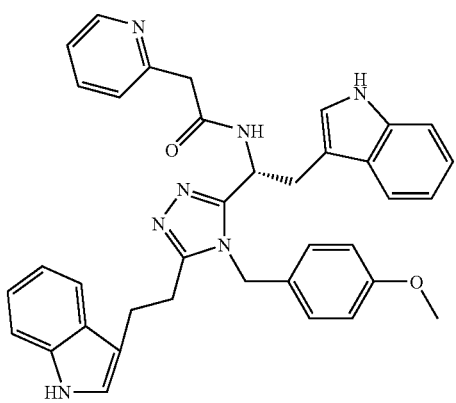 [SMILES: COc1ccc(Cn2c(CCc3c[nH]c4ccccc34)nnc2[C@@H](Cc2c[nH]c3ccccc23)NC(=O)Cc2ccccn2)cc1]

compound 92 (R)—N-(1-(5-(2-(1H-indol-3-yl)ethyl)-4-(4-bromobenzyl)-4H-1,2,4-triazol-3-yl)-2-(1H-indol-3-yl)ethyl)-2-amino-2-methylpropanamide,

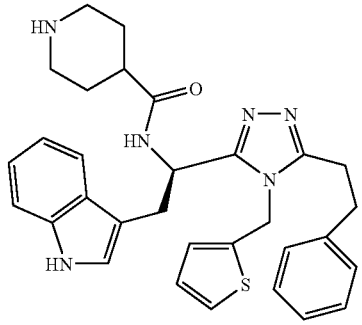

compound 95 (R)—N-(1-(4-(2-(1H-indol-3-yl)ethyl)-4H-1,2,4-triazol-3-yl)-2-(1H-indol-3-yl)ethyl)-2-amino-2-methylpropanamide,

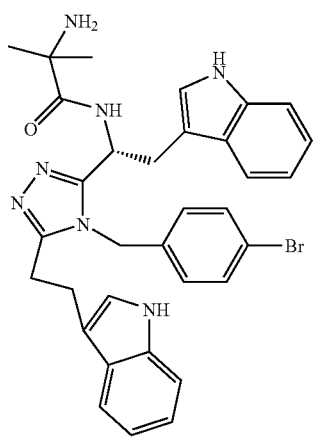 [SMILES: CC(C)(N)C(=O)N[C@H](Cc1c[nH]c2ccccc12)c1nnc(CCc2c[nH]c3ccccc23)n1Cc1ccc(Br)cc1]

compound 93 (R)—N-(1-(5-(2-(1H-indol-3-yl)ethyl)-4-(4-methoxybenzyl)-4H-1,2,4-triazol-3-yl)-2-phenylethyl)-2-amino-2-methylpropanamide,

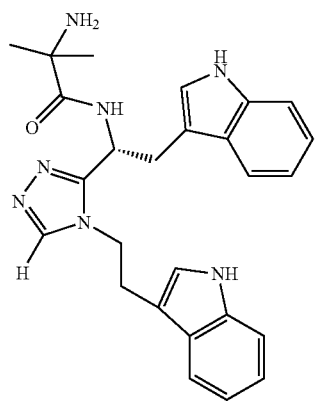

compound 96 (R)—N-(1-(5-((1H-indol-3-yl)methyl)-4-methyl-4H-1,2,4-triazol-3-yl)-2-(1H-indol-3-yl)ethyl)-2-amino-2-methylpropanamide,

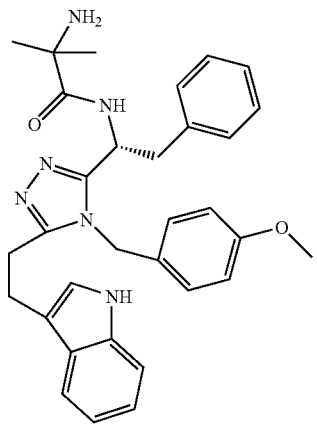 [SMILES: COc1ccc(Cn2c(CCc3c[nH]c4ccccc34)nnc2[C@@H](Cc2ccccc2)NC(=O)C(C)(C)N)cc1]

compound 94 (R)—N-(2-(1H-indol-3-yl)-1-(5-phenethyl-4-(thiophen-2-ylmethyl)-4H-1,2,4-triazol-3-yl)ethyl)piperidine-4-carboxamide,

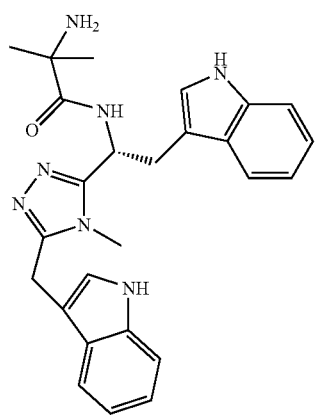 [SMILES: Cn1c(Cc2c[nH]c3ccccc23)nnc1[C@@H](Cc1c[nH]c2ccccc12)NC(=O)C(C)(C)N]

compound 97 (R)—N-(1-(5-(2-(1H-indol-3-yl)ethyl)-4-methyl-4H-1,2,4-triazol-3-yl)-2-(1H-indol-3-yl)ethyl)-2-amino-2-methylpropanamide,

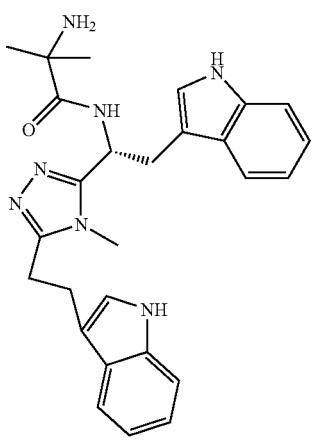 [SMILES: Cn1c(CCc2c[nH]c3ccccc23)nnc1[C@@H](Cc1c[nH]c2ccccc12)NC(=O)C(C)(C)N]

compound 98 (R)—N-(1-(5-(((1H-indol-3-yl)methyl)-4H-1,2,4-triazol-3-yl)-2-(1H-indol-3-yl)ethyl)-2-amino-2-methylpropanamide,

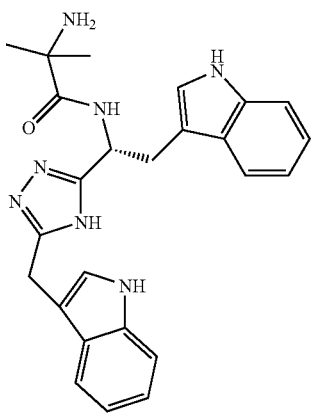 [SMILES: CC(C)(N)C(=O)N[C@H](Cc1c[nH]c2ccccc12)c1nnc(Cc2c[nH]c3ccccc23)[nH]1]

compound 99 (R)—N-(1-(5-(((1H-indol-3-yl)methyl)-4-(2,4-dimethoxybenzyl)-4H-1,2,4-triazol-3-yl)-2-(1H-indol-3-yl)ethyl)-2-amino-2-methylpropanamide,

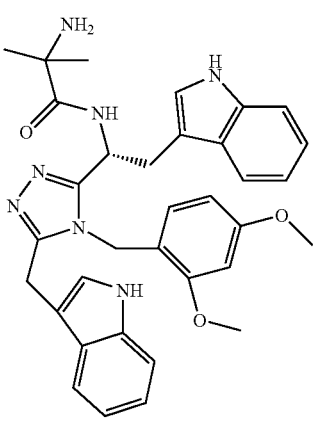 [SMILES: COc1ccc(Cn2c(Cc3c[nH]c4ccccc34)nnc2[C@@H](Cc2c[nH]c3ccccc23)NC(=O)C(C)(C)N)c(OC)c1]

compound 100 (R)—N-(1-(4-(2,4-dimethoxybenzyl)-5-methyl-4H-1,2,4-triazol-3-yl)-2-(1H-indol-3-yl)ethyl)-2-amino-2-methylpropanamide,

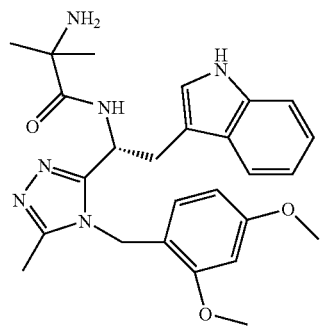 [SMILES: COc1ccc(Cn2c(C)nnc2[C@@H](Cc2c[nH]c3ccccc23)NC(=O)C(C)(C)N)c(OC)c1]

compound 101 (R)—N-(1-(5-(((1H-indol-3-yl)methyl)-4-(4-methoxybenzyl)-4H-1,2,4-triazol-3-yl)-2-(1H-indol-3-yl)ethyl)-2-amino-2-methylpropanamide,

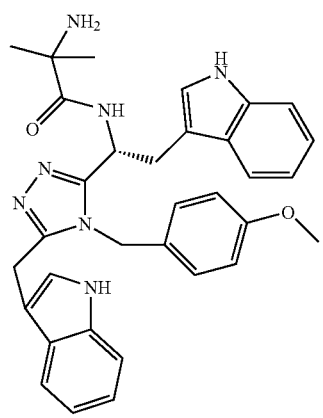 [SMILES: COc1ccc(Cn2c(Cc3c[nH]c4ccccc34)nnc2[C@@H](Cc2c[nH]c3ccccc23)NC(=O)C(C)(C)N)cc1]

compound 102 (R)—N-(1-(4-(2,4-dimethoxybenzyl)-5-benzyl-4H-1,2,4-triazol-3-yl)-2-(1H-indol-3-yl)ethyl)-2-amino-2-methylpropanamide,

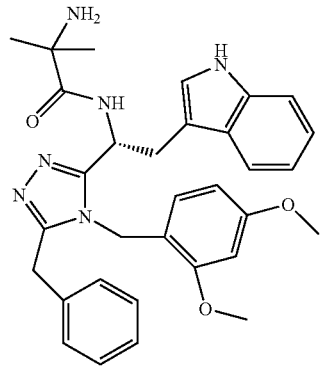 [SMILES: COc1ccc(Cn2c(Cc3ccccc3)nnc2[C@@H](Cc2c[nH]c3ccccc23)NC(=O)C(C)(C)N)c(OC)c1]

compound 103 (R)—N-(1-(5-(3-(1H-indol-3-yl)propyl)-4-(2,4-dimethoxybenzyl)-4H-1,2,4-triazol-3-yl)-2-(1H-indol-3-yl)ethyl)-2-amino-2-methylpropanamide,

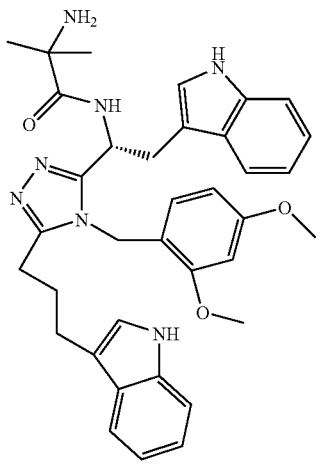 [SMILES: COc1ccc(Cn2c(CCCc3c[nH]c4ccccc34)nnc2[C@@H](Cc2c[nH]c3ccccc23)NC(=O)C(C)(C)N)c(OC)c1]

compound 104 (R)—N-(1-(5-((1H-indol-3-yl)methyl)-4-phenethyl-4H-1,2,4-triazol-3-yl)-2-(1H-indol-3-yl)ethyl)-2-amino-2-methylpropanamide,

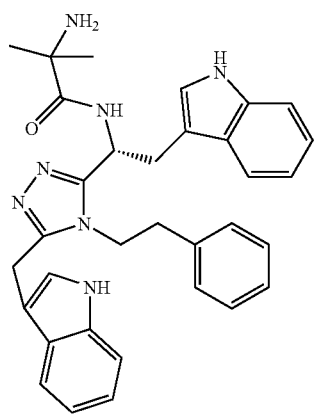 [SMILES: CC(C)(N)C(=O)N[C@H](Cc1c[nH]c2ccccc12)c1nnc(Cc2c[nH]c3ccccc23)n1CCc1ccccc1]

compound 105 (R)—N-(1-(5-benzyl-4-phenethyl-4H-1,2,4-triazol-3-yl)-2-(1H-indol-3-yl)ethyl)-2-amino-2-methylpropanamide,

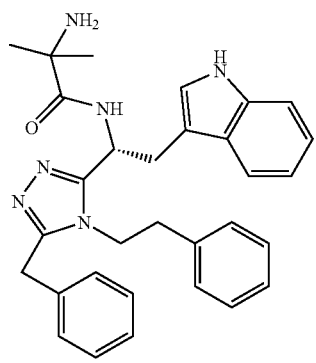 [SMILES: CC(C)(N)C(=O)N[C@H](Cc1c[nH]c2ccccc12)c1nnc(Cc2ccccc2)n1CCc1ccccc1]

compound 106 (R)—N-(1-(5-benzyl-4-(2,2-diphenylethyl)-4H-1,2,4-triazol-3-yl)-2-(1H-indol-3-yl)ethyl)-2-amino-2-methylpropanamide,

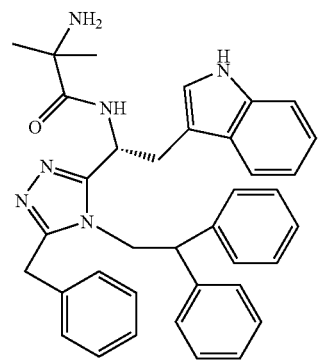 [SMILES: CC(C)(N)C(=O)N[C@H](Cc1c[nH]c2ccccc12)c1nnc(Cc2ccccc2)n1CC(c1ccccc1)c1ccccc1]

compound 107 (R)—N-(1-(5-(2-(1H-indol-3-yl)ethyl)-4-(2,2-diphenylethyl)-4H-1,2,4-triazol-3-yl)-2-(1H-indol-3-yl)ethyl)-2-amino-2-methylpropanamide,

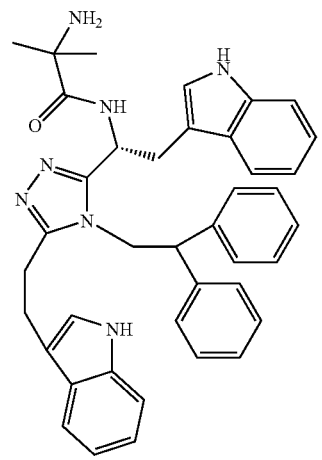 [SMILES: CC(C)(N)C(=O)N[C@H](Cc1c[nH]c2ccccc12)c1nnc(CCc2c[nH]c3ccccc23)n1CC(c1ccccc1)c1ccccc1]

compound 108 (R)—N-(1-(4-(3,5-dimethoxybenzyl)-5-benzyl-4H-1,2,4-triazol-3-yl)-2-(1H-indol-3-yl)ethyl)-2-amino-2-methylpropanamide,

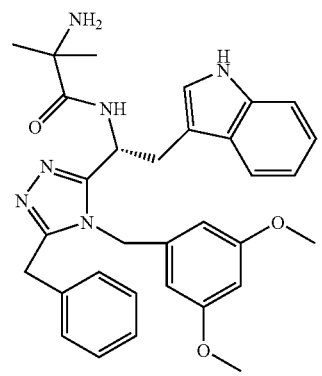 [SMILES: COc1cc(Cn2c(Cc3ccccc3)nnc2[C@@H](Cc2c[nH]c3ccccc23)NC(=O)C(C)(C)N)cc(OC)c1]

compound 109 (R)—N-(1-(4,5-dibenzyl-4H-1,2,4-triazol-3-yl)-2-(1H-indol-3-yl)ethyl)-2-amino-2-methylpropanamide,

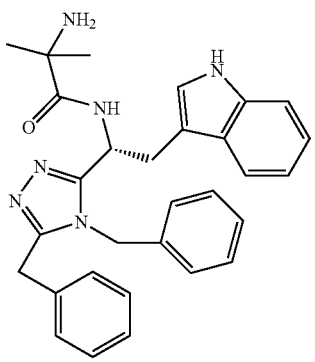 [SMILES: CC(C)(N)C(=O)N[C@H](Cc1c[nH]c2ccccc12)c1nnc(Cc2ccccc2)n1Cc1ccccc1]

compound 110 (R)—N-(1-(5-benzyl-4-hexyl-4H-1,2,4-triazol-3-yl)-2-(1H-indol-3-yl)ethyl)-2-amino-2-methylpropanamide,

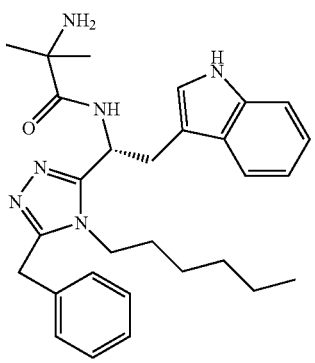 [SMILES: CCCCCCn1c(Cc2ccccc2)nnc1[C@@H](Cc1c[nH]c2ccccc12)NC(=O)C(C)(C)N]

compound 111 (R)—N-(1-(4-(2-(1H-indol-3-yl)ethyl)-5-benzyl-4H-1,2,4-triazol-3-yl)-2-(1H-indol-3-yl)ethyl)-2-amino-2-methylpropanamide,

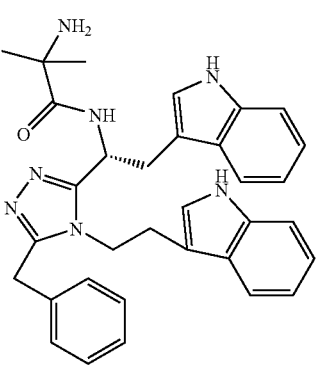 [SMILES: CC(C)(N)C(=O)N[C@H](Cc1c[nH]c2ccccc12)c1nnc(Cc2ccccc2)n1CCc1c[nH]c2ccccc12]

compound 112 (S)—N-(1-(4-(2,4-dimethoxybenzyl)-5-benzyl-4H-1,2,4-triazol-3-yl)-2-(1H-indol-3-yl)ethyl)-2-amino-2-methylpropanamide,

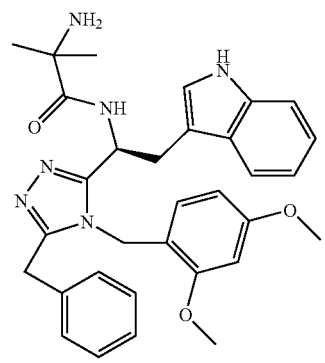 [SMILES: COc1ccc(Cn2c(Cc3ccccc3)nnc2[C@H](Cc2c[nH]c3ccccc23)NC(=O)C(C)(C)N)c(OC)c1]

compound 113 (R)—N-(1-(4-(3,5-dimethoxybenzyl)-5-phenethyl-4H-1,2,4-triazol-3-yl)-2-(1H-indol-3-yl)ethyl)-2-amino-2-methylpropanamide,

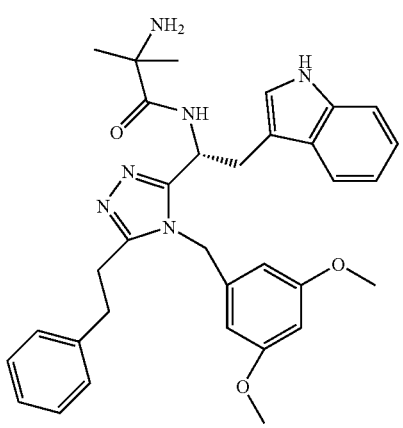 [SMILES: COc1cc(Cn2c(CCc3ccccc3)nnc2[C@@H](Cc2c[nH]c3ccccc23)NC(=O)C(C)(C)N)cc(OC)c1]

compound 114 (R)—N-(1-(4-(4-bromobenzyl)-5-benzyl-4H-1,2,4-triazol-3-yl)-2-(1H-indol-3-yl)ethyl)-2-amino-2-methylpropanamide,

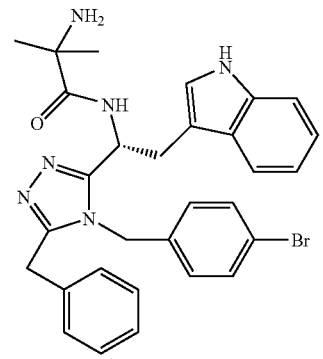 [SMILES: CC(C)(N)C(=O)N[C@H](Cc1c[nH]c2ccccc12)c1nnc(Cc2ccccc2)n1Cc1ccc(Br)cc1]

compound 115 (R)—N-(1-(4-(2-methoxybenzyl)-5-benzyl-4H-1,2,4-triazol-3-yl)-2-(1H-indol-3-yl)ethyl)-2-amino-2-methylpropanamide,

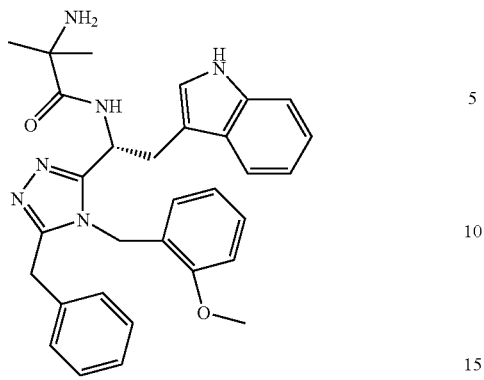

compound 116 (S)—N-(1-(4-(2,4-dimethoxybenzyl)-5-phenethyl-4H-1,2,4-triazol-3-yl)-2-(1H-indol-3-yl)ethyl)-2-amino-2-methylpropanamide,

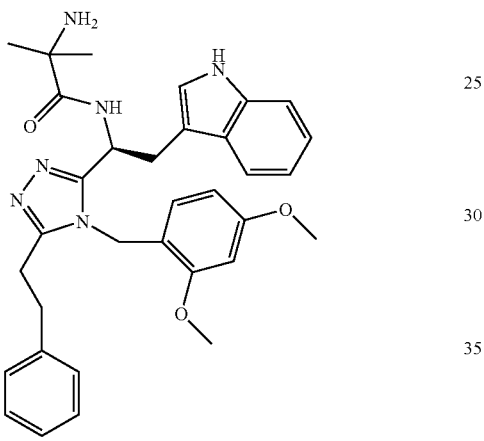

compound 117 (R)—N-(1-(4,5-diphenethyl-4H-1,2,4-triazol-3-yl)-2-(1H-indol-3-yl)ethyl)-2-amino-2-methylpropanamide,

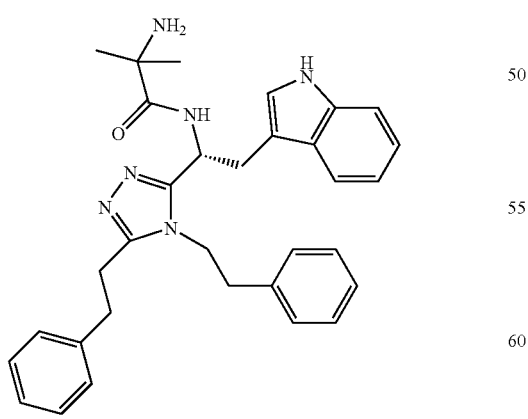

compound 118 (R)—N-(1-(4-(3,4-dichlorobenzyl)-5-benzyl-4H-1,2,4-triazol-3-yl)-2-(1H-indol-3-yl)ethyl)-2-amino-2-methylpropanamide,

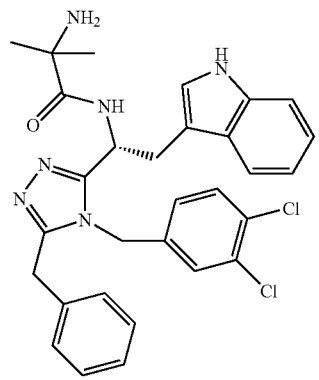 [SMILES: CC(C)(N)C(=O)N[C@H](Cc1c[nH]c2ccccc12)c1nnc(Cc2ccccc2)n1Cc1ccc(Cl)c(Cl)c1]

compound 119 (R)-1-(5-(2-(1H-indol-3-yl)ethyl)-4-(2,4-dimethoxybenzyl)-4H-1,2,4-triazol-3-yl)-2-(1H-indol-3-yl)ethanamine,

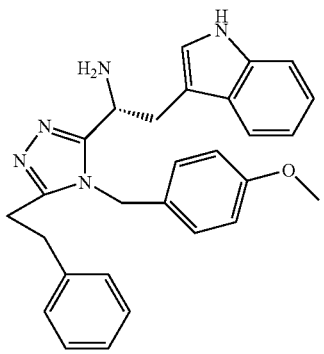 [SMILES: COc1ccc(Cn2c(CCc3ccccc3)nnc2[C@H](N)Cc2c[nH]c3ccccc23)cc1]

compound 120 (R)—N-(1-(4-(4-methoxybenzyl)-5-benzyl-4H-1,2,4-triazol-3-yl)-2-phenylethyl)-2-amino-2-methylpropanamide,

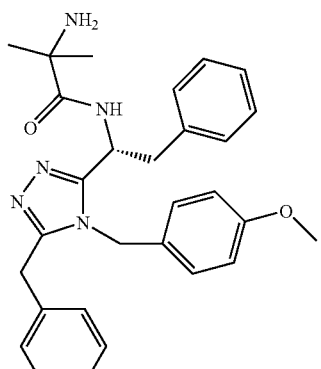

compound 121 (R)—N-(1-(4-(4-fluorobenzyl)-5-phenethyl-4H-1,2,4-triazol-3-yl)-2-(1H-indol-3-yl)ethyl)-2-amino-2-methylpropanamide,

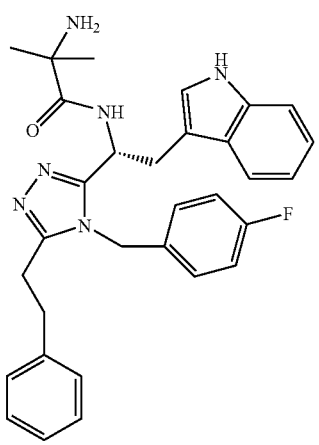 [SMILES: CC(C)(N)C(=O)N[C@H](Cc1c[nH]c2ccccc12)c1nnc(CCc2ccccc2)n1Cc1ccc(F)cc1]

compound 122 (R)—N-(1-(4-(3,4-dichlorobenzyl)-5-phenethyl-4H-1,2,4-triazol-3-yl)-2-(1H-indol-3-yl)ethyl)-2-amino-2-methylpropanamide,

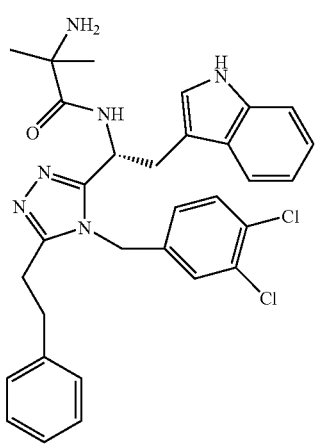 [SMILES: CC(C)(N)C(=O)N[C@H](Cc1c[nH]c2ccccc12)c1nnc(CCc2ccccc2)n1Cc1ccc(Cl)c(Cl)c1]

compound 124 (R)—N-(1-(4-(4-methylbenzyl)-5-benzyl-4H-1,2,4-triazol-3-yl)-2-(1H-indol-3-yl)ethyl)-2-amino-2-methylpropanamide,

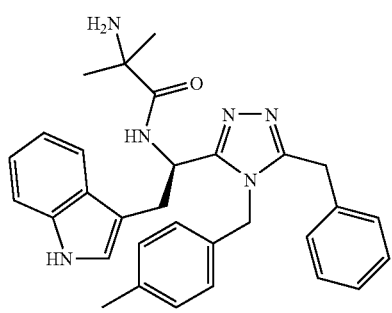 [SMILES: Cc1ccc(Cn2c(Cc3ccccc3)nnc2[C@@H](Cc2c[nH]c3ccccc23)NC(=O)C(C)(C)N)cc1]

compound 125 (S)—N-(1-(4-(4-methoxybenzyl)-5-(3-phenylpropyl)-4H-1,2,4-triazol-3-yl)-2-(1H-indol-3-yl)ethyl)-2-amino-2-methylpropanamide,

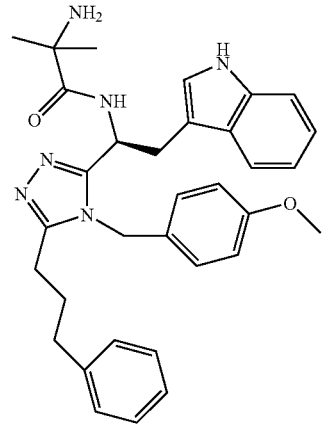 [SMILES: COc1ccc(Cn2c(CCCc3ccccc3)nnc2[C@H](Cc2c[nH]c3ccccc23)NC(=O)C(C)(C)N)cc1]

compound 126 (S)—N-(1-(4-(4-methoxybenzyl)-5-benzyl-4H-1,2,4-triazol-3-yl)-2-(1H-indol-3-yl)ethyl)-2-amino-2-methylpropanamide,

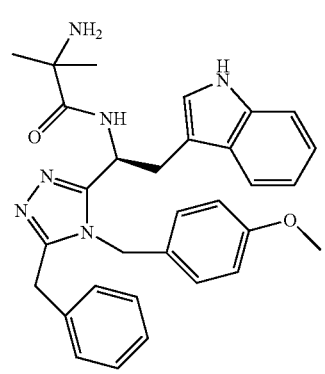 [SMILES: COc1ccc(Cn2c(Cc3ccccc3)nnc2[C@H](Cc2c[nH]c3ccccc23)NC(=O)C(C)(C)N)cc1]

compound 128 N—((R)-1-(4-(4-nitrobenzyl)-5-phenethyl-4H-1,2,4-triazol-3-yl)-2-(1H-indol-3-yl)ethyl)-2-amino-2-methylpropanamide,

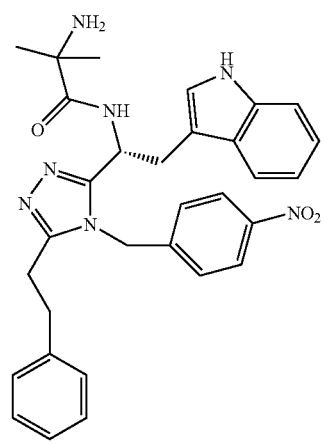 [SMILES: CC(C)(N)C(=O)N[C@H](Cc1c[nH]c2ccccc12)c1nnc(CCc2ccccc2)n1Cc1ccc([N+](=O)[O-])cc1]

compound 129 (S)—N-(1-(4-(4-methoxybenzyl)-5-phenethyl-4H-1,2,4-triazol-3-yl)-2-(1H-indol-3-yl)ethyl)-2-amino-2-methylpropanamide,

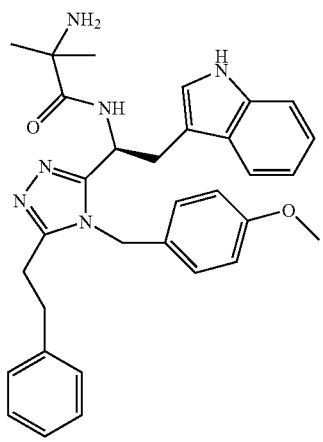 [SMILES: COc1ccc(Cn2c(CCc3ccccc3)nnc2[C@H](Cc2c[nH]c3ccccc23)NC(=O)C(C)(C)N)cc1]

compound 130 (R)—N-(1-(4-(4-methoxyphenethyl)-5-phenethyl-4H-1,2,4-triazol-3-yl)-2-(1H-indol-3-yl)ethyl)-2-amino-2-methylpropanamide,

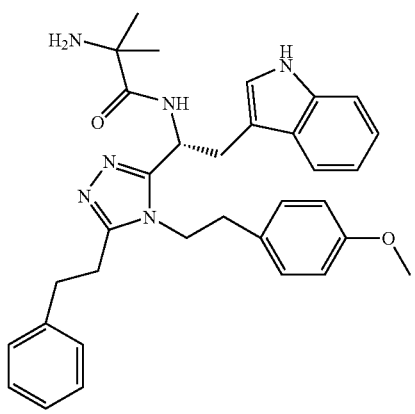 [SMILES: COc1ccc(CCn2c(CCc3ccccc3)nnc2[C@@H](Cc2c[nH]c3ccccc23)NC(=O)C(C)(C)N)cc1]

compound 131 (R)—N-(2-(1H-indol-3-yl)-1-(5-phenethyl-4-(thiophen-2-ylmethyl)-4H-1,2,4-triazol-3-yl)ethyl)-2-amino-2-methylpropanamide,

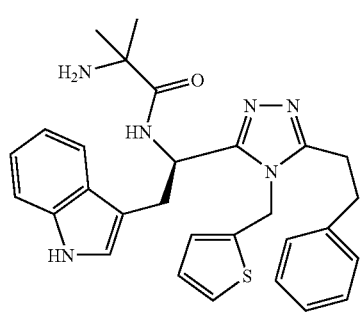 [SMILES: CC(C)(N)C(=O)N[C@H](Cc1c[nH]c2ccccc12)c1nnc(CCc2ccccc2)n1Cc1cccs1]

compound 132 (R)—N-(2-(1H-indol-3-yl)-1-(5-phenethyl-4-(pyridin-2-ylmethyl)-4H-1,2,4-triazol-3-yl)ethyl)-2-amino-2-methylpropanamide,

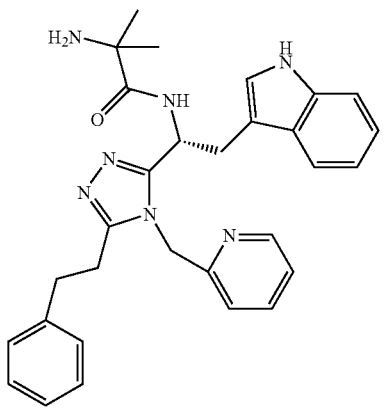 [SMILES: CC(C)(N)C(=O)N[C@H](Cc1c[nH]c2ccccc12)c1nnc(CCc2ccccc2)n1Cc1ccccn1]

compound 133 (R)—N-(2-(1H-indol-3-yl)-1-(5-phenethyl-4-(pyridin-2-ylmethyl)-4H-1,2,4-triazol-3-yl)ethyl)piperidine-3-carboxamide,

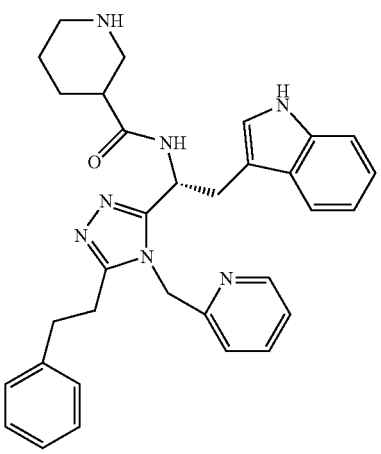 [SMILES: O=C(N[C@H](Cc1c[nH]c2ccccc12)c1nnc(CCc2ccccc2)n1Cc1ccccn1)C1CCCNC1]

compound 134 (S)—N—((R)-1-(4-(4-ethylbenzyl)-5-phenethyl-4H-1,2,4-triazol-3-yl)-2-(1H-indol-3-yl)ethyl)pyrrolidine-2-carboxamide,

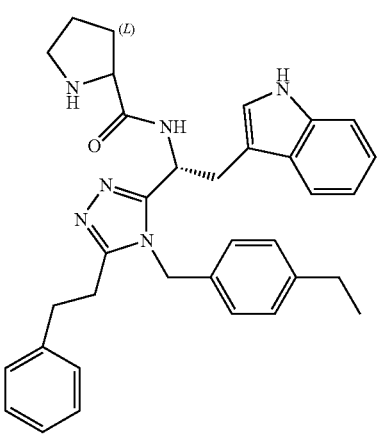

compound 135 N—((R)-1-(4-(4-ethylbenzyl)-5-phenethyl-4H-1,2,4-triazol-3-yl)-2-(1H-indol-3-yl)ethyl)-2-aminoacetamide,

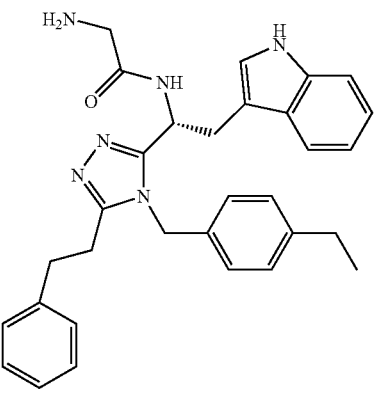 [SMILES: CCc1ccc(Cn2c(CCc3ccccc3)nnc2[C@@H](Cc2c[nH]c3ccccc23)NC(=O)CN)cc1]

compound 136 N—((R)-1-(5-(2-(1H-indol-3-yl)ethyl)-4-(4-methoxybenzyl)-4H-1,2,4-triazol-3-yl)-2-(1H-indol-3-yl)ethyl)-2-(pyridin-4-yl)acetamide,

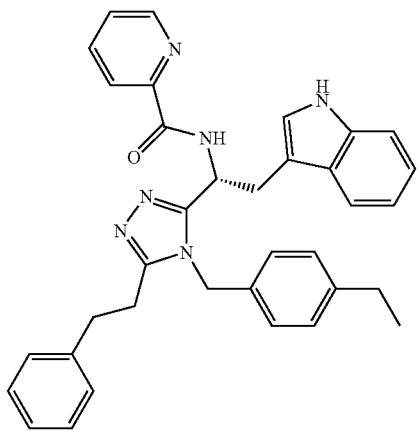

compound 139 N—((R)-1-(4-(4-ethylbenzyl)-5-phenethyl-4H-1,2,4-triazol-3-yl)-2-(1H-indol-3-yl)ethyl)-2-aminopyridine-3-carboxamide,

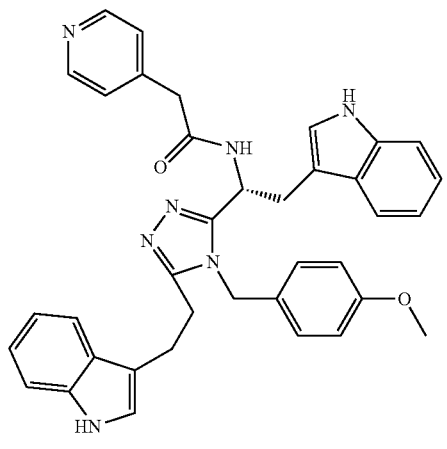 [SMILES: COc1ccc(Cn2c(CCc3c[nH]c4ccccc34)nnc2[C@@H](Cc2c[nH]c3ccccc23)NC(=O)Cc2ccncc2)cc1]

compound 137 (2R)—N—((R)-1-(4-(4-ethylbenzyl)-5-phenethyl-4H-1,2,4-triazol-3-yl)-2-(1H-indol-3-yl)ethyl)piperidine-2-carboxamide,

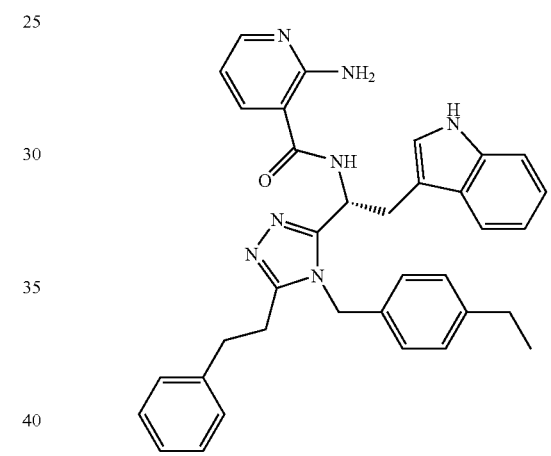

compound 140 (2S)—N—((R)-1-(4-(4-ethylbenzyl)-5-phenethyl-4H-1,2,4-triazol-3-yl)-2-(1H-indol-3-yl)ethyl)-2-aminopropanamide,

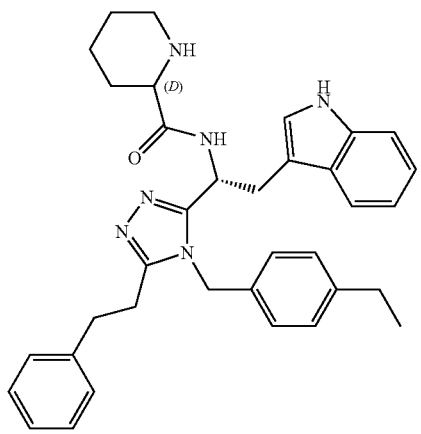

compound 138 N—((R)-1-(4-(4-ethylbenzyl)-5-phenethyl-4H-1,2,4-triazol-3-yl)-2-(1H-indol-3-yl)ethyl)picolinamide,

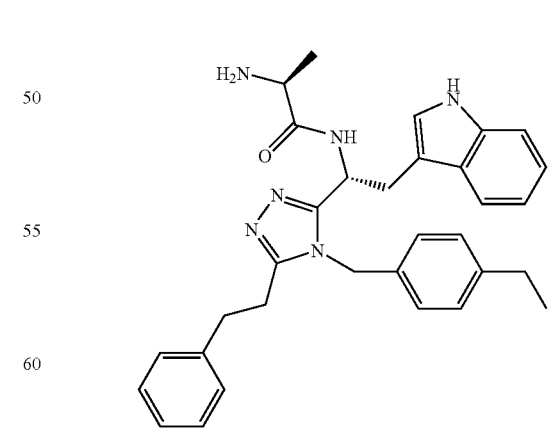

compound 141 N—((R)-1-(4-(4-ethylbenzyl)-5-phenethyl-4H-1,2,4-triazol-3-yl)-2-(1H-indol-3-yl)ethyl)isonicotinamide,

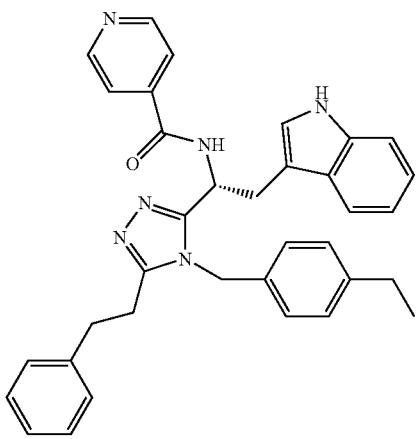 [SMILES: CCc1ccc(Cn2c(CCc3ccccc3)nnc2[C@@H](Cc2c[nH]c3ccccc23)NC(=O)c2ccncc2)cc1]

compound 142 N—((R)-2-(1H-indol-3-yl)-1-(5-phenethyl-4-phenyl-4H-1,2,4-triazol-3-yl)ethyl)piperidine-4-carboxamide,

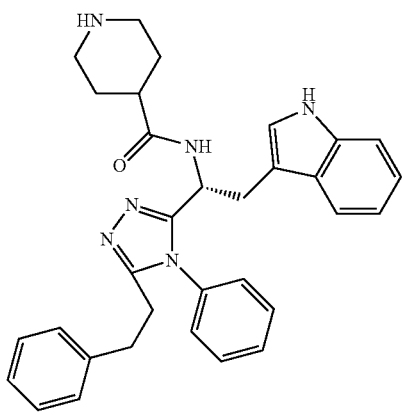 [SMILES: O=C(N[C@H](Cc1c[nH]c2ccccc12)c1nnc(CCc2ccccc2)n1-c1ccccc1)C1CCNCC1]

compound 143 (2S)—N—((R)-2-(1H-indol-3-yl)-1-(5-phenethyl-4-phenyl-4H-1,2,4-triazol-3-yl)ethyl)pyrrolidine-2-carboxamide,

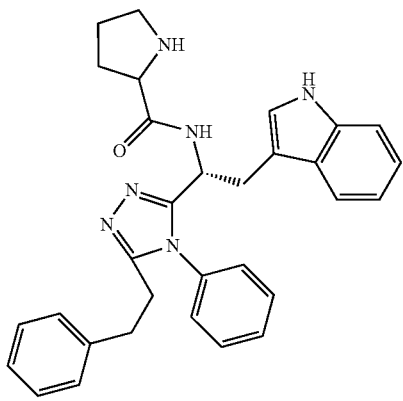 [SMILES: O=C(N[C@H](Cc1c[nH]c2ccccc12)c1nnc(CCc2ccccc2)n1-c1ccccc1)C1CCCN1]

compound 144 N—((R)-2-(1H-indol-3-yl)-1-(5-phenethyl-4-phenyl-4H-1,2,4-triazol-3-yl)ethyl)-2-aminoacetamide,

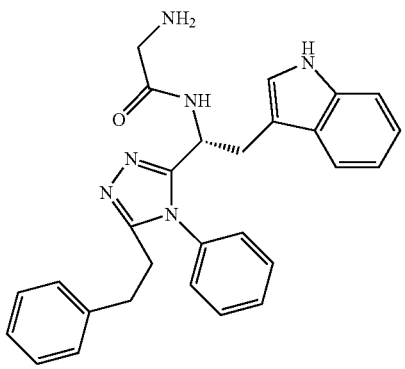 [SMILES: NCC(=O)N[C@H](Cc1c[nH]c2ccccc12)c1nnc(CCc2ccccc2)n1-c1ccccc1]

compound 145 N—((R)-2-(1H-indol-3-yl)-1-(5-phenethyl-4-phenyl-4H-1,2,4-triazol-3-yl)ethyl)-2-(pyridin-2-yl)acetamide,

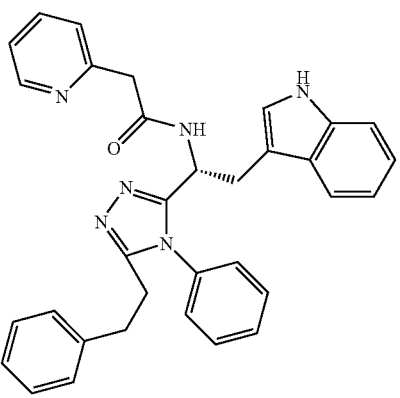 [SMILES: O=C(Cc1ccccn1)N[C@H](Cc1c[nH]c2ccccc12)c1nnc(CCc2ccccc2)n1-c1ccccc1]

compound 146 N—((R)-2-(1H-indol-3-yl)-1-(5-phenethyl-4-phenyl-4H-1,2,4-triazol-3-yl)ethyl)picolinamide,

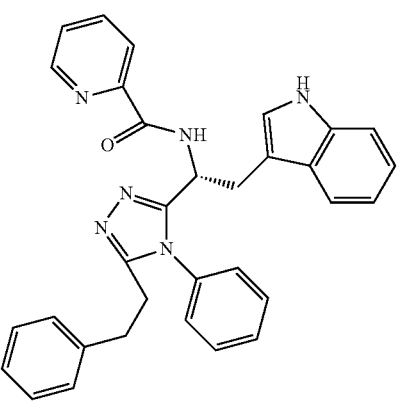 [SMILES: O=C(N[C@H](Cc1c[nH]c2ccccc12)c1nnc(CCc2ccccc2)n1-c1ccccc1)c1ccccn1]

compound 147 N—((R)-1-(5-(2-(1H-indol-3-yl)ethyl)-4-(4-ethylphenyl)-4H-1,2,4-triazol-3-yl)-2-(1H-indol-3-yl)ethyl)picolinamide,

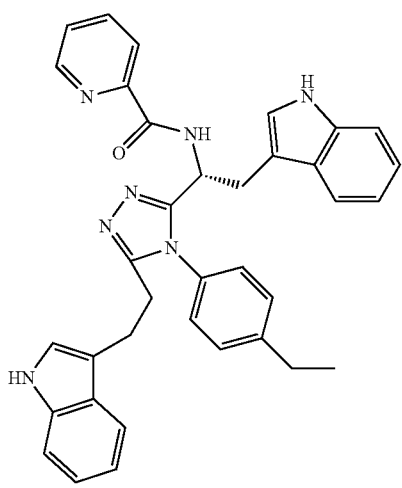 [SMILES: CCc1ccc(-n2c(CCc3c[nH]c4ccccc34)nnc2[C@@H](Cc2c[nH]c3ccccc23)NC(=O)c2ccccn2)cc1]

compound 148 N—((R)-1-(5-(2-(1H-indol-3-yl)ethyl)-4-(4-ethylphenyl)-4H-1,2,4-triazol-3-yl)-2-(1H-indol-3-yl)ethyl)-2-(pyridin-2-yl)acetamide,

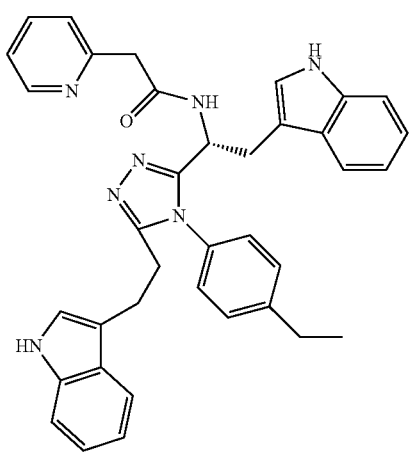 [SMILES: CCc1ccc(-n2c(CCc3c[nH]c4ccccc34)nnc2[C@@H](Cc2c[nH]c3ccccc23)NC(=O)Cc2ccccn2)cc1]

compound 149 N—((R)-1-(5-(2-(1H-indol-3-yl)ethyl)-4-(4-ethylphenyl)-4H-1,2,4-triazol-3-yl)-2-(1H-indol-3-yl)ethyl)-2-aminoacetamide,

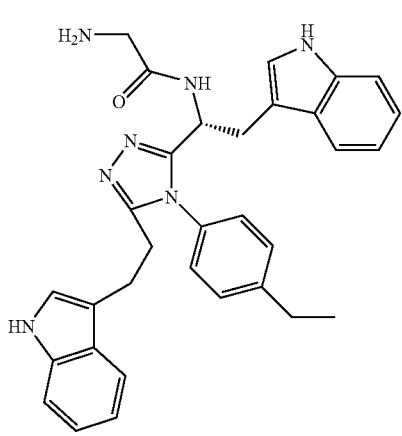 [SMILES: CCc1ccc(-n2c(CCc3c[nH]c4ccccc34)nnc2[C@@H](Cc2c[nH]c3ccccc23)NC(=O)CN)cc1]

compound 150 (2S)—N—((R)-1-(5-(2-(1H-indol-3-yl)ethyl)-4-(4-ethyl phenyl)-4H-1,2,4-triazol-3-yl)-2-(1H-indol-3-yl)ethyl)pyrrolidine-2-carboxamide,

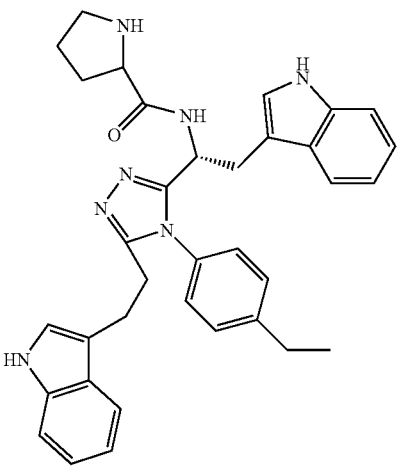 [SMILES: CCc1ccc(-n2c(CCc3c[nH]c4ccccc34)nnc2[C@@H](Cc2c[nH]c3ccccc23)NC(=O)C2CCCN2)cc1]

compound 152 N—((R)-1-(5-(2-(1H-indol-3-yl)ethyl)-4-(4-methoxybenzyl)-4H-1,2,4-triazol-3-yl)-2-(1H-indol-3-yl)ethyl)-2-aminoacetamide, compound 153 N—((R)-1-(4-(4-methoxybenzyl)-5-phenethyl-4H-1,2,4-triazol-3-yl)-2(1H-indol-3-yl)ethyl)-2-trans-aminocyclohexanecarboxamide,

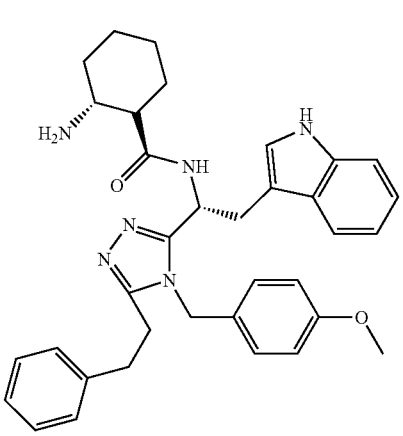

compound 154 N—((R)-1-(4-(4-ethylbenzyl)-5-phenethyl-4H-1,2,4-triazol-3-yl)-2-(1H-indol-3-yl)ethyl)-2-(pyridin-3-yl)acetamide,

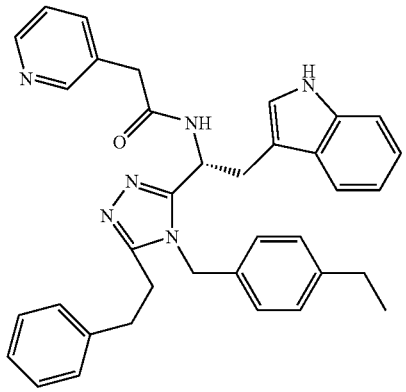 [SMILES: CCc1ccc(Cn2c(CCc3ccccc3)nnc2[C@@H](Cc2c[nH]c3ccccc23)NC(=O)Cc2cccnc2)cc1]

compound 155 (3S)—N—((R)-1-(4-(4-ethylbenzyl)-5-phenethyl-4H-1,2,4-triazol-3-yl)-2-(1H-indol-3-yl)ethyl)piperidine-3-carboxamide,

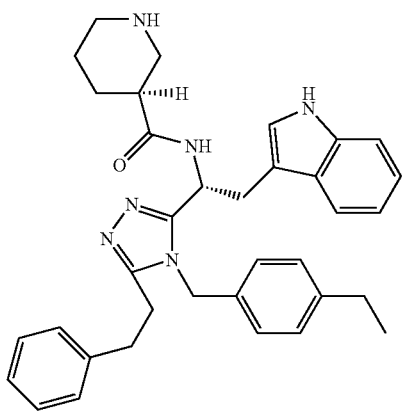 [SMILES: CCc1ccc(Cn2c(CCc3ccccc3)nnc2[C@@H](Cc2c[nH]c3ccccc23)NC(=O)[C@H]2CCCNC2)cc1]

compound 156 N—((R)-1-(4-(4-ethylbenzyl)-5-phenethyl-4H-1,2,4-triazol-3-yl)-2-(1H-indol-3-yl)ethyl)-2-aminobenzamide,

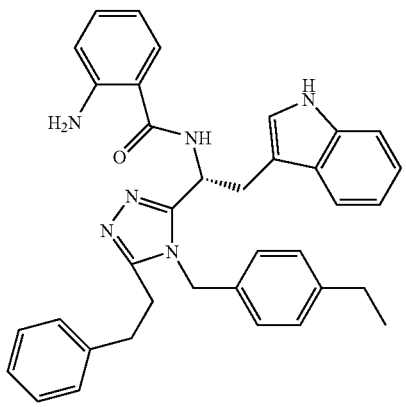 [SMILES: CCc1ccc(Cn2c(CCc3ccccc3)nnc2[C@@H](Cc2c[nH]c3ccccc23)NC(=O)c2ccccc2N)cc1]

compound 157 N—((R)-1-(5-(2-(1H-indol-3-yl)ethyl)-4-phenyl-4H-1,2,4-triazol-3-yl)-2-(1H-indol-3-yl)ethyl)picolinamide,

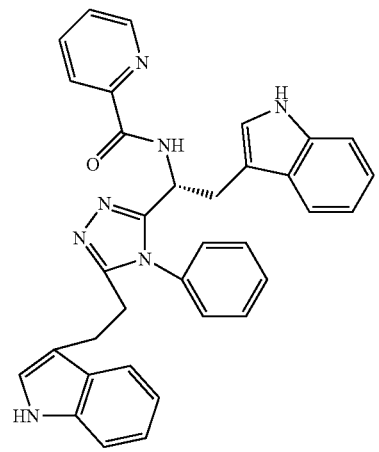 [SMILES: O=C(N[C@H](Cc1c[nH]c2ccccc12)c1nnc(CCc2c[nH]c3ccccc23)n1-c1ccccc1)c1ccccn1]

compound 158 N—((R)-1-(5-(2-(1H-indol-3-yl)ethyl)-4-phenyl-4H-1,2,4-triazol-3-yl)-2-(1H-indol-3-yl)ethyl)piperidine-4-carboxamide,

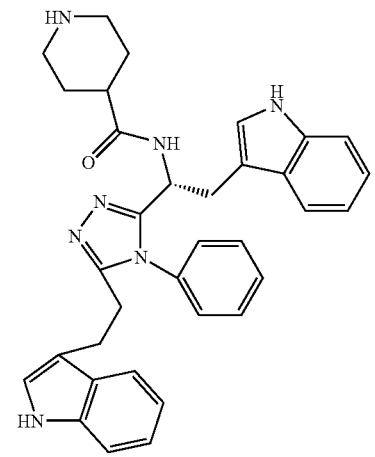 [SMILES: O=C(N[C@H](Cc1c[nH]c2ccccc12)c1nnc(CCc2c[nH]c3ccccc23)n1-c1ccccc1)C1CCNCC1]

compound 159 N—((R)-2-(1H-indol-3-yl)-1-(4-(2,4-dimethoxyphenyl)-5-phenethyl-4H-1,2,4-triazol-3-yl)ethyl)picolinamide,

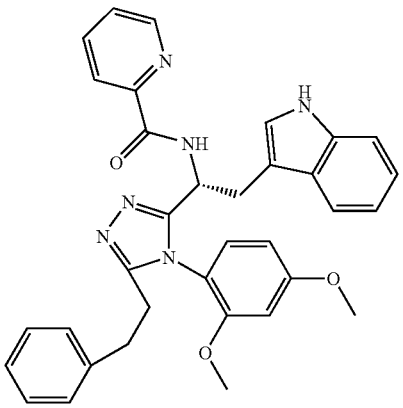 [SMILES: COc1ccc(-n2c(CCc3ccccc3)nnc2[C@@H](Cc2c[nH]c3ccccc23)NC(=O)c2ccccn2)c(OC)c1]

compound 160 N—((R)-2-(1H-indol-3-yl)-1-(4-(2,4-dimethoxyphenyl)-5-phenethyl-4H-1,2,4-triazol-3-yl)ethyl)-2-(pyridin-2-yl)acetamide,

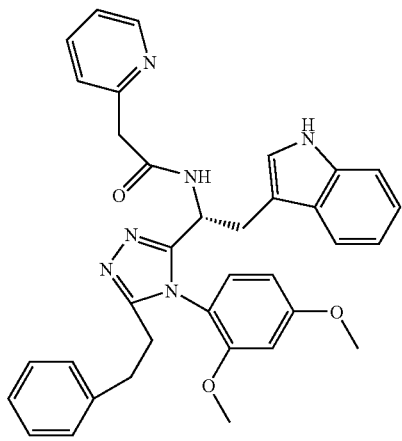 [SMILES: COc1ccc(-n2c(CCc3ccccc3)nnc2[C@@H](Cc2c[nH]c3ccccc23)NC(=O)Cc2ccccn2)c(OC)c1]

compound 161 N—((R)-2-(1H-indol-3-yl)-1-(4-(2,4-dimethoxyphenyl)-5-phenethyl-4H-1,2,4-triazol-3-yl)ethyl)pyrazine-2-carboxamide,

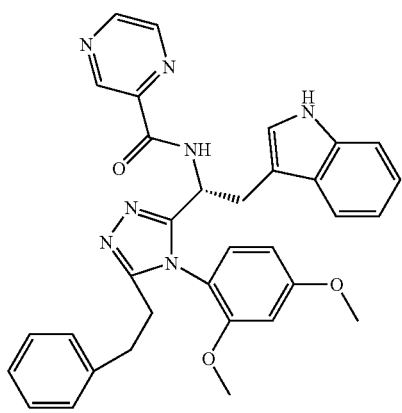 [SMILES: COc1ccc(-n2c(CCc3ccccc3)nnc2[C@@H](Cc2c[nH]c3ccccc23)NC(=O)c2cnccn2)c(OC)c1]

compound 162 N—((R)-2-(1H-indol-3-yl)-1-(4-(2,4-dimethoxyphenyl)-5-phenethyl-4H-1,2,4-triazol-3-yl)ethyl)-2-aminoacetamide,

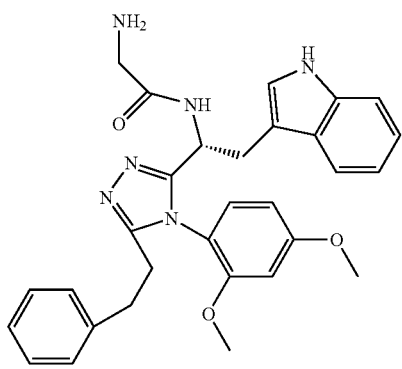 [SMILES: COc1ccc(-n2c(CCc3ccccc3)nnc2[C@@H](Cc2c[nH]c3ccccc23)NC(=O)CN)c(OC)c1]

compound 163 N—((R)-2-(1H-indol-3-yl)-1-(4-(2,4-dimethoxyphenyl)-5-phenethyl-4H-1,2,4-triazol-3-yl)ethyl)piperidine-4-carboxamide,

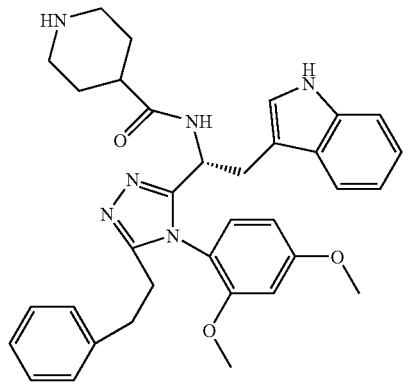 [SMILES: COc1ccc(-n2c(CCc3ccccc3)nnc2[C@@H](Cc2c[nH]c3ccccc23)NC(=O)C2CCNCC2)c(OC)c1]

compound 164 N—((R)-1-(5-benzyl-4-((pyridin-2-yl)methyl)-4H-1,2,4-triazol-3-yl)-2-(1H-indol-3-yl)ethyl)picolinamide,

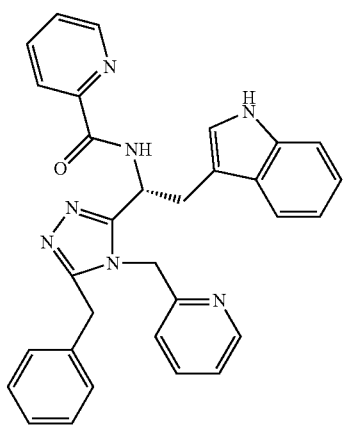 [SMILES: O=C(N[C@H](Cc1c[nH]c2ccccc12)c1nnc(Cc2ccccc2)n1Cc1ccccn1)c1ccccn1]

compound 165 N—((R)-1-(5-benzyl-4-((pyridin-2-yl)methyl)-4H-1,2,4-triazol-3-yl)-2-(1H-indol-3-yl)ethyl)-2-amino-acetamide,

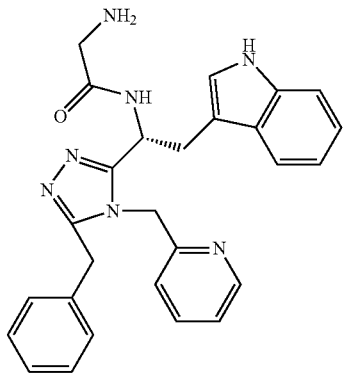 [SMILES: NCC(=O)N[C@H](Cc1c[nH]c2ccccc12)c1nnc(Cc2ccccc2)n1Cc1ccccn1]

compound 166 N—((R)-1-(5-benzyl-4-((pyridin-2-yl)methyl)-4H-1,2,4-triazol-3-yl)-2-(1H-indol-3-yl)ethyl)piperidine-4-carboxamide,

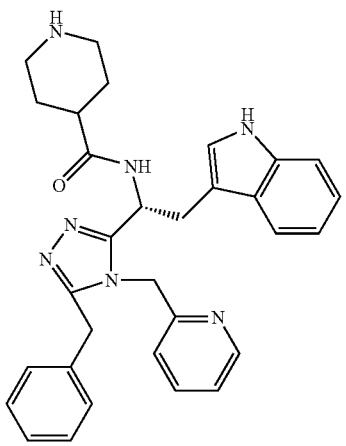 [SMILES: O=C(N[C@H](Cc1c[nH]c2ccccc12)c1nnc(Cc2ccccc2)n1Cc1ccccn1)C1CCNCC1]

compound 167 N—((R)-1-(5-benzyl-4-((pyridin-4-yl)methyl)-4H-1,2,4-triazol-3-yl)-2-(1H-indol-3-yl)ethyl)-2-amino-2-methylpropanamide,

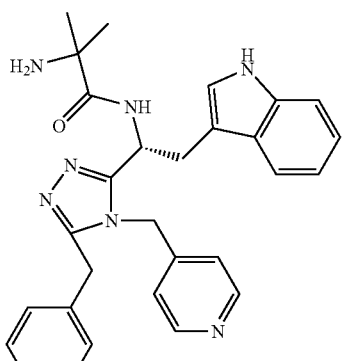

compound 168 N—((R)-1-(5-(4-methoxybenzyl)-4-phenethyl-4H-1,2,4-triazol-3-yl)-2-(1H-indol-3-yl)ethyl)-2-amino-2-methylpropanamide,

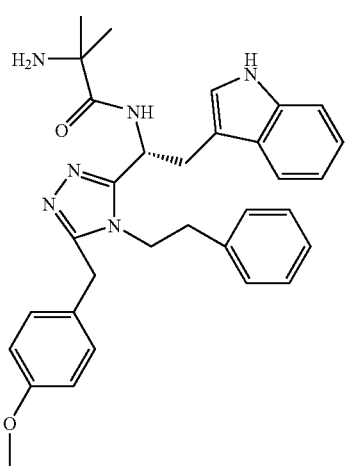 [SMILES: COc1ccc(Cc2nnc([C@@H](Cc3c[nH]c4ccccc34)NC(=O)C(C)(C)N)n2CCc2ccccc2)cc1]

compound 169 N—((R)-1-(5-benzyl-4-((pyridin-4-yl)methyl)-4H-1,2,4-triazol-3-yl)-2-(1H-indol-3-yl)ethyl)picolinamide,

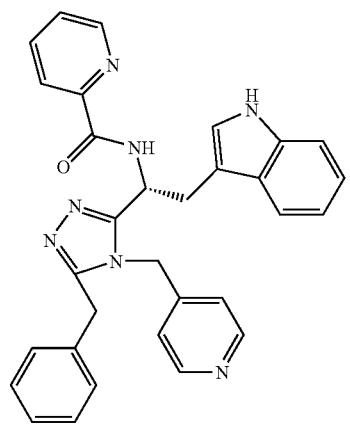 [SMILES: O=C(N[C@H](Cc1c[nH]c2ccccc12)c1nnc(Cc2ccccc2)n1Cc1ccncc1)c1ccccn1]

compound 170 N—((R)-1-(5-benzyl-4-((pyridin-4-yl)methyl)-4H-1,2,4-triazol-3-yl)-2-(1H-indol-3-yl)ethyl)-2-amino-acetamide,

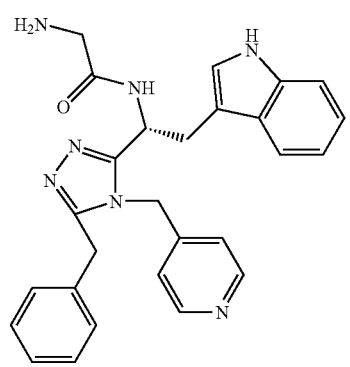 [SMILES: NCC(=O)N[C@H](Cc1c[nH]c2ccccc12)c1nnc(Cc2ccccc2)n1Cc1ccncc1]

compound 171 (R)-benzyl-3-(2-aminoisobutyramido)-3-(5-(2-(1H-indol-3-yl)ethyl)-4-(4-methoxybenzyl)-4H-1,2,4-triazol-3-yl)-propanoate,

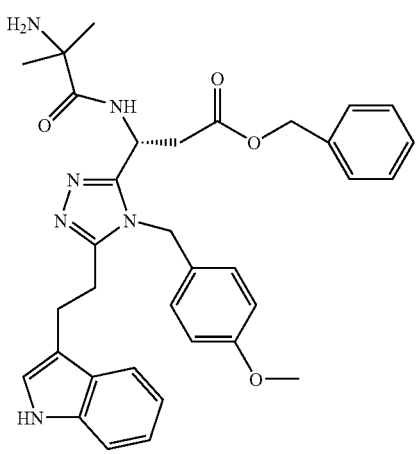 [SMILES: COc1ccc(Cn2c(CCc3c[nH]c4ccccc34)nnc2[C@@H](CC(=O)OCc2ccccc2)NC(=O)C(C)(C)N)cc1]

compound 172 N—((R)-1-(5-benzyl-4-((pyridin-3-yl)methyl)-4H-1,2,4-triazol-3-yl)-2-(1H-indol-3-yl)ethyl)-2-amino-2-methylpropanamide,

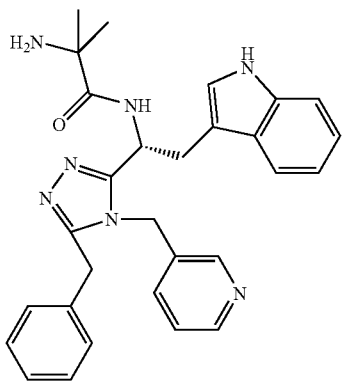 [SMILES: CC(C)(N)C(=O)N[C@H](Cc1c[nH]c2ccccc12)c1nnc(Cc2ccccc2)n1Cc1cccnc1]

compound 173 N—((R)-1-(4-benzyl-5-phenethyl-4H-1,2,4-triazol-3-yl)-2-(1H-indol-3-yl)ethyl)-2-amino-2-methyl-propanamide,

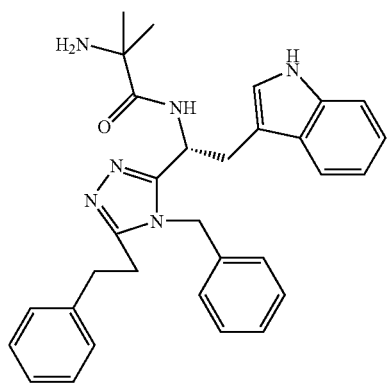 [SMILES: CC(C)(N)C(=O)N[C@H](Cc1c[nH]c2ccccc12)c1nnc(CCc2ccccc2)n1Cc1ccccc1]

compound 174 N—((R)-2-(1H-indol-3-yl)-1-(4-methyl-5-phenethyl-4H-1,2,4-triazol-3-yl)ethyl)picolinamide,

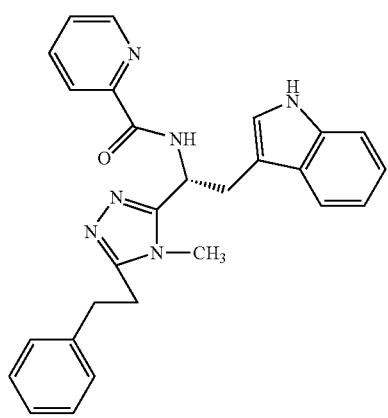 [SMILES: Cn1c(CCc2ccccc2)nnc1[C@@H](Cc1c[nH]c2ccccc12)NC(=O)c1ccccn1]

compound 175 N—((R)-1-(5-(2-(1H-indol-3-yl)ethyl)-4-phenyl-4H-1,2,4-triazol-3-yl)-2-(1H-indol-3-yl)ethyl)-2-amino-2-methylpropanamide,

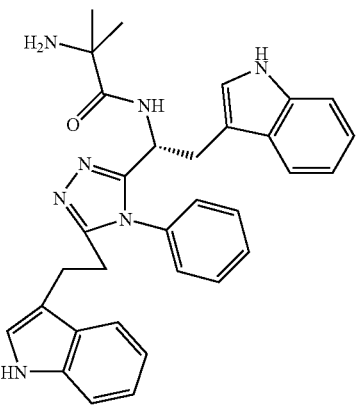 [SMILES: CC(C)(N)C(=O)N[C@H](Cc1c[nH]c2ccccc12)c1nnc(CCc2c[nH]c3ccccc23)n1-c1ccccc1]

compound 176 N—((R)-1-(4-(4-methoxybenzyl)-5-phenethyl-4H-1,2,4-triazol-3-yl)-2-(1H-indol-3-yl)ethyl)benzamide,

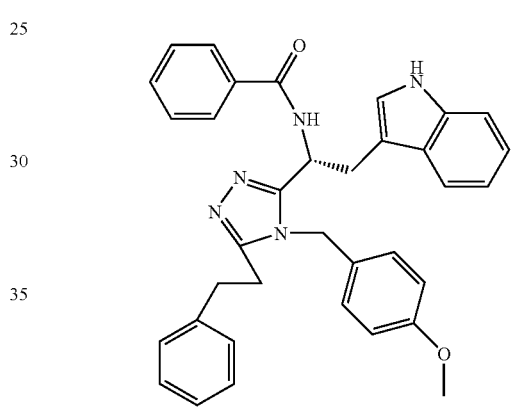

compound 177 (R)-1-(4-(2,4-dimethoxybenzyl)-5-phenethyl-4H-1,2,4-triazol-3-yl)-2-(1H-indol-3-yl)-N-phenyl-methanesulfonylamine,

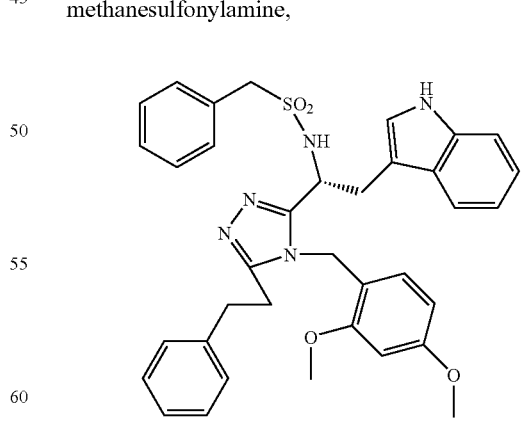

compound 178 (R)-1-(4-(2,4-dimethoxybenzyl)-5-phenethyl-4H-1,2,4-triazol-3-yl)-2-(1H-indol-3-yl)-N-tosyle-thanamine,

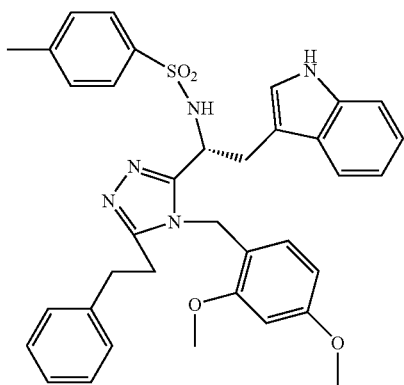 [SMILES: COc1ccc(Cn2c(CCc3ccccc3)nnc2[C@@H](Cc2c[nH]c3ccccc23)NS(=O)(=O)c2ccc(C)cc2)c(OC)c1]

compound 179 N—((R)-1-(4-(2,4-dimethoxybenzyl)-5-phenethyl-4H-1,2,4-triazol-3-yl)-2-(1H-indol-3-yl)ethyl)-2-amino-2-methylpropanamide,

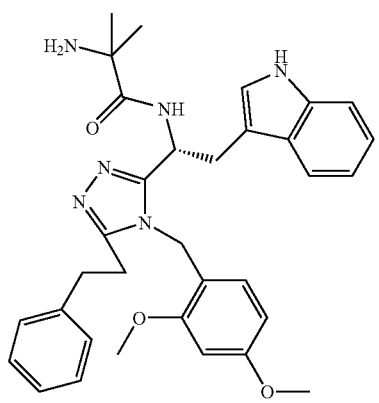 [SMILES: COc1ccc(Cn2c(CCc3ccccc3)nnc2[C@@H](Cc2c[nH]c3ccccc23)NC(=O)C(C)(C)N)c(OC)c1]

compound 180 N-1-((R)-1-(4-(2,4-dimethoxybenzyl)-5-phenethyl-4H-1,2,4-triazol-3-yl)-2-(1H-indol-3-yl)ethyl)ethane-1,2-diamine,

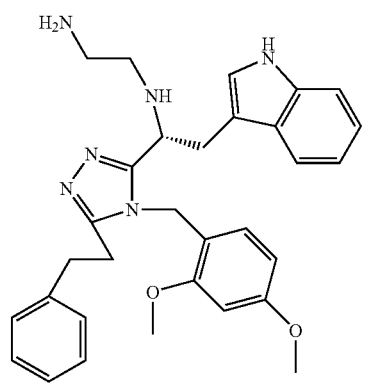 [SMILES: COc1ccc(Cn2c(CCc3ccccc3)nnc2[C@@H](Cc2c[nH]c3ccccc23)NCCN)c(OC)c1]

compound 181 N—((R)-1-(4-((furan-2-yl)methyl)-5-phenethyl-4H-1,2,4-triazol-3-yl)-2-(1H-indol-3-yl)ethyl)-2-amino-2-methylpropanamide,

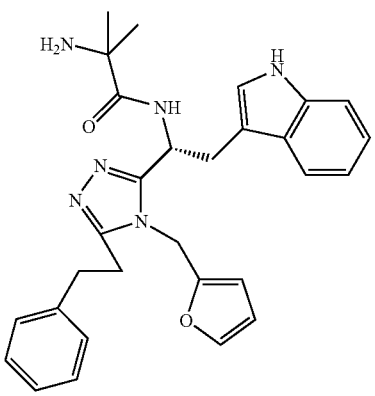 [SMILES: CC(C)(N)C(=O)N[C@H](Cc1c[nH]c2ccccc12)c1nnc(CCc2ccccc2)n1Cc1ccco1]

compound 182 N—((R)-1-(4-((furan-2-yl)methyl)-5-phenethyl-4H-1,2,4-triazol-3-yl)-2-(1H-indol-3-yl)ethyl)picolinamide,

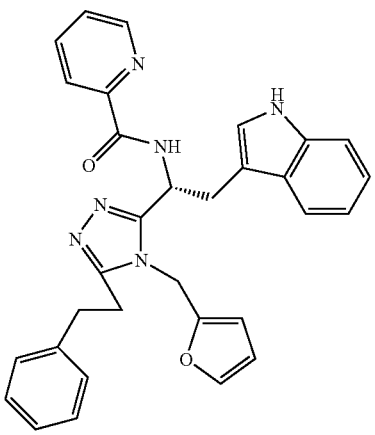 [SMILES: O=C(N[C@H](Cc1c[nH]c2ccccc12)c1nnc(CCc2ccccc2)n1Cc1ccco1)c1ccccn1]

compound 183 N—((R)-1-(4-((furan-2-yl)methyl)-5-phenethyl-4H-1,2,4-triazol-3-yl)-2-(1H-indol-3-yl)ethyl)piperidine-4-carboxamide,

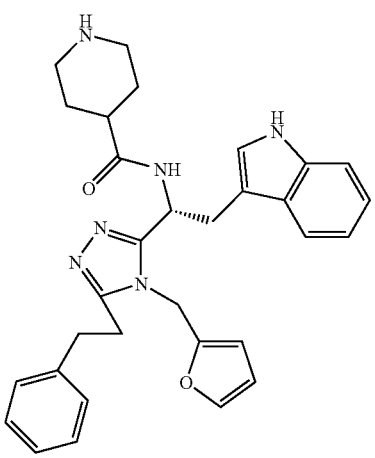 [SMILES: O=C(N[C@H](Cc1c[nH]c2ccccc12)c1nnc(CCc2ccccc2)n1Cc1ccco1)C1CCNCC1]

compound 184 N—((R)-1-(4-(4-methoxybenzyl)-5-phenethyl-4H-1,2,4-triazol-3-yl)-2-(1H-indol-3-yl)ethyl)tetrahydro-2H-pyran-4-carboxamide,

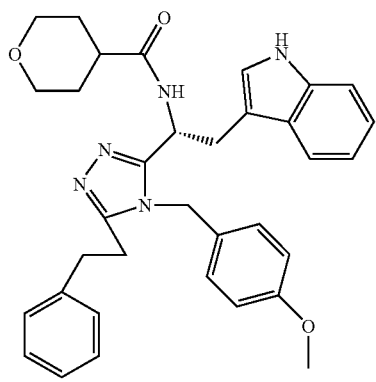 [SMILES: COc1ccc(Cn2c(CCc3ccccc3)nnc2[C@@H](Cc2c[nH]c3ccccc23)NC(=O)C2CCOCC2)cc1]

compound 185 N—((R)-1-(5-((1H-indol-3-yl)methyl)-4-(3-methoxybenzyl)-4H-1,2,4-triazol-3-yl)-2-(1H-indol-3-yl)ethyl)-2-amino-2-methylpropanamide,

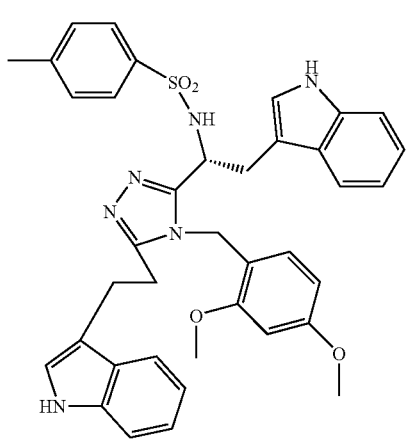

compound 188 N—((R)-1-(4-(2,4-dimethoxybenzyl)-5-phenethyl-4H-1,2,4-triazol-3-yl)-2-(1H-indol-3-yl)ethyl)-4-azidobenzamide,

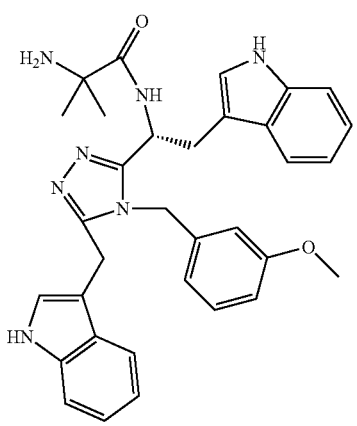 [SMILES: COc1cccc(Cn2c(Cc3c[nH]c4ccccc34)nnc2[C@@H](Cc2c[nH]c3ccccc23)NC(=O)C(C)(C)N)c1]

compound 186 (2S)—N—((R)-1-(4-(4-methoxybenzyl)-5-phenethyl-4H-1,2,4-triazol-3-yl)-2-(1H-indol-3-yl)ethyl)-2-amino-3-phenylpropanamide,

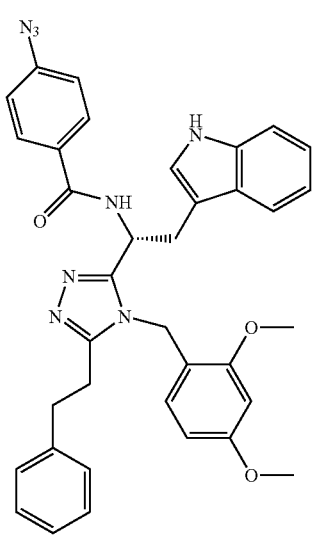

compound 189 N-benzyl-(R)-1-(4-(2,4-dimethoxybenzyl)-5-phenethyl-4H-1,2,4-triazol-3-yl)-2-(1H-indol-3-yl)ethanamine,

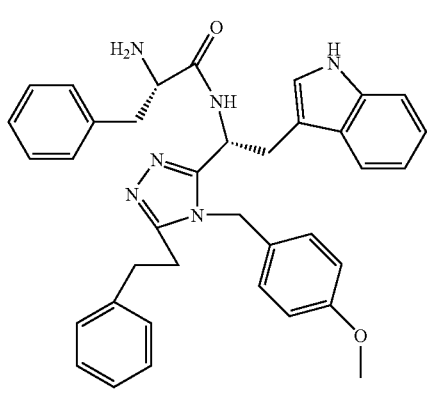 [SMILES: COc1ccc(Cn2c(CCc3ccccc3)nnc2[C@@H](Cc2c[nH]c3ccccc23)NC(=O)[C@@H](N)Cc2ccccc2)cc1]

compound 187 (R)-1-(5-(2-(1H-indol-3-yl)ethyl)-4-(2,4-dimethoxybenzyl)-4H-1,2,4-triazol-3-yl)-2-(1H-indol-3-yl)-N-tosylethanamine,

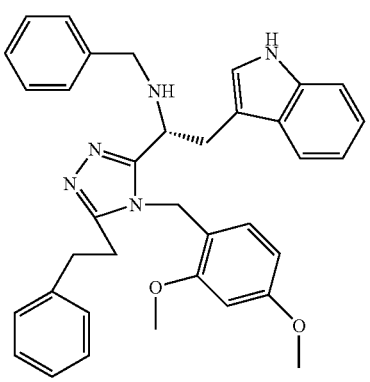 [SMILES: COc1ccc(Cn2c(CCc3ccccc3)nnc2[C@@H](Cc2c[nH]c3ccccc23)NCc2ccccc2)c(OC)c1]

compound 190 (2S)—N—((R)-1-(5-(2-(1H-indol-3-yl) ethyl)-4-(4-methoxybenzyl)-4H-1,2,4-triazol-3-yl)-2-(1H-indol-3-yl)ethyl)-2,5-dihydro-1H-pyrrole-2-carboxamide,

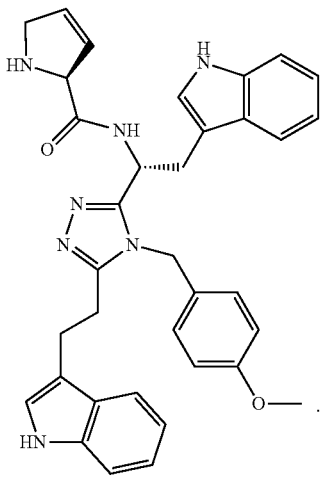 [SMILES: COc1ccc(Cn2c(CCc3c[nH]c4ccccc34)nnc2[C@@H](Cc2c[nH]c3ccccc23)NC(=O)[C@@H]2C=CCN2)cc1]

For the avoidance of doubt, if chemical name and chemical structure of the above illustrated compounds do not correspond by mistake, the chemical structure is regarded to unambigously define the compound.

In a preferred embodiment these compounds can be used for the manufacture of a medicament for the treatment or prophylaxis of physiological and/or pathophysiological conditions in mammals that are mediated by GHS receptors.

In a further preferred embodiment all triazole compounds as illustrated herein, i.e. generically (by above formula (I) and different R radicals) and explicitly, in the following referred to as the compounds of the (present) invention, can be used for the manufacture of a medicament for the treatment or prophylaxis of physiological and/or pathophysiological conditions in mammals that are mediated by GHS receptors and where the treatment is achieved by modulation of GHS receptors.

In yet another preferred embodiment all compounds of the invention are antagonists of GHS receptors.

More preferably, antagonists of GHS receptors are compounds selected from the group consisting of:
compound 1, 3, 12, 13, 14, 18, 20, 22, 23, 33, 36, 37, 38, 41, 46, 47, 48, 49, 50, 51, 52, 53, 57, 58, 59, 60, 61, 63, 64, 65, 66, 68, 69, 70, 71, 72, 73, 74, 75, 76, 77, 79, 80, 82, 85, 86, 87, 88, 89, 90, 91, 93, 101, 102, 109, 114, 116, 119, 134, 135, 136, 137, 138, 139, 140, 145, 146, 147, 148, 150, 152, 153, 154, 156, 157, 159, 160, 161, 164, 171, 174, 176, 178, 179, 182, 184, 186, 188 and/or compound 190.

In yet a further preferred embodiment all compounds of the invention are agonists of GHS receptors.

More preferably, agonists of GHS receptors are compounds selected from the group consisting of:
compound 2, 4, 5, 6, 7, 8, 9, 10, 11, 15, 16, 17, 19, 21, 24, 25, 26, 27, 28, 29, 30, 31, 32, 34, 39, 40, 42, 43, 44, 45, 54, 55, 56, 62, 67, 78, 81, 83, 84, 87, 92, 94, 99, 103, 104, 105, 106, 107, 108, 110, 111, 115, 117, 118, 121, 122, 124, 130, 131, 142, 155, 158, 163, 173, 175, 180, 181, 183, 185 and/or compound 187.

The terms indicated for explanation of the above compounds of formula (I) always, unless indicated otherwise in the description or in the claims, have the following meanings:

The term substituted means that the corresponding radical or group has one or more substituents. Where a radical has a plurality of substituents, and a selection of various substituents is specified, the substituents are selected independently of one another and need not be identical. The term unsubstituted means that the corresponding group has no substituent. The term optionally substituted means that the corresponding group is either unsubstituted or substituted by one or more substituents. The term substituted by up to 3 substituents means that the corresponding radical or group is substituted either by one or by two or three substituents.

The term alkyl includes for the purposes of this invention acyclic saturated hydrocarbons having C1-C12 carbon atoms, which may be straight-chain or branched. The term alkyl preferably stands for alkyl chains of 1 to 8, particularly preferably 1 to 6, carbon atoms. Examples of suitable alkyl radicals are methyl, ethyl, n-propyl, isopropyl, n-butyl, isobutyl. sec-butyl, tert-butyl, n-pentyl, tert-pentyl, 2- or 3-methylpentyl, n-hexyl, isohexyl, n-heptyl, n-octyl, n-nonyl, n-decyl, n-undecyl, n-dodecyl.

The term cycloalkyl stands for a saturated or partially unsaturated non-aromatic cyclic hydrocarbon group/radical, containing 1 to 3 rings, including monocyclic alkyl, bicyclic alkyl and tricyclic alkyl, and containing a total of 3 to 20 carbon atoms forming the rings, preferably 3 to 10, most preferably (C3-C8)-cycloalkyl. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl, cyclooctadienyl.

The term cycloalkylalkyl refers to a radical in which the cycloalkyl group is linked via an alkyl group, where the alkyl and cycloalkyl groups have the meanings defined herein, preferably a (C3-C8)-cycloalkyl-(C1-C4)-alkyl radical. Examples thereof are cyclopropylmethyl, cyclohexylmethyl, cyclopentylethyl, cyclohexenylethyl.

The term alkenyl includes for the purposes of this invention acyclic unsaturated or partially unsaturated hydrocarbons having C2-C12 carbon atoms, which may be straight-chain or branched and contain one or more double bonds. The term alkenyl preferably stands for alkenyl chains of 2 to 8, particularly preferably 2 to 6, carbon atoms. Examples are vinyl, propenyl, butenyl, pentenyl, hexenyl, and octadienyl and the like.

The term alkynyl refers to acyclic unsaturated or partially unsaturated hydrocarbons having C2-C12 carbon atoms, which may be straight-chain or branched and contain one or more triple bonds. The term alkynyl preferably stands for alkynyl chains of 2 to 8, particularly preferably 2 to 6, carbon atoms. Examples are propynyl, butynyl, pentynyl, hexynyl.

The term aryl refers to aromatic hydrocarbon systems having 3 to 14, preferably 5 to 14, carbon atoms, which may also be fused to further saturated, (partially) unsaturated or aromatic cyclic systems. Examples of aryl are inter alia phenyl, biphenyl, naphthyl and anthracenyl, but also indanyl, indenyl, or 1,2,3,4-tetrahydronaphthyl.

The term heteroaryl refers to a 5-, 6- or 7-membered cyclic aromatic radical which comprises at least 1, where appropriate also 2, 3, 4 or 5 heteroatoms, preferably nitrogen, oxygen and/or sulfur, where the heteroatoms are identical or different. The number of nitrogen atoms is preferably between 0 and 3, and that of the oxygen and sulfur atoms is between 0 and 1. The term heteroaryl also includes systems in which the aromatic cycle is part of a bi- or polycyclic system, such as were the aromatic cycle is fused to an aryl, cycloalkyl, heteroaryl or heterocyclyl group as defined herein via any desired and possible ring member of the heteroaryl radical. Examples of heteroaryl include pyrrolyl, thienyl, furyl, imidazolyl, thiazolyl, isothiazolyl, oxazolyl, isoxazolyl, pyrazolyl, pyridinyl, pyrimidinyl, pyrazinyl, indolyl, quinolinyl, and isoquinolinyl.

The terms arylalkyl and heteroarylalkyl refer to radicals in which the aryl or heteroaryl radical is linked via an alkyl group, where the alkyl, aryl and heteroaryl groups have the meanings defined herein. Preferred arylalkyl groups are phenyl-($C_1$-$C_4$)-alkyl radicals, preferably benzyl or phenylethyl radicals. Preferred heteroarylalkyl groups are indolyl-($C_1$-$C_4$)-alkyl radicals, preferably 1H-indole-3-yl-methyl or 2(1H-indole-3-yl)-ethyl.

The term heterocyclyl refers to a mono- or polycyclic system of 3 to 14, preferably 5 or 6 to 14 ring atoms which may be exclusively carbon atoms. However, the cyclic system may also comprise 1, 2, 3, 4, or 5 heteroatoms, in particular nitrogen, oxygen and/or sulfur. The cyclic system may be saturated, mono- or polyunsaturated but may not be aromatic. In the case of a cyclic system consisting of at least two rings the rings may be fused or spiro- or otherwise connected. The heterocyclyl radical may be attached at any carbon or heteroatom which results in the creation of a stable structure. Examples include pyrrolidinyl, thiapyrrolidinyl, piperidinyl, piperazinyl, oxapiperazinyl, oxapiperidinyl and oxadiazolyl.

The term heterocyclylalkyl refers to radicals in which the heterocyclyl group is linked via an alkyl group, where the alkyl and heterocyclyl groups have the meanings defined herein.

The terms alkylsulfonyl, arylsulfonyl and arylalkylsulfonyl refer to radicals in which the alkyl, aryl or arylalkyl group is linked via a —$SO_2$— group, where the alkyl, aryl and arylalkyl groups have the meanings defined herein. Examples are methylsulfonyl and phenylsulfonyl.

The term halogen, halogen atom or halogen substituent (Hal-) refers to one, where appropriate, a plurality of fluorine (F, fluoro), bromine (Br, bromo), chlorine (Cl, chloro), or iodine (I, iodo) atoms. The designations dihalogen, trihalogen and perhalogen refer respectively to two, three and four substituents, where each substituent can be selected independently from the group consisting of fluorine, chlorine, bromine and iodine. Halogen preferably means a fluorine, chlorine or bromine atom.

The term natural alpha-amino acid side chain for the purpose of the present invention refers to all side chains of the known 20 proteinogenic alpha-amino acids as well as to side chains of naturally occurring (i.e. in any biological systems) alpha-amino acids, such as for instance selenocystein, pyrrolysine, citrulline, ornithine, homocysteine, N-methylariginine, N-acetyllysine, gamma-carboxyglutamate, 5-hydroxylysine, 3-methylhistidine and/or N,N,N-trimethyllysine. In this connection side chain refers to the residue that is attached to the alpha-carbon atom, e.g. methyl in case of an Ala side chain or benzyl in case of a Phe side chain.

The term unnatural alpha amino acid side chain for the purpose of the present invention refers to all side chains of known alpha-amino acids that are not proteinogenic nor are known to occur naturally (i.e. in any biological systems). Examples are norleucine, cyclohexylglycine, 2-naphthylalanine, substituted alpha-amino acids (e.g. halogen substituted Tyr or Phe) as well as protected alpha-amino acid side chains, where a protection group such as Fmoc, Boc, Z, CBZ, Aloc, trityl, acetyl and/or benzyl is directly attached/reacted to a functionalization (e.g. amino, hydroxy and/or carboxy residue). In this connection side chain is referred to as for natural alpha amino acid side chains.

Above embodiments of radicals R1 to R10 that possess functionalization (e.g. amino, hydroxy and/or carboxy residues), such as alkyl-CO—$NH_2$, -alkyl-CO—OH, -alkyl-$NH_2$, -alkyl-NH—C(NH)—$NH_2$, —CO—C*(R9R10)-$NH_2$, —CO—$CH_2$—C*(R9R10)-$NH_2$, —CO—C*(R9R10)-$CH_2$—$NH_2$ and/or 2-amino-2-carbonyl-propane (2-amino-isobutyric acid/Aib residue), may be protected with protection groups as mentioned above. Such protection group carrying embodiments are regarded as belonging to/within the scope and spirit of the invention.

All stereoisomers of the compounds of the invention are contemplated, either in a mixture or in pure or substantially pure form. The compounds of the present invention can have asymmetric centers at any of the carbon atoms including any one of the R radicals. Consequently, compounds of the invention can exist in the form of their racemates, in the form of the pure enantiomers and/or diastereomers or in the form of mixtures of these enantiomers and/or diastereomers. The mixtures may have any desired mixing ratio of the stereoisomers. All these different stereochemical forms and mixtures are within the scope of the present invention.

Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or nonchiral phases or by recrystallization from an optionally optically active solvent or with use of an optically active acid or base or by derivatization with an optically active reagent such as, for example, an optically active alcohol, and subsequent elimination of the radical.

Where possible, the compounds of the invention may be in the form of the tautomers.

It is likewise possible for the compounds of the invention to be in the form of any desired prodrugs such as, for example, esters, carbonates or phosphates, in which cases the actually biologically active form is released only through metabolism. Any compound that can be converted in vivo to provide the bioactive agent (i.e. a compound of the invention) is a prodrug within the scope and spirit of the invention.

Various forms of prodrugs are well known in the art and are described for instance in:
(i) The Practice of Medicinal Chemistry (Wermuth C G et al., Chapter 31, Academic Press 1996);
(ii) Design of Prodrugs (editor: Bundgaard H, Elsevier 1985); and
(iii) A Textbook of Drug Design and Development (Krogsgaard-Larson P and Bundgaard H, eds., Chapter 5: 113-191, Harwood Academic Publishers 1991).
Said references are incorporated herein by reference.

It is further known that chemical substances are converted in the body into metabolites which may where appropriate likewise elicit the desired biological effect—in some circumstances even in more pronounced form.

Any biologically active compound that was converted in vivo by metabolism from any compound of the invention is a metabolite within the scope and spirit of the invention.

The compounds of the invention can, if they have a sufficiently basic group such as, for example, a primary, secondary or tertiary amine, be converted with inorganic and organic acids into salts. The pharmaceutically acceptable salts of the compounds of the invention are preferably formed with hydrochloric acid, hydrobromic acid, iodic acid, sulfuric acid, phosphoric acid, methanesulfonic acid, p-toluenesulfonic acid, carbonic acid, formic acid, acetic acid, sulfoacetic acid, trifluoroacetic acid, oxalic acid, malonic acid, maleic acid, succinic acid, tartaric acid, racemic acid, malic acid, embonic acid, mandelic acid, fumaric acid, lactic acid, citric acid, taurocholic acid, glutaric acid, stearic acid, glutamic acid or aspartic acid. The salts which are formed are, inter alia, hydrochlorides, chlorided, hydrobromides, bromides, iodides, sulfates, phosphates, methanesulfonates, tosylates, carbonates, bicarbonates, formates, acetates, sulfoacetates, triflates, oxalates, malonates, maleates, succinates, tartrates, malates, embonates, mandelates, fumarates, lactates, citrates, glutarate, stearate, aspartates and glutamates. The stoichiometry of the salts formed from the compounds of the invention may moreover be an integral or non-integral multiple of one.

The compounds of the invention can, if they contain a sufficiently acidic group such as, for example, the carboxy, sulfonic acid, phosphoric acid or a phenolic group, be converted with inorganic and organic bases into their physiologically tolerated salts. Examples of suitable inorganic bases are ammonium, sodium hydroxide, potassium hydroxide, calcium hydroxide, and of organic bases are ethanolamine, diethanolamine, triethanolamine, ethylenediamine, t-butylamine, t-octylamine, dehydroabietylamine, cyclohexylamine, dibenzylethylene-diamine and lysine. The stoichiometry of the salts formed from the compounds of the invention can moreover be an integral or non-integral multiple of one.

It is likewise possible for the compounds of the invention to be in the form of their solvates and, in particular, hydrates which can be obtained for example by crystallization from a solvent or from aqueous solution. It is moreover possible for one, two, three or any number of solvate or water molecules to combine with the compounds of the invention to give solvates and hydrates.

It is known that chemical substances form solids which exist in different order states which are referred to as polymorphic forms or modifications. The various modifications of a polymorphic substance may differ greatly in their physical properties. The compounds of the invention can exist in various polymorphic forms, and certain modifications may moreover be metastable. All these polymorphic forms of the compounds of the invention are to be regarded as belonging to the invention.

The triazole derivatives (compounds of the invention) as illustrated herein are ghrelin analogue ligands of GHS receptors. Thus, the aforementioned compounds of the invention are suitable for the treatment or prophylaxis of physiological and/or pathophysiological conditions mediated by GHS receptors and/or physiological and/or pathophysiological conditions which can be influenced by modulation of these receptors, and thus prevented, treated and/or alleviated.

For the purpose of the present invention, the term treatment is also intended to include prophylactic treatment or alleviation.

The term ghrelin analogue ligand or ligand is intended to refer for the purposes of the present invention to every compound which binds in any way to a receptor (the receptors in the present invention being GHS receptors) and induces either activation, inhibition and/or another conceivable effect at this receptor. The term ghrelin analogue ligand or ligand thus includes agonists, antagonists, partial agonists/antagonists, inverse agonists and other ligands which cause an effect at the receptor which is similar to the effect of agonists, antagonists, partial agonists/antagonists or inverse agonist.

For the purpose of the present invention, the term GHS receptor antagonist or antagonist of GHS receptors refers to compounds of the invention that bind to GHS receptors but do not elicit a proper activation of the receptors as assessed by recording an increase of intracellular calcium which is characteristic for activation of G-protein coupled receptors (GPCRs).

The ability to properly activate the receptors is assessed for any compound of the invention by comparing the degree of activation (increase of intracellular calcium) of GHS-R 1a by the compound to be tested (at $10^{-6}$ M concentration) to the degree of activation (increase of intracellular calcium) of GHS-R 1a by $10^{-6}$ M ghrelin (100%) and to the basal level (0%). Such assessment can be readily performed by the skilled artisan due to his expert knowledge. The output is a percentage value for each compound to be tested.

Any compound of the invention that does not show a degree of activation (increase of intracellular calcium) of GHS-R 1a of at least 20% as assessed in accordance with above specification is regarded as not eliciting a proper activation and therefore as GHS receptor antagonist. Preferably such compounds do show an antagonizing effect (counteraction/decrease) on ghrelin and/or other GHS stimulated intracellular calcium increase, prevent such stimulation or even act as inverse agonists (an inverse agonists is an ligand which binds to the same receptor binding-site as an agonist or antagonist but causes an inhibition of the basal/constitutive activity of the receptor, in principle an agonists with a negative intrinsic activity). Such compounds may furthermore exhibit an inhibitory activity on GH secretion and/or on other physiological or pathophysiological conditions or effects, such as food intake or lipogenesis. Their effects may be dissociated. Thus, they may have no impact at all on GH secretion while inhibiting other physiological effects. They may even stimulate other physiological effects.

For the purpose of the present invention, the term GHS receptor agonist or agonist of GHS receptors refers to compounds of the invention that bind to GHS receptors and elicit a proper activation of the receptor as assessed by recording an increase of intracellular calcium which is characteristic for activation of G-protein coupled receptors.

Any compound of the invention that shows a degree of activation (increase of intracellular calcium) of GHS-R 1a of at least 20% as assessed in accordance with above specification is regarded as eliciting a proper activation and therefore as GHS receptor agonist.

Such compounds may mimic the effects of ghrelin and/or GHS on GH secretion and for instance food intake or lipogenesis. Like for antagonists, the effects of agonist compounds may be dissociated from the GH secretory effect. Such compounds may even antagonize (counteract/decrease) ghrelin and/or other GHS stimulated intracellular calcium increase.

The term GHS receptor or GHS-R is intended to comprise for the purposes of the present invention receptors that bind at least one known peptidyl and/or non-peptidyl GHS and/or ghrelin. The term GHS receptor or GHS-R is also intended to comprise different GHS binding sites in the various tissues and/or organs as illustrated herein, that bind at least one known peptidyl and/or non-peptidyl GHS and/or ghrelin and which are probably not yet characterized GHS-R subtypes.

Binding of a given known peptidyl and/or non-peptidyl GHS and/or ghrelin can be easily verified by the skilled artisan on the basis of his expert knowledge, e.g. by appropriate binding assays which represent only routine experimentation.

Such GHS receptors may be stimulated/activated by ghrelin (ghrelin responsive) or may not be stimulated/activated by ghrelin (ghrelin non-responsive)—with regard to both acylated and non-acylated ghrelin, respectively. Stimulation/activation of such receptors may cause but does not compulsorily have to elicit GH production and/or GH secretion and/or increase GH plasma levels.

Preferably such GHS receptors are selected from the group consisting of GHS type 1 receptor, GHS-R 1a, GHS-R1b, motilin receptor, motilin receptor 1a, neurotensin receptor, TRH receptor, GPR38 (FM1), GPR39 (FM2), FM3, GHS binding site, GHS-R subtype, cardiac GHS-R, mammary GHS-R.

More preferably, such GHS receptors are selected from the group consisting of GHS type 1 receptor, GHS-R 1a, GHS-R 1b and most preferably are GHS-R 1a.

As discussed herein, GHS receptors (including GHS binding sites and GHS-R subtypes) are known to be concentrated in the hypothalamus-pituitary area but also appear to be distributed in other central and peripheral tissues. Furthermore, they are also expressed in various tumoral tissues, even in tumoral tissues from organs that do not express these receptors under physiological conditions.

For the purposes of the present invention, all these GHS receptor (including GHS binding sites and GHS-R subtypes) expressing organs and/or tissues are intended to be comprised by the scope of the present invention. Expression of GHS receptors (including GHS binding sites and GHS-R subtypes) in a given organ and/or tissue can be easily verified by the skilled artisan on the basis of his expert knowledge, e.g. by appropriate molecular biologic assays, such as immunofluorescence or immunoprecipitation assays, which represent only routine experimentation.

Preferably, such GHS receptors are located in tissues and/or organs selected from the group consisting of endocrine tissue, exocrine tissue, peripheral tissue, adipose/fat tissue, brain, hypothalamus, thalamus, hippocampus, striatum, cortex, pituitary, central nervous system, spinal cord, gland, adrenal gland, thyroid gland, salivary gland, mammary gland, neuron, bowel, intestine, stomach, heart, liver, pancreas, kidney, bile, gall, bladder, prostate, spleen, muscle, skeletal muscle, aorta, artery, vein, immune cell, leukocyte, lymphocyte, T cell, B cell, granulocyte, monocyte, macrophage, dendritic cell, mast cell, NK cell, neutrophil, eosinophil, basophil, lymph node, bone, bone marrow, tonsil, thymus, placenta, testes, ovary, uterus, lung, adipocyte, tumor/cancer cell, carcinoma cell, prostate cancer cell, thyroid cancer cell, lung cancer cell, breast cancer cell.

As illustrated supra, the compounds of the invention are ghrelin analogue ligands of GHS receptors. They can be administered to various mammalian species, including human, for the treatment or prophylaxis of physiological and/or pathophysiological condition in such mammals.

For the purpose of the present invention, all mammalian species are regarded as being comprised. Preferably, such mammals are selected from the group consisting of human, domestic animals, cattle, livestock, pets, cow, sheep, pig, goat, horse, pony, donkey, hinny, mule, hare, rabbit, cat, dog, guinea pig, hamster, rat, mouse. More preferably, such mammals are human.

The compounds of the invention being non-peptidic ghrelin analogue ligands of GHS receptors are surprisingly characterized by a strong binding affinity to such receptors. Such compounds for instance may preferably exhibit an $IC_{50}$ value of less than 1000 nM for binding to GHS-R 1a. More preferably, such compounds may exhibit an $IC_{50}$ value of less than 500 nM, even more preferably of less than 300 nM and most preferably of less than 100 nM for binding to GHS-R 1a.

Due to their surprisingly strong receptor binding, the compounds of the invention can be advantageously administered at lower doses compared to other less potent binders while still achieving equivalent or even superior desired biological effects. In addition, such a dose reduction may advantageously lead to less or even no medicinal adverse effects.

Further, the high binding specificity of the compounds of the invention may translate into a decrease of undesired side effects on its own regardless of the dose applied.

Furthermore, the compounds of the invention, being of non-peptidic nature, are resistant to degradation by enzymes of the gastro-intestinal tract. Hence, they offer the advantage to be given by oral route. They surprisingly display an improved metabolic stability and/or an improved bioavailability. Hence, again an advantageous dose reduction may be achievable which may cause less or even no side effects.

The compounds of the invention can either be antagonists or agonists of GHS receptors as illustrated and defined herein.

GHS receptor antagonists of the present invention can for instance be employed for the inhibition of GHS receptors stimulated by ghrelin and/or other GHS thus decreasing and/or blocking GH production and/or secretion and/or GH plasma levels. In addition, such GHS receptor antagonists may also be employed for the inhibition or prevention of physiological or pathophysiological effects of ghrelin which are not related to GH production and/or GH secretion.

Therefore, GHS receptor antagonists of the present invention are suitable for the treatment and/or prophylaxis of various physiological and pathophysiological conditions as disclosed herein, in particular for the short-, medium- and/or long term regulation of energy balance, the short-, medium- and/or long term regulation (stimulation and/or inhibition) of food intake, the treatment of adipogenesis, adiposity and/or obesity, body weight gain and/or reduction and the treatment of tumor cell proliferation.

In contrast, GHS receptor agonists of the present invention can for instance be employed for the activation of GHS receptors and stimulation/increase of GH production and/or GH secretion and would thus have similar effects or uses as growth hormone itself, ghrelin and/or known GHS.

Thus, GHS receptor agonists of the present invention are suitable for the treatment and/or prophylaxis of various physiological and pathophysiological conditions as disclosed herein, in particular for growth retardation, cachexia, inflammation, inflammatory effects, gastric postoperative ileus, postoperative ileus and/or gastrectomy (ghrelin replacement therapy).

For the purpose of the present invention, all physiological and/or pathophysiological conditions are intended to be comprised that are known to be mediated by GHS receptors.

Preferably, these physiological and/or pathophysiological conditions are selected from the group consisting of acute fatigue syndrome and muscle loss following election surgery, adipogenesis, adiposity, age-related decline of thymic function, age-related functional decline (ARFD) in the elderly, aging disorder in companion animals, Alzheimer's disease, anorexia (e.g. associated with cachexia or aging); anxiety, blood pressure (lowering), body weight gain/reduction, bone fracture repair (acceleration), bone remodeling stimulation, cachexia and protein loss reduction due to chronic illness such as cancer or AIDS, cardiac dysfunctions (e.g. associated with valvular disease, myocardial infarction, cardiac hypertrophy or congestive heart failure), cardiomyopathy, cartilage growth stimulation, catabolic disorders in connection with pulmonary dysfunction and ventilator dependency, catabolic side effects of glucocorticoids, catabolic state of aging, central nervous system disorders (in combination with antidepressants), chronic dialysis, chronic fatigue syndrome (CFS), cognitive function improvement (e.g. in dementia, Alzheimer's disease), complicated fractures (e.g. disctraction osteogenesis), complications associated with transplantation, congestive heart failure (alone/in combination with corticotropin releasing factor antagonists), Crohn's disease and ulcerative colits, Cushing's syndrome, dementia, depressions, short-, medium- and/or long-term regulation of energy balance, short-, medium- and/or long-term regulation of food intake (stimulation and/or inhibition), fraility (e.g. in elderly humans), gastrectomy (ghrelin replacement therapy), gastric postoperative ileus, glycemic control improvement, growth hormone release stimulation in the elderly, growth hormone replacement in stressed patients, growth promotion in livestock, growth retardation associated with the Prader-Willi syndrome and Turner's syndrome, growth retardation in connection with Crohn's disease, growth retardation, hair/nail growth maintenance, hip fractures, hunger, hypercortisolism, hyperinsulinemia including nesidioblastosis, hypothermia, immune deficiency in individuals with a depressed T4/T8 cell ratio, immune response improvement to vaccination, immune system stimulation in companion animals, immune system stimulation, immunosuppression in immunosuppressed patients, inflammation or inflammatory effects, inflammatory bowel disease, insulin resistance in the heart, insulin resistance in type 2 diabetic patients, insulin resistance including NIDDM, diabetes, diabetes type I, diabetes type II, intrauterine growth retardation, irritable bowel syndrome, lipodystrophy (e.g. HIV-induced), metabolic homeostasis maintenance, milk production increase in livestock, muscle mass/strength increase, muscle mobility improvement, muscle strength improvement, muscle strength/function maintenance in elderly humans, muscular atrophy, musculoskeletal impairment (e.g. in elderly), Noonan's syndrome, obesity and growth retardation associated with obesity, osteoblast stimulation, osteochondrodysplasias, osteoporosis, ovulation induction (adjuvant treatment), physiological short stature including growth hormone deficient children, postoperative ileus, protein catabolic response attenuation after major surgery/trauma, protein kinase B activity enhancement, psychosocial deprivation, pulmonary dysfunction and ventilator dependency, pulmonary function improvement, pulsatile growth hormone release induction, recovery of burn patients and reducing hospitalization of burn patients (acceleration), renal failure or insufficiency resulting from growth retardation, renal homeostasis maintenance in the frail elderly, sarcopenia, schizophrenia, sensory function maintenance (e.g. hearing, sight, olefaction and taste), short bowel syndrome, short stature associated with chronic illness, skeletal dysplasia, skin thickness maintenance, sleep disorders, sleep quality improvement, thrombocytopenia, thymic development stimulation, tooth repair or growth, tumor cell proliferation, ventricular dysfunction or reperfusion events, wasting in connection with AIDS, wasting in connection with chronic liver disease, wasting in connection with chronic obstructive pulmonary disease (COPD), wasting in connection with multiple sclerosis or other neurodegenerative disorders, wasting secondary to fractures, wool growth stimulation in sheep, wound healing (acceleration), wound healing delay. More preferably these physiological and/or pathophysiological conditions are selected from the group consisting of growth retardation, cachexia, short-, medium- and/or long term regulation of energy balance; short-, medium- and/or long term regulation (stimulation and/or inhibition) of food intake; adipogenesis, adiposity and/or obesity; body weight gain and/or reduction; diabetes, diabetes type I, diabetes type II, tumor cell proliferation; inflammation, inflammatory effects, gastric postoperative ileus, postoperative ileus and/or gastrectomy (ghrelin replacement therapy).

In a further aspect of the present invention, the compounds of the invention may be used in combination with at least one additional pharmacologically active substance.

Such additional pharmacologically active substance may be other compounds of the present invention and/or other suitable therapeutic agents useful in the treatment and/or prophylaxis of the aforementioned physiological and/or pathophysiological conditions. The additional pharmacologically active substance may be an antagonist of GHS receptors and/or an agonist of GHS receptors depending on the purpose of the combined use. Selection and combination of the additional pharmacologically active substance(s) can be easily performed by the skilled artisan on the basis of his expert knowledge and depending on the purpose of the combined use and physiological and/or pathophysiological conditions targeted.

In a preferred embodiment, the compounds of the invention are used for the treatment and/or prophylaxis of the aforementioned physiological and/or pathophysiological conditions in the form of a medicament, where such medicament comprises at least one additional pharmacologically active substance.

In another preferred embodiment, the compounds of the invention are used for the treatment and/or prophylaxis of the aforementioned physiological and/or pathophysiological conditions in the form of a medicament, where the medicament is applied before and/or during and/or after treatment with at least one additional pharmacologically active substance.

The above mentioned suitable therapeutic agents include: GHS, anti-diabetic agents; anti-osteoporosous agents; anti-obesity agents; anti-inflammatory agents; anti-anxiety agents; anti-depressants; anti-hypertensive agents; anti-platelet agents; antithrombotic and thrombolytic agents; cardiac glycosides; cholesterol/lipid lowering agents; mineralocorticoid receptor antagonists; phosphodiesterase inhibitors; protein tyrosine kinase inhibitors; thyroid mimetics (including thyroid receptor antagonists); anabolic agents; HIV or AIDS therapies; therapies useful in the treatment of Alzheimer's disease and other cognitive disorders; therapies useful in the treatment of sleeping disorders; anti-proliferative agents; anti-tumor agents; anti-ulcer and gastroesopheageal reflux disease agents; progestin receptor agonists (PRA); estrogen; testosterone; a selective estrogen receptor modulator; a selective androgen receptor modulator; parathyroid hormone; and/or bisphosphonate, and preferably, a suitable therapeutic agents is selected of the group consisting of this agents.

Examples of suitable GHS for use in combination with the compounds of the present invention include GHRP-6, GHRP-1 as described in U.S. Pat. No. 4,411,890; and publications WO 89/07110 and WO 89/07111 and B-HT920 or growth hormone releasing factor and its analogs or growth hormone and its analogs or somatomedins including IGF-1 and IGF-2 as well as GHS described in WO 01/96300.

Examples of suitable anti-diabetic agents for use in combination with the compounds of the present invention include biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Pat. No. 6,548,529, glucagon-like peptide-1 (GLP-1), and dipeptidyl peptidase IV (DP4) inhibitors.

Examples of suitable anti-osteoporosous agents for use in combination with the compounds of the present invention include alendronate, risedronate, raloxifene, calcitonin, nonsteroidal progestin receptor agonists, RANK ligand agonists, calcium sensing receptor antagonists, TRAP inhibitors, selective estrogen receptor modulators (SERM), estrogen and AP-1 inhibitors.

Examples of suitable anti-obesity agents for use in combination with the compounds of the present invention include endocannabinoid receptor antagonists, e.g. CB1 receptor antagonists such as rimonabant (1H-Pyrazole-3-carboxamide, 5-(4-chlorophenyl)-1-(2,4-dichlorophenyl)-4-methyl-N-1-piperidinyl-, monohydrochloride; CAS Registry Number: 158681-13-1; SR-141716A; U.S. Pat. No. 5,624,941), aP2 inhibitors such as those disclosed in U.S. Pat. No. 6,548,529, PPAR gamma antagonists, PPAR delta agonists, and orlistat.

Examples of suitable antinflammatory agents for use in combination with the compounds of the present invention include prednisone, dexamethasone, Enbrel, cyclooxygenase inhibitors (i.e., COX-1 and/or COX-2 inhibitors such as NSAIDs, aspirin, indomethacin, ibuprofen, piroxicam, Naproxen, Celebrex, Vioxx), CTLA4-Ig agonists/antagonists, CD40 ligand antagonists, integrin antagonists, alpha4 beta7 integrin antagonists, cell adhesion inhibitors, interferon gamma antagonists, ICAM-1, tumor necrosis factor (TNF) antagonists (e.g., infliximab, OR1384), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., zelmac and Maxi-K openers such as those disclosed in U.S. Pat. No. 6,184,231).

Examples of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradii), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265, Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-platelet agents for use in combination with the compounds of the present invention include GPIIb/IIIa blockers (e.g., abciximab, eptifibatide, tirofiban), P2Y12 antagonists (e.g., clopidogrel, ticlopidine, CS-747), thromboxane receptor antagonists (e.g., ifetroban), aspirin, and PDE-III inhibitors (e.g., dipyridamole) with or without aspirin.

Examples of suitable cardiac glycosides for use in combination with the compounds of the present invention include digitalis and ouabain.

Examples of suitable cholesterol/lipid lowering agents for use in combination with the compounds of the present invention include HMG-CoA reductase inhibitors [e.g., pravastatin lovastatin, atorvastatin, simvastatin, NK-104 (a.k.a. itavastatin, or nisvastatin or nisbastatin] and ZD-4522 (a.k.a. rosuvastatin, or atavastatin or visastatin)), squalene synthetase inhibitors, fibrates, bile acid sequestrants, ACAT inhibitors, MTP inhibitors, lipooxygenase inhibitors, cholesterol absorption inhibitors, and cholesterol ester transfer protein inhibitors (e.g., CP-529414).

Examples of suitable mineralocorticoid receptor antagonists for use in combination with the compounds of the present invention include spironolactone and eplerinone.

Examples of suitable phosphodiesterase inhibitors for use in combination with the compounds of the present invention include PDE III inhibitors such as cilostazol, and PDE V inhibitors such as sildenafil.

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone and SARMs.

Examples of suitable HIV or AIDS therapies for use in combination with the compounds of the present invention include indinavir sulfate, saquinavir, saquinavir mesylate, amprenavir, ritonavir, lopinavir, ritonavir/lopinavir combinations, lamivudine, zidovudine, lamivudine/zidovudine combinations, zalcitabine, didanosine, stavudine, and megestrol acetate.

Examples of suitable therapies for treatment of Alzheimer's disease and cognitive disorders for use in combination with the compounds of the present invention include donepezil, tacrine, revastigmine, 5HT6, gamma secretase inhibitors, beta secretase inhibitors, SK channel blockers, Maxi-K blockers, and KCNQs blockers.

Examples of suitable therapies for treatment of sleeping disorders for use in combination with the compounds of the present invention include melatonin analogs, melatonin receptor antagonists, ML1B agonists, and GABA/NMDA receptor antagonists.

Examples of suitable anti-proliferative agents for use in combination with the compounds of the present invention include cyclosporin A, taxol, FK 506, and adriamycin.

Examples of suitable anti-tumor agents for use in combination with the compounds of the present invention include taxol, adriamycin, epothilones, cisplatin and carboplatin.

Examples of suitable a selective estrogen receptor modulator for use in combination with the compounds of the present invention include tamoxifen and raloxifene.

Examples of suitable a selective androgen receptor modulator for use in combination with the compounds of the present invention include such disclosed in Edwards, J. P. et al., Bio. Med. Chem. Let., 9, 1003-1008 (1999) and Hamann, L. G. et al., J. Med. Chem., 12, 210-212 (1999).

Examples of suitable a bisphosphonate for use in combination with the compounds of the present invention include MK-217 (alendronate).

The above other therapeutic agents, when employed in combination with the compounds of the present invention, may be used, for example, in those amounts indicated in the Physicians' Desk Reference (PDR) or as otherwise determined by one of ordinary skill in the art.

In a preferred embodiment, the compounds of the invention are used for the treatment and/or prophylaxis of the aforementioned physiological and/or pathophysiological conditions in the form of a medicament, where such medicament comprises as additional pharmacologically active substance an endocannabinoid receptor antagonist, preferably a CB1 receptor antagonist, most preferably rimonabant (1H-Pyrazole-3-carboxamide, 5-(4-chlorophenyl)-1-(2,4-dichlorophenyl)-4-methyl-N-1-piperidinyl-, monohydrochloride; CAS Registry Number: 158681-13-1; SR-141716A; U.S. Pat. No. 5,624,941) and as compound of the invention a GHS-R antagonist.

In another preferred embodiment, the compounds of the invention are used for the treatment and/or prophylaxis of the aforementioned physiological and/or pathophysiological conditions in the form of a medicament, where the medicament is applied before and/or during and/or after treatment with at least one additional pharmacologically active substance, where such additional pharmacologically active substance is an endocannabinoid receptor antagonist, preferably a CB1 receptor antagonist, most preferably rimonabant (1H-Pyrazole-3-carboxamide, 5-(4-chlorophenyl)-1-(2,4-dichlorophenyl)-4-methyl-N-1-piperidinyl-, monohydrochloride; CAS Registry Number: 158681-13-1; SR-141716A; U.S. Pat. No. 5,624,941) and the compound of the invention is a GHS-R antagonist.

The compounds of the present invention can be administered in a known manner. The route of administration may thereby be any route which effectively transports the active compound to the appropriate or desired site of action, for example orally or non-orally, in particular topically, transdermally, pulmonary, rectally, intravaginally, nasally or parenteral or by implantation. Oral administration is preferred.

The compounds of the invention are converted into a form which can be administered and are mixed where appropriate with pharmaceutically acceptable carriers or diluents. Suitable excipients and carriers are described for example in Ullman's Encyclopedia of Technical Chemistry, Vol. 4, (1953), 1-39; Journal of Pharmaceutical Sciences, Vol. 52 (1963), 918 et seq.; H. v. Czetsch-Lindenwald, Hilfsstoffe für Pharmazie and angrenzende Gebiete; Pharm. Ind. 2, 1961, 72 et seq.; Dr. H. P. Fiedler, "Lexikon der Hilfsstoffe für Pharmazie, Kosmetik and angrenzende Gebiete, Cantor K G, Aulendorf in Württemberg, 1971.

Oral administration can take place for example in solid form as tablet, capsule, gel capsule, coated tablet, granulation or powder, but also in the form of a drinkable solution. The compounds of the invention can for oral administration be combined with known and ordinarily used, physiologically tolerated excipients and carriers such as, for example, gum arabic, talc, starch, sugars such as, for example, mannitol, methylcellulose, lactose, gelatin, surface-active agents, magnesium stearate, cyclodextrins, aqueous or nonaqueous carriers, diluents, dispersants, emulsifiers, lubricants, preservatives and flavorings (e.g. essential oils). The compounds of the invention can also be dispersed in a microparticulate, e.g. nanoparticulate, composition.

Non-oral administration can take place for example by intravenous, subcutaneous, intramuscular injection of sterile aqueous or oily solutions, suspensions or emulsions, by means of implants or by ointments, creams or suppositories. Administration as sustained release form is also possible where appropriate. Implants may comprise inert materials, e.g. biodegradable polymers or synthetic silicones such as, for example, silicone rubber. Intravaginal administration is possible for example by means of vaginal rings. Intrauterine administration is possible for example by means of diaphragms or other suitable intrauterine devices. Transdermal administration is additionally provided, in particular by means of a formulation suitable for this purpose and/or suitable means such as, for example, patches.

The dosage may vary within a wide range depending on type and/or severity of the physiological and/or pathophysiological condition, the mode of administration, the age, gender, bodyweight and sensitivity of the subject to be treated. It is within the ability of a skilled worker to determine a pharmacologically effective amount of a compound of the invention and/or additional pharmacologically active substance. Administration can take place in a single dose or a plurality of separate dosages.

A suitable unit dose is, for example, from 0.001 mg to 100 mg of the active ingredient, i.e. at least one compound of the invention and, where appropriate, at least one additional pharmacologically active substance, per kg of a patient's bodyweight.

In another aspect, the present invention relates to a pharmaceutical composition comprising a pharmacologically active amount of at least one triazole compound selected from the group consisting of: compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 124, 125, 126, 128, 129, 130, 131, 132, 133, 134, 135, 136, 137, 138, 139, 140, 141, 142, 143, 144, 145, 146, 147, 148, 149, 150, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189 and/or compound 190.

In a further aspect, such a pharmaceutical composition may additionally comprise at least one pharmaceutically acceptable carrier and/or excipient and/or may comprise at least one further pharmacologically active substance.

In a preferred embodiment, such further pharmacologically active substance is an endocannabinoid receptor antagonist, preferably a CB1 receptor antagonist, most preferably rimonabant [1H-Pyrazole-3-carboxamide, 5-(4-chlorophenyl)-1-(2,4-dichlorophenyl)-4-methyl-N-1-piperidinyl-, monohydrochloride].

Concerning the pharmaceutical compositions of the invention, at least one of the triazole compounds as listed above is present in a pharmacologically effective amount, preferably in a unit dose, e.g. the aforementioned unit dose, specifically and preferably in an administration form which makes oral administration possible. Furthermore, reference may be made to that already said in connection with the possible uses and administrations of the compounds of the invention.

General Syntheses Schemes

The compounds of the present invention may be prepared according to the following general synthetic schemes, as well as relevant published literature procedures that are known to the one skilled in the art (e.g. WO 00/54729 and cited references therein).

Exemplary reagents and procedures for these reactions appear hereinafter and in the working examples. Unless otherwise specified, the various substituents (radicals) of the compounds have the meanings as defined for formula (I) herein.

Amide bond formation (peptide coupling) is conducted under standard peptide coupling procedures known in the prior art. Optimally, the reaction is conducted in a solvent such as dichloromethane (DCM) at room temperature using benzotriazol-1-yl-oxytris(dimethylamino)phosphoniumhexafluoorophosphate (BOP) (Castro B et al., Tetrahedron Lett. 1975, 14:1219-1222) and a base, for example N-methylmorpholine or diisopropylethylamine.

Thionation of the formed amide was performed using Lawesson's reagent (Pons J F et al., Tetrahedron Lett. 2000, 41: 4965-4968).

Cyclisation: the obtained thioamide was then submitted to the conditions reported by Hitosuyanagi et al. (Hitotsuyanagi Y. et al., J. Org. Chem. 2002, 67: 3266-3271) which were slightly modified (5 eq. of hydrazide and 1.1 eq. of mercury (II) acetate in acetonitrile). Cyclisation into triazoles was generally achieved within three hours. When the hydrazide was not commercially available, it was prepared by known methods from its acid or methyl ester precursors.

Deprotection of the tert-butyloxycarbonyl group (Boc) was performed at room temperature in acidic medium as usually described.

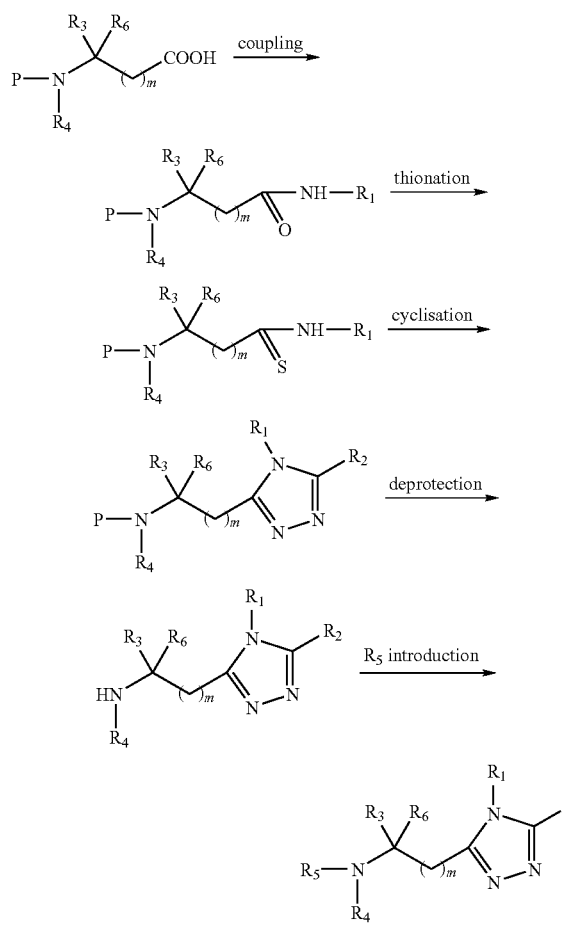

P: protecting group

For R5=—CO-alkyl, —CO-cycloalkyl, —CO-cycloalkylalkyl, —CO-aryl, —CO-arylalkyl, —CO-heteroaryl, —CO-heteroarylalkyl, —CO-heterocyclyl, —CO-heterocyclylalkyl, —CO—C*(R9R10)-NH$_2$, —CO—CH$_2$—C*(R9R10)-NH$_2$, —CO—C*(R9R10)-CH$_2$—NH$_2$ (R):

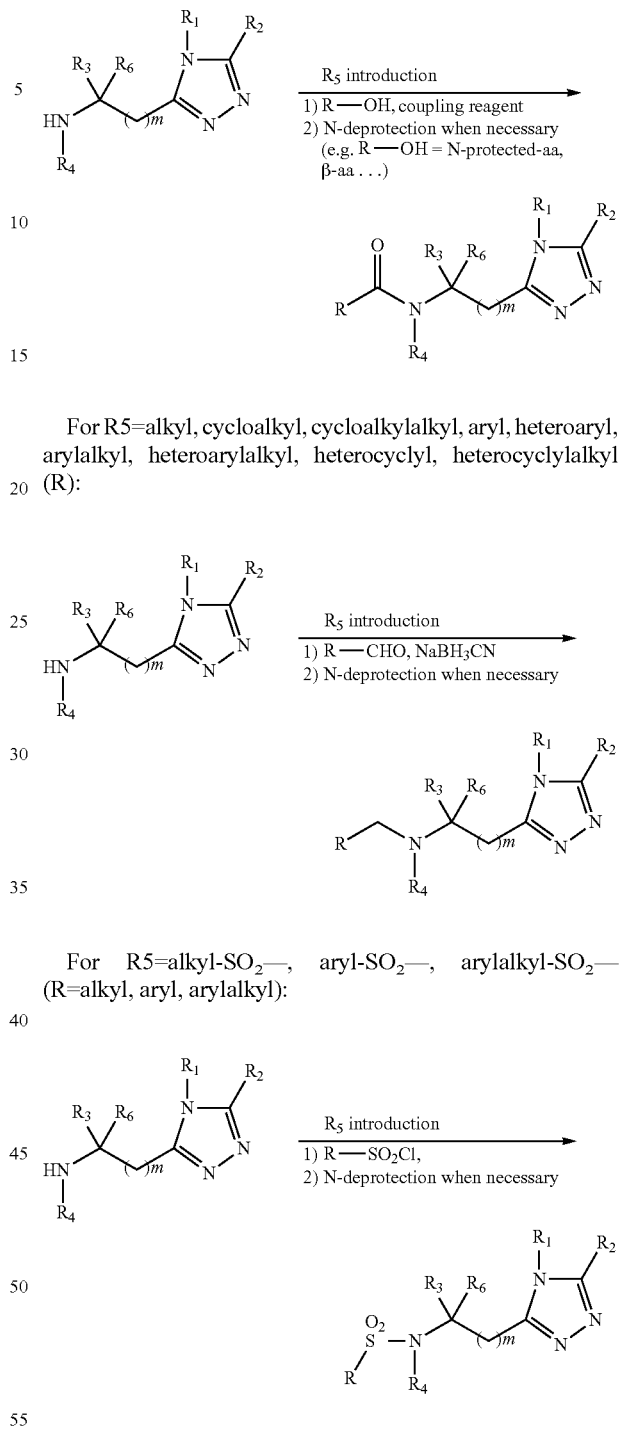

For R5=alkyl, cycloalkyl, cycloalkylalkyl, aryl, heteroaryl, arylalkyl, heteroarylalkyl, heterocyclyl, heterocyclylalkyl (R):

For R5=alkyl-SO$_2$—, aryl-SO$_2$—, arylalkyl-SO$_2$— (R=alkyl, aryl, arylalkyl):

The compounds of the invention, especially compounds 1 to 190 were named from the drawn formula using the Chem Draw Ultra 8 software (CambridgeSoft Corporation, Cambridge, USA).

The contents of all cited references and patents are hereby incorporated by reference. The invention is explained in more detail by means of the following examples without, however, being restricted thereto.

EXAMPLES

I) Synthesis of Compounds of the Invention

Example 1

(R)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-amino-2-methylpropanamide (Compound 1)

Compound 1 was obtained from Boc-(D)-Trp (10 mmoles), (2,4-dimethoxyphenyl)-methanamine, 3-(1H-indol-3-yl)propane hydrazide and Boc-2-amino-2-methylpropanoic acid according to the general synthetic schemes with a total yield after purification by HPLC of 35%.

$^1$H NMR (400 MHz, 300° K, DMSO-d$^6$):

δ 1.32 (3H, s, CH$_3$ Aib), 1.36 (3H, s, CH$_3$ Aib), 2.93 (2H, m, CH$_2$—CH$_2$-indole), 2.97 (2H, m, CH$_2$—CH$_2$-indole), 3.31 (1H, dd, J=14.5, J=6.1, 1H CH$_2$ βTrp), 3.38 (1H, dd, J=14.5, J=9.1, 1H CH$_2$ βTrp), 3.66 (3H, s, o-OCH$_3$), 3.72 (3H, s, p-OCH$_3$), 4.93 (1H, d, J=16.9, 1H CH$_2$ o,p-dimethoxybenzyl), 5.10 (1H, d, J=16.9, 1H CH$_2$ o,p-dimethoxybenzyl), 5.23 (1H, m, CαH Trp), 6.31 (1H, dd, J=8.5, J=1.7, H$_5$ o,p-dimethoxybenzyl), 6.45 (1H, d, J=8.5, H$_6$ o,p-dimethoxybenzyl), 6.59 (1H, d, J=1.7, H$_3$ o,p-dimethoxybenzyl), 6.88 (1H, t, J=7.5, H$_5$ Trp), 6.94 (1H, t, J=7.5, H$_5$ indole), 7.04 (1H, t, H$_6$ Trp), 7.06 (1H, t, H$_6$ indole), 7.08 (1H, s, H$_2$ indole), 7.11 (1H, s, H$_2$ Trp), 7.18 (1H, d, J=7.9, H$_4$ Trp), 7.33 (3H, H$_4$, H$_7$ indole, H$_7$ Trp), 8.05 (2H, s, NH$_2$ Aib), 8.95 (1H, d, J=7.9, NH Trp), 10.80 (1H, s, NH indole), 10.82 (1H, s, NH indole Trp).

$^{13}$C NMR (400 MHz, DMSO-d$^6$):

δ 22.4 (CH$_2$—CH$_2$ indole), 23.2 (CH$_3$ Aib), 23.3 (CH$_3$ Aib), 25.4 (CH$_2$—CH$_2$ indole), 28.7 (Cβ Trp), 41.3 (CH$_2$-o,p-dimethoxybenzyl), 45.3 (Cα Trp), 55.2 (p-OCH$_3$), 55.4 (o-OCH$_3$), 56.3 (Cq Aib), 98.6 (C$_3$ o,p-dimethoxybenzyl), 104.7 (C$_6$ o,p-dimethoxybenzyl), 109.5 (C$_3$ Trp), 111.3 (C$_7$ Trp, C$_7$ indole), 112.9 (C$_3$ indole), 115.2 (C$_1$ o,p-dimethoxybenzyl), 117.8 (C$_4$ indole), 117.9 (C$_4$ Trp), 118.2 (C$_6$ Trp, C$_5$ indole), 120.9 (C$_6$ Trp, C$_6$ indole), 122.4 (C$_2$ indole), 124.3 (C$_2$ Trp), 126.8 (C$_9$ Indole), 126.9 (C$_9$ Trp), 127.5 (C$_6$ o,p-dimethoxybenzyl), 136.0 (C$_8$ Trp), 136.2 (C$_8$ indole), 154.6 (2Cq triazole), 157.3 (C$_2$ o,p-dimethoxybenzyl), 160.4 (C$_4$ o,p-dimethoxybenzyl), 171.3 (CO Aib).

ESI-MS: found: m/z 606.3 [M+H]$^+$/calculated: 604.3 g/mol.

Example 2

(R)—N-(1-(5-benzyl-4-(naphthalen-1-ylmethyl)-4H-1,2,4-triazol-3-yl)-2-(1H-indol-3-yl)ethyl)-2-amino-2-methylpropanamide (Compound 4)

Compound 4 was obtained from Boc-(D)-Trp (10 mmoles), naphthalen-1-yl-methanamine, 2-phenylacetohydrazide and Boc-2-amino-2-methylpropanoic acid according to the general synthetic schemes with a total yield after purification by HPLC of 42%.

$^1$H NMR (300 MHz, DMSO-d$^6$, 300° K):

δ (ppm) 1.18 (3H, s, CH$_3$ Aib), 1.24 (3H, s, CH$_3$ Aib), 3.17 (1H, dd, J=14 Hz and 5 Hz, CH$_2$ βTrp), 3.36 (1H, dd, J=14 and 9 Hz, CH$_2$ βTrp), 4.05 (2H, m, CH$_2$-benzyl), 4.90 (1H, m, CH αTrp), 5.65 (1H, d, J=18 Hz, CH$_2$-naphtyl), 5.81 (1H, d, J=18 Hz, CH$_2$-naphtyl), 6.12 (1H, d, J$_o$=7 Hz, H$_2$ naphtyl), 6.38 (1H, t, J$_o$=7 Hz, H$_5$ Trp), 6.47 (1H, d, J$_o$=8 Hz, H$_4$ Trp), 6.85 (1H, t, J$_o$=8 Hz, H$_6$ Trp), 7.03 (1H, d, J$_m$=2 Hz, H$_2$ Trp), 7.05-7.12 (5H, m, CHar benzyl), 7.15 (1H, d, J$_o$=8 Hz, H$_7$ Trp), 7.19 (1H, d, J$_o$=8 Hz, H$_3$ naphtyl), 7.58 (2H, m, H$_6$ and H$_7$ naphtyl), 7.81 (1H, d, J$_o$=8 Hz, H$_4$ naphtyl), 7.89-8.01 (5H, m, NH$_2$ Aib, H$_5$ and H$_8$ naphtyl), 8.92 (1H, d, J=8 Hz, NH amide), 10.73 (1H, s, NH indole Trp).

$^{13}$C NMR (75 MHz, DMSO-d$^6$, 300° K):

δ (ppm) 23.5 (CH$_3$ Aib), 23.6 (CH$_3$ Aib), 29.2 (CH$_2$ βTrp), 30.5 (CH$_2$-benzyl), 44.0 (CH$_2$-naphtyl), 45.6 (CH αTrp), 56.6 (Cq Aib), 109.7 (C$_3$ Trp), 111.7 (C$_7$ Trp), 117.9 (C$_4$ Trp), 118.4 (C$_5$ Trp), 121.1 (C$_6$ Trp), 122.1 (C$_2$ naphtyl), 122.8 (C$_8$ naphtyl), 124.9 (C$_2$ Trp), 125.7 (C$_3$ naphtyl), 126.7 (C$_6$ naphtyl), 126.9 (C$_9$ Trp), 127.0 (C$_7$ naphtyl), 128.2 (C$_4$ benzyl), 128.7-129.1 (C$_2$, C$_3$, C$_5$ and C$_6$ benzyl, C$_4$ and C$_5$ naphtyl), 129.9 (C$_9$ naphtyl), 131.5 (C$_1$ naphtyl), 133.5 (C$_{10}$ naphtyl), 136.2 (C$_1$ benzyl), 136.4 (C$_8$ Trp), 154.2 (Cq triazole), 155.7 (Cq triazole), 171.9 (CO Aib).

ESI-MS: found: m/z 543.4 [M+H]$^+$/calculated: 542.2 g/mol.

Example 3

(R)—N-(1-(5-(2-(1H-indol-3-yl)ethyl)-4-(naphthalen-1-ylmethyl)-4H-1,2,4-triazol-3-yl)-2-(1H-indol-3-yl)ethyl)-2-amino-2-methylpropanamide (Compound 5)

Compound 5 was obtained from Boc-(D)-Trp (10 mmoles), naphthalen-1-yl-methanamine, 3-(1H-indol-3-yl) propane hydrazide and Boc-2-amino-2-methylpropanoic acid according to the general synthetic schemes with a total yield after purification by HPLC of 33%.

$^1$H NMR (400 MHz, DMSO-d$^6$, 300° K):

δ(ppm) 1.25 (3H, s, CH$_3$ Aib), 1.28 (3H, s, CH$_3$ Aib), 2.93 (2H, m, CH$_2$—CH$_2$-indole), 3.01 (2H, m, CH$_2$—CH$_2$-indole), 3.30 (1H, dd, $^3$J=14.3 and 5.8 Hz, CH$_2$ βTrp), 3.40 (1H, dd, $^3$J=14.3 and 8.8 Hz, CH$_2$ βTrp), 5.03 (1H, m, CH αTrp), 5.62 (1H, d, J=18.0 Hz, CH$_2$-naphtyl), 5.76 (1H, J=18.0 Hz, CH$_2$-naphtyl), 3.36 (1H, d, J$_o$=7.2 Hz, H$_2$ naphtyl), 6.51 (1H, t, J$_o$=7.4 Hz, H$_5$ Trp), 6.72 (1H, d, J$_o$=7.9 Hz, H$_4$ Trp), 6.76 (1H, t, J$_o$=7.5 Hz, H$_5$ indole), 6.92 (1H, t, J$_o$=7.5 Hz, H$_6$ Trp), 7.0 (1H, t, J$_o$=7.5 Hz, H$_6$ indole), 7.02 (1H, d, J=2.0 Hz, H$_2$ indole), 7.09 (1H, d, J=2.0 Hz, H$_2$ Trp), 7.13 (1H, d, J$_o$=7.9 Hz, H$_4$ indole), 7.26 (1H, J$_o$=7.9 Hz, H$_7$ Trp), 7.27 (1H, t, J$_o$=8.2 Hz, H$_3$ naphtyl), 7.29 (1H, d, H$_7$ indole), 7.58-7.64 (2, m, H$_6$ and H$_7$ naphtyl), 7.88 (1H, d, J$_o$=8.2 Hz, H$_4$ naphtyl), 7.93 (1H, d, J$_o$=7.9 Hz, H$_8$ naphtyl), 7.98 (3H, brs, NH$_2$ Aib), 8.03 (1H, d, J$_o$=8.2 Hz, H$_5$ naphtyl), 8.96 (1H, d, J$_o$=7.9 Hz, NH Trp), 10.75 (1H, brs, NH indole), 10.77 (1H, brs, NH indole Trp).

$^{13}$C NMR (100 MHz, DMSO-d$^6$, 300° K):

δ (ppm) 22.6 (CH$_2$—CH$_2$-indole), 23.1 (CH$_3$ Aib), 23.2 (CH$_3$ Aib), 25.3 (CH$_2$—CH$_2$-indole), 28.8 (CH$_2$ βTrp), 43.3 (CH$_2$-naphtyl), 45.3 (CH αTrp), 56.2 (Cq Aib), 109.4 (C$_3$ Trp), 111.2 (C$_7$ indole and C$_7$ Trp), 112.9 (C$_3$ indole), 117.5 (C$_4$ Trp), 117.8 (C$_4$ indole), 118.0 (C$_6$ Trp), 118.1 (C$_5$ indole), 120.7 (C$_6$ Trp), 120.8 (C$_6$ indole), 121.6 (C$_2$ naphtyl), 122.5 (C$_2$ indole and C$_8$ naphtyl), 124.4 (C$_2$ Trp), 125.4 (C$_3$ naphtyl), 126.3 (C$_6$ naphtyl), 126.6 (C$_9$ indole, C$_9$ Trp and C$_7$ naphtyl), 127.9 (C$_4$ naphtyl), 128.6 (C$_5$ naphtyl), 129.5 (C$_9$ naphtyl), 131.4 (C$_1$ naphtyl), 133.1 (C$_{10}$ naphtyl), 135.9 (C$_8$ Trp), 136.1 (C$_8$ indole), 154.7 (2 Cq triazole), 171.4 (CO Aib).

ESI-MS: found: m/z 596.4 [M+H]$^+$/calculated: 595.3 g/mol.

Example 4

(R)—N-(1-(5-(2-(1H-indol-3-yl)ethyl)-4-(3-methoxybenzyl)-4H-1,2,4-triazol-3-yl)-2-(1H-indol-3-yl)ethyl)-2-amino-2-methylpropanamide (Compound 6)

Compound 6 was obtained from Boc-(D)-Trp (10 mmoles), (3-methoxyphenyl)-methenamine, 3-(1H-indol-3-yl)propane hydrazide and Boc-2-amino-2-methylpropanoic acid according to the general synthetic schemes with a total yield after purification by HPLC of 25%.

$^1$H NMR (400 MHz, DMSO-d$^6$):

δ (ppm) 1.28 (3H, s, CH$_3$ Aib), 1.30 (3H, s, CH$_3$ Aib), 2.92 (2H, m, CH$_2$—CH$_2$-indole), 2.98 (2H, m, CH$_2$—CH$_2$-indole), 3.33 (1H, dd, J=14.5, J=6.2, 1H CH$_2$ βTrp), 3.40 (1H, dd, J=14.5, J=8.8, 1H CH$_2$ βTrp), 3.66 (3H, s, OCH$_3$), 5.09 (2H, m, CH$_2$ m-methoxybenzyl), 5.22 (1H, m, CαH Trp), 6.38 (1H, d, J=7.5, H$_6$ m-methoxybenzyl), 6.59 (1H, s, H$_2$ m-methoxybenzyl), 6.86 (1H, t, H$_5$ Trp), 6.87 (1H, d, H$_4$ m-methoxybenzyl), 6.92 (1H, t, J=7.5, H$_5$ indole), 7.03 (1H, t, J=7.9, H$_6$ Trp), 7.05 (1H, t, H$_6$ indole), 7.07 (1H, s, H$_2$ indole), 7.11 (1H, s, H$_2$ Trp), 7.18 (1H, t, H$_5$ m-methoxybenzyl), 7.19 (1H, d, H$_4$ Trp), 7.31 (1H, H$_4$ indole), 7.32 (2H, H$_7$ Trp, H$_7$ indole), 8.00 (2H, s, NH$_2$ Aib), 8.96 (1H, d, J=8.1, NH Trp), 10.78 (1H, s, NH indole), 10.80 (1H, s, NH indole Trp).

$^{13}$C NMR (400 MHz, DMSO-d$^6$):

δ (ppm) 22.4 (CH$_2$—CH$_2$ indole), 23.1 (CH$_3$ Aib), 23.3 (CH$_3$ Aib), 25.4 (CH$_2$—CH$_2$ indole), 28.7 (Cβ Trp), 45.3 (CH$_2$ m-methoxybenzyl), 45.4 (Cα Trp), 55.0 (OCH$_3$), 56.3 (CqAib), 109.5 (C$_3$ Trp), 111.3 (C$_7$ Trp, C$_7$ indole), 112.0 (C$_2$ m-methoxybenzyl), 113.0 (C$_4$ m-methoxybenzyl, C$_3$ indole), 117.8 (C$_4$ Trp, C$_6$ m-methoxybenzyl), 118.0 (C$_4$ indole), 118.2 (C$_5$ indole), 118.3 (C$_5$ Trp), 120.8 (C$_6$ indole), 120.9 (C$_6$ Trp), 122.4 (C$_2$ indole), 124.3 (C$_2$ Trp), 126.7 (C$_9$ indole), 126.9 (C$_9$ Trp), 130.0 (C$_5$ m-methoxybenzyl), 136.0 (C$_8$ indole), 136.1 (C$_8$ Trp), 137.2 (C$_1$ m-methoxybenzyl), 154.3 (2Cq triazole), 159.6 (C$_3$ m-methoxybenzyl), 171.4 (CO Aib).

ESI-MS: found: m/z 576.6 [M+H]$^+$/calculated: 575.3 g/mol.

Example 5

(R)—N-(1-(4-(3-methoxybenzyl)-5-benzyl-4H-1,2,4-triazol-3-yl)-2-(1H-indol-3-yl)ethyl)-2-amino-2-methylpropanamide (Compound 7)

Compound 7 was obtained from Boc-(D)-Trp (10 mmoles), (3-methoxyphenyl)-methanamine, 2-phenylacetohydrazide and Boc-2-amino-2-methylpropanoic acid according to the general synthetic schemes with a total yield after purification by HPLC of 30%.

$^1$H NMR (400 MHz, DMSO-d$^6$):

δ (ppm) 1.25 (3H, s, CH$_3$ Aib), 1.29 (3H, s, CH$_3$ Aib), 3.24 (1H, dd, J=14.3, J=5.8, 1H CH$_2$ βTrp), 3.38 (1H, dd, J=14.3, J=9.1, 1H CH$_2$ βTrp), 3.61 (3H, s, m-OCH$_3$), 4.04 (2H, m, CH$_2$ benzyl), 5.07 (1H, d, J=17.4, 1H CH$_2$ m-methoxybenzyl), 5.13 (1H, d, J=17.4, 1H CH$_2$ m-methoxybenzyl), 5.14 (1H, m, CαH Trp), 6.32 (1H, d, J=7.8, H$_6$ m-methoxybenzyl), 6.40 (1H, m, H$_2$ m-methoxybenzyl), 6.82 (1H, t, H$_5$ Trp), 6.83 (1H, d, J=7.8, H$_4$ m-methoxybenzyl), 7.01 (1H, t, J=8.2, H$_6$ Trp), 7.04 (1H, d, J=8.2, H$_4$ Trp), 7.06 (1H, d, J=2.0, H$_2$ Trp), 7.12 (2H, m, H$_6$-Benzyl), 7.13 (1H, t, J=7.9, H$_5$ m-methoxybenzyl), 7.20 (1H, m, H$_4$ benzyl), 7.24 (2H, m, H$_3$, H$_5$ benzyl), 7.29 (1H, d, J=8.2, H$_7$ Trp), 7.99 (2H, s, NH$_2$ Aib), 8.92 (1H, d, J=8.2, NH Trp), 10.77 (1H, s, NH indole Trp).

$^{13}$C NMR (400 MHz, DMSO-d$^6$):

δ (ppm) 23.0 (CH$_3$ Aib), 23.3 (CH$_3$ Aib), 28.6 (Cβ Trp), 30.1 (CH$_2$ benzyl), 45.2 (Cα Trp), 45.6 (CH$_2$-m-methoxybenzyl), 54.9 (m-OCH$_3$), 56.2 (CqAib), 109.4 (C$_3$ Trp), 111.2 (C$_7$ Trp), 111.7 (C$_2$ m-methoxybenzyl), 113.1 (C$_4$ m-methoxybenzyl), 117.9 (C$_4$ Trp, C$_6$ m-methoxybenzyl), 118.2 (C$_5$ Trp), 120.8 (C$_6$ Trp), 124.3 (C$_2$ Trp), 126.6 (C$_4$ benzyl), 126.8 (C$_9$ Trp), 128.3 (C$_3$, C$_5$ benzyl), 128.4 (C$_2$, C$_6$ benzyl), 129.9 (C$_5$ m-methoxybenzyl), 135.9 (C$_1$ benzyl, C$_8$ Trp), 137.0 (C$_1$ m-methoxybenzyl), 153.5 (Cq triazole), 154.8 (Cq triazole), 159.5 (C$_3$ m-methoxybenzyl), 171.3 (CO Aib).

ESI-MS: found: m/z 523.3 [M+H]$^+$/calculated: 522.3 g/mol.

Example 6

(R)—N-(1-(5-(2-(1H-indol-3-yl)ethyl)-4-benzyl-4H-1,2,4-triazol-3-yl)-2-(1H-indol-3-yl)ethyl)-2-amino-2-methylpropanamide (Compound 8)

Compound 8 was obtained from Boc-(D)-Trp (10 mmoles), phenylmethanamine, 3-(1H-indol-3-yl)propane hydrazide and Boc-2-amino-2-methylpropanoic acid according to the general synthetic schemes with a total yield after purification by HPLC of 45%.

$^1$H NMR (400 MHz, DMSO-d$^6$):

δ (ppm) 1.29 (3H, s, CH$_3$ Aib), 1.30 (3H, s, CH$_3$ Aib), 2.88 (2H, m, CH$_2$—CH$_2$-indole), 2.97 (2H, m, CH$_2$—CH$_2$-indole), 3.37 (2H, m, CH$_2$ βTrp), 5.11 (2H, s, CH$_2$ benzyl), 5.21 (1H, m, CαH Trp), 6.86 (1H, t, J=7.4, H$_5$ Trp), 6.88 (2H, H$_2$, H$_6$ benzyl), 6.92 (1H, t, J=7.6, H$_5$ indole), 7.03 (1H, t, J=7.6, H$_6$ Trp), 7.05 (2H, H$_6$ indole, H$_2$ indole), 7.09 (1H, d, J=1.8, H$_2$ Trp), 7.17 (1H, d, J=7.9, H$_4$ Trp), 7.26 (2H, H$_3$, H$_5$ benzyl), 7.27 (1H, H$_4$ benzyl), 7.30 (1H, H$_4$ indole), 7.32 (2H, H$_7$ Trp, H$_7$ indole), 8.03 (2H, brs, NH$_2$ Aib), 8.95 (1H, d, J=8.1, NH Trp), 10.77 (1H, s, NH indole), 10.81 (1H, s, NH indole Trp).

$^{13}$C NMR (400 MHz, DMSO-d$^6$):

δ (ppm) 22.4 (CH$_2$—CH$_2$ indole), 23.1 (CH$_3$ Aib), 23.3 (CH$_3$ Aib), 25.4 (CH$_2$—CH$_2$ indole), 28.7 (Cβ Trp), 45.3 (Cα Trp, CH$_2$-benzyl), 56.3 (Cq Aib), 109.5 (C$_3$ Trp), 111.3 (C$_7$ Trp, C$_7$ indole), 113.0 (C$_3$ indole), 117.8 (C$_4$ Trp), 118.0 (C$_4$ indole), 118.2 (C$_5$ indole), 118.3 (C$_5$ Trp), 120.9 (C$_6$ Trp, C$_6$ indole), 122.4 (C$_2$ indole), 124.3 (C$_2$ Trp), 125.9 (C$_2$, C$_6$ benzyl), 126.7 (C$_9$ Indole), 126.9 (C$_9$ Trp), 127.6 (C$_4$ benzyl), 128.8 (C$_3$, C$_5$ benzyl), 135.7 (C$_1$ benzyl), 136.0 (C$_8$ Trp), 136.1 (C$_8$ indole), 154.3 (Cq triazole), 154.5 (Cq triazole), 171.4 (CO Aib).

ESI-MS: found: m/z 546.3 [M+H]$^+$/calculated: 545.3 g/mol.

Example 7

(R)—N-(1-(5-(3-(1H-indol-3-yl)propyl)-4-benzyl-4H-1,2,4-triazol-3-yl)-2-(1H-indol-3-yl)ethyl)-2-amino-2-methylpropanamide (Compound 9)

Compound 9 was obtained from Boc-(D)-Trp (10 mmoles), phenylmethanamine, 4-(1H-indol-3-yl)butanehydrazide and Boc-2-amino-2-methylpropanoic acid according to the general synthetic schemes with a total yield after purification by HPLC of 38%.

$^1$H NMR (400 MHz, DMSO-d$^6$):

δ (ppm) 1.29 (3H, s, CH$_3$ Aib), 1.31 (3H, s, CH$_3$ Aib), 1.90 (2H, m, CH$_2$—CH$_2$—CH$_2$-indole), 2.61 (2H, m, CH$_2$—CH$_2$—CH$_2$-indole), 2.69 (2H, m, CH$_2$—CH$_2$—CH$_2$-indole), 3.37 (2H, m, CH$_2$ βTrp), 5.09 (2H, s, CH$_2$ benzyl), 5.20 (1H, m, CαH Trp), 6.85 (3H, m, H$_2$, H$_6$ benzyl, H$_5$ Trp), 6.94 (1H, t, J=7.5, H$_5$ indole), 7.01 (1H, s, H$_2$ indole), 7.02 (1H, t, J=7.8, H$_6$ Trp), 7.05 (1H, t, J=8, H$_6$ indole), 7.08 (1H, d, J=2.0, H$_2$ Trp), 7.14 (1H, d, J=8.0, H$_4$ Trp), 7.25 (3H, m, H$_3$, H$_4$, H$_5$ benzyl), 7.31 (1H, d, J=8.0, H$_7$ Trp), 7.32 (1H, d, J=8.0, H$_7$ indole), 7.42 (1H, d, J=7.8, H$_4$ indole), 8.03 (2H, s, NH$_2$ Aib), 8.95 (1H, d, J=8.1, NH Trp), 10.73 (1H, s, NH indole), 10.80 (1H, d, J=2.0, NH indole Trp).

$^{13}$C NMR (400 MHz, DMSO-d$^6$):

δ (ppm) 23.1 (CH$_3$ Aib), 23.3 (CH$_3$ Aib), 23.8 (CH$_2$—CH$_2$—CH$_2$-indole), 24.1 (CH$_2$—CH$_2$—CH$_2$-indole), 27.2 (CH$_2$—CH$_2$—CH$_2$-indole), 28.7 (Cβ Trp), 45.4 (Cα Trp), 45.5 (CH$_2$ benzyl), 56.3 (Cq Aib), 109.4 (C$_3$ Trp), 111.3 (C$_7$ Trp, C$_7$ indole), 113.6 (C$_3$ indole), 117.8 (C$_4$ Trp), 118.0 (C$_5$ indole), 118.2 (C$_4$ indole), 118.3 (C$_5$ Trp), 120.8 (C$_6$ indole, C$_6$ Trp), 122.2 (C$_2$ indole), 124.3 (C$_2$ Trp), 125.9 (C$_2$, C$_6$ benzyl), 126.8 (C$_9$ Trp), 127.0 (C$_9$ indole), 127.7 (C$_4$ benzyl), 128.7 (C$_3$, C$_5$ benzyl), 135.5 (C$_1$ benzyl), 136.0 (C$_8$ Trp), 136.2 (C$_8$ indole), 154.3 (Cq triazole), 154.7 (Cq triazole), 171.4 (CO Aib).

ESI-MS: found: m/z 560.4 [M+H]$^+$/calculated: 559.3 g/mol.

Example 8

(R)—N-(1-(5-(3-(1H-indol-3-yl)propyl)-4-(3-methoxybenzyl)-4H-1,2,4-triazol-3-yl)-2-(1H-indol-3-yl)ethyl)-2-amino-2-methylpropanamide (Compound 10)

Compound 10 was obtained from Boc-(D)-Trp (10 mmoles), (3-methoxyphenyl)-methanamine, 4-(1H-indol-3-yl)butanehydrazide and Boc-2-amino-2-methylpropanoic acid according to the general synthetic schemes with a total yield after purification by HPLC of 25%.

$^1$H NMR (400 MHz, DMSO-d$^6$):

δ (ppm) 1.27 (3H, s, CH$_3$ Aib), 1.30 (3H, s, CH$_3$ Aib), 1.92 (2H, m, CH$_2$—CH$_2$—CH$_2$-indole), 2.62 (2H, m, CH$_2$—CH$_2$—CH$_2$-indole), 2.68 (2H, m, CH$_2$—CH$_2$—CH$_2$-indole), 3.24 (1H, dd, J=14.5, J=5.8, 1H CH$_2$ βTrp), 3.39 (1H, dd, J=14.5, J=9.0, 1H CH$_2$βTrp), 3.66 (3H, s, m-OCH$_3$), 5.07 (2H, s, CH$_2$ m-methoxybenzyl), 5.18 (1H, m, CαH Trp), 6.35 (1H, d, J=7.5, H$_6$ m-methoxybenzyl), 6.54 (1H, bs, H$_2$ m-methoxybenzyl), 6.84 (1H, t, J=7.5, H$_5$ Trp), 6.87 (1H, dd, J=8.0, J=2.1, H$_4$ m-methoxybenzyl), 6.94 (1H, t, J=7.3, H$_5$ indole), 7.02 (1H, t, H$_6$ Trp), 7.02 (1H, s, H$_2$ indole), 7.05 (1H, t, J=7.8, H$_6$ indole), 7.08 (1H, d, J=2.1, H$_2$ Trp), 7.13 (1H, d, J=8.1, H$_4$ Trp), 7.17 (1H, t, J=8.1, H$_5$ m-methoxybenzyl), 7.30 (1H, d, H$_7$ Trp), 7.32 (1H, d, J=8, H$_7$ indole), 7.42 (1H, d, J=7.6, H$_4$ indole), 7.98 (2H, s, NH$_2$ Aib), 8.93 (1H, d, J=8.2, NH Trp), 10.71 (1H, s, NH indole), 10.77 (1H, s, NH indole Trp).

$^{13}$C NMR (400 MHz, DMSO-d$^6$):

δ (ppm) 23.1 (CH$_3$ Aib), 23.3 (CH$_3$ Aib), 23.9 (CH$_2$—CH$_2$—CH$_2$-indole), 24.3 (CH$_2$—CH$_2$—CH$_2$-indole), 27.4 (CH$_2$—CH$_2$—CH$_2$ indole), 28.8 (Cβ Trp), 45.2 (CH$_2$-m-methoxybenzyl), 45.4 (Cα Trp), 55.1 (m-OCH$_3$), 56.3 (Cq Aib), 109.5 (C$_3$ Trp), 111.3 (C$_7$ Trp, C$_7$ indole), 111.8 (C$_2$ m-methoxybenzyl), 113.0 (C$_4$ m-methoxybenzyl), 113.8 (C$_3$ indole), 117.8 (C$_6$ m-methoxybenzyl), 117.9 (C$_4$ Trp), 118.1 (C$_5$ indole), 118.2 (C$_5$ Trp, C$_4$ indole), 120.8 (C$_6$ Trp), 120.9 (C$_6$ indole), 122.2 (C$_2$ indole), 124.3 (C$_2$ Trp), 126.8 (C$_9$ Trp), 127.0 (C$_9$ Indole), 130.0 (C$_5$ m-methoxybenzyl), 136.0 (C$_8$ Trp), 136.2 (C$_8$ indole), 137.4 (C$_1$ m-methoxybenzyl), 154.3 (Cq triazole), 154.6 (Cq triazole), 159.7 (C$_3$ m-methoxybenzyl), 171.4 (CO Aib).

ESI-MS: found: m/z 590.3 [M+H]$^+$/calculated: 589.3 g/mol.

Example 9

(R)—N-(1-(5-(3-(1H-indol-3-yl)propyl)-4-(naphthalen-1-ylmethyl)-4H-1,2,4-triazol-3-yl)-2-(1H-indol-3-yl)ethyl)-2-amino-2-methylpropanamide (Compound 11)

Compound 11 was obtained from Boc-(D)-Trp (10 mmoles), naphthalen-1-ylmethanamine, 4-(1H-indol-3-yl)butanehydrazide and Boc-2-amino-2-methylpropanoic acid according to the general synthetic schemes with a total yield after purification by HPLC of 22%.

$^1$H NMR (300 MHz, DMSO-d$^6$, 300° K):

δ (ppm) 1.20 (3H, s, CH$_3$ Aib), 1.25 (3H, s, CH$_3$ Aib), 1.93 (2H, m, CH$_2$—CH$_2$—CH$_2$-indole), 2.66 (4H, m, CH$_2$—CH$_2$—CH$_2$-indole), 3.25 (1H, dd, J=14 Hz and 5 Hz, CH$_2$ βTrp), 3.40 (1H, dd, J=14 Hz and 9 Hz, CH$_2$ βTrp), 4.95 (1H, m, CH αTrp), 5.66 (1H, d, J=18 Hz, CH$_2$-naphtyl), 5.81 (1H, d, J=18 Hz, CH$_2$-naphtyl), 6.37 (1H, d, J$_o$=7 Hz, H$_2$ naphtyl), 6.43 (1H, t, J$_o$=7 Hz, H$_5$ Trp), 6.59 (1H, d, J$_o$=8 Hz, H$_4$ Trp), 6.86 (3H, m, H$_5$ and H$_6$ indole, H$_6$ Trp), 6.95 (1H, d, J=2 Hz, H$_2$ indole), 7.00 (1H, d, J$_o$=8 Hz, H$_4$ indole), 7.06 (1H, d, J=2 Hz, H$_2$ Trp), 7.20-7.33 (4H, m, H$_4$ and H$_7$ indole, H$_7$ Trp, H$_3$ naphtyl), 7.60 (2H, m, H$_6$ and H$_7$ naphtyl), 7.87 (1H, d, J$_o$=8 Hz, H$_4$ naphtyl), 7.99 (5H, m, NH$_2$ Aib, H$_5$ and H$_8$ naphtyl), 8.95 (1H, d, J=8 Hz, NH amide), 10.70 (1H, s, NH indole), 10.77 (1H, s, NH indole Trp).

$^{13}$C NMR (75 MHz, DMSO-d$^6$, 300° K):

δ (ppm) 23.5 (CH$_3$ Aib), 23.6 (CH$_3$ Aib), 24.1 (CH$_2$—CH$_2$—CH$_2$-indole), 24.5 (CH$_2$—CH$_2$—CH$_2$-indole), 27.6 (CH$_2$—CH$_2$—CH$_2$-indole), 29.1 (CH$_2$ βTrp), 44.1 (CH$_2$-naphtyl), 45.7 (CH α Trp), 56.7 (Cq Aib), 109.7 (C$_3$ Trp), 111.7 (C$_7$ indole and C$_7$ Trp), 113.9 (C$_3$ indole), 117.9 (C$_4$ Trp), 118.5 (C$_4$ indole, C$_5$ Trp), 118.6 (C$_5$ indole), 121.1 (C$_6$ Trp), 121.2 (C$_6$ indole), 122.1 (C$_2$ naphtyl), 122.7 (C$_2$ indole), 122.9 (C$_8$ naphtyl), 125.0 (C$_2$ Trp), 125.9 (C$_3$ naphtyl), 126.8 (C$_6$ naphtyl), 127.0 (C$_9$ indole), 127.1 (C$_7$ naphtyl), 127.4 (C$_9$ Trp), 128.5 (C$_4$ naphtyl), 129.2 (C$_5$ naphtyl), 129.9 (C$_9$ naphtyl), 131.6 (C$_1$ naphtyl), 133.6 (C$_{10}$ naphtyl), 136.4 (C$_8$ Trp), 136.7 (C$_8$ indole), 155.4 (Cqs triazole), 171.9 (CO Aib).

ESI-MS: found: m/z 610.3 [M+H]$^+$/calculated: 609.3 g/mol.

Example 10

(R)—N-(1-(5-(2-(1H-indol-3-yl)ethyl)-4-(4-methoxybenzyl)-4H-1,2,4-triazol-3-yl)-2-(1H-indol-3-yl)ethyl)-2-amino-2-methylpropanamide (Compound 12)

Compound 12 was obtained from Boc-(D)-Trp (10 mmoles), (4-methoxyphenyl)-methanamine, 3-(1H-indol-3-yl)propane hydrazide and Boc-2-amino-2-methylpropanoic acid according to the general synthetic schemes with a total yield after purification by HPLC of 28%.

$^1$H NMR (400 MHz, DMSO-d$^6$):

δ (ppm) 1.30 (3H, s, CH$_3$ Aib), 1.33 (3H, s, CH$_3$ Aib), 2.91 (2H, m, CH$_2$—CH$_2$-indole), 2.97 (2H, m, CH$_2$—CH$_2$-indole), 3.37 (2H, d, CH$_2$βTrp), 3.71 (3H, s, OCH$_3$), 5.02 (2H, s, CH$_2$ p-methoxybenzyl), 5.23 (1H, m, CαH Trp), 6.78 (4H, m, CHar p-methoxybenzyl), 6.87 (1H, t, J=7.5, H$_5$ Trp), 6.93 (1H, t, J=7.5, H$_5$ indole), 7.03 (1H, t, H$_6$ Trp), 7.05 (1H, t, H$_6$ indole), 7.07 (1H, s, H$_2$ indole), 7.09 (1H, s, H$_2$ Trp), 7.21 (1H, d, J=8, H$_4$ Trp), 7.32 (3H, H$_4$ indole, H$_7$ Trp, H$_7$ indole), 8.02 (2H, s, NH$_2$ Aib), 8.97 (1H, d, J=8.1, NH Trp), 10.77 (1H, s, NH indole), 10.80 (1H, s, NH indole Trp).

$^{13}$C NMR (400 MHz, DMSO-d$^6$):

δ (ppm) 22.4 (CH$_2$—CH$_2$ indole), 23.1 (CH$_3$ Aib), 23.4 (CH$_3$ Aib), 25.5 (CH$_2$—CH$_2$ indole), 28.9 (Cβ Trp), 44.9 (CH$_2$ p-methoxybenzyl), 45.3 (Cα Trp), 55.0 (OCH$_3$), 56.3 (CqAib), 109.5 (C$_3$ Trp), 111.3 (C$_7$ Trp, C$_7$ indole), 113.0 (C$_3$ indole), 114.1 (C$_3$, C$_5$ p-methoxybenzyl), 117.9 (C$_4$ Trp), 118.0 (C$_4$ indole), 118.2 (C$_5$ indole), 118.3 (C$_5$ Trp), 120.9 (C$_6$ indole, C$_6$ Trp), 122.0 (C$_2$ indole), 124.4 (C$_2$ Trp), 126.7 (C$_9$ indole), 126.9 (C$_9$ Trp), 127.3 (C$_2$, C$_6$ p-methoxybenzyl), 127.4 (C$_1$ p-methoxybenzyl), 135.9 (C$_8$ Trp), 136.1 (C$_8$ indole), 154.2 (Cq triazole), 154.5 (Cq triazole), 158.4 C$_4$ p-methoxybenzyl), 171.4 (CO Aib).

ESI-MS: found: m/z 576.3 [M+H]$^+$/calculated: 575.3 g/mol.

Example 11

(R)—N-(1-(4-(4-methoxybenzyl)-5-benzyl-4H-1,2,4-triazol-3-yl)-2-(1H-indol-3-yl)ethyl)-2-amino-2-methylpropanamide (Compound 13)

Compound 13 was obtained from Boc-(D)-Trp (10 mmoles), (4-methoxyphenyl)-methanamine, 2-phenylacetohydrazide and Boc-2-amino-2-methylpropanoic acid according to the general synthetic schemes with a total yield after purification by HPLC of 37%.

$^1$H NMR (300 MHz, DMSO-d$^6$, 300° K):

δ (ppm) 1.24 (3H, s, CH$_3$ Aib), 1.28 (3H, s, CH$_3$ Aib), 3.26 (1H, dd, $^3$J=14 Hz and 6 Hz, CH$_2$ βTrp), 3.31 (1H, dd, $^3$J=14 Hz and 9 Hz, CH$_2$ βTrp), 3.67 (3H, s, OCH$_3$), 3.99 (2H, s, CH$_2$-benzyl), 4.99 (2H, s, CH$_2$-p-methoxybenzyl), 5.12 (1H, m, CH αTrp), 6.67 (4H, m, CHar p-methoxybenzyl), 6.80 (1H, t, J$_o$=8 Hz, H$_5$ Trp), 6.98 (1H, t, J$_o$=8 Hz, H$_6$ Trp), 7.02-7.06 (4H, m, H$_2$ and H$_6$ benzyl, H$_2$ and H$_4$ Trp), 7.12-7.25 (3H, m, H$_3$, H$_4$ and H$_5$ benzyl), 7.26 (1H, d, J$_o$=8 Hz, H$_7$ Trp), 8.01 (3H, brs, NH$_2$ Aib), 8.92 (1H, d, J=8 Hz, NH Trp), 10.77 (1H, s, NH indole Trp).

$^{13}$C NMR (75 MHz, DMSO-d$^6$, 300° K):

δ (ppm) 23.5 (CH$_3$ Aib), 23.7 (CH$_3$ Aib), 29.1 (CH$_2$ βTrp), 30.6 (CH$_2$-benzyl), 45.7 (CH$_2$-p-methoxybenzyl), 45.7 (CH αTrp), 55.5 (OCH$_3$), 56.7 (CqAib), 109.8 (C$_3$ Trp), 111.7 (C$_7$ Trp), 114.5 (C$_3$ and C$_5$ p-methoxybenzyl), 118.3 (C$_4$ Trp), 118.7 (C$_5$ Trp), 121.3 (C$_6$ Trp), 124.8 (C$_2$ Trp), 127.1 (C$_2$ and C$_6$ benzyl), 127.3 (C$_9$ Trp), 127.6 (C$_1$ p-methoxybenzyl), 127.8 (C$_2$ and C$_6$ p-methoxybenzyl), 128.8 (C$_3$, C$_4$ and C$_5$ p-methoxybenzyl), 136.3 (C$_1$ benzyl), 136.4 (C$_8$ Trp), 153.8 (Cq triazole), 155.2 (Cq triazole), 159.1 (C$_4$ p-methoxybenzyl), 171.9 (CO Aib).

ESI-MS: found: m/z 524.1 [M+H]$^+$/calculated: 522.3 g/mol.

Example 12

(R)—N-(1-(5-(2-(1H-indol-3-yl)ethyl)-4-hexyl-4H-1,2,4-triazol-3-yl)-2-(1H-indol-3-yl)ethyl)-2-amino-2-methylpropanamide (Compound 15)

Compound 15 was obtained from Boc-(D)-Trp (10 mmoles), hexan-1-amine, 3-(1H-indol-3-yl)propane hydrazide and Boc-2-amino-2-methylpropanoic acid according to the general synthetic schemes with a total yield after purification by HPLC of 28%.

$^1$H NMR (400 MHz, DMSO-d$^6$):

δ (ppm) 0.77 (3H, t, J=7.2 (CH$_2$)$_5$—CH$_3$), 1.01 (4H, m, 2CH$_2$), 1.11 (2H, m, CH$_2$—CH$_3$), 1.14 (1H, m, 1H N—CH$_2$—CH$_2$), 1.33 (1H, m, 1H N—CH$_2$—CH$_2$), 1.40 (3H, s, CH$_3$ Aib), 1.42 (3H, s, CH$_3$ Aib), 3.05 (2H, m, CH$_2$—CH$_2$-indole), 3.10 (2H, m, CH$_2$—CH$_2$-indole), 3.37 (1H, dd, J=14.2, J=7.6, 1H CH$_2$ βTrp), 3.44 (1H, dd, J=14.2, J=7.6, 1H CH$_2$βTrp), 3.58 (1H, m, 1H N—CH$_2$), 3.71 (1H, m, 1H N—CH$_2$), 5.21 (1H, m, CαH Trp), 6.96 (1H, H$_5$ Trp), 6.97 (1H, H$_5$ indole), 7.06 (2H, H$_6$ Trp, H$_6$ indole), 7.09 (1H, s, H$_2$ Trp), 7.13 (1H, s, H$_2$ indole), 7.34 (2H, H$_7$ Trp, H$_7$ indole), 7.48 (1H, d, H$_4$ indole), 7.50 (1H, H$_4$ Trp), 8.14 (2H, s, NH$_2$ Aib), 9.08 (1H, d, J=7.8, NH Trp), 10.84 (1H, s, NH indole), 10.88 (1H, s, NH indole Trp).

$^{13}$C NMR (400 MHz, DMSO-d$^6$):

δ (ppm) 13.7 (CH$_2$)$_6$—CH$_3$), 21.7 (CH$_2$—CH$_3$), 22.4 (CH$_2$—CH indole), 23.1 (CH$_3$ Aib), 23.3 (CH$_3$ Aib), 25.1 (CH$_2$—CH, indole), 25.5 (CH$_3$—CH$_2$—CH$_2$—CH$_2$), 29.1 (Cβ Trp), 29.3 (N—CH$_2$—CH$_2$), 30.4 (CH$_3$—CH$_2$—CH$_2$), 42.6 (N—CH$_2$—CH$_2$), 45.6 (Cα Trp), 56.3 (Cq Aib), 109.2 (C$_3$ Trp), 111.4-111.5 (C$_7$ Trp, C$_7$ indole), 112.8 (C$_3$ indole), 117.7 (C$_4$ Trp), 118.0 (C$_5$ Trp), 118.2 (C$_4$ indole), 118.4 (C$_5$ Trp), 120.9 (C$_6$ indole, C$_6$ Trp), 122.6 (C$_2$ indole), 124.3 (C$_2$ Trp), 126.8 (C$_9$ Trp), 126.9 (C$_9$ indole), 136.0 (C$_8$ Trp), 136.2 (C$_8$ indole), 154.0 (Cq triazole), 154.1 (Cq triazole), 171.4 (CO Aib). ESI-MS: found: m/z 540.3 [M+H]$^+$/calculated: 539.3 g/mol.

Example 13

(S)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-amino-2-methylpropanamide (Compound 18)

Compound 18 was obtained from Boc-(L)-Trp (10 mmoles), (2,4-dimethoxyphenyl)-methanamine, 3-(1H-indol-3-yl)propane hydrazide and Boc-2-amino-2-methylpropanoic acid according to the general synthetic schemes with a total yield after purification by HPLC of 30%.

$^1$H NMR (300 MHz, DMSO-d$^6$, 300° K):

δ (ppm) 1.27 (3H, s, CH$_3$ Aib), 1.31 (3H, s, CH$_3$ Aib), 2.89 (2H, m, CH$_2$CH$_2$-indole), 2.93 (2H, m, CH$_2$CH$_2$-indole), 3.27 (2H, m, CH$_2$ βTrp), 3.62 (3H, s, o-OCH$_3$), 3.68 (3H, s, p-OCH$_3$), 4.89 (1H, d, $^3$J=17 Hz, CH$_2$-o,p-dimethoxybenzyl), 5.06 (1H, d, $^3$J=17 Hz, CH$_2$-o,p-dimethoxybenzyl), 5.18 (1H, m, CH αTrp), 6.27 (1H, dd, J$_o$=8 Hz and J$_P$=2 Hz, H$_5$ o,p-dimethoxybenzyl), 6.40 (1H, d, 8 Hz, H$_6$ o,p-dimethoxybenzyl), 6.56 (1H, d, J$_P$=2 Hz, H$_3$ o,p-dimethoxybenzyl), 6.83 (1H, t, J$_o$=7 Hz, H$_5$ Trp), 6.90 (1H, t, J$_o$=7 Hz, H$_5$ indole), 7.02 (1H, t, H$_6$ Trp), 7.04 (1H, t, H$_6$ indole), 7.07 (1H S, H$_2$ indole), 7.08 (1H, s, H$_2$ Trp), 7.12 (1H, d, J$_o$=8 Hz, H$_4$ Trp), 7.29 (3H, H$_4$ and H$_7$ indole, H$_7$ Trp), 8.00 (3H, brs, NH$_2$ Aib), 8.93 (1H, d, J=8 Hz, NH amide), 10.76 (1H, s, NH indole), 10.79 (1H, s, NH indole Trp).

$^{13}$C NMR (75 MHz, DMSO-d$^6$, 300° K):

δ (ppm) 22.9 (CH$_2$CH$_2$-indole), 23.6 (CH$_3$ Aib), 23.7 (CH$_3$ Aib), 25.8 (CH$_2$CH$_2$-indole), 29.2 (CH$_2$ βTrp), 41.4 (CH$_2$-o, p-dimethoxybenzyl), 45.7 (CαTrp), 55.7 (p-OCH$_3$), 55.9 (o-OCH$_3$), 56.7 (Cq Aib), 99.0 (C$_3$ o,p-dimethoxybenzyl), 105.1 (C$_6$ o,p-dimethoxybenzyl), 109.9 (C$_3$ Trp), 111.8 (C$_7$ Trp, C$_7$ indole), 113.4 (C$_3$ indole), 115.6 (C$_1$ o,p-dimethoxybenzyl), 118.3 (C$_4$ Trp), 118.4 (C$_4$ Trp), 118.6 (C$_5$ Trp, C$_5$ indole), 121.3 (C$_6$ Trp, C$_6$ indole), 122.6 (C$_2$ indole), 124.4 (C$_2$ Trp), 127.2 (C$_9$ indole), 127.3 (C$_9$ Trp), 128.0 (C$_6$ o,p-dimethoxybenzyl), 136.4 (C$_8$Trp), 136.6 (C$_8$ indole), 155.0 (2 Cq triazole), 157.7 (C$_2$ o,p-dimethoxybenzyl), 160.9 (C$_4$ o,p-dimethoxybenzyl), 171.6 (CO Aib).

ESI-MS: found: m/z 606.2 [M+H]$^+$/calculated: 605.3 g/mol.

Example 14

(R)—N-(1-(5-(3-(1H-indol-3-yl)propyl)-4-(4-methoxybenzyl)-4H-1,2,4-triazol-3-yl)-2-(1H-indol-3-yl)ethyl)-2-amino-2-methylpropanamide (Compound 23)

Compound 23 was obtained from Boc-(D)-Trp (10 mmoles), (4-methoxyphenyl)-methenamine, 4-(1H-indol-3-yl)butanehydrazide and Boc-2-amino-2-methylpropanoic acid according to the general synthetic schemes with a total yield after purification by HPLC of 25%.

$^1$H NMR (300 MHz, DMSO-d$^6$, 300° K):

δ (ppm) 1.27 (3H, s, CH$_3$ Aib), 1.30 (3H, s, CH$_3$ Aib), 1.84 (2H, m, CH$_2$CH$_2$CH$_2$-indole), 2.58 (2H, m, CH$_2$CH$_2$CH$_2$-indole), 2.65 (2H, m, CH$_2$CH$_2$CH$_2$-indole), 3.34 (2H, d, $^3$J=7 Hz, CH$_2$ βTrp), 3.67 (3H, s, OCH$_3$), 4.96 (2H, s, CH$_2$-p-methoxybenzyl), 5.19 (1H, m, CH αTrp), 6.71 (4H, s, CH ar p-methoxybenzyl), 6.89 (1H, t, J$_o$=7 Hz, H$_5$ Trp), 6.92 (1H, t, J$_o$=7 Hz, H$_5$ indole), 7.02 (1H, s, H$_2$ indole), 7.05 (1H, s, H$_2$ Trp), 7.14 (1H, d, J$_o$=8 Hz, H$_4$ Trp), 7.33 (3H, H$_4$ indole, H$_7$ Trp, H$_7$ indole), 8.02 (3H, brs, NH$_2$ Aib), 7.90 (1H, d, J=8 Hz, NH amide), 10.73 (1H, s, NH indole), 10.79 (1H, s, NH indole Trp).

$^{13}$C NMR (75 MHz, DMSO-d$^6$, 300° K):

δ (ppm) 23.6 (CH$_3$ Aib), 23.8 (CH$_3$ Aib), 24.3 (CH$_2$CH$_2$CH$_2$-indole), 24.8 (CH$_2$CH$_2$CH$_2$-indole), 27.7 (CH$_2$CH$_2$CH$_2$-indole), 29.1 (Cβ Trp), 45.5 (N—CH$_2$-p-methoxybenzyl), 45.8 (Cα Trp), 55.5 (OCH$_3$), 56.8 (Cq Aib), 109.8 (C$_3$ Trp), 111.7 (C$_7$ Trp, C$_7$ indole), 114.0 (C$_3$ indole), 114.5 (C$_3$, C$_5$ p-methoxybenzyl), 118.3 (C$_4$ indole, C$_4$ Trp), 118.5 (C$_5$ indole), 118.8 (C$_5$ Trp), 121.3 (C$_6$ indole, C$_6$ Trp), 127.3 (C$_9$ indole), 127.4 (C$_9$ Trp), 127.6 (C$_1$ p-methoxybenzyl), 127.9 (C$_2$, C$_6$ p-methoxybenzyl, C$_2$ Trp, C$_2$ indole), 136.1 (C$_8$ indole), 136.4 (C$_8$ Trp), 154.7 (Cq triazole), 155.1 (Cq triazole), 159.2 (C$_4$ p-methoxybenzyl), 171.9 (CO Aib).

ESI-MS: found: m/z 590.0 [M+H]$^+$/calculated: 589.3 g/mol.

Example 15

(R)—N-(1-(5-(2-(1H-indol-3-yl)ethyl)-4-(2-methoxy)benzyl)-4H-1,2,4-triazol-3-yl)-2-(1H-indol-3-yl)ethyl)-2-amino-2-methylpropanamide (Compound 25)

Compound 25 was obtained from Boc-(D)-Trp (10 mmoles), (2-methoxyphenyl)-methanamine, 3-(1H-indol-3-yl)propane hydrazide and Boc-2-amino-2-methylpropanoic acid according to the general synthetic schemes with a total yield after purification by HPLC of 28%.

$^1$H NMR (300 MHz, DMSO-d$^6$, 300° K):

δ (ppm) 1.27 (3H, s, CH$_3$ Aib), 1.29 (3H, s, CH$_3$ Aib), 2.90 (2H, m, CH$_2$—CH$_2$-indole), 2.96 (2H, m, CH$_2$—CH$_2$-indole), 3.29 (2H, m, CH$_2$ βTrp), 3.65 (3H, s, OCH$_3$), 5.09 (3H, m, CH$_2$—O-methoxybenzyl and CH αTrp), 6.49 (1H, d, J$_o$=8 Hz, H$_3$ o-methoxybenzyl), 6.76 (1H, t, J$_o$=8 Hz, H$_5$ Trp), 6.81 (1H, t, J$_o$=8 Hz, H$_5$ indole), 6.89 (1H, t, J$_o$=7 Hz, H$_6$ Trp), 6.96 (1H, t, J$_o$=8 Hz, H$_6$ indole), 6.98 (1H, s, H$_2$ indole), 7.02 (3H, m, H$_4$, H$_5$ and H$_6$ o-methoxybenzyl), 7.07 (1H, d, J$_o$=6 Hz, H$_4$ Trp), 7.18 (1H, m, H$_4$ indole), 7.29 (2H, m, H$_7$ indole and H$_7$ Trp), 8.07 (3H, brs, NH$_2$ Aib), 8.97 (1H, d, J=8 Hz, NH amide), 10.80 (1H, s, NH indole), 10.82 (1H, s, NH indole Trp).

$^{13}$C NMR (75 MHz, DMSO-d$^6$, 300° K):

δ (ppm) 22.8 (CH$_2$—CH$_2$-indole), 23.6 (CH$_3$ Aib), 23.7 (CH$_3$ Aib), 25.8 (CH$_2$—CH$_2$-indole), 29.1 (CH$_2$ βTrp), 42.3 (CH$_2$—O-methoxybenzyl), 45.7 (CH α Trp), 55.8 (OCH$_3$), 56.7 (Cq Aib), 109.8 (C$_3$ Trp), 111.5 (C$_3$ o-methoxybenzyl), 111.8 (C$_7$ indole and C$_7$ Trp), 113.2 (C$_3$ indole), 118.2 (C$_4$ Trp), 118.4 (C$_4$ indole), 118.7 (C$_5$ indole and C$_5$ Trp), 121.0 (C$_6$ indole), 121.3 (C$_6$ Trp), 121.4 (C$_5$ o-methoxybenzyl), 123.0 (C$_2$ indole and C$_2$ Trp), 123.3 (C$_1$ o-methoxybenzyl), 127.0 (C$_4$ o-methoxybenzyl), 127.1 (C$_9$ indole), 127.3 (C$_9$ Trp), 129.8 (C$_6$ o-methoxybenzyl), 136.4 (C$_8$ indole), 136.6 (C$_8$ Trp), 155.2 (Cq triazole), 171.9 (CO Aib).

ESI-MS: found: m/z 576.1 [M+H]$^+$/calculated: 575.3 g/mol.

Data on further exemplary embodiments that were synthesized according to the general synthesis schemes are compiled below (please refer also to Table 1):

(R)—N-(1-(5-(3-(1H-indol-3-yl)propyl)-4-phenethyl-4H-1,2,4-triazol-3-yl)-2-(1H-indol-3-yl)ethyl)-2-amino-2-methylpropanamide (Compound 3)

$^1$H NMR (300 MHz, DMSO-d$^6$, 300° K):

δ (ppm) 1.32 (s, 3H, CH$_3$ Aib), 1.37 (s, 3H, CH$_3$ Aib), 1.86 (2H, m, CH$_2$—CH$_2$—CH$_2$-indole), 2.38 (2H, m, CH$_2$—CH$_2$-indole), 2.65 (4H, m, CH$_2$—CH$_2$—CH$_2$-indole and CH$_2$—CH$_2$-phenyl), 3.38 (2H, m, CH$_2$—CH$_2$-phenyl), 3.74 (1H, m, CH$_2$βTrp), 3.92 (1H, m, CH$_2$ βTrp), 5.23 (1H, m, CH αTrp), 6.78 (2H, m, H$_5$ indole and H$_5$ Trp), 6.93 (1H, t, J$_o$=8 Hz, H$_6$ Trp), 7.01 (3H, m, H$_6$ indole, H$_2$ and H$_6$ phenyl), 7.05 (1H, d, J=2 Hz, H$_2$ Trp), 7.08 (1H, d, J=2 Hz, H$_2$ indole), 7.15 (3H, m, H$_3$, H$_4$ and H$_5$ phenyl), 7.29 (1H, d, J$_o$=8 Hz, H$_4$ Trp), 7.31 (1H, d, Jo=8 Hz, H$_7$ Trp), 7.44 (1H, d, J$_o$=8 Hz, H$_7$ indole), 7.46 (1H, d, J$_o$=8 Hz, H$_4$ indole), 8.06 (3H, brs, NH$_2$ Aib), 9.05 (1H, d, 8 Hz, NH amide), 10.76 (1H, s, NH indole), 10.85 (1H, d, J=2 Hz, NH indole Trp).

$^{13}$C NMR (75 MHz, DMSO-d$^6$, 300° K):

δ (ppm) 23.5 (CH$_3$ Aib), 23.6 (CH$_2$—CH$_2$—CH$_2$-indole), 23.9 (CH$_3$ Aib), 24.5 (CH$_2$—CH$_2$—CH$_2$-indole), 27.3 (CH$_2$—CH$_2$—CH$_2$-indole), 29.4 (CH$_2$ βTrp), 35.7 (CH$_2$—CH$_2$-phenyl), 44.5 (CH$_2$—CH$_2$-phenyl), 46.1 (CH αTrp), 56.8 (Cq Aib), 109.6 (C$_3$ Trp), 111.8 (C$_7$ indole), 111.9 (C$_7$ indole), 113.9 (C$_3$ indole), 118.3 (C$_4$ Trp), 118.6 (C$_5$ indole), 118.7 (C$_4$ indole), 118.9 (C$_5$ Trp), 121.3 (C$_6$ Trp), 121.4 (C$_6$ indole), 122.8 (C$_2$ indole and C$_2$ Trp), 127.1 (C$_4$ phenyl), 127.3 (C$_9$ Trp), 127.5 (C$_9$ indole), 128.8 (C$_2$ and C$_6$ phenyl), 129.1 (C$_3$ and C$_5$ phenyl), 136.5 (C$_1$ phenyl), 136.8 (C$_8$ Trp), 137.2 (C$_8$ indole), 154.7 (Cq triazole), 172.0 (CO Aib).

(R)—N-(1-(5-(3-(1H-indol-3-yl)propyl)-4-hexyl-4H-1,2,4-triazol-3-yl)-2-(1H-indol-3-yl)ethyl)-2-amino-2-methylpropanamide (Compound 16)

$^1$H NMR (300 MHz, DMSO-d$^6$, 300° K):

δ (ppm) 0.74 (3H, t, J=6 Hz, CH$_3$—CH$_2$—CH$_2$—CH$_2$—CH$_2$—CH$_2$), 0.95 (4H, brs, CH$_3$—CH$_2$—CH$_2$—CH$_2$—CH$_2$—CH$_2$), 1.06 (3H, m, CH$_3$—CH$_2$—CH$_2$—CH$_2$—CH$_2$—CH$_2$ and 1H N—CH$_2$—CH$_2$), 1.38 (7H, s, CH$_3$ Aib and 1H N—CH$_2$—CH$_2$), 1.97 (2H, m, CH$_2$—CH$_2$—CH$_2$-indole), 2.71 (4H, m, CH$_2$—CH$_2$—CH$_2$-indole), 3.37 (2H, m, CH$_2$ βTrp), 3.56 (2H, m, N—CH$_2$), 5.15 (1H, m, CH αTrp), 6.91 (2H, m, H$_5$ indole and H$_5$ Trp), 7.00 (2H, m, H$_6$ indole and H$_6$ Trp), 7.07 (2H, s, H$_2$ indole and H$_2$ Trp), 7.29 (2H, d, J$_o$=8 Hz, H$_7$ indole and H$_7$ Trp), 7.45 (2H, d, Jo=7 Hz, H$_4$ indole and H$_4$ Trp), 8.15 (3H, brs, NH$_2$ Aib), 9.10 (1H, d, J=6 Hz, NH amide), 10.77 (1H, s, NH indole), 10.85 (1H, s, NH indole Trp).

$^{13}$C NMR (75 MHz, DMSO-d$^6$, 300° K):

δ (ppm) 14.2 (CH$_3$—CH$_2$—CH$_2$—CH$_2$—CH$_2$—CH$_2$), 22.2 (CH$_3$—CH$_2$—CH$_2$—CH$_2$—CH$_2$—CH$_2$ and CH$_2$—CH$_2$—CH$_2$-indole), 23.6 (CH$_3$ Aib), 23.7 (CH$_3$ Aib), 24.5 (CH$_2$—CH$_2$—CH$_2$-indole), 25.9 (CH$_3$—CH$_2$—CH$_2$—CH$_2$—CH$_2$—CH$_2$), 27.5 (CH$_2$ βTrp and CH$_2$—CH$_2$—CH$_2$-indole), 29.7 (N—CH$_2$—CH$_2$), 30.8 (CH$_3$—CH$_2$—CH$_2$—CH$_2$—CH$_2$—CH$_2$), 43.2 (N—CH$_2$), 46.1 (CH αTrp), 56.8 (Cq Aib), 109.5 (C$_3$ Trp), 111.8 (C$_7$ Trp), 111.9 (C$_7$ indole), 113.9 (C$_3$ indole), 118.1 (C$_4$ Trp), 118.5 (C$_5$ indole), 118.6 (C$_4$ indole), 118.9 (C$_5$ Trp), 121.3 (C$_6$ indole and C$_6$ Trp), 122.8 (C$_2$ indole and C$_2$ Trp), 127.3 (C$_9$ Trp), 127.4 (C$_9$ indole), 136.5 (C$_8$ Trp), 136.8 (C$_8$ indole), 154.7 (Cq triazole), 172.0 (CO Aib).

(R)—N-(1-(4,5-bis(2-(1H-indol-3-yl)ethyl)-4H-1,2,4-triazol-3-yl)-2-(1H-indol-3-yl)ethyl)-2-amino-2-methylpropanamide (Compound 17)

$^1$H NMR (300 MHz, DMSO-d$^6$, 300° K):

δ (ppm) 1.30 (3H, s, CH$_3$ Aib), 1.37 (3H, s, CH$_3$ Aib), 2.50 (2H, m, N—CH$_2$—CH$_2$-indole), 2.68 (2H, t, J$_o$=8 Hz, C—CH$_2$—CH$_2$-indole), 2.91 (2H, t, J$_o$=8 Hz, C—CH$_2$—CH$_2$-indole), 3.34 (2H, m, N—CH$_2$—CH$_2$-indole), 3.93 (2H, m, CH$_2$ βTrp), 5.25 (1H, m, CH αTrp), 6.72-6.94 (4H, m, H$_5$ and H$_6$ Trp, H$_5$ indole from C—CH$_2$—CH$_2$-indole and H$_5$ indole from N—CH$_2$—CH$_2$-indole), 6.98-7.04 (4H, m, H$_2$ Trp, H$_6$ indole from C—CH$_2$—CH$_2$-indole, H$_2$ and H$_6$ indole from N—CH$_2$—CH$_2$-indole), 7.11 (1H, s, H$_2$ indole from C—CH$_2$—CH$_2$-indole), 7.19 (1H, d, J$_o$=8 Hz, H$_4$ indole from N—CH$_2$—CH$_2$-indole), 7.28 (3H, m, H$_4$ and H$_7$ Trp, H$_7$ indole from N—CH$_2$—CH$_2$-indole), 7.40 (1H, d, J$_o$=8 Hz, H$_7$ indole from C—CH$_2$—CH$_2$-indole), 7.44 (1H, d, J$_o$=8 Hz, H$_4$ indole from C—CH$_2$—CH$_2$-indole), 8.04 (3H, brs, NH$_2$ Aib), 9.69 (1H, d, J=8 Hz, NH amide), 10.73 (1H, s, NH indole from C—CH$_2$—CH$_2$-indole), 10.82 (1H, d, J=2 Hz, NH indole Trp), 10.84 (1H, s, NH indole from N—CH$_2$—CH$_2$-indole).

$^{13}$C NMR (75 MHz, DMSO-d$^6$, 300° K):

δ (ppm) 22.7 (C—CH$_2$—CH$_2$-indole), 23.6 (CH$_3$ Aib), 23.8 (CH$_3$ Aib), 25.4 (C—CH$_2$—CH$_2$-indole), 26.0 (N—CH$_2$—CH$_2$-indole), 29.6 (CH$_2$ βTrp), 43.9 (N—CH$_2$—CH$_2$-indole), 46.0 (CH αTrp), 56.8 (Cq Aib), 109.5 (C$_3$ indole from N—CH$_2$—CH$_2$-indole), 109.9 (C$_3$ Trp), 111.7 (C$_7$ Trp), 111.9 (C$_7$ indole from N—CH$_2$—CH$_2$-indole and C$_7$ indole from C—CH$_2$—CH$_2$-indole), 113.5 (C$_3$ indole from C—CH$_2$—CH$_2$-indole), 118.3 (C$_4$ indole from N—CH$_2$—CH$_2$-indole), 118.4 (C$_4$ Trp), 118.5 (C$_5$ indole from C—CH$_2$—CH$_2$-indole), 118.7 (C$_4$ indole from C—CH$_2$—CH$_2$-indole), 118.9 (C$_5$ Trp), 119.0 (C$_5$ indole from N—CH$_2$—CH$_2$-indole), 121.3 (C$_6$ Trp), 121.5 (C$_6$ indole from C—CH$_2$—CH$_2$-indole and C$_6$ indole from N—CH$_2$—CH$_2$-indole), 122.8 (C$_2$ Trp, C$_2$ indole from C—CH$_2$—CH$_2$-indole and indole from N—CH$_2$—CH$_2$-indole), 127.1 (C$_9$ Trp), 127.2 (C$_9$ indole from C—CH$_2$—CH$_2$-indole), 127.4 (C$_9$ indole from N—CH$_2$—CH$_2$-indole), 136.5 (C$_8$ Trp and C$_8$ indole from C—CH$_2$—CH$_2$-indole), 136.6 (C$_8$ indole from N—CH$_2$—CH$_2$-indole), 154.5 (Cq triazole), 154.8 (Cq triazole), 171.8 (CO amide).

(R)—N-(1-(4-(3-methoxybenzyl)-5-phenethyl-4H-1,2,4-triazol-3-yl)-2-(1H-indol-3-yl)ethyl)-2-amino-2-methylpropanamide (Compound 19)

$^1$H NMR (300 MHz, DMSO-d$^6$, 300° K):

δ (ppm) 1.24 (3H, s, CH$_3$ Aib), 1.27 (3H, s, CH$_3$ Aib), 2.82 (4H, m, CH$_2$—CH$_2$-phenyl), 3.32 (2H, m, CH$_2$ βTrp), 3.63 (3H, s, OCH$_3$), 5.08 (2H, m, CH$_2$-m-methoxybenzyl), 5.18 (1H, m, CH αTrp), 6.35 (1H, d, J$_o$=8 Hz, H$_6$ m-methoxybenzyl), 6.57 (1H, s, H$_2$ m-methoxybenzyl), 6.82 (1H, t, J$_o$=8 Hz, H$_5$ Trp), 6.84 (1H, d, J$_o$=8 Hz, H$_4$ m-methoxybenzyl), 6.99 (1H, t, J$_o$=8 Hz, H$_6$ Trp), 7.08 (1H, m, H$_4$ phenyl), 7.11-7.16 (5H, m, H$_2$ and H$_4$ Trp, H$_2$ and H$_6$ phenyl, H$_5$ m-methoxybenzyl), 7.20 (2H, m, H$_3$ and H$_5$ phenyl), 7.27 (1H, d, J$_o$=8 Hz, H$_7$ Trp), 8.01 (3H, brs, NH$_2$ Aib), 8.96 (1H, d, J=8 Hz, NH amide), 10.81 (1H, d, J=2 Hz, NH indole).

$^{13}$C NMR (75 MHz, DMSO-d$^6$, 300° K):

δ (ppm) 23.5 (CH$_3$ Aib), 23.8 (CH$_3$ Aib), 26.4 (CH$_2$—CH$_2$-phenyl), 29.1 (CH$_2$ βTrp), 32.7 (CH$_2$—CH$_2$-phenyl), 45.7 (CH αTrp), 45.8 (CH$_2$-m-methoxybenzyl), 55.5 (OCH$_3$), 56.7 (Cq Aib), 109.8 (C$_3$ Trp), 111.8 (C$_7$ Trp), 112.5 (C$_2$ m-methoxybenzyl), 113.5 (C$_4$ m-methoxybenzyl), 118.2 (C$_4$ Trp), 118.4 (C$_6$ m-methoxybenzyl), 118.7 (C$_5$ Trp), 121.3 (C$_6$ Trp), 124.8 (C$_2$ Trp), 126.5 (C$_4$ phenyl), 127.3 (C$_9$ Trp), 128.7 (C$_2$, C$_3$, C$_5$ and C$_6$ phenyl), 130.5 (C$_5$ m-methoxybenzyl), 136.4 (C$_8$ Trp), 137.7 (C$_1$ m-methoxybenzyl), 170.9 (C$_1$ phenyl), 154.6 (Cq triazole), 154.9 (Cq triazole), 160.1 (C$_3$ m-methoxybenzyl), 171.9 (CO amide).

(R)—N-(1-(4-(4-methoxybenzyl)-5-phenethyl-4H-1,2,4-triazol-3-yl)-2-(1H-indol-3-yl)ethyl)-2-amino-2-methylpropanamide (Compound 20)

$^1$H NMR (300 MHz, DMSO-d$^6$, 300° K):

δ (ppm) 1.28 (3H, s, CH$_3$ Aib), 1.32 (3H, s, CH$_3$ Aib), 2.46 (2H, m, CH$_2$—CH$_2$-phenyl), 2.82 (2H, m, CH$_2$—CH$_2$-phenyl), 3.35 (2H, d, J=7 Hz, CH$_2$ βTrp), 3.68 (3H, s, OCH$_3$), 5.02 (2H, s, CH$_2$-p-methoxybenzyl), 5.22 (1H, m, CH αTrp), 6.73-6.81 (4H, m, CHar p-methoxybenzyl), 6.84 (1H, t, J$_o$=7 Hz, H$_5$ Trp), 7.00 (1H, t, J$_o$=7 Hz, H$_6$ Trp), 7.05-7.11 (4H, m, H$_2$ and H$_6$ phenyl, H$_2$ and H$_4$ Trp), 7.14-7.22 (3H, m, H$_3$, H$_4$ and H$_5$ phenyl), 7.29 (1H, d, J$_a$=8 Hz, H$_7$ Trp), 8.09 (3H, brs, NH$_2$ Aib), 8.99 (1H, d, J=8 Hz, NH amide), 10.83 (1H, s, NH indole Trp).

$^{13}$C NMR (75 MHz, DMSO-d$^6$, 300° K):

δ (ppm) 23.5 (CH$_3$ Aib), 23.8 (CH$_3$ Aib), 26.5 (CH$_2$—CH$_2$-phenyl), 29.1 (CH$_2$ βTrp), 32.6 (CH$_2$—CH$_2$-phenyl), 45.5 (CH$_2$-p-methoxybenzyl), 45.7 (CH αTrp), 55.5 (OCH$_3$), 56.8 (Cq Aib), 109.7 (C$_3$ Trp), 111.8 (C$_7$ Trp), 114.6 (C$_3$ and C$_5$ p-methoxybenzyl), 118.3 (C$_4$ Trp), 118.7 (C$_5$ Trp), 121.3 (C$_6$ Trp), 124.9 (C$_2$ Trp), 126.6 (C$_2$ and C$_6$ phenyl), 127.3 (C$_9$ Trp), 127.6 (C$_1$ p-methoxybenzyl), 128.0 (C$_2$ and C$_6$ p-methoxybenzyl), 128.7 (C$_3$, C$_4$ and C$_5$ phenyl), 136.4 (C$_8$ Trp), 140.8 (C$_1$ phenyl), 154.5 (Cq triazole), 154.8 (Cq triazole), 159.2 (C$_4$ p-methoxybenzyl), 172.0 (CO Aib).

(R)—N-(1-(4-(4-methoxybenzyl)-5-(3-phenylpropyl)-4H-1,2,4-triazol-3-yl)-2-(1H-indol-3-yl)ethyl)-2-amino-2-methylpropanamide (Compound 22)

$^1$H NMR (300 MHz, DMSO-d$^6$, 300° K):

δ (ppm) 1.27 (3H, s, CH$_3$ Aib), 1.31 (3H, s, CH$_3$ Aib), 1.73 (2H, m, CH$_2$—CH$_2$—CH$_2$-phenyl), 2.47 (2H, m, CH$_2$—CH$_2$—CH$_2$-phenyl), 2.52 (2H, t, $^3$J=7 Hz, CH$_2$—CH$_2$—CH$_2$-phenyl), 3.35 (2H, d, J=7 Hz, CH$_2$ βTrp), 3.68 (3H, s, OCH$_3$), 4.98 (2H, s, methoxybenzyl), 5.20 (1H, m, CH αTrp), 6.75 (4H, m, CHar p-methoxybenzyl), 6.82 (1H, t, J$_o$=7 Hz, H$_5$ Trp), 6.99 (1H, t, J$_o$=7 Hz, H$_6$ Trp), 7.04-7.07 (4H, m, H$_2$ and H$_6$ phenyl, H$_2$ and H$_4$ Trp), 7.13-7.24 (3H, m, H$_3$, H$_4$ and H$_5$ phenyl), 7.29 (1H, d, J$_o$=8 Hz, H$_7$ Trp), 8.03 (3H, brs, NH$_2$ Aib), 8.96 (1H, d, J=8 Hz, NH amide), 10.80 (1H, d, J=2 Hz, NH indole Trp).

$^{13}$C NMR (75 MHz, DMSO-d$^6$, 300° K):

δ (ppm) 23.6 (CH$_3$ Aib), 23.6 (CH$_3$ Aib), 24.06 (CH$_2$—CH$_2$—CH$_2$-phenyl), 28.5 (CH$_2$—CH$_2$—CH$_2$-phenyl), 29.2 (CH$_2$ βTrp), 34.7 (CH$_2$—CH$_2$—CH$_2$-phenyl), 45.5 (CH$_2$-p-methoxybenzyl), 45.8 (CH αTrp), 55.5 (OCH$_3$), 56.8 (Cq Aib), 109.8 (C$_3$ Trp), 111.8 (C$_7$ Trp), 114.6 (C$_3$ and C$_5$ p-methoxybenzyl), 118.3 (C$_4$ Trp), 118.7 (C$_5$ Trp), 121.3 (C$_6$ Trp), 124.9 (C$_2$ Trp), 126.2 (C$_2$ and C$_6$ phenyl), 127.3 (C$_9$ Trp), 127.8 (C$_1$ p-methoxybenzyl), 127.9 (C$_2$ and C$_6$ p-methoxybenzyl), 128.7 (C$_3$, C$_4$ and C$_5$ phenyl), 136.4 (C$_8$ Trp), 141.7 (C$_1$ phenyl), 154.8 (Cq triazole), 159.2 (C$_4$ p-methoxybenzyl), 171.9 (CO Aib).

(R)—N-(1-(4-(2-(1H-indol-3-yl)ethyl)-5-(3-(1H-indol-3-yl)propyl)-4H-1,2,4-triazol-3-yl)-2-(1H-indol-3-yl)ethyl)-2-amino-2-methylpropanamide (Compound 24)

$^1$H NMR (300 MHz, DMSO-d$^6$, 300° K):

δ (ppm) 1.29 (3H, s, CH$_3$ Aib), 1.35 (3H, s, CH$_3$ Aib), 1.78 (2H, m, CH$_2$—CH$_2$—CH$_2$-indole), 2.34 (2H, m, CH$_2$—CH$_2$—CH$_2$-indole), 2.48 (2H, m, N—CH$_2$—CH$_2$-indole), 2.80 (2H, m, CH$_2$—CH$_2$—CH$_2$-indole), 3.34 (2H, m, N—CH$_2$—CH$_2$-indole), 3.94 (2H, m, CH$_2$ βTrp), 5.27 (1H, m, CH αTrp), 6.73-6.94 (4H, m, H$_5$ and H$_6$ Trp, H$_5$ indole from N—CH$_2$—CH$_2$-indole and H$_5$ indole from CH$_2$—CH$_2$—CH$_2$-indole), 6.99-7.04 (5H, m, H$_2$ Trp, H$_2$ and H$_6$ indole from N—CH$_2$—CH$_2$-indole, H$_2$ and H$_6$ indole from CH$_2$—CH$_2$—CH$_2$-indole), 7.20 (1H, d, J$_o$=8 Hz, H$_4$ indole from N—CH$_2$—CH$_2$-indole), 7.29 (3H, m, H$_4$ and H$_7$ Trp, H$_7$ indole from N—CH$_2$—CH$_2$-indole), 7.40 (1H, d, J$_o$=8 Hz, H$_7$ indole from CH$_2$—CH$_2$—CH$_2$-indole), 7.44 (1H, d, J$_o$=8 Hz, H$_4$ indole from CH$_2$—CH$_2$—CH$_2$-indole), 8.05 (3H, brs, NH$_2$ Aib), 9.07 (1H, d, J=8 Hz, NH amide), 10.75 (1H, s, NH indole from CH$_2$—CH$_2$—CH$_2$-indole), 10.86 (1H, s, NH indole Trp), 10.90 (1H, s, NH indole from N—CH$_2$—CH$_2$-indole).

$^{13}$C NMR (75 MHz, DMSO-d$^6$, 300° K):

δ (ppm) 23.6 (CH$_3$ Aib), 23.8 (CH$_3$ Aib), 24.5 (CH$_2$—CH$_2$—CH$_2$-indole), 25.8 (CH$_2$—CH$_2$—CH$_2$-indole), 27.2 (CH$_2$—CH$_2$—CH$_2$-indole), 29.4 (CH$_2$ βTrp), 44.1 (N—CH$_2$—CH$_2$-indole), 46.0 (CH αTrp), 52.9 (N—CH$_2$—CH$_2$-indole), 56.8 (Cq Aib), 109.7 (C$_3$ Trp and C$_3$ indole from N—CH$_2$—CH$_2$-indole), 111.8 (C$_7$ Trp), 111.9 (C$_7$ indole from N—CH$_2$—CH$_2$-indole and C$_7$ indole from CH$_2$—CH$_2$—CH$_2$-indole), 114.0 (C$_3$ indole from CH$_2$—CH$_2$—CH$_2$-indole), 118.2 (C$_4$ indole from N—CH$_2$—CH$_2$-indole), 118.3 (C$_4$ Trp), 118.5 (C$_5$ indole from CH$_2$—CH$_2$—CH$_2$-indole), 118.6 (C$_4$ indole from CH$_2$—CH$_2$—CH$_2$-indole), 118.9 (C$_5$ Trp), 119.0 (C$_5$ indole from N—CH$_2$—CH$_2$-indole), 121.3 (C$_6$ Trp), 121.4 (C$_6$ indole from CH$_2$—CH$_2$—CH$_2$-indole), 121.6 (C$_6$ indole from N—CH$_2$—CH$_2$-indole), 122.7 (C$_2$ Trp, C$_2$ indole from N—CH$_2$—CH$_2$-indole and C$_2$ indole from CH$_2$—CH$_2$—CH$_2$-indole), 127.1 (C$_9$ Trp), 127.4 (C$_g$ indole from N—CH$_2$—CH$_2$-indole and C$_9$ indole from CH$_2$—CH$_2$—CH$_2$-indole), 136.4 (C$_8$ Trp), 136.5 (C$_8$ indole from CH$_2$—CH$_2$—CH$_2$-indole), 136.7 (C$_8$ indole from N—CH$_2$—CH$_2$-indole), 154.7 (2 Cq triazole), 171.9 (CO amide).

(R)—N-(1-(4-(2-methoxybenzyl)-5-phenethyl-4H-1,2,4-triazol-3-yl)-2-(1H-indol-3-yl)ethyl)-2-amino-2-methylpropanamide (Compound 26)

$^1$H NMR (300 MHz, DMSO-d$^6$, 300° K):

δ (ppm) 1.26 (3H, s, CH$_3$ Aib), 1.29 (3H, s, CH$_3$ Aib), 2.78-2.92 (4H, m, CH$_2$—CH$_2$-phenyl), 3.29 (2H, m, CH$_2$ βTrp), 3.65 (3H, s, OCH$_3$), 4.97-5.21 (3H, m, CH αTrp and CH$_2$-o-methoxybenzyl), 6.52 (1H, d, J$_o$=7 Hz, H$_3$ o-methoxybenzyl), 6.78 (1H, t, J$_o$=7 Hz, H$_5$ Trp), 6.82 (1H, t, J$_o$=8 Hz, H$_6$ Trp), 6.84-7.04 (3H, m, H$_4$, H$_5$ and H$_6$ o-methoxybenzyl), 7.15 (1H, d, J$_o$=7 Hz, H$_4$ Trp), 7.19-7.29 (4H, m, H$_3$, H$_4$ and H$_5$ phenyl, H$_7$ Trp), 8.03 (3H, brs, NH$_2$ Aib), 8.94 (1H, d, J=8 Hz, NH amide), 10.82 (1H, s, NH indole Trp).

$^{13}$C NMR (75 MHz, DMSO-d$^6$, 300° K):

δ (ppm) 23.6 (CH$_3$ Aib), 23.7 (CH$_3$ Aib), 26.3 (CH$_2$—CH$_2$-phenyl), 29.0 (CH$_2$ βTrp), 32.5 (CH$_2$—CH$_2$-phenyl), 42.3 (CH$_2$—O-methoxybenzyl), 45.7 (CH αTrp), 55.8 (OCH$_3$), 56.7 (Cq Aib), 109.7 (C$_3$ Trp), 111.5 (C$_7$ Trp), 111.8 (C$_3$ o-methoxybenzyl), 118.2 (C$_4$ Trp), 118.7 (C$_5$ Trp), 121.0 (C$_6$ Trp), 121.3 (C$_5$ o-methoxybenzyl), 123.2 (C$_1$ o-methoxybenzyl), 124.9 (C$_2$ Trp), 126.6 (C$_2$ and C$_6$ phenyl), 127.2 (C$_9$ Trp and C$_4$ o-methoxybenzyl), 128.7 (C$_3$, C$_4$ and C$_5$ phenyl), 129.9 (C$_6$ o-methoxybenzyl), 136.4 (C$_8$ Trp), 140.6 (C$_1$ phenyl), 154.8 (Cq triazole), 155.2 (Cq triazole), 156.7 (C$_2$ o-methoxybenzyl), 171.9 (CO Aib).

(R)—N-(2-(1H-indol-3-yl)-1-(4-(naphthalen-1-ylmethyl)-5-phenethyl-4H-1,2,4-triazol-3-yl)ethyl)-2-amino-2-methylpropanamide (Compound 27)

$^1$H NMR (300 MHz, DMSO-d$^6$, 300° K):

δ (ppm) 1.21 (3H, s, CH$_3$ Aib), 1.25 (3H, s, CH$_3$ Aib), 2.46 (2H, m, CH$_2$—CH$_2$-phenyl), 2.88 (2H, m, CH$_2$—CH$_2$-phenyl), 3.26 (2H, dd, $^3$J=14 Hz and 6 Hz, CH$_2$ βTrp), 3.36 (2H, dd, $^3$J=14 Hz and 9 Hz, CH$_2$ βTrp), 4.99 (1H, m, CH αTrp), 5.65 (1H, d, $^3$J=18 Hz, CH$_2$-naphtyl), 5.78 (1H, d, $^3$J=18 Hz, CH$_2$-naphtyl), 6.29 (1H, d, J$_o$=7 Hz, H$_2$ naphtyl), 6.45 (1H, t, J$_o$=7 Hz, H$_5$ Trp), 6.62 (1H, d, J$_o$=8 Hz, H$_4$ Trp), 6.88 (1H, t, J$_o$=8 Hz, H$_6$ Trp), 7.04-7.06 (4H, m, H$_2$ and H$_7$ Trp, H$_2$ and H$_6$ phenyl), 7.07-7.25 (H$_3$ naphtyl, H$_3$, H$_4$ and H$_5$ phenyl), 7.57-7.60 (2H, m, H$_6$ and H$_7$ naphtyl), 7.86 (1H, d, J$_o$=8 Hz, H$_4$ naphtyl), 7.98-8.00 (4H, m, H$_5$ and H$_8$ naphtyl, NH$_2$ Aib), 8.96 (1H, d, J=8 Hz, NH amide), 10.77 (1H, s, NH indole Trp).

$^{13}$C NMR (75 MHz, DMSO-d$^6$, 300° K):

δ (ppm) 23.5 (CH$_3$ Aib), 23.6 (CH$_3$ Aib), 26.3 (CH$_2$CH$_2$-phenyl), 29.2 (CH$_2$ βTrp), 32.6 (CH$_2$—CH$_2$-phenyl), 43.8 (CH$_2$-naphtyl), 45.6 (CH αTrp), 56.7 (Cq Aib), 109.7 (C$_3$ Trp), 111.7 (C$_7$ Trp), 117.9 (C$_4$ Trp), 118.4 (C$_5$ Trp), 121.1 (C$_6$ Trp), 122.1 (C$_2$ naphtyl), 123.0 (C$_8$ naphtyl), 124.9 (C$_2$ Trp), 125.9 (C$_3$ naphtyl), 126.5 (C$_6$ naphtyl), 126.9 (C$_2$ and C$_6$ phenyl), 127.0 (C$_8$ Trp and C$_7$ naphtyl), 127.1 (C$_4$ naphtyl), 128.4 (C$_5$ naphtyl), 128.7 (C$_3$, C$_4$ and C$_5$ phenyl), 130.0 (C$_8$ naphtyl), 131.7 (C$_1$ naphtyl), 133.6 (C$_{18}$ naphtyl), 136.4 (C$_8$ Trp), 140.8 (C$_1$ phenyl), 154.8 (Cq triazole), 155.3 (Cq triazole), 171.9 (CO Aib).

(R)—N-(1-(5-(2-(1H-indol-3-yl)ethyl)-4-(3,4-dichlorobenzyl)-4H-1,2,4-triazol-3-yl)-2-(1H-indol-3-yl)ethyl)-2-amino-2-methylpropanamide (Compound 28)

$^1$H NMR (300 MHz, DMSO-d$^6$, 300° K):

δ (ppm) 1.26 (6H, s, CH$_3$ Aib), 2.87 (2H, m, CH$_2$—CH$_2$-indole), 2.96 (2H, m, CH$_2$—CH$_2$-indole), 3.32 (2H, m, CH$_2$ βTrp), 5.13 (3H, m, CH αTrp and CH$_2$-m,p-dichlorobenzyl), 6.58 (1H, d, J$_o$=8 Hz, H$_6$ m,p-dichlorobenzyl), 6.85 (1H, t, J$_o$=7 Hz, H$_5$ Trp), 6.96 (1H, t, J$_o$=7 Hz, H$_5$ indole), 7.01 (2H, m, H$_6$ indole and H$_6$ Trp), 7.04 (1H, s, H$_2$ Trp), 7.08 (1H, s, H$_2$ indole), 7.13 (1H, d, J$_o$=8 Hz, H$_5$ m,p-dichlorobenzyl), 7.20-7.30 (4H, m, H$_4$ and H$_7$ indole, H$_7$ Trp and H$_2$ m,p-dichlorobenzyl), 7.36 (1H, d, J$_o$=8 Hz, H$_4$ Trp), 8.08 (3H, brs, NH$_2$ Aib), 8.98 (1H, d, J=8 Hz, NH amide), 10.80 (1H, s, NH indole), 10.82 (1H, s, NH indole Trp).

$^{13}$C NMR (75 MHz, DMSO-d$^6$, 300° K):

δ (ppm) 22.8 (CH$_2$—CH$_2$-indole), 23.4 (CH$_3$ Aib), 23.8 (CH$_3$ Aib), 25.8 (CH$_2$—CH$_2$-indole), 29.0 (CH$_2$ β Trp), 44.8 (CH$_2$-m,p-dichlorobenzyl), 45.6 (CH αTrp), 56.8 (Cq Aib), 109.7 (C$_3$ indole), 111.8 (C$_7$ indole and C$_7$ Trp), 118.1 (C$_4$ Trp), 118.4 (C$_5$ indole), 118.6 (C$_4$ indole and C$_5$ Trp), 121.3 (C$_6$ indole and C$_6$ Trp), 123.0 (C$_2$ indole and C$_2$ Trp), 126.4 (C$_6$ m,p-dichlorobenzyl), 127.1 (C$_9$ Trp), 127.3 (C$_9$ indole), 128.6 (C$_2$ m,p-dichlorobenzyl), 130.9 (C$_4$ m,p-dichlorobenzyl), 131.3 (C$_5$ m,p-dichlorobenzyl), 132.0 (C$_3$ m,p-dichlorobenzyl), 136.4 (C$_8$ Trp), 136.6 (C$_8$ indole), 137.2 (C$_1$ m,p-dichlorobenzyl), 154.7 (Cq triazole), 155.1 (Cq triazole), 172.0 (CO Aib).

(R)—N-(1-(4-(4-fluorobenzyl)-5-benzyl-4H-1,2,4-triazol-3-yl)-2-(1H-indol-3-yl)ethyl)-2-amino-2-methylpropanamide (Compound 30)

$^1$H NMR (300 MHz, DMSO-d$^6$, 300° K):

δ (ppm) 1.27 (3H, s, CH$_3$ Aib), 1.29 (3H, s, CH$_3$ Aib), 3.33 (2H, m, CH$_2$ βTrp), 4.02 (2H, s, CH$_2$-benzyl), 5.10 (3H, m, CH$_2$-p-fluorobenzyl and CH αTrp), 6.71 (2H, m, H$_3$ and H$_5$ p-fluorobenzyl), 6.80 (1H, t, J$_o$=8 Hz, H$_5$ Trp), 6.90 (2H, d, J$_o$=8 Hz, H$_2$ and H$_6$ p-fluorobenzyl), 6.94 (1H, t, J$_o$=8 Hz, H$_6$ Trp), 6.99-7.10 (4H, m, H$_2$ and H$_4$ Trp, H$_2$ and H$_6$ benzyl), 7.20 (3H, m, H$_3$, H$_4$ and H$_5$ benzyl), 7.27 (1H, d, J$_o$=8 Hz, H$_7$ Trp), 8.09 (3H, brs, NH$_2$ Aib), 8.97 (1H, d, J=8 Hz, NH amide), 10.79 (1H, s, NH indole Trp).

$^{13}$C NMR (75 MHz, DMSO-d$^6$, 300° K):

δ (ppm) 23.5 (CH$_3$ Aib), 23.8 (CH$_3$ Aib), 29.0 (CH$_2$ βTrp), 31.1 (CH$_2$-benzyl), 45.7 (CH$_2$-p-fluorobenzyl), 45.8 (CH αTrp), 56.8 (Cq Aib), 109.6 (C$_3$ Trp), 111.8 (C$_7$ Trp), 115.6 and 115.9 (C$_3$ and C$_5$ p-fluorobenzyl), 118.2 (C$_4$ Trp), 118.7 (C$_5$ Trp), 121.3 (C$_6$ Trp), 124.8 (C$_2$ Trp), 127.1 (C$_4$ benzyl), 127.2 (C$_9$ Trp), 128.8 and 128.9 (C$_2$ and C$_6$ p-fluorobenzyl), 129.4 (C$_2$, C$_3$, C$_5$ and C$_6$ p-fluorobenzyl), 131.6 (C$_1$ p-fluorobenzyl), 135.9 (C$_1$ benzyl), 136.4 (C$_8$ Trp), 154.0 (C$_4$ p-fluorobenzyl), 155.3 (Cq triazole), 172.0 (CO amide).

(R)—N-(1-(4-(4-methylbenzyl)-5-(3-phenylpropyl)-4H-1,2,4-triazol-3-yl)-2-(1H-indol-3-yl)ethyl)-2-amino-2-methylpropanamide (Compound 33)

$^1$H NMR (300 MHz, DMSO-d$^6$, 300° K):

δ (ppm) 1.25 (3H, s, CH$_3$ Aib), 1.28 (3H, s, CH$_3$ Aib), 1.73 (2H, m, CH$_2$—CH$_2$—CH$_2$-phenyl), 2.23 (3H, s, CH$_3$ p-methylbenzyl), 2.49-2.54 (4H, m, CH$_2$—CH$_2$—CH$_2$-phenyl), 3.33 (2H, m, CH$_2$ βTrp), 5.04 (2H, s, CH$_2$-p-methylbenzyl), 5.16 (1H, m, CH αTrp), 6.74 (2H, d, J$_o$=8 Hz, H$_3$ and H$_5$ p-methylbenzyl), 6.80 (1H, t, J$_o$=7 Hz, H$_5$ Trp), 6.98 (1H, t, J$_o$=7 Hz, H$_6$ Trp), 7.03 (1H, d, J=2 Hz, H$_2$ Trp), 7.06 (5H, m, CHar phenyl), 7.14 (1H, d, J$_o$=7 Hz, H$_4$ Trp), 7.20 (2H, d, J$_o$=7 Hz, H$_2$ and H$_6$ p-methylbenzyl), 7.27 (1H, d, 8 Hz, H$_7$ Trp), 8.01 (3H, brs, NH$_2$ Aib), 8.95 (1H, d, J=8 Hz, NH amide), 10.80 (1H, d, J=2 Hz, NH indole Trp).

$^{13}$C NMR (75 MHz, DMSO-d$^6$, 300° K):

δ (ppm) 21.0 (CH$_3$ p-methylbenzyl), 23.5 (CH$_3$ Aib), 23.8 (CH$_3$ Aib), 24.0 (CH$_2$—CH$_2$—CH$_2$-phenyl), 28.5 (CH$_2$—CH$_2$—CH$_2$-phenyl), 29.1 (CH$_2$ βTrp), 34.7 (CH$_2$—CH$_2$—CH$_2$-phenyl), 45.7 (CH αTrp), 45.8 (CH$_2$-p-methylbenzyl), 56.8 (Cq Aib), 109.8 (C$_3$ Trp), 111.8 (C$_7$ Trp), 118.3 (C$_4$ Trp), 118.7 (C$_5$ Trp), 121.3 (C$_6$ Trp), 124.9 (C$_2$ Trp), 126.2 (C$_4$ phenyl), 126.4 (C$_3$ and C$_5$ p-methylbenzyl), 127.3 (C$_6$ Trp), 128.7 (C$_2$, C$_3$, C$_5$ and C$_6$ phenyl), 129.8 (C$_2$ and C$_6$ p-methylbenzyl), 133.0 (C$_1$ p-methylbenzyl), 136.4 (C$_8$ Trp), 137.5 (C$_4$ p-methylbenzyl), 141.7 (C$_1$ phenyl), 154.8 (Cq triazole), 171.9 (CO Aib).

(R)—N-(1-(5-(2-(1H-indol-3-yl)ethyl)-4-(4-methylbenzyl)-4H-1,2,4-triazol-3-yl)-2-(1H-indol-3-yl)ethyl)-2-amino-2-methylpropanamide (Compound 34)

$^1$H NMR (300 MHz, DMSO-d$^6$, 300° K):

δ (ppm) 1.25 (3H, s, CH$_3$ Aib), 1.28 (3H, s, CH$_3$ Aib), 2.23 (3H, s, CH$_3$-p-methylbenzyl), 2.84-2.97 (4H, m, CH$_2$—CH$_2$-indole), 3.32 (2H, m, CH$_2$ βTrp), 5.04 (2H, s, CH$_2$-p-methylbenzyl), 5.16 (1H, m, CH αTrp), 6.79-6.86 (4H, m, CH ar p-methylbenzyl), 6.99-7.05 (4H, m, H$_5$ and H$_6$ indole, H$_5$ and H$_6$ Trp), 7.08 (3H, m, H$_2$ indole, H$_2$ and H$_4$ Trp), 7.25-7.30 (3H, m, H$_4$ and H$_7$ indole, H$_7$ Trp), 8.00 (3H, brs, NH$_2$ Aib), 8.94 (1H, d, J=8 Hz, NH amide), 10.76 (1H, s, NH indole), 10.78 (1H, s, NH indole Trp).

$^{13}$C NMR (75 MHz, DMSO-d$^6$, 300° K):

δ (ppm) 21.0 (CH$_3$-p-methylbenzyl), 22.8 (CH$_2$—CH$_2$-indole), 23.8 (CH$_3$ Aib), 23.9 (CH$_3$ Aib), 25.9 (CH$_2$—CH$_2$-indole), 28.5 (CH$_2$ βTrp), 45.7 (CH$_2$-p-methylbenzyl and CH αTrp), 56.7 (CqAib), 109.9 (C$_3$ Trp), 111.8 (C$_7$ indole and C$_7$ Trp), 113.4 (C$_3$ indole), 118.1 (C$_4$ Trp), 118.3 (C$_4$ indole), 118.5 (C$_5$ indole), 118.7 (C$_5$ Trp), 120.9 (C$_6$ indole and C$_6$ Trp), 121.3 (C$_2$ indole and C$_2$ Trp), 126.3 (C$_3$ and C$_5$ p-methylbenzyl), 127.2 (C$_9$ indole), 127.3 (C$_9$ Trp), 129.8 (C$_2$ and C$_6$ p-methylbenzyl), 133.1 (C$_1$ p-methylbenzyl), 135.8 (C$_8$ indole, C$_8$ Trp), 136.4 (C$_4$ p-methylbenzyl), 154.8 (Cq triazole), 155.0 (Cq triazole), 171.9 (CO Aib).

(R)—N-(1-(4-(4-methylbenzyl)-5-phenethyl-4H-1,2,4-triazol-3-yl)-2-(1H-indol-3-yl)ethyl)-2-amino-2-methylpropanamide (Compound 37)

$^1$H NMR (300 MHz, DMSO-d$^6$, 300° K):

δ (ppm) 1.25 (3H, s, CH$_3$ Aib), 1.28 (3H, s, CH$_3$ Aib), 2.23 (3H, s, CH$_3$ p-methylbenzyl), 2.83 (4H, m, CH$_2$—C2-phenyl), 3.32 (2H, m, CH$_2$ βTrp), 5.05 (2H, s, CH$_2$-p-methylbenzyl), 5.18 (1H, m, CH αTrp), 6.75 (2H, d, J$_o$=8 Hz, H$_3$ and H$_5$ p-methylbenzyl), 6.82 (1H, t, J$_o$=8 Hz, H$_5$ Trp), 6.99 (1H, t, J$_o$=8 Hz, H$_6$ Trp), 7.02-7.11 (6H, m, H$_2$ Trp and CHar phenyl), 7.15 (1H, d, J$_o$=7 Hz, H$_4$ Trp), 7.20 (2H, d, J$_o$=7 Hz, H$_2$ and H$_6$ p-methylbenzyl), 7.28 (1H, d, J$_o$=8 Hz, H$_7$ Trp), 8.01 (3H, brs, NH$_2$ Aib), 8.93 (1H, d, J=8 Hz, NH amide), 10.77 (1H, s, NH indole Trp).

$^{13}$C NMR (75 MHz, DMSO-d$^6$, 300° K):

δ (ppm) 21.0 (CH$_3$ p-methylbenzyl), 23.6 (CH$_3$ Aib), 23.8 (CH$_3$ Aib), 26.5 (CH$_2$—CH$_2$-phenyl), 29.1 (CH$_2$ βTrp), 32.7 (CH$_2$—CH$_2$-phenyl), 45.7 (CH αTrp and CH$_2$-p-methylbenzyl), 56.8 (Cq Aib), 109.8 (C$_3$ Trp), 111.8 (C$_7$ Trp), 118.3 (C$_4$ Trp), 118.7 (C$_5$ Trp), 121.3 (C$_6$ Trp), 124.8 (C$_2$ Trp), 126.4 (C$_3$ and C$_5$ p-methylbenzyl), 126.6 (C$_4$ phenyl), 127.3 (C$_9$ Trp), 128.7 (C$_2$, C$_3$, C$_5$ and C$_6$ phenyl), 129.8 (C$_2$ and C$_6$ p-methylbenzyl), 133.0 (C$_1$ p-methylbenzyl), 136.4 (C$_8$ Trp), 137.5 (C$_4$ p-methylbenzyl), 140.9 (C$_1$ phenyl), 154.5 (Cq triazole), 154.9 (Cq triazole), 171.9 (CO amide).

(R)—N-(1-(5-benzyl-4-(pyridin-2-ylmethyl)-4H-1,2,4-triazol-3-yl)-2-(1H-indol-3-yl)ethyl)-2-amino-2-methylpropanamide (Compound 39)

$^1$H NMR (300 MHz, DMSO-d$^6$, 300° K):

δ (ppm) 1.23 (3H, s, CH$_3$ Aib), 1.27 (3H, s, CH$_3$ Aib), 3.34 (1H, dd, J=14 Hz and 6 Hz, CH$_2$ βTrp), 3.43 (1H, dd, J=14 Hz and 9 Hz, CH$_2$ βTrp), 4.13 (2H, s, CH$_2$-benzyl), 5.22 (1H, s, CH αTrp), 5.35 (2H, s, CH$_2$-o-pyridyl), 6.80 (1H, t, J$_o$=8 Hz, H$_5$ Trp), 6.92 (1H, t, J$_o$=8 Hz, H$_5$ pyridyl), 6.97 (1H, t, J$_o$=8 Hz, H$_6$ Trp), 7.04 (1H, d, J$_o$=8 Hz, H$_4$ Trp), 7.07 (1H, d, J=2 Hz, H$_2$ Trp), 7.10-7.16 (5H, m, CHar benzyl), 7.19 (1H, s, H$_3$ o-pyridyl), 7.26 (1H, d, J$_o$=8 Hz, H$_7$ Trp), 7.57 (1H, t, J$_o$=9 Hz, H$_4$ o-pyridyl), 8.16 (3H, brs, NH$_2$ Aib), 8.36 (1H, d, J$_{αβ}$=5 Hz, H$_6$ o-pyridyl), 9.01 (1H, d, J=8 Hz, NH amide), 10.85 (1H, s, NH indole Trp).

$^{13}$C NMR (75 MHz, DMSO-d$^6$, 300° K):

δ (ppm) 23.4 (CH$_3$ Aib), 23.7 (CH$_3$ Aib), 28.6 (CH$_2$ βTrp), 30.4 (CH$_2$-benzyl), 45.7 (CH αTrp), 47.7 (CH$_2$—o-pyridyl), 56.7 (Cq Aib), 109.8 (C$_3$ Trp), 111.8 (C$_7$ Trp), 118.3 (C$_4$ Trp), 118.6 (C$_5$ Trp), 121.2 (C$_6$ Trp), 121.7 (C$_3$ o-pyridyl), 123.3 (C$_5$ o-pyridyl), 124.8 (C$_2$ Trp), 127.1 (C$_4$ benzyl), 127.3 (C$_9$ Trp), 128.8 (C$_2$ and C$_6$ benzyl), 129.0 (C$_3$ and C$_5$ benzyl), 135.6 (C$_1$ benzyl), 136.4 (C$_8$ Trp), 137.5 (C$_4$ o-pyridyl), 149.5 (C$_6$ o-pyridyl), 154.1 (Cq triazole), 154.2 (Cq triazole), 155.7 (C$_2$ o-pyridyl), 172.0 (CO amide).

(R)—N-(1-(4-(4-ethylbenzyl)-5-phenethyl-4H-1,2,4-triazol-3-yl)-2-(1H-indol-3-yl)ethyl)-2-amino-2-methylpropanamide (Compound 43)

$^1$H NMR (300 MHz, DMSO-d$^6$, 300° K):

δ (ppm) 1.10 (3H, t, J=8 Hz, CH$_3$—CH$_2$ p-ethylbenzyl), 1.25 (3H, s, CH$_3$ Aib), 1.28 (3H, s, CH$_3$ Aib), 2.53 (2H, q, J=8 Hz, CH$_3$—CH$_2$ p-ethylbenzyl), 2.83 (4H, m, CH$_2$—CH$_2$-phenyl), 3.34 (2H, m, CH$_2$ βTrp), 5.07 (2H, s, CH$_2$-p-ethylbenzyl), 5.19 (1H, m, CH αTrp), 6.77 (2H, d, J$_o$=8 Hz, H$_3$ and H$_5$ p-ethylbenzyl), 6.81 (1H, t, J$_o$=7 Hz, H$_5$ Trp), 6.99 (1H, t, J$_o$=8 Hz, H$_6$ Trp), 7.05-7.10 (7H, m, CHar phenyl, H$_2$ and H$_6$ p-ethylbenzyl), 7.13 (1H, d, J=2 Hz, H$_2$ Trp), 7.20 (1H, d, J$_o$=7 Hz, H$_4$ Trp), 7.28 (1H, d, J$_o$=8 Hz, H$_7$ Trp), 8.03 (3H, brs, NH$_2$ Aib), 8.94 (1H, d, J=8 Hz, NH amide), 10.79 (1H, s NH indole Trp).

$^{13}$C NMR (75 MHz, DMSO-d$^6$, 300° K):

δ (ppm) 15.9 (CH$_3$—CH$_2$ p-ethylbenzyl), 23.5 (CH$_3$ Aib), 23.8 (CH$_3$ Aib), 26.5 (CH$_2$—CH$_2$-phenyl), 28.1 (CH$_3$—CH$_2$ p-ethylbenzyl), 29.1 (CH$_2$ βTrp), 32.7 (CH$_2$—CH$_2$-phenyl), 45.7 (CH αTrp), 45.8 (CH$_2$-p-ethylbenzyl), 56.8 (Cq Aib), 109.8 (C$_3$ Trp), 111.8 (C$_7$ Trp), 118.3 (C$_4$ Trp), 118.7 (C$_5$ Trp), 121.3 (C$_6$ Trp), 124.9 (C$_2$ Trp), 126.5 (C$_3$ and C$_5$ p-ethylbenzyl), 126.6 (C$_4$ phenyl), 127.3 (C$_9$ Trp), 128.6 (C$_2$ and C$_6$ p-ethylbenzyl, C$_2$, C$_3$, C$_5$ and C$_6$ phenyl), 133.1 (C$_1$ p-ethylbenzyl), 136.5 (C$_8$ Trp), 140.8 (C$_1$ phenyl), 143.8 (C$_4$ p-ethylbenzyl), 154.6 (Cq triazole), 154.9 (Cq triazole), 171.9 (CO amide).

(R)—N-(1-(4-(4-methoxybenzyl)-5-phenethyl-4H-1,2,4-triazol-3-yl)-2-(1H-indol-3-yl)ethyl)piperidine-4-carboxamide (Compound 44)

$^1$H NMR (300 MHz, DMSO d$^6$, 300° K):

δ (ppm) 1.42 (m, 2H, H$_3$ and H$_5$ piperidyl), 1.55 (m, 1H, H$_5$ piperidyl), 2.23 (m, 1H, H$_4$ piperidyl), 2.75 (m, 5H, H$_2$ piperidyl and CH$_2$—CH$_2$-phenyl), 3.04 (m, 1H, H$_6$ piperidyl), 3.13 (m, 1H, H$_2$ piperidyl), 3.32 (m, 2H, CH$_2$ βTrp), 3.66 (s, 3H, OCH$_3$), 4.97 (m, 2H, CH$_2$-p-methoxybenzyl), 5.23 (m, 1H, CH αTrp), 6.70 (s, 4H, CHar p-methoxybenzyl), 6.87 (t, 1H, J$_o$=8 Hz, H$_5$ Trp), 7.00 (m, 2H, H$_2$ and H$_6$ Trp), 7.07 (d, 2H, J$_o$=8 Hz, H$_2$ and H$_6$ phenyl), 7.14 (d, 1H, J$_o$=7 Hz, H$_4$ Trp), 7.18-7.30 (m, 4H, H$_7$ Trp, H$_3$, H$_4$ and H$_5$ phenyl), 8.16 and 8.46 (2 m, 2H, NH piperidyl TFA salt), 8.66 (d, 1H, J=8 Hz, NH amide), 10.75 (1H, s, NH indole Trp).

$^{13}$C NMR (75 MHz, DMSO d$^6$, 300° K):

δ (ppm) 24.9 (C$_3$ piperidyl), 25.4 (C$_5$ piperidyl), 26.5 (CH$_2$—CH$_2$-phenyl), 29.2 (CH$_2$ βTrp), 32.7 (CH$_2$—CH$_2$-phenyl), 38.7 (C$_4$ piperidyl), 42.7 (C$_2$ and C$_6$ piperidyl), 44.7 (CH Trp), 45.3 (CH$_2$-p-methoxybenzyl), 55.5 (OCH$_3$), 110.2 (C$_3$ Trp), 111.7 (C$_7$ Trp), 114.4 (C$_3$ and C$_5$ p-methoxybenzyl), 118.5 (C$_4$ Trp), 118.7 (C$_5$ Trp), 121.3 (C$_6$ Trp), 124.4 (C$_2$ Trp), 126.5 (C$_2$ and C$_6$ phenyl), 127.5 (C$_9$ Trp), 127.8 (C$_1$, C$_2$ and C$_6$ p-methoxybenzyl), 128.7 (C$_3$, C$_4$ and C$_5$ phenyl), 136.4 (C$_8$ Trp), 140.8 (C$_1$ phenyl), 155.3 (Cq triazole), 155.4 (Cq triazole), 159.1 (C$_4$ p-methoxybenzyl), 173.1 (CO amide).

(R)—N-(1-(5-(2-(1H-indol-3-yl)ethyl)-4-(4-methoxybenzyl)-4H-1,2,4-triazol-3-yl)-2-(1H-indol-3-yl)ethyl)piperidine-4-carboxamide (Compound 45)

$^1$H NMR (300 MHz, DMSO d$^6$, 300° K):

δ (ppm) 1.41 (m, 2H, H$_3$ and H$_5$ piperidyl), 1.54 (dd, 1H, J=13 Hz and 2 Hz, H$_5$ piperidyl), 2.23 (m, 1H, H$_4$ piperidyl), 2.72 (m, 2H, H$_2$ and H$_6$ piperidyl), 2.77-2.93 (m, 4H, CH$_2$—CH$_2$-indole), 3.06 (m, 2H, H$_2$ and H$_6$ piperidyl), 3.32 (m, 2H, CH$_2$ βTrp), 3.65 (s, 3H, OCH$_3$), 4.94 (s, 2H, CH$_2$-p-methoxybenzyl), 5.22 (m, 1H, CH αTrp), 6.68 (s, 4H, CHar p-methoxybenzyl), 6.87 (m, 3H, H$_5$ and H$_6$ Trp, H$_5$ indole), 6.98 (m, 4H, H$_2$ and H$_6$ indole, H$_2$ and H$_4$ Trp), 7.20-7.33 (m, 3H, H$_4$ and H$_7$ indole, H$_7$ Trp), 8.15 and 8.46 (2 m, 2H, NH piperidyl TFA salt), 8.64 (d, 1H, J=8 Hz, NH amide), 10.74 (s, 2H, NH indole and NH indole Trp).

$^{13}$C NMR (75 MHz, DMSO d$^6$, 300° K):

δ (ppm) 22.9 (CH$_2$—CH$_2$-indole), 24.9 (C$_3$ piperidyl), 25.4 (C$_5$ piperidyl), 26.0 (CH$_2$—CH$_2$-indole), 29.3 (CH$_2$ βTrp), 39.1 (C$_4$ piperidyl), 42.7 (C$_2$ and C$_6$ piperidyl), 44.7 (CH αTrp), 45.3 (CH$_2$-p-methoxybenzyl), 55.5 (OCH$_3$), 109.5 (C$_3$ Trp), 111.7 (C$_7$ indole and C$_7$ Trp), 113.5 (C$_3$ indole), 114.4 (C$_3$ and C$_5$ p-methoxybenzyl), 118.5 (C$_4$ indole and C$_4$ Trp), 118.6 (C$_5$ indole and C$_5$ Trp), 121.2 (C$_6$ indole), 121.3 (C$_6$ Trp), 122.9 (C$_2$ indole and C$_2$ Trp), 127.2 (C$_9$ indole), 127.6 (C$_9$ Trp, C$_2$ and C$_6$ p-methoxybenzyl), 127.9 (C$_1$ p-methoxybenzyl), 136.4 (C$_8$ Trp), 136.6 (C$_8$ indole), 154.9 (Cq triazole), 155.2 (Cq triazole), 159.0 (C$_4$ p-methoxybenzyl), 173.0 (CO amide).

(R)—N-(1-(4-(4-methoxybenzyl)-5-phenethyl-4H-1,2,4-triazol-3-yl)-2-(1H-indol-3-yl)ethyl)-2-aminoacetamide (Compound 50)

$^1$H NMR (300 MHz, DMSO d$^6$, 300° K):

δ (ppm) 2.78 (m, 4H, CH$_2$—CH$_2$-phenyl), 3.26 (1H, dd, J=14 Hz and 7 Hz, CH$_2$ βTrp), 3.39 (m, 3H, CH$_2$ βTrp and CH$_2$—NH$_2$), 3.65 (s, 3H, OCH$_3$), 4.95 (m, 2H, CH$_2$-p-methoxybenzyl), 5.20 (m, 1H, CH αTrp), 6.63 (s, 4H, CHar p-methoxybenzyl), 6.86 (t, 1H, J$_o$=7 Hz, H$_5$ Trp), 6.99 (s, 1H, H$_2$ Trp), 7.02 (t, 1H, J$_o$=7 Hz, H$_6$ Trp), 7.10 (m, 2H, H$_2$ and H$_6$ phenyl), 7.15 (d, 1H, J$_o$=7 Hz, H$_4$ Trp), 7.23 (m, 3H, H$_3$, H$_4$ and H$_5$ Trp), 7.31 (d, 1H, J$_o$=8 Hz, H$_7$ Trp), 7.95 (brs, 3H, NH$_2$ Gly, TFA salt), 9.20 (d, 1H, J=8 Hz, NH amide), 10.82 (s, 1H, NH indole Trp).

$^{13}$C NMR (75 MHz, DMSO d$^6$, 300° K):

δ (ppm) 26.5 (CH$_2$—CH$_2$-phenyl), 29.8 (CH$_2$ βTrp), 32.7 (CH$_2$—CH$_2$-phenyl), 39.0 (CH$_2$—NH$_2$), 45.3 (CH$_2$-p-methoxybenzyl), 45.4 (CH αTrp), 55.4 (OCH$_3$), 109.7 (C$_3$ Trp), 111.8 (C$_7$ Trp), 114.5 (C$_3$ and C$_5$ p-methoxybenzyl), 118.3 (C$_4$ Trp), 118.9 (C$_5$ Trp), 121.4 (C$_6$ Trp), 124.6 (C$_2$ Trp), 126.5 (C$_2$ and C$_6$ phenyl), 127.3 (C$_9$ Trp), 127.7 (C$_1$ p-methoxybenzyl), 127.8 (C$_2$ and C$_6$ p-methoxybenzyl), 128.7 (C$_3$, C$_4$ and C$_5$ phenyl), 136.4 (C$_8$ Trp), 140.9 (C$_1$ phenyl), 154.3 (Cq triazole), 154.8 (Cq triazole), 159.0 (C$_4$ p-methoxybenzyl), 166.1 (CO amide).

(R)—N-(1-(4-(4-methoxybenzyl)-5-phenethyl-4H-1,2,4-triazol-3-yl)-2-(1H-indol-3-yl)ethyl)-2-(pyridin-2-yl)acetamide (Compound 51)

$^1$H NMR (300 MHz, DMSO d$^6$, 300° K):

δ (ppm) 2.77-2.88 (m, 4H, CH$_2$—CH$_2$-phenyl), 3.37 (m, 2H, CH$_2$ βTrp), 3.64 (s, 3H, OCH$_3$), 3.74 (m, 2H, CH$_2$-o-pyridyl), 5.03 (m, 2H, CH$_2$-p-methoxybenzyl), 5.24 (m, 1H, CH αTrp), 6.65 (s, 4H, CHar p-methoxybenzyl), 6.85 (t, 1H, J$_o$=7 Hz, H$_5$ Trp), 7.01 (m, 2H, H$_2$ and H$_6$ Trp), 7.08 (d, 2H, J$_o$=7 Hz, H$_2$ and H$_6$ phenyl), 7.15 (d, 1H, J$_o$=7 Hz, H$_4$ Trp), 7.21 (m, 3H, H$_3$, H$_4$ and H$_5$ phenyl), 7.27-7.36 (m, 2H, H$_7$ Trp and H$_3$ o-pyridyl), 7.58 (t, 1H, J=6 Hz, H$_5$ o-pyridyl), 8.04 (t, 1H, J$_o$=8 Hz, H$_4$ o-pyridyl), 8.62 (d, 1H, J$_{αβ}$=5 Hz, H$_6$ o-pyridyl), 9.17 (d, 1H, J=8 hz, NH amide), 10.81 (s, 1H, NH indole Trp).

$^{13}$C NMR (75 MHz, DMSO d$^6$, 300° K):

δ (ppm) 26.4 (CH$_2$—CH$_2$-phenyl), 29.2 (CH$_2$ βTrp), 32.4 (CH$_2$—CH$_2$-phenyl), 41.7 (CH$_2$—O— pyridyl), 45.3 (CH αTrp), 45.7 (CH$_2$-p-methoxybenzyl), 55.5 (OCH$_3$), 109.7 (C$_3$ Trp), 111.8 (C$_7$ Trp), 114.4 (C$_3$ and C$_5$ p-methoxybenzyl), 118.4 (C$_4$ Trp), 118.8 (C$_5$ Trp), 121.4 (C$_6$ Trp), 124.1 (C$_3$ o-pyridyl), 124.6 (C$_2$ Trp), 126.4 (C$_5$ o-pyridyl), 126.6 (C$_2$ and C$_6$ phenyl), 127.2 (C$_9$ Trp), 127.4 (C$_1$ p-methoxybenzyl), 127.9 (C$_2$ and C$_6$ p-methoxybenzyl), 128.7 (C$_3$, C$_4$ and C$_5$ phenyl), 136.4 (C$_8$ Trp), 140.5 (C$_1$ phenyl), 142.1 (C$_4$ o-pyridyl), 145.3 (C$_6$ o-pyridyl), 153.0 (C$_2$ o-pyridyl), 154.5 (Cq triazole), 155.3 (Cq triazole), 159.1 (C$_4$ p-methoxybenzyl), 167.9 (CO amide).

(R)—N-(1-(4-(2,4-dimethoxybenzyl)-5-phenethyl-4H-1,2,4-triazol-3-yl)-2-(1H-indol-3-yl)ethyl)picolinamide (Compound 64)

$^1$H NMR (300 MHz, DMSO d$^6$, 300° K):

δ (ppm) 2.83 (m, 2H, CH$_2$—CH$_2$-phenyl), 2.90 (m, 2H, CH$_2$—CH$_2$-phenyl), 3.48 (m, 2H, CH$_2$ βTrp), 3.57 (s, 3H, OCH$_3$), 3.61 (s, 3H, OCH$_3$), 4.97 (d, 1H, J=17 Hz, CH$_2$-o,p-dimethoxybenzyl), 5.09 (d, 1H, J=17 Hz, CH$_2$-o,p-dimethoxybenzyl), 5.56 (m, 1H, CH αTrp), 6.18 (dd, 1H, J$_o$=8 Hz and J$_m$=2 Hz, H$_5$ o,p-dimethoxybenzyl), 6.41 (d, 1H, J$_m$=2 Hz, H$_3$ o,p-dimethoxybenzyl), 6.55 (d, 1H, J$_o$=8 Hz, H$_6$ o,p-dimethoxybenzyl), 6.87 (t, 1H, J$_o$=8 Hz, H$_5$ Trp), 7.01 (t, 1H, J$_o$=8 Hz, H$_6$ Trp), 7.08 (m, 3H, H$_2$ Trp, H$_2$ and H$_6$ phenyl), 7.14 (d, 1H, J$_o$=7 Hz, H$_4$ Trp), 7.19-7.31 (m, 4H, H$_7$ Trp, H$_3$, H$_4$ and H$_5$ phenyl), 7.56 (t, 1H, J=8 Hz, NH amide), 7.91 (m, 2H, H$_4$ and H$_5$ o-pyridyl), 8.57 (d, 1H, J$_{up}$=5 Hz, H$_6$ o-pyridyl), 9.16 (d, 1H, J$_o$=8 Hz, H$_3$ o-pyridyl), 10.80 (s, 1H, NH indole Trp).

$^{13}$C NMR (75 MHz, DMSO d$^6$, 300° K):

δ (ppm) 26.2 (CH$_2$—CH$_2$-phenyl), 28.8 (CH$_2$ βTrp), 32.1 (CH$_2$—CH$_2$-phenyl), 43.0 (CH$_2$-o,p-dimethoxybenzyl), 45.5 (CH αTrp), 55.6 (OCH$_3$), 55.8 (OCH$_3$), 98.9 (C$_3$ o,p-dimethoxybenzyl), 105.0 (C$_5$ o,p-dimethoxybenzyl), 109.5 (C$_3$ Trp), 111.8 (C$_7$ Trp), 114.4 (C$_1$ o,p-dimethoxybenzyl), 118.4 (C$_4$ Trp), 118.8 (C$_5$ Trp), 121.4 (C$_6$ Trp), 122.4 (C$_3$ o-pyridyle), 124.4 (C$_2$ Trp), 126.7 (C$_6$ o,p-dimethoxybenzyl), 127.2 (C$_5$ o-pyridyle), 127.5 (C$_9$ Trp), 128.6-128.8 (C$_2$, C$_3$, C$_4$, C$_5$ and C$_6$ phenyl), 136.4 (C$_8$ Trp), 138.1 (C$_4$ o-pyridyle), 140.2 (C$_1$ phenyl), 148.8 (C$_6$ o-pyridyle), 149.3 (C$_2$ o-pyridyle), 155.2 (Cq triazole), 155.4 (Cq triazole), 157.9 (C$_2$ o,p-dimethoxybenzyl), 161.0 (C$_4$ o,p-dimethoxybenzyl), 163.9 (CO amide).

(R)—N-(1-(4-(2,4-dimethoxybenzyl)-5-phenethyl-4H-1,2,4-triazol-3-yl)-2-(1H-indol-3-yl)ethyl)pyrazine-2-carboxamide (Compound 66)

$^1$H NMR (300 MHz, DMSO d$^6$, 300° K):

δ (ppm) 2.87 (m, 4H, CH$_2$—CH$_2$-phenyl), 3.51 (m, 2H, CH$_2$ βTrp), 3.58 (s, 3H, OCH$_3$), 3.59 (s, 3H, OCH$_3$), 4.97 (d, 1H, J=17 Hz, CH$_2$-o,p-dimethoxybenzyl), 5.08 (d, 1H, J=17 Hz, CH$_2$-o,p-dimethoxybenzyl), 5.56 (s, 1H, CH αTrp), 6.10 (dd, 1H, J$_o$=8 Hz and J$_m$=2 Hz, H$_5$ o,p-dimethoxybenzyl), 6.36 (d, 1H, Jm=2 Hz, H$_3$ o,p-dimethoxybenzyl), 6.40 (d, 1H, J$_o$=8 Hz, H$_6$ o,p-dimethoxybenzyl), 6.87 (t, 1H, J$_o$=8 Hz, H$_5$ Trp), 7.00 (t, 1H, J$_o$=7 Hz, H$_6$ Trp), 7.09 (m, 3H, H$_2$ Trp, H$_2$ and H$_6$ phenyl), 7.15 (d, 1H, J$_o$=7 Hz, H$_4$ Trp), 7.19-7.28 (m, 3H, H$_3$, H$_4$ and H$_5$ phenyl), 7.36 (d, 1H, J$_o$=8 Hz, H$_7$ Trp), 8.61 (t, 1H, J=2 Hz, H$_3$ o-pyrazinyl), 8.78 (d, 1H, J=2 Hz, H$_5$ o-pyrazinyl), 8.94 (d, 1H, J=1 Hz, H$_6$ o-pyrazinyl), 9.26 (d, 1H, J=8 Hz, NH amide), 10.78 (s, 1H, NH indole Trp).

$^{13}$C NMR (75 MHz, DMSO d$^6$, 300° K):

δ (ppm) 26.1 (CH$_2$—CH$_2$-phenyl), 28.4 (CH$_2$ βTrp), 32.1 (CH$_2$—CH$_2$-phenyl), 42.9 (CH$_2$-o,p-dimethoxybenzyl), 45.5 (CH αTrp), 55.5 (OCH$_3$), 55.8 (OCH$_3$), 98.7 (C$_3$ o,p-dimethoxybenzyl), 104.9 (C$_5$ o,p-dimethoxybenzyl), 109.7 (C$_3$ o,p-dimethoxybenzyl), 111.8 (C$_7$ Trp), 114.5 (C$_1$ o,p-dimethoxybenzyl), 118.5 (C$_4$ Trp), 118.8 (C$_5$ Trp), 121.4 (C$_6$ Trp), 124.4 (C$_2$ Trp), 126.7 (C$_6$ o,p-dimethoxybenzyl), 127.5 (C$_9$ Trp), 128.1 (C$_4$ phenyl), 128.7-128.8 (C$_2$, C$_3$, C$_5$ and C$_6$ phenyl), 136.4 (C$_8$ Trp), 140.3 (C$_1$ phenyl), 141.2 (C$_6$ o,p-dimethoxybenzyl), 144.2 (C$_2$ o-pyrazinyl), 144.3 (C$_3$ o-pyrazinyl), 146.8 (C$_5$ o-pyrazinyl), 155.2 (Cqs triazole), 157.7 (C$_2$ o,p-dimethoxybenzyl), 160.7 (CO amide), 162.9 (C$_4$ o,p-dimethoxybenzyl).

(S)—N—((R)-1-(5-(2-(1H-indol-3-yl)ethyl)-4-(2,4-dimethoxybenzyl)-4H-1,2,4-triazol-3-yl)-2-(1H-indol-3-yl)ethyl)pyrrolidine-2-carboxamide (Compound 70)

$^1$H NMR (300 MHz, DMSO d$^6$, 300° K):

δ (ppm) 1.40 (m, 1H, H$_3$ Pro), 1.53 (m, 1H, H$_4$ Pro), 1.71 (m, 1H, H$_4$ Pro), 2.09 (m, 1H, H$_3$ Pro), 2.90 (m, 4H, CH$_2$—CH$_2$-indole), 3.06 (t, 2H, J=6 Hz, H$_5$ Pro), 3.28 (m, 2H, CH$_2$ βTrp), 3.40 (s, 3H, OCH$_3$), 3.80 (s, 3H, OCH$_3$), 3.80 (m, 1H, CH αPro), 4.80 (d, 1H, J=17 Hz, CH$_2$-o,p-dimethoxybenzyl), 5.4 (d, 1H, J=17 Hz, CH$_2$-o,p-dimethoxybenzyl), 5.1 (m, 1H, CH αTrp), 6.26 (dd, 1H, J$_o$=8 Hz and J$_m$=2 Hz, H$_5$ o,p-dimethoxybenzyl), 6.38 (d, 1H, J$_o$=8 Hz, H$_6$ o,p-dimethoxybenzyl), 6.53 (d, 1H, J$_m$=2 Hz, H$_3$ o,p-dimethoxybenzyl), 6.84 (t, 1H, H$_5$ indole), 6.91 (t, 1H, J$_o$=8 Hz, H$_5$ Trp), 6.93-7.07 (m, 4H, H$_2$ and H$_6$ indole, H$_2$ and H$_6$ Trp), 7.16 (d, 1H, J$_o$=8 Hz, H$_4$ Trp), 7.29 (m, 3H, H$_4$ and H$_7$ indole, H$_7$ Trp), 8.39 and 9.10 (2 m, 2H, NH Pro TFA salt), 9.22 (d, 1H, J=8 Hz, NH amide), 10.76 (s, 1H, NH indole), 10.80 (s, 1H, NH indole Trp).

$^{13}$C NMR (75 MHz, DMSO d$^6$, 300° K):

δ (ppm) 22.9 (CH$_2$—CH$_2$-indole), 23.5 (C$_4$ Pro), 25.8 (CH$_2$—CH$_2$-indole), 29.6 (CH$_2$ βTrp), 29.8 (C$_3$ Pro), 41.9 (CH$_2$-o,p-dimethoxybenzyl), 45.2 (CH αTrp), 46.0 (C$_5$ Pro), 55.7 (OCH$_3$), 55.9 (OCH$_3$), 59.3 (CH αPro), 99.0 (C$_3$ o,p-dimethoxybenzyl), 105.1 (C$_5$ o,p-dimethoxybenzyl), 109.7 (C$_3$ Trp), 111.8 (C$_7$ indole and C$_7$ Trp), 113.4 (C$_3$ indole), 115.6 (C$_1$ o,p-dimethoxybenzyl), 118.4 (C$_4$ indole and C$_4$ Trp), 118.7 (C$_5$ indole and C$_5$ Trp), 121.4 (C$_6$ indole and C$_6$ Trp), 123.0 (C$_2$ indole and C$_2$ Trp), 127.2 (C$_9$ indole), 127.3 (C$_9$ Trp), 128.1 (C$_6$ o,p-dimethoxybenzyl), 136.5 (C$_8$ Trp), 136.6 (C$_8$ indole), 155.0 (Cq triazole), 157.8 (C$_2$ o,p-dimethoxybenzyl), 160.9 (C$_4$ o,p-dimethoxybenzyl), 168.1 (CO amide).

(R)—N-(1-(5-(2-(1H-indol-3-yl)ethyl)-4-(2,4-dimethoxybenzyl)-4H-1,2,4-triazol-3-yl)-2-(1H-indol-3-yl)ethyl)pyrazine-2-carboxamide (Compound 71)

$^1$H NMR (300 MHz, DMSO d$^6$, 300° K):

δ (ppm) 3.01 (m, 2H, CH$_2$—CH$_2$-indole), 3.10 (m, 2H, CH$_2$—CH$_2$-indole), 3.51 (m, 2H, CH$_2$ βTrp), 3.55 (s, 3H, OCH$_3$), 3.57 (s, 3H, OCH$_3$), 5.15 (d, 2H, J=7 Hz, CH$_2$-o,p-dimethoxybenzyl), 5.63 (m, 1H, CH αTrp), 6.08 (dd, 1H, J$_o$=8 Hz and J$_m$=2 Hz, H$_5$ o,p-dimethoxybenzyl), 6.35 (d, 1H, J$_m$=2 Hz, H$_3$ o,p-dimethoxybenzyl), 6.53 (d, 1H, J$_o$=8 Hz, H$_6$ o,p-dimethoxybenzyl), 6.89 (m, 2H, H$_5$ indole and H$_5$ Trp), 6.99 (m, 2H, H$_6$ indole and H$_6$ Trp), 7.08 (m, 2H, H$_2$ indole and H$_2$ Trp), 7.29 (m, 3H, H$_4$ Trp, H$_4$ and H$_7$ indole), 7.41 (d, 1H, J$_o$=8 Hz, H$_7$ Trp), 8.61 (t, 1H, J=2 Hz, H$_3$ o-pyrazine), 8.79 (d, 1H, J=2 Hz, H$_5$ o-pyrazine), 8.94 (d, 1H, J=1 Hz, H$_6$ o-pyrazine), 9.43 (d, 1H, J=8 Hz, NH amide), 10.84 (s, 2H, NH indole and NH indole Trp).

$^{13}$C NMR (75 MHz, DMSO d$^6$, 300° K):

δ (ppm) 22.0 (CH$_2$—CH$_2$-indole), 25.3 (CH$_2$—CH$_2$-indole), 27.9 (CH$_2$ βTrp), 44.1 (CH$_2$-o,p-dimethoxybenzyl), 45.5 (CH αTrp), 55.5 (OCH$_3$), 55.8 (OCH$_3$), 98.8 (C$_3$ o,p-dimethoxybenzyl), 104.9 (C$_5$ o,p-dimethoxybenzyl), 109.3 (C$_3$ Trp), 111.8 (C$_7$ indole and C$_7$ Trp), 112.1 (C$_3$ indole), 113.4 (C$_1$ o,p-dimethoxybenzyl), 118.4 (C$_4$ indole), 118.5 (C$_4$ Trp), 118.8 (C$_5$ indole and C$_5$ Trp), 121.5 (C$_6$ indole and C$_6$ Trp), 127.0 (C$_9$ indole), 127.4 (C$_9$ Trp), 136.4 (C$_8$ Trp), 136.6 (C$_8$ indole), 141.2 (C$_6$ o-pyrazine), 144.1 (C$_2$ o-pyrazine), 144.3 (C$_3$ o-pyrazine), 146.8 (C$_5$ o-pyrazine), 155.4 (Cq triazole), 156.0 (Cq triazole), 157.8 (C$_2$ o,p-dimethoxybenzyl), 161.0 (CO amide), 163.2 (C$_4$ o,p-dimethoxybenzyl).

(R)—N-(1-(5-(2-(1H-indol-3-yl)ethyl)-4-(2,4-dimethoxybenzyl)-4H-1,2,4-triazol-3-yl)-2-(1H-indol-3-yl)ethyl)picolinamide (Compound 73)

$^1$H NMR (300 MHz, DMSO d$^6$, 300° K):

δ (ppm) 2.94 (m, 4H, CH$_2$—CH$_2$-indole), 3.47 (m, 2H, CH$_2$ βTrp), 3.57 (s, 3H, OCH$_3$), 3.60 (s, 3H, OCH$_3$), 5.05 (m, 2H, CH$_2$-o,p-dimethoxybenzyl), 5.56 (m, 1H, CH αTrp), 6.14 (dd, 1H, J$_o$=8 Hz and J$_m$=2 Hz, H$_5$ o,p-dimethoxybenzyl), 6.41 (d, 1H, J$_m$=2 Hz, H$_3$ o,p-dimethoxybenzyl), 6.52 (d, 1H, J$_o$=8 Hz, H$_6$ o,p-dimethoxybenzyl), 6.88 (t, 2H, J$_o$=7 Hz, H$_5$ indole and H$_5$ Trp), 6.99 (t, 1H, J$_o$=8 Hz, H$_6$ Trp), 7.01 (t, 1H, J$_o$=8 Hz, H$_6$ indole), 7.04 (d, 1H, J=2 Hz, H$_2$ Trp), 7.07 (d, 1H, J=2 Hz, H$_2$ indole), 7.27-7.33 (m, 4H, H$_4$ and H$_7$ Trp, H$_4$ and H$_7$ indole), 7.55 (m, 1H, NH amide), 7.90 (m, 2H, H$_4$ and H$_5$ o-pyridyl), 8.57 (d, 1H, J$_{αβ}$=4 Hz, H$_6$ o-pyridyl), 9.15 (d, 1H, J=8 Hz, H$_3$ o-pyridyl), 10.78 (brs, 2H NH indole and NH indole Trp).

$^{13}$C NMR (75 MHz, DMSO d$^6$, 300° K):

δ (ppm) 22.3 (CH$_2$—CH$_2$-indole), 25.6 (CH$_2$—CH$_2$-indole), 28.9 (CH$_2$ βTrp), 43.1 (CH$_2$-o,p-dimethoxybenzyl), 45.5 (CH αTrp), 55.5 (OCH$_3$), 55.8 (OCH$_3$), 98.9 (C$_3$ o,p-dimethoxybenzyl), 105.0 (C$_5$ o,p-dimethoxybenzyl), 109.5 (C$_3$ Trp), 111.8 (C$_7$ indole and C$_7$ Trp), 112.8 (C$_3$ indole), 114.4 (C$_1$ o,p-dimethoxybenzyl), 118.4 (C$_4$ indole and C$_4$ Trp), 118.7 (C$_5$ indole), 118.8 (C$_6$ Trp), 121.4 (C$_6$ indole and C$_6$ Trp), 122.5 (O$_2$ indole and C$_3$ o-pyridyl), 123.1 (C$_2$ Trp), 127.1 (C$_5$ o-pyridyl), 127.2 (C$_9$ indole), 127.5 (C$_9$ Trp), 128.6 (C$_6$ o,p-dimethoxybenzyl), 136.4 (C$_8$ Trp), 136.6 (C$_8$ indole), 139.1 (C$_4$ o-pyridyl), 146.6 (C$_6$ o-pyridyl), 150.6 (C$_2$ o-pyridyl), 155.5 (Cq triazole), 155.6 (Cq triazole), 157.8 (C$_2$ o,p-dimethoxybenzyl), 161.0 (C$_4$ o,p-dimethoxybenzyl), 163.9 (CO amide).

(R)-1-(5-(2-(1H-indol-3-yl)ethyl)-4-(2,4-dimethoxybenzyl)-4H-1,2,4-triazol-3-yl)-2-(1H-indol-3-yl)ethanamine (Compound 74)

$^1$H NMR (300 MHz, DMSO d$^6$, 300° K):

δ (ppm) 2.79 (m, 2H, CH$_2$—CH$_2$-indole), 2.86 (m, 2H, CH$_2$—CH$_2$-indole), 3.30 (dd, 1H, $^3$J=14 Hz and 5 Hz, CH$_2$ βTrp), 3.38 (dd, 1H, $^3$J=14 Hz and 6 Hz, CH$_2$ βTrp), 3.62 (s, 3H, OCH$_3$), 3.63 (s, 3H, OCH$_3$), 4.47 (d, 1H, $^3$J=17 Hz, CH$_2$-o,p-dimethoxybenzyl), 4.59 (d, 1H, $^3$J=17 Hz, CH$_2$-o,p-dimethoxybenzyl), 6.11 (dd, 1H, J$_o$=8 Hz and J$_m$=2 Hz, H$_5$ o,p-dimethoxybenzyl), 6.20 (d, 1H, J$_o$=8 Hz, H$_6$ o,p-dimethoxybenzyl), 6.45 (d, 1H, J$_m$=2 Hz, H$_3$ o,p-dimethoxybenzyl), 6.87 (t, 1H, J$_o$=8 Hz, H$_5$ Trp), 6.91 (t, 1H, J$_o$=8 Hz, H$_5$ indole), 7.00-7.04 (m, 2H, H$_6$ indole and H$_6$ Trp), 7.07 (s, 1H, H$_2$ indole), 7.09 (s, 1H, H$_2$ Trp), 7.17-7.35 (m, 4H, H$_4$ and H$_7$ indole, H$_4$ and H$_7$ Trp), 8.75 (brs, 3H, NH$_2$ TFA salt), 10.78 (s, 1H, NH indole), 11.00 (s, 1H, NH indole Trp).

$^{13}$C NMR (75 MHz, DMSO d$^6$, 300° K):

δ (ppm) 22.9 (CH$_2$—CH$_2$-indole), 25.7 (CH$_2$—CH$_2$-indole), 29.9 (CH$_2$ βTrp), 41.5 (CH$_2$-o,p-dimethoxybenzyl), 46.5 (CH αTrp), 55.6 (OCH$_3$), 55.9 (OCH$_3$), 98.8 (C$_3$ o,p-dimethoxybenzyl), 105.0 (C$_6$ o,p-dimethoxybenzyl), 107.4 (C$_3$ Trp), 111.8 (C$_7$ indole and C$_7$ Trp), 113.4 (C$_3$ indole), 115.1 (C$_1$ o,p-dimethoxybenzyl), 118.0 (C$_4$ indole), 118.4 (C$_4$ Trp), 118.6 (C$_5$ Trp), 119.0 (C$_5$ indole), 121.3 (C$_6$ Trp), 121.6 (C$_6$ indole), 122.9 (C$_2$ indole), 125.4 (C$_2$ Trp), 127.1 (C$_9$ indole and C$_9$ Trp), 128.5 (C$_6$ o,p-dimethoxybenzyl), 136.5 (C$_8$ Trp), 136.6 (C$_8$ indole), 152.3 (Cq triazole), 155.6 (Cq triazole), 157.6 (C$_2$ o,p-dimethoxybenzyl), 160.8 (C$_4$ o,p-dimethoxybenzyl).

(R)—N-(1-(4-(4-methoxybenzyl)-5-phenethyl-4H-1,2,4-triazol-3-yl)-2-(1H-indol-3-yl)ethyl)picolinamide (Compound 79)

$^1$H NMR (300 MHz, DMSO d$^6$, 300° K):

δ (ppm) 2.85 (m, 4H, CH$_2$—CH$_2$-phenyl), 3.51 (m, 2H, CH$_2$ βTrp), 3.59 (s, 3H, OCH$_3$), 5.11 (d, 1H, J=17 Hz, CH$_2$-p-methoxybenzyl), 5.23 (d, 1H, J=17 Hz, CH$_2$-p-methoxybenzyl), 5.51 (m, 1H, CH αTrp), 6.59 (d, 2H, J$_o$=8 Hz, H$_3$ and H$_5$ p-methoxybenzyl), 6.73 (d, 2H, J$_o$=8 Hz, H$_2$ and H$_6$ p-methoxybenzyl), 6.87 (t, 1H, J$_o$=8 Hz, H$_5$ Trp), 7.01 (t, 1H, J$_o$=8 Hz, H$_6$ Trp), 7.06 (m, 2H, H$_2$ and H$_6$ phenyl), 7.10 (d, 1H, J=2 Hz, H$_2$ Trp), 7.14 (d, 1H, J$_o$=7 Hz, H$_4$ Trp), 7.24 (m, 3H, H$_3$, H$_4$ and H$_5$ phenyl), 7.34 (d, 1H, J$_o$=8 Hz, H$_7$ Trp), 7.55 (m, 1H, NH amide), 7.88 (m, 2H, H$_4$ and H$_5$ o-pyridyl), 8.56 (d, 1H, J$_{αβ}$=4 Hz, H6 o-pyridyl), 9.20 (d, 1H, J$_o$=8 Hz, H$_3$ o-pyridyl), 10.80 (s, 1H, NH indole Trp).

$^{13}$C NMR (75 MHz, DMSO d$^6$, 300° K):

δ (ppm) 26.2 (CH$_2$—CH$_2$-phenyl), 28.6 (CH$_2$ βTrp), 32.1 (CH$_2$—CH$_2$-phenyl), 45.5 (CH αTrp), 46.2 (CH$_2$-p-methoxybenzyl), 55.4 (OCH$_3$), 109.6 (C$_3$ Trp), 111.8 (C$_7$ Trp), 114.3 (C$_3$ and C$_5$ p-methoxybenzyl), 118.5 (C$_4$ Trp), 118.8 (C$_5$ Trp), 121.4 (C$_6$ Trp), 122.5 (C$_3$ o-pyridyl), 124.5 (C$_2$ Trp), 127.2 (C$_2$ and C$_6$ phenyl), 127.4 (C$_9$ Trp and C$_1$ p-methoxybenzyl), 127.8 (C$_5$ o-pyridyl), 128.7 (C$_2$ and C$_6$ p-methoxybenzyl), 128.8 (C$_3$, C$_4$ and C$_5$ phenyl), 136.4 (C$_8$ Trp), 138.1 (C$_4$ o-pyridyl), 140.3 (C$_1$ phenyl), 148.7 (C$_6$ o-pyridyl), 149.3 (C$_2$ o-pyridyl), 155.0 (Cq triazole), 155.3 (Cq triazole), 159.0 (C$_4$ p-methoxybenzyl), 164.1 (CO amide).

(R)—N-(1-(5-(2-(1H-indol-3-yl)ethyl)-4-(4-methoxybenzyl)-4H-1,2,4-triazol-3-yl)-2-(1H-indol-3-yl)ethyl)picolinamide (Compound 80)

$^1$H NMR (300 MHz, DMSO d$^6$, 300° K):

δ (ppm) 2.95 (m, 4H, CH$_2$—CH$_2$-indole), 3.48 (m, 2H, CH$_2$ βTrp), 3.58 (s, 3H, OCH$_3$), 5.16 (m, 2H, CH$_2$-p-methoxybenzyl), 5.50 (m, 1H, CH αTrp), 6.57 (d, 2H, J$_o$=8 Hz, H$_3$ and H$_5$ p-methoxybenzyl), 6.72 (d, 2H, J$_o$=8 Hz, H$_2$ and H$_6$ p-methoxybenzyl), 6.87 (t, 2H, J$_o$=8 Hz, H$_5$ Trp and H$_5$ indole), 6.96-7.07 (m, 5H, H$_2$ and H$_6$ indole, H$_2$, H$_4$ and H$_6$ Trp), 7.27-7.34 (m, 3H, H$_4$ and H$_7$ indole, H$_7$ Trp), 7.55 (m, 1H, NH amide), 7.88 (m, 2H, H$_4$ and H$_5$ o-pyridyl), 8.56 (d, 1H, J$_{αβ}$=4 Hz, H$_6$ o-pyridyl), 9.18 (d, 1H, J$_o$=8 Hz, H$_3$ o-pyridyl), 10.77 (brs, 2H, NH indole Trp and NH indole).

$^{13}$C NMR (75 MHz, DMSO d$^6$, 300° K):

δ (ppm) 22.4 (CH$_2$—CH$_2$-indole), 25.7 (CH$_2$—CH$_2$-indole), 28.9 (CH$_2$ βTrp), 45.5 (CH αTrp), 46.2 (CH$_2$-p-methoxybenzyl), 55.4 (OCH$_3$), 109.7 (C$_3$ Trp), 111.8 (C$_7$ Trp and C$_7$ indole), 112.6 (C$_3$ indole), 114.3 (C$_3$ and C$_5$ p-methoxybenzyl), 118.4 (C$_4$ Trp and C$_4$ indole), 118.7 (C$_5$ indole), 118.8 (C$_5$ Trp), 121.4 (C$_6$ Trp and C$_6$ indole), 122.4 (C$_3$ o-pyridyl and C$_2$ indole), 124.5 (C$_2$ Trp), 126.7 (C$_9$ indole), 127.1 (C$_9$ Trp), 127.2 (C$_5$ o-pyridyl), 127.5 (C$_1$ p-methoxybenzyl), 127.7 (C$_2$ and C$_6$ p-methoxybenzyl), 136.4 (C$_8$ Trp), 136.6 (C$_8$ indole), 138.1 (C$_4$ o-pyridyl), 148.7 (C$_6$ o-pyridyl), 149.3 (C$_2$ o-pyridyl), 155.3 (Cq triazole), 159.0 (C$_4$ p-methoxybenzyl), 164.0 (CO amide).

(R)—N-1-(5-(2-(1H-indol-3-yl)ethyl)-4-(4-methoxybenzyl)-4H-1,2,4-triazol-3-yl)-2-(1H-indol-3-yl)ethyl)piperazine-2-carboxamide (Compound 81)

$^1$H NMR (300 MHz, DMSO d$^6$, 300° K):

δ (ppm) 2.18 (m, 2H, NH piperazine), 2.96 (m, 6H, H$_2$, H$_5$ and H$_6$ piperazine), 3.34 (d, 2H, J=7 Hz, CH$_2$ βTrp), 3.57 (m, 4H, CH$_2$—CH$_2$-indole), 3.61 (s, 3H, OMe), 3.64 (m, 1H, H$_3$ piperazine), 4.82 (m, 2H, CH$_2$-p-methoxybenzyl), 5.40 (m, 1H, CH αTrp), 6.45 (d, 2H, J$_o$=8 Hz, H$_3$ and H$_5$ p-methoxybenzyl), 6.51 (d, 2H, J$_o$=8 Hz, H$_2$ and H$_6$ p-methoxybenzyl), 6.65-7.47 (m, 10H, CHar, indole and indole Trp), 8.95 (m, 1H, NH amide), 10.88 (d, 1H, J=2 Hz, NH indole), 10.91 (s, 1H, NH indole Trp).

$^{13}$C NMR (75 MHz, DMSO d$^6$, 300° K):

δ (ppm) 22.5 (CH$_2$—CH$_2$-indole), 25.6 (CH$_2$—CH$_2$-indole), 31.3 (CH$_2$ βTrp), 41.9 (CH$_2$-p-methoxybenzyl), 47.7 (CH αTrp, C$_5$ and C$_6$ piperazine), 55.5 (OCH$_3$ and C$_2$ piperazine), 61.1 (C$_3$ piperazine), 109.3 (C$_3$ Trp), 111.7 (C$_7$ indole and C$_7$ Trp), 114.0 (C$_3$ indole), 114.3 (C$_3$ and C$_5$ p-methoxybenzyl), 118.6 (C$_4$ indole), 118.7 (C$_4$ Trp), 118.9 (C$_5$ indole and C$_5$ Trp), 121.4 (C$_6$ indole), 121.5 (C$_6$ Trp), 123.9 (C$_2$ indole and C$_2$ Trp), 127.0 (C$_9$ indole), 127.2 (C$_9$ Trp), 127.7 (C$_1$ p-methoxybenzyl), 128.1 (C$_2$ and C$_6$ p-methoxybenzyl), 136.3 (C$_8$ Trp), 136.5 (C$_8$ indole), 155.5 (Cq triazole), 162.2 (C$_4$ p-methoxybenzyl), 171.1 (CO amide).

(S)—N—((R)-1-(5-(2-(1H-indol-3-yl)ethyl)-4-(4-methoxybenzyl)-4H-1,2,4-triazol-3-yl)-2-(1H-indol-3-yl)ethyl)pyrrolidine-2-carboxamide (Compound 89)

$^1$H NMR (300 MHz, DMSO d$^6$, 300° K):

δ (ppm) 1.42 (m, 1H, H$_3$ Pro), 1.52 (m, 1H, H$_4$ Pro), 1.72 (m, 1H, H$_4$ Pro), 2.07 (m, 1H, H$_3$ Pro), 2.94 (m, 4H, CH$_2$—CH$_2$-indole), 3.05 (t, 2H, J=6 Hz, H$_5$ Pro), 3.30 (m, 2H, CH$_2$ βTrp), 3.67 (s, 3H, OCH$_3$), 3.96 (m, 1H, CH αPro), 5.02 (s, 2H, CH$_2$-p-methoxybenzyl), 5.19 (m, 1H, CH αTrp), 6.73 (s, 4H, CHar p-methoxybenzyl), 6.84 (t, 1H, J$_o$=8 Hz, H$_5$ indole), 6.90 (t, 1H, J$_o$=8 Hz, H$_5$ Trp), 6.93-7.06 (m, 4H, H$_2$ and H$_6$ indole, H$_2$ and H$_6$ Trp), 7.17 (d, 1H, J$_o$=8 Hz, H$_4$ Trp), 7.29 (d, 3H, J$_o$=8 Hz, H$_4$ and H$_7$ indole, H$_7$ Trp), 8.39 and 9.10 (2 m, 2H, NH Pro TFA salt), 9.25 (d, 1H, J=8 Hz, NH amide), 10.76 (s, 1H, NH indole), 10.80 (d, 1H, J=2 Hz, NH indole Trp).

$^{13}$C NMR (75 MHz, DMSO d$^6$, 300° K):

δ (ppm) 22.8 (CH$_2$—CH$_2$-indole), 23.5 (C$_4$ Pro), 25.8 (CH$_2$—CH$_2$-indole), 29.4 (CH$_2$ βTrp), 29.8 (C$_3$ Pro), 45.2 (CH αTrp), 45.5 (CH$_2$-p-methoxybenzyl), 46.0 (C$_5$ Pro), 55.5 (OCH$_3$), 59.3 (CH αPro), 109.6 (C$_3$ Trp), 111.8 (C$_7$ indole and C$_7$ Trp), 113.4 (C$_3$ indole), 114.6 (C$_3$ and C$_5$ p-methoxybenzyl), 118.4 (C$_4$ indole), 118.5 (C$_4$ Trp), 118.7 (C$_5$ indole and C$_5$ Trp), 121.4 (C$_6$ indole and C$_6$ Trp), 123.0 (C$_2$ Trp), 124.7 (C$_2$ indole), 127.2 (C$_9$ indole), 127.3 (C$_9$ Trp), 127.7 (C$_1$ p-methoxybenzyl), 127.8 (C$_2$ and C$_6$ p-methoxybenzyl), 126.5 (C$_8$ Trp), 136.6 (C$_8$ indole), 154.8 (Cq triazole), 154.9 (Cq triazole), 159.2 (C$_4$ p-methoxybenzyl), 168.2 (CO amide).

(R)—N—((R)-1-(5-(2-(1H-indol-3-yl)ethyl)-4-(4-methoxybenzyl)-4H-1,2,4-triazol-3-yl)-2-(1H-indol-3-yl)ethyl)pyrrolidine-2-carboxamide (Compound 90)

$^1$H NMR (300 MHz, DMSO d$^6$, 300° K):

δ (ppm) 1.23 (m, 1H, H$_3$ Pro), 1.52 (m, 1H, H$_4$ Pro), 1.74 (m, 1H, H$_4$ Pro), 2.08 (m, 1H, H$_3$ Pro), 2.81 (m, 2H, H$_5$ Pro), 2.90-3.14 (m, 4H, CH$_2$—CH$_2$-indole), 3.31 (dd, 1H, J=14 Hz and 7 Hz, CH$_2$±3Trp), 3.41 (dd, 1H, J=14 Hz and 8 Hz, CH$_2$ βTrp), 3.63 (s, 3H, OCH$_3$), 4.05 (m, 1H, CH αPro), 4.86 (s, 2H, CH$_2$-p-methoxybenzyl), 5.21 (m, 1H, CH αTrp), 6.63 (s, 4H, CHar p-methoxybenzyl), 6.88 (t, 2H, J$_o$=7 Hz, H$_5$ indole and H$_5$ Trp), 7.02 (m, 4H, H$_2$ and H$_6$ indole, H$_2$ and H$_6$ Trp), 7.26-7.34 (m, 4H, H$_4$ and H$_7$ indole, H$_4$ and H$_7$ Trp), 8.51 and 9.18 (2 m, 2H, NH Pro, TFA salt), 9.27 (d, 1H, J=8 Hz, NH amide), 10.73 (s, 1H, NH indole), 10.80 (s, 1H, NH indole Trp).

$^{13}$C NMR (75 MHz, DMSO d$^6$, 300° K):

δ (ppm) 22.8 (CH$_2$—CH$_2$-indole), 23.8 (C$_4$ Pro), 25.9 (CH$_2$—CH$_2$-indole), 29.7 (CH$_2$ βTrp and C$_3$ Pro), 45.4 (CH$_2$-p-methoxybenzyl), 45.8 (CH αTrp), 46.1 (C$_5$ Pro), 55.5 (OCH$_3$), 59.2 (CH αPro), 109.7 (C$_3$ Trp), 111.8 (C$_7$ Trp), 111.9 (C$_7$ indole), 113.4 (C$_3$ indole), 114.4 (C$_3$ and C$_5$ p-methoxybenzyl), 118.3 (C$_4$ indole), 118.5 (C$_4$ Trp), 118.6 (C$_5$ indole), 118.9 (C$_5$ Trp), 121.4 (C$_6$ indole and C$_6$ Trp), 122.9 (C$_2$ indole and C$_2$ Trp), 127.2 (C$_9$ indole), 127.4 (C$_9$ Trp), 127.6 (C$_1$, C$_2$ and C$_6$ p-methoxybenzyl), 136.5 (C$_8$ Trp), 136.6 (C$_8$ indole), 154.4 (Cq triazole), 155.0 (Cq triazole), 159.1 (C$_4$ p-methoxybenzyl), 168.3 (CO amide).

(R)—N-(1-(5-(2-(1H-indol-3-yl)ethyl)-4-(4-bromobenzyl)-4H-1,2,4-triazol-3-yl)-2-(1H-indol-3-yl)ethyl)-2-amino-2-methylpropanamide (Compound 92)

$^1$H NMR (400 MHz, DMSO-d$^6$):

δ (ppm) 1.28 (3H, s, CH$_3$ Aib), 1.30 (3H, s, CH$_3$ Aib), 2.90 (2H, m, CH$_2$—CH$_2$-indole), 3.00 (2H, m, CH$_2$—CH$_2$-indole), 3.37 (2H, m, CH$_2$ βTrp), 5.10 (2H, s, CH$_2$ 4-bromobenzyl), 5.13 (1H, m, CαH Trp), 6.75 (2H, d, J=8.1, H$_2$, H$_6$ 4-bromobenzyl), 6.88 (1H, t, J=7.3, H$_5$ Trp), 6.93 (1H, t, J=7.5, H$_5$ indole), 7.03 (1H, t, J=7.0, H$_6$ Trp), 7.05 (1H, H$_6$ indole), 7.07 (1H, d, J=1.7, H$_2$ indole), 7.09 (1H, d, J=1.8, H$_2$ Trp), 7.12 (1H, d, J=8.2, H$_4$ Trp), 7.28 (1H, d, J=7.9, H$_4$ indole), 7.32 (2H, d, J=8.2, H$_7$ Trp, H$_7$ indole), 7.41 (2H, d, J=8.1, H₃, H₅ 4-bromobenzyl), 8.01 (2H, s, NH₂ Aib), 8.95 (1H, d, J=7.9, NH Trp), 10.77 (1H, brs, NH indole), 10.80 (1H, brs, NH indole Trp).

¹³C NMR (400 MHz, DMSO-d⁶):

δ (ppm) 22.4 (CH₂—CH indole), 23.1 (CH₃ Aib), 23.4 (CH₃ Aib), 25.4 (CH₂—CH indole), 28.7 (Cβ Trp), 44.8 (CH₂ 4-bromobenzyl), 45.2 (Cα Trp), 56.3 (Cq Aib), 109.4 (C₃ Trp), 111.3 (C₇ Trp, C₇ indole), 113.0 (C₃ indole), 117.8 (C₄ Trp), 118.0 (C₄ indole), 118.2 (C₅ indole), 118.3 (C₅ Trp), 120.8 (C₄ 4-bromobenzyl), 120.9 (C₆ Trp, C₆ indole), 122.5 (C₂ indole), 124.4 (C₂ Trp), 126.7 (C₆ Indole), 126.8 (C₉ Trp), 128.0 (O₂, C₆ 4-bromobenzyl), 131.6 (C₃, C₅ 4-bromobenzyl), 135.1 (C₁ 4-bromobenzyl), 136.1 (C₈ Trp, C₈ indole), 154.2 (Cq triazole), 154.5 (Cq triazole), 171.4 (CO Aib).

(R)—N-(1-(5-(2-(1H-indol-3-yl)ethyl)-4-(4-methoxybenzyl)-4H-1,2,4-triazol-3-yl)-2-phenylethyl)-2-amino-2-methylpropanamide (Compound 93)

¹H NMR (300 MHz, DMSO-d⁶, 300° K):

δ (ppm) 1.18 (3H, s, CH₃ Aib), 1.27 (3H, s, CH₃ Aib), 2.91 (4H, m, CH₂—CH₂-indole), 3.19 (2H, m, CH₂ βPhe), 3.69 (3H, s, OCH₃), 5.05 (2H, m, CH₂-p-methoxybenzyl), 5.20 (1H, m, CH αPhe), 6.82 (2H, d, J₀=8 Hz, H₃ and H₅ p-methoxybenzyl), 6.88 (2H, d, J₀=8 Hz, H₂ and H₆ p-methoxybenzyl), 6.92 (1H, t, J₀=8 Hz, H₅ indole), 7.02 (1H, t, J₀=7 Hz, H₆ indole), 7.03 (1H, d, J=2 Hz, H₂ indole), 7.11-7.20 (5H, m, CHar Phe), 7.29 (2H, d, J₀=8 Hz, H₄ and H₇ indole), 7.99 (3H, brs, NH₂ Aib), 8.93 (1H, d, J=8 Hz, NH amide), 10.77 (1H, s, NH indole).

¹³C NMR (75 MHz, DMSO-d⁶, 300° K):

δ (ppm) 22.8 (CH₂—CH₂-indole), 23.5 (CH₃ Aib), 23.9 (CH₃ Aib), 25.9 (CH₂—CH₂-indole), 38.7 (CH₂ βPhe), 45.7 (CH₂-p-methoxybenzyl), 46.4 (CH αPhe), 55.6 (OCH₃), 56.8 (CqAib), 111.8 (C₇ indole), 113.4 (C₃ indole), 114.7 (C₃ and C₅ p-methoxybenzyl), 118.5 (C₄ Trp), 118.6 (C₅ Trp), 121.4 (C₆ Trp), 123.0 (C₂ Trp), 127.0 (C₄ phenyl), 127.2 (C₉ indole), 127.9 (C₁ p-methoxybenzyl), 128.1 (C₂ and C₆ phenyl), 128.5 (C₃ and C₅ phenyl), 129.8 (C₂ and C₆ p-methoxybenzyl), 136.6 (C₈ indole), 137.7 (C₁ phenyl), 155.2 (Cq triazole), 154.4 (Cq triazole), 159.3 (C₄ p-methoxybenzyl), 171.7 (CO Aib).

(R)—N-(1-(4-(2-(1H-indol-3-yl)ethyl)-4H-1,2,4-triazol-3-yl)-2-(1H-indol-3-yl)ethyl)-2-amino-2-methylpropanamide (Compound 95)

¹H NMR (400 MHz, DMSO-d⁶):

δ (ppm) 1.29 (3H, s, CH₃ Aib), 1.35 (3H, s, CH₃ Aib), 2.85 (1H, m, 1H N—CH₂—CH₂—In), 2.89 (1H, m, 1H, —N—CH₂—CH₂—In), 3.28 (1H, dd, J=14.2, J=6.8, 1H CH₂ βTrp), 3.40 (1H, dd, J=14.2, J=8.4, 1H CH₂β Trp), 4.10 (2H, m, —N—CH₂—CH₂—In), 5.25 (1H, m, CHα Trp), 6.85 (1H, d, J=2.0, H₂ indole), 6.90-6.98 (2H, m, H₅ indole), 7.01 (1H, d, J=2.0, H₂ indole), 7.02-7.12 (2H, m, H₆ indole), 7.30 (1H, d, J=8.2, H₇ indole), 7.33 (1H, d, J=8.3, H₇ indole), 7.40 (1H, d, J=7.9, H₄ indole), 7.47 (1H, d, J=7.8, H₄ indole), 8.04 (2H, brs, NH₂ Aib), 8.42 (1H, s, H triazole), 9.01 (1H, d, J=8.0, NH Trp), 10.81 (1H, s, NH indole), 10.90 (1H, s, NH indole).

(R)—N-(1-(5-((1H-indol-3-yl)methyl)-4-methyl-4H-1,2,4-triazol-3-yl)-2-(1H-indol-3-yl)ethyl)-2-amino-2-methylpropanamide (Compound 96)

¹H NMR (400 MHz, DMSO-d⁶):

δ (ppm) 1.20 (3H, s, CH₃ Aib), 1.28 (3H, s, CH₃ Aib), 3.32 (3H, d, N—CH₃), 3.30-3.45 (2H, m, CH₂β Trp), 4.22 (2H, s, —CH₂—In), 5.30 (1H, m, CHα Trp), 6.91 (1H, t, J=7.5, H₅ indole), 6.94 (1H, d, J=7.5, H₅ indole), 7.02 (1H, t, J=7.9, H₆ indole), 7.05 (1H, t, J=7.9, H₆ indole), 7.08 (1H, d, J=1.9, H₂ indole), 7.12 (1H, d, J=1.9, H₂ indole), 7.29 (1H, d, J=8.1, H₇ indole), 7.33 (1H, d, J=8.2, H₇ indole), 7.48 (1H, d, J=7.9, H₄ indole), 7.57 (1H, d, J=7.9 H₄ indole), 8.00 (2H, brs, NH₂ Aib), 8.85 (1H, d, J=8.2, NH Trp), 10.82 (1H, s, NH indole), 10.98 (1H, s, NH indole).

(R)—N-(1-(5-(2-(1H-indol-3-yl)ethyl)-4-methyl-4H-1,2,4-triazol-3-yl)-2-(1H-indol-3-yl)ethyl)-2-amino-2-methylpropanamide (Compound 97)

¹H NMR (400 MHz, DMSO-d⁶):

δ (ppm) 1.30 (3H, s, CH₃ Aib), 1.40 (3H, s, CH₃ Aib), 3.00-3.20 (4H, m, —CH₂—CH₂—In), 3.36 (3H, s, N—CH₃), 3.45-3.50 (2H, m, CH₂β Trp), 5.30 (1H, m, CHα Trp), 6.95-7.04 (2H, t, H₅ indole), 7.06-7.13 (2H, m, H₆ indole), 7.18 (2H, brs, H₂ indole), 7.34 (1H, d, J=8.0, H₇ indole), 7.36 (1H, d, J=8.0, H₇ indole), 7.48 (1H, d, J=7.8, H₄ indole), 7.58 (1H, d, J=7.8, H₄ indole), 8.10 (2H, brs, NH₂ Aib), 8.95 (1H, d, J=8.1, NH Trp), 10.95 (1H, s, NH indole), 10.96 (1H, s, NH indole).

¹³C NMR (100 MHz, DMSO-d⁶):

δ (ppm) 22.9-25.9 (—CH₂—CH₂-indole), 24.1 (CH₃ Aib), 24.3 (CH₃ Aib), 28.8 (CH₂β Trp), 30.7 (—NCH₃), 46.2 (CHα Trp), 57.2 (Cq Aib), 110.2 (C₃ indole), 112.3 (2C₇ indole), 113.5 (C₃ indole), 118.9-119.2 (2C₅, 2C₄ indole), 121.9 (2C₆ indole), 123.6 (C₂ indole), 125.3 (C₂ indole), 127.7 (C₉ indole), 128.0 (C₉ indole), 136.9 (C₈ indole), 137.1 (C₈ indole), 155.3 (Cq triazole), 155.8 (Cq triazole), 172.2 (CO Aib).

(R)—N-(1-(5-((1H-indol-3-yl)methyl)-4H-1,2,4-triazol-3-yl)-2-(1H-indol-3-yl)ethyl)-2-amino-2-methylpropanamide (Compound 98)

¹H NMR (400 MHz, DMSO-d⁶):

δ (ppm) 1.31 (3H, s, CH₃ Aib), 1.42 (3H, s, CH₃ Aib), 3.19 (1H, dd, J=14.5, J=9.6, 1H CH₂ βTrp), 3.35 (1H, dd, J=14.5, J=5.3, 1H CH₂ βTrp), 4.15 (2H, s, CH₂ indole), 5.26 (1H, m, CαH Trp), 6.95 (1H, t, H₅ indole), 6.96 (1H, t, H₅ indole), 7.05 (1H, t, H₆ Trp), 7.06 (1H, s, H₂ Trp), 7.07 (1H, t, H₆ indole), 7.21 (1H, s, H₂ indole), 7.32 (1H, d, H₇ Trp), 7.37 (1H, d, H₇ indole), 7.51 (1H, d, J=7.8, H₄ indole), 7.58 (1H, d, J=7.8, H₄ Trp), 8.00 (2H, s, NH₂ Aib), 8.64 (1H, d, J=8.7, NH Trp), 10.77 (1H, s, NH indole Trp), 10.92 (1H, s, NH indole).

¹³C NMR (400 MHz, DMSO-d⁶):

δ (ppm) 22.9 (CH₂ indole), 23.2 (CH₃ Aib), 23.3 (CH₃ Aib), 29.4 (Cβ Trp), 48.3 (Cα Trp), 56.3 (Cq Aib), 109.7 (C₃ indole), 110.3 (C₃ Trp), 111.2 (C₇ Trp), 111.3 (C₇ indole), 118.1 (C₄ Trp, C₅ Trp), 118.3 (C₄ indole), 118.4 (C₅ indole), 120.7 (C₆ Trp), 121.0 (C₆ indole), 123.4 (C₂ indole), 123.6 (C₂ Trp), 126.8 (C₉ indole), 127.1 (C₉ Trp), 136.0 (C₈ Trp), 136.2 (C₈ indole), 157.5 (Cq triazole), 161.7 (Cq triazole), 170.8 (CO Aib).

(R)—N-(1-(5-((1H-indol-3-yl)methyl)-4-(2,4-dimethoxybenzyl)-4H-1,2,4-triazol-3-yl)-2-(1H-indol-3-yl)ethyl)-2-amino-2-methylpropanamide (Compound 99)

¹H NMR (400 MHz, DMSO-d⁶):

δ (ppm) 1.27 (3H, s, CH₃ Aib), 1.29 (3H, s, CH₃ Aib), 3.25 (1H, dd, J=14.3, J=5.6, 1H CH₂ βTrp), 3.38 (1H, dd, J=14.3, J=9.1, 1H CH₂ βTrp), 3.68 (3H, s, OCH₃), 3.72 (3H, s, OCH₃), 4.10 (1H, d, J=16.5, 1H CH₂ indole), 4.16 (1H, d, J=16.5, 1H CH₂ indole), 4.96 (1H, d, J=16.8, 1H CH₂ o,p-dimethoxybenzyl), 5.12 (1H, d, J=16.8, 1H CH₂ o,p-dimethoxybenzyl), 5.16 (1H, m, CαH Trp), 6.21 (1H, dd, J=8.5, J=2.1, H₅ o,p-dimethoxybenzyl), 6.27 (1H, d, J=8.5, H₆ o,p-dimethoxybenzyl), 6.57 (1H, d, J=2.1, H₃ o,p-dimethoxybenzyl), 6.83 (1H, t, H₅ Trp), 6.94 (1H, t, H₅ indole), 7.02 (1H, t, H₆ Trp), 7.05 (1H, t, H₂ indole), 7.06 (1H, t, H₆ indole), 7.07 (1H, s, H₂ Trp), 7.07 (1H, t, H₄ Trp), 7.31 (1H, d, H₇ Trp), 7.33 (1H, d, H₇ indole), 7.36 (1H, d, J=7.8, H₄ indole), 8.00 (2H, br s, NH₂ Aib), 8.92 (1H, d, J=8.2, NH Trp), 10.79 (1H, s, NH indole Trp), 10.89 (1H, s, NH indole).

¹³C NMR (400 MHz, DMSO-d⁶):

δ (ppm) 21.2 (CH₂indole), 23.1 (CH₃ Aib), 23.2 (CH₃ Aib), 28.6 (Cβ Trp), 41.4 (N—CH₂ o,p-dimethoxybenzyl), 45.1 (Cα Trp), 55.2 (OCH₃), 55.4 (OCH₃), 56.2 (Cq Aib), 98.5 (C₃ o,p-dimethoxybenzyl), 104.6 (C₅ o,p-dimethoxybenzyl), 107.9 (C₃ indole), 109.5 (C₃ Trp), 111.2 (C₇ Trp), 111.3 (C₇ indole), 115.1 (C₁ o,p-dimethoxybenzyl), 117.8 (C₄ Trp), 118.1 (C₅ Trp), 118.3 (C₄ indole), 118.4 (C₅ indole), 120.8 (C₆ Trp), 121.1 (C₆ indole), 123.5 (C₂ indole), 124.3 (C₂ Trp), 126.6 (C₉ indole), 126.8 (C₉ Trp), 127.2 (C₆ o,p-dimethoxybenzyl), 136.0 (C₈ Trp), 136.2 (C₈ indole), 157.5 (Cq triazole), 154.9 (Cq triazole), 157.2 (C₂ o,p-dimethoxybenzyl), 160.3 (C₄ o,p-dimethoxybenzyl), 171.2 (CO Aib).

(R)—N-(1-(5-((1H-indol-3-yl)methyl)-4-(4-methoxybenzyl)-4H-1,2,4-triazol-3-yl)-2-(1H-indol-3-yl)ethyl)-2-amino-2-methylpropanamide (Compound 101)

¹H NMR (300 MHz, DMSO-d⁶, 300° K):

δ (ppm) 1.22 (3H, s, CH₃ Aib), 1.25 (3H, s, CH₃ Aib), 3.22 (1H, dd, J=14 Hz and 6 Hz, CH₂ βTrp), 3.34 (1H, dd, J=14 Hz and 9 Hz, CH₂ βTrp), 3.68 (3H, s, OCH₃), 4.11 (2H, m, CH₂-indole), 5.09 (3H, m, CH αTrp and CH₂-p-methoxybenzyl), 6.70 (4H, s, CHar p-methoxybenzyl), 6.78 (2H, m, H₅ indole and H₅ Trp), 6.93 (2H, m, H₆ indole and H₆ Trp), 7.01-7.06 (3H, m, H₂ indole, H₂ and H₄ Trp), 7.31 (3H, m, H₄ and H₇ indole, H₇ Trp), 7.98 (3H, brs, NH₂ Aib), 8.92 (1H, d, J=8 Hz, NH amide), 10.77 (1H, s, NH indole), 10.89 (1H, s, NH indole Trp).

¹³C NMR (75 MHz, DMSO-d⁶, 300° K):

δ (ppm) 21.7 (CH₂-indole), 23.5 (CH₃ Aib), 23.7 (CH₃ Aib), 28.9 (CH₂ βTrp), 45.6 (CH αTrp), 45.8 (CH₂-p-methoxybenzyl), 55.5 (OCH₃), 56.7 (Cq Aib), 108.1 (C₃ indole), 109.7 (C₃ Trp), 111.7 (C₇ Trp), 111.9 (C₇ indole), 114.5 (C₃ and C₅ p-methoxybenzyl), 118.3 (C₄ Trp), 118.7 (C₄ indole), 118.8 (C₅ indole), 118.9 (C₅ Trp), 121.3 (C₆ indole), 121.6 (C₆ Trp), 124.2 (C₂ indole), 125.3 (C₂ Trp), 127.1 (C₉ indole), 127.2 (C₉ Trp), 127.6 (C₁ p-methoxybenzyl), 127.8 (C₂ and C₆ p-methoxybenzyl), 136.4 (C₈ Trp), 136.7 (C₈ indole), 154.2 (Cq triazole), 155.2 (Cq triazole), 159.2 (C₄ p-methoxybenzyl), 171.9 (CO Aib).

(R)—N-(1-(4-(2,4-dimethoxybenzyl)-5-benzyl-4H-1,2,4-triazol-3-yl)-2-(1H-indol-3-yl)ethyl)-2-amino-2-methylpropanamide (Compound 102)

¹H NMR (400 MHz, DMSO-d⁶):

δ (ppm) 1.30 (3H, s, CH₃ Aib), 1.33 (3H, s, CH₃ Aib), 3.26 (1H, dd, J=14.2, J=5.9, 1H CH₂ βTrp), 3.38 (1H, dd, J=14.2, J=8.7, 1H CH₂ βTrp), 3.69 (3H, s, OCH₃), 3.72 (3H, s, OCH₃), 4.02 (2H, s, CH₂ benzyl), 4.87 (1H, d, J=16.7, 1H CH₂ o,p-dimethoxybenzyl), 5.08 (1H, d, J=16.7, 1H CH₂ o,p-dimethoxybenzyl), 5.17 (1H, m, CαH Trp), 6.24 (1H, dd, J=8.4, J=1.7, H₅ o,p-dimethoxybenzyl), 6.28 (1H, d, J=8.4, H₆ o,p-dimethoxybenzyl), 6.56 (1H, d, J=1.7, H₃ o,p-dimethoxybenzyl), 6.85 (1H, t, J=7.5, H₅ Trp), 7.02 (1H, t, H₆ Trp), 7.07 (2H, m, H₂, H₆ benzyl), 7.08 (1H, s, H₂ Trp), 7.09 (1H, d, H₄ Trp), 7.16-7.29 (3H, m, H₃, H₄, H₅ benzyl), 7.31 (1H, d, J=8.2, H₇ Trp), 8.01 (2H, s, NH₂ Aib), 8.92 (1H, d, J=7.9, NH Trp), 11.79 (1H, s, NH indole Trp).

¹³C NMR (400 MHz, DMSO-d⁶):

δ (ppm) 23.2 (2CH₃ Aib), 28.7 (Cβ Trp), 30.2 (CH₂-benzyl), 41.3 (CH₂-o,p-dimethoxybenzyl), 45.2 (Cα Trp), 55.2 (OCH₃), 55.4 (OCH₃), 56.2 (Cq Aib), 98.5 (C₃ o,p-dimethoxybenzyl), 104.7 (C₅ o,p-dimethoxybenzyl), 109.5 (C₃ Trp), 111.3 (C₇ Trp), 115.1 (C₁ o,p-dimethoxybenzyl), 117.8 (C₄ Trp), 118.2 (C₅ Trp), 120.8 (C₆ Trp), 124.3 (C₂ Trp), 126.5 (O₂, C₆ benzyl), 126.8 (C₉ Trp), 127.3 (C₆ o,p-dimethoxybenzyl), 128.3 (C₃, C₄, C₅ Benzyl), 135.8 (C₁ benzyl), 136.0 (C₈ Trp), 153.4 (Cq triazole), 155.0 (Cq triazole), 157.2 (C₂ o,p-dimethoxybenzyl), 160.3 (C₄ o,p-dimethoxybenzyl), 171.3 (CO Aib).

(R)—N-(1-(5-((1H-indol-3-yl)methyl)-4-phenethyl-4H-1,2,4-triazol-3-yl)-2-(1H-indol-3-yl)ethyl)-2-amino-2-methylpropanamide (Compound 104)

¹H NMR (300 MHz, DMSO-d⁶, 300° K):

δ (ppm) 1.27 (3H, s, CH₃ Aib), 1.29 (3H, s, CH₃ Aib), 2.39-2.53 (4H, m, CH₂—CH₂-phenyl), 3.74 (1H, m, CH₂ βTrp), 3.92 (1H, m, CH₂ βTrp), 3.99 (2H, s, CH₂-indole), 5.21 (1H, m, CH αTrp), 6.74 (2H, m, H₅ indole and H₅ Trp), 6.90 (1H, t, J₀=8 Hz, H₆ Trp), 6.92 (1H, t, J₀=8 Hz, H₆ indole), 7.01-7.06 (4H, m, H₂ and H₆ phenyl, H₂ indole and H₂ Trp), 7.16 (3H, m, H₃, H₄ and H₅ phenyl), 7.27 (1H, d, J₀=8 Hz, H₄ Trp), 7.32 (1H, d, J₀=8 Hz, H₇ Trp), 7.36 (1H, d, J₀=8 Hz, H₇ indole), 7.50 (1H, d, J₀=8 Hz, H₄ indole), 7.99 (3H, brs, NH₂ Aib), 9.02 (1H, s, J=8 Hz, NH amide), 10.79 (1H, s, NH indole Trp), 10.94 (1H, s, NH indole).

¹³C NMR (75 MHz, DMSO-d⁶, 300° K):

δ (ppm) 21.4 (CH₂-indole), 23.5 (CH₃ Aib), 23.8 (CH₃ Aib), 29.5 (CH₂ βTrp), 35.8 (CH₂—CH₂-phenyl), 44.5 (CH₂—CH₂-phenyl), 45.8 (CH αTrp), 56.7 (Cq Aib), 108.5 (C₃ indole), 109.9 (C₃ Trp), 114.0 (C₇ indole and C₇ Trp), 118.4 (C₄ Trp), 118.8 (C₄ indole and C₅ Trp), 119.0 (C₅ indole), 121.4 (C₆ Trp), 121.7 (C₆ indole), 124.0 (C₂ indole and C₂ Trp), 127.1 (C₄ phenyl), 127.7 (C₉ indole and C₉ Trp), 128.8 (C₂ and C₆ phenyl), 129.1 (C₃ and C₅ phenyl), 136.5 (C₈ Trp), 136.6 (C₈ indole), 137.5 (C₁ phenyl), 153.6 (Cq triazole), 155.0 (Cq triazole), 171.8 (CO Aib).

(R)—N-(1-(5-benzyl-4-(2,2-diphenylethyl)-4H-1,2,4-triazol-3-yl)-2-(1H-indol-3-yl)ethyl)-2-amino-2-methylpropanamide (Compound 106)

¹H NMR (300 MHz, DMSO-d⁶, 300° K):

δ (ppm) 1.29 (3H, s, CH₃ Aib), 1.34 (3H, s, CH₃ Aib), 3.37 (4H, m, CH₂ βTrp and CH₂-benzyl), 3.74 (1H, t, J=7 Hz, CH₂—CH(Phe)₂), 4.21 (1H, dd, J=14 Hz and 8 Hz, CH₂—

CH(Phe)$_2$), 4.51 (1H, dd, J=14 Hz and 8 Hz, CH$_2$—CH (Phe)$_2$), 5.08 (1H, m, CH αTrp), 6.72 (2H, m, H$_2$ and H$_6$ benzyl), 6.86-6.93 (5H, m, H$_3$, H$_4$ and H$_5$ benzyl, H$_5$ and H$_6$ Trp), 7.03 (1H, s, H$_2$ Trp), 7.06-7.25 (CHar phenyl from CH(Phe)$_2$), 7.33 (1H, d, J$_o$=8 Hz, H$_4$ Trp), 7.47 (1H, d, J$_o$=8 Hz, H$_7$ indole), 8.10 (3H, brs, NH$_2$ Aib), 8.98 (1H, d, J=8 Hz, NH amide), 10.94 (1H, s, NH indole Trp).

$^{13}$C NMR (75 MHz, DMSO-d$^6$, 300° K):

δ (ppm) 23.5 (CH$_3$ Aib), 23.7 (CH$_3$ Aib), 29.4 (CH$_2$ βTrp), 30.1 (CH$_2$-benzyl), 46.0 (CH αTrp), 47.7 (CH$_2$—CH(Phe)$_2$), 51.3 (CH(Phe)$_2$), 56.8 (Cq Aib), 109.8 (C$_3$ Trp), 112.0 (C$_7$ Trp), 118.5 (C$_4$ Trp), 119.0 (C$_5$ Trp), 121.5 (C$_6$ Trp), 124.8 (C$_2$ Trp), 127.1 (C$_4$ phenyl from CH(Phe)$_2$), 127.4 (C$_9$ Trp, C$_2$ and C$_6$ benzyl), 128.3 (C$_2$ and C$_6$ phenyl from CH(Phe)$_2$), 128.8-129.1 (C$_3$ and C$_5$ phenyl from CH(Phe)$_2$, C$_3$, C$_4$ and C$_5$ benzyl), 136.2 (C$_1$ benzyl), 136.5 (C$_8$ Trp), 141.0 (C$_1$ phenyl from CH(Phe)$_2$), 153.5 (Cq triazole), 155.1 (Cq triazole), 172.0 (CO Aib)

(R)—N-(1-(5-(2-(1H-indol-3-yl)ethyl)-4-(2,2-diphenylethyl)-4H-1,2,4-triazol-3-yl)-2-(1H-indol-3-yl)ethyl)-2-amino-2-methylpropanamide (Compound 107)

$^1$H NMR (300 MHz, DMSO-d$^6$, 300° K):

δ (ppm) 1.34 (3H, s, CH$_3$ Aib), 1.38 (3H, s, CH$_3$ Aib), 2.06 (1H, m, CH$_2$—CH$_2$-indole), 2.30 (1H, m, CH$_2$—CH$_2$-indole), 2.78 (2H, m, CH$_2$—CH$_2$-indole), 3.35 (1H, dd, J=14 Hz and 7 Hz, CH$_2$ βTrp), 3.46 (1H, dd, J=14 Hz and 9 Hz, CH$_2$ βTrp), 3.58 (1H, t, J=7 Hz, CH$_2$—CH(Phe)$_2$), 4.14 (1H, dd, J=14 Hz and 8 Hz, CH$_2$—CH(Phe)$_2$), 4.39 (1H, dd, J=14 Hz and 7 Hz, CH$_2$—CH(Phe)$_2$), 5.12 (1H, m, CH αTrp), 6.50 (2H, m, H$_5$ indole and H$_5$ Trp), 6.76 (2H, m, H$_6$ indole and H$_6$ Trp), 6.87 (2H, m, H$_2$ indole and H$_2$ Trp), 6.89-6.96 (2H, m, H$_4$ phenyl), 7.03-7.15 (8H, m, H$_2$, H$_3$, H$_5$ and H$_6$ phenyl), 7.33 (3H, m, H$_4$ indole, H$_4$ and H$_7$ Trp), 7.47 (1H, d, J=8 Hz, H$_7$ indole), 8.11 (3H, brs, NH$_2$ Aib), 9.04 (1H, d, J=8 Hz, NH amide), 10.76 (1H, s, NH indole), 10.96 (1H, s, NH indole Trp).

$^{13}$C NMR (75 MHz, DMSO-d$^6$, 300° K):

δ (ppm) 22.4 (CH$_2$—CH$_2$-indole), 23.6 (CH$_3$ Aib), 23.8 (CH$_3$ Aib), 24.9 (CH$_2$—CH$_2$-indole), 29.6 (CH$_2$ βTrp), 46.1 (CH αTrp), 47.5 (CH$_2$—CH(Phe)$_2$), 51.5 (CH$_2$—CH(Phe)$_2$), 56.8 (Cq Aib), 109.8 (C$_3$ Trp), 111.8 (C$_7$ Trp), 112.1 (C$_7$ indole), 113.5 (C$_3$ indole), 118.4 (C$_4$ Trp), 118.7 (C$_4$ and C$_5$ indole), 119.0 (C$_5$ Trp), 121.4 (C$_6$ indole and C$_6$ Trp), 122.8 (C$_2$ indole), 125.0 (C$_2$ Trp), 127.2 (C$_9$ indole and C$_9$ Trp), 127.3 (C$_4$ phenyl), 128.2 (C$_2$ and C$_6$ phenyl), 128.7 (C$_3$ and C$_5$ phenyl), 136.6 (C$_8$ indole and C$_8$ Trp), 141.0 (C$_1$ phenyl), 154.6 (2 Cq triazole), 172.0 (CO Aib).

(R)—N-(1-(4,5-dibenzyl-4H-1,2,4-triazol-3-0)-2-(1H-indol-3-yl)ethyl)-2-amino-2-methylpropanamide (Compound 109)

$^1$H NMR (300 MHz, DMSO-d$^6$, 300° K):

δ (ppm) 1.23 (3H, s, CH$_3$ Aib), 1.26 (3H, s, CH$_3$ Aib), 3.23 (1H, dd, J=14 Hz and 6 Hz, CH$_2$ βTrp), 3.35 (1H, dd, J=14 Hz and 9 Hz, CH$_2$ βTrp), 3.99 (2H, s, C—CH$_2$-phenyl), 5.10 (3H, m, N—CH$_2$-phenyl and CH αTrp), 6.77 (3H, m, H$_5$ Trp, H$_2$ and H$_6$ phenyl from N—CH$_2$-phenyl), 6.99 (2H, m, H$_2$ and H$_6$ Trp), 7.01-7.07 (3H, m, H$_4$ Trp, H$_2$ and H$_6$ from C—CH$_2$-phenyl), 7.15-7.23 (6H, m, H$_3$, H$_4$ and H$_5$ phenyl from N—CH$_2$-phenyl and from C—CH$_2$-phenyl), 7.25 (1H, d, J=8 Hz, H$_7$ Trp), 8.01 (3H, brs, NH$_2$ Aib), 8.91 (1H, d, J=8 Hz, NH amide), 10.78 (1H, s, NH indole Trp).

$^{13}$C NMR (75 MHz, DMSO-d$^6$, 300° K):

δ (ppm) 23.5 (CH$_3$ Aib), 23.7 (CH$_3$ Aib), 29.0 (CH$_2$ βTrp), 30.6 (C—CH$_2$-phenyl), 45.7 (CH αTrp), 46.1 (N—CH$_2$-phenyl), 56.7 (Cq Aib), 109.8 (C$_3$ Trp), 111.7 (C$_7$ Trp), 118.3 (C$_4$ Trp), 118.7 (C$_5$ Trp), 121.2 (C$_6$ Trp), 124.8 (C$_2$ Trp), 126.3 (C$_2$ and C$_6$ phenyl from N—CH$_2$-phenyl), 127.0 (C$_2$ and C$_6$ phenyl from C—CH$_2$-phenyl), 127.2 (C$_9$ Trp), 128.0 (C$_4$ phenyl from N—CH$_2$-phenyl), 128.8 (C$_3$, C$_4$ and C$_5$ phenyl from C—CH$_2$-phenyl), 128.9 (C$_3$ and C$_5$ phenyl from N—CH$_2$-phenyl), 135.8 (C$_1$ phenyl from N—CH$_2$-phenyl), 136.2 (C$_1$ phenyl from C—CH$_2$-phenyl), 136.4 (C$_8$ Trp), 153.9 (Cq triazole), 155.3 (Cq triazole), 171.9 (CO Aib).

(R)—N-(1-(5-benzyl-4-hexyl-4H-1,2,4-triazol-3-yl)-2-(1H-indol-3-yl)ethyl)-2-amino-2-methylpropanamide (Compound 110)

$^1$H NMR (300 MHz, DMSO-d$^6$, 300° K):

δ (ppm) 0.71 (3H, t, $^3$J=7 Hz, (CH$_2$)$_5$—CH$_3$), 0.87 (4H, m, 2 CH$_2$), 0.95 (2H, m, CH$_2$—CH$_3$), 1.00 (2H, m, N—CH$_2$—CH$_2$), 1.36 (6H, s, CH$_3$ Aib), 3.36 (1H, dd, $^3$J=14 Hz and 7 Hz, CH$_2$ βTrp), 3.41 (1H, dd, $^3$J=14 Hz and 7 Hz, CH$_2$ βTrp), 3.50 (1H, m, N—CH$_2$), 3.65 (1H, m, N—CH$_2$), 4.11 (2H, s, CH$_2$-benzyl), 5.14 (1H, m, CH αTrp), 6.90 (1H, t, J$_o$=7 Hz, H$_5$ Trp), 7.01 (1H, t, J$_o$=7 Hz, H$_6$ Trp), 7.04 (1H, s, H$_2$ Trp), 7.09 (2H, m, H$_2$ and H$_6$ benzyl), 7.17-7.29 (4H, m, H$_4$ Trp, H$_3$, H$_4$ and H$_5$ benzyl), 7.47 (1H, d, J$_o$=8 Hz, H$_7$ Trp), 8.10 (3H, brs, NH$_2$ Aib), 9.05 (1H, d, J=7 Hz, NH amide), 10.84 (1H, s, NH indole Trp).

$^{13}$C NMR (75 MHz, DMSO-d$^6$, 300° K):

δ (ppm) 14.1 ((CH$_2$)$_6$—CH$_3$), 22.1 (CH$_2$—CH$_3$), 23.8 (CH$_3$ Aib), 23.5 (CH$_3$ Aib), 25.8 (CH$_3$—CH$_2$—CH$_2$—CH$_2$), 29.5 (CH$_2$ βTrp), 30.3 (N—CH$_2$—CH$_2$), 30.8 (CH$_2$-benzyl and CH$_3$—CH$_2$—CH$_2$), 43.3 (N—CH$_2$—CH$_2$), 46.1 (CH αTrp), 56.8 (Cq Aib), 109.6 (C$_3$ Trp), 111.9 (C$_7$ Trp), 118.2 (C$_4$ Trp), 118.8 (C$_5$ Trp), 121.4 (C$_6$ Trp), 124.7 (C$_2$ Trp), 127.2 (C$_2$ and C$_6$ benzyl), 127.3 (C$_9$ Trp), 128.8 (C$_3$, C$_4$ and C$_5$ benzyl), 136.2 (C$_1$ benzyl), 136.5 (C$_8$ Trp), 153.1 (Cq triazole), 155.1 (Cq triazole), 171.9 (CO Aib).

(R)—N-(1-(4-(2-(1H-indol-3-yl)ethyl)-5-benzyl-4H-1,2,4-triazol-3-yl)-2-(1H-indol-3-yl)ethyl)-2-amino-2-methylpropanamide (Compound 111)

$^1$H NMR (400 MHz, DMSO-d$^6$, 300° K):

δ (ppm) 1.31 (3H, s, CH$_3$ Aib), 1.35 (3H, s, CH$_3$ Aib), 2.51 (2H, m, CH$_2$—CH$_2$-indole), 3.37 (2H, m, CH$_2$ βTrp), 3.76-3.90 (4H, m, CH$_2$-benzyl and CH$_2$—CH$_2$-indole), 5.25 (1H, m, CH αTrp), 6.88 (2H, t, J$_o$=7 hz, H$_5$ indole and H$_5$ Trp), 6.95 (2H, t, J$_o$=7 Hz, H$_6$ indole and H$_6$ Trp), 7.03 (4H, m, H$_2$ Trp, H$_2$ indole, H$_2$ and H$_6$ benzyl), 7.16 (2H, d, J$_o$=8 Hz, H$_4$ indole and H$_4$ Trp), 7.20-7.30 (4H, 3, H$_7$ indole, H$_3$, H$_4$ and H$_5$ benzyl), 7.47 (1H, d, J$_o$=8 Hz, H$_7$ Trp), 8.05 (3H, brs, NH$_2$ Aib), 9.05 (1H, d, J=8 Hz, NH amide), 10.83 (1H, s, NH indole), 10.88 (1H, s, NH indole Trp).

$^{13}$C NMR (100 MHz, DMSO-d$^6$, 300° K):

δ (ppm) 23.5 (CH$_3$ Aib), 23.7 (CH$_3$ Aib), 29.6 (CH$_2$ βTrp), 30.3 (CH$_2$-benzyl and CH$_2$—CH$_2$-indole), 44.1 (CH$_2$—CH$_2$-indole), 46.1 (CH αTrp), 56.8 (CqAib), 109.8 (C$_3$ Trp), 109.9 (C$_3$ indole), 111.9 (C$_7$ indole and C$_7$ Trp), 118.3 (C$_4$ Trp), 118.4 (C$_4$ indole), 118.9 (C$_5$ indole and C$_5$ Trp), 121.3 (C$_6$ Trp), 121.5 (C$_6$ indole), 123.7 (C$_2$ indole), 124.7 (O$_2$ Trp), 127.0 (C$_9$ indole), 127.2 (C$_2$ and C$_6$ benzyl), 127.4 (C$_9$ Trp), 128.8 (C$_3$ and C$_5$ benzyl), 129.0 (C$_4$ benzyl), 136.3 (C$_1$ benzyl), 136.4 (C$_8$ indole and C$_8$ Trp), 153.1 (Cq triazole), 155.3 (Cq triazole), 171.8 (CO Aib).

(S)—N-(1-(4-(2,4-dimethoxybenzyl)-5-benzyl-4H-1,2,4-triazol-3-yl)-2-(1H-indol-3-yl)ethyl)-2-amino-2-methylpropanamide (Compound 112)

$^1$H NMR (300 MHz, DMSO-d$^6$, 300° K):

δ (ppm) 1.26 (3H, s, CH$_3$ Aib), 1.29 (3H, s, CH$_3$ Aib), 3.24 (1H, dd, J=14 Hz and 6 Hz, CH$_2$ βTrp), 3.33 (1H, dd, J=14 Hz and 9 Hz, CH$_2$ βTrp), 3.64 (3H, s, OCH$_3$), 3.68 (3H, s, OCH$_3$), 3.99 (2H, s, CH$_2$ phenyl), 4.84 (1H, d, J=17 Hz, CH$_2$-o,p-dimethoxybenzyl), 5.05 (1H, d, J=17 Hz, CH$_2$-o,p-dimethoxybenzyl), 5.13 (1H, m, CH αTrp), 6.24 (2H, m, H$_5$ and H$_6$ o,p-dimethoxybenzyl), 6.52 (1H, d, J$_m$=2 Hz, H$_3$ o,p-dimethoxybenzyl), 6.83 (1H, t, J$_o$=7 Hz, H$_5$ Trp), 7.01 (1H, t, J$_o$=8 Hz, H$_6$ Trp), 7.04 (1H, s, H$_2$ Trp), 7.05-7.23 (6H, m, H4 Trp and CHar phenyl), 7.27 (1H, d, J$_o$=8 Hz, H$_7$ Trp), 8.01 (3H, brs, NH$_2$ Aib), 8.90 (1H, d, J=8 Hz, NH amide), 10.77 (1H, d, J=2 Hz, NH indole Trp).

$^{13}$C NMR (75 MHz, DMSO-d$^6$, 300° K):

δ (ppm) 23.6 (CH$_3$ Aib), 29.1 (CH$_2$ βTrp), 30.6 (CH$_2$-phenyl), 41.9 (CH$_2$-o,p-dimethoxybenzyl), 45.7 (CH αTrp), 55.7 (OCH$_3$), 55.9 (OCH$_3$), 56.7 (Cq Aib), 99.9 (C$_3$ o,p-dimethoxybenzyl), 105.1 (C$_5$ o,p-dimethoxybenzyl), 109.9 (C$_3$ Trp), 111.7 (C$_7$ Trp), 115.5 (C$_1$ o,p-dimethoxybenzyl), 118.3 (C$_4$ Trp), 118.6 (C$_5$ Trp), 121.3 (C$_6$ Trp), 124.2 (C$_2$ Trp), 127.0 (C$_6$ o,p-dimethoxybenzyl), 127.3 (C$_9$ Trp), 127.8 (C$_4$ phenyl), 128.8 (C$_2$, C$_3$, C$_5$ and C$_6$ phenyl), 136.2 (C$_8$ Trp), 136.4 (C$_1$ phenyl), 153.9 (Cq triazole), 155.5 (Cq triazole), 157.6 (C$_2$ o,p-dimethoxybenzyl), 160.8 (C$_4$ o,p-dimethoxybenzyl), 171.8 (CO amide).

(R)—N-(1-(4-(3,5-dimethoxybenzyl)-5-phenethyl-4H-1,2,4-thiazol-3-yl)-2-(1H-indol-3-yl)ethyl)-2-amino-2-methylpropanamide (Compound 113)

$^1$H NMR (300 MHz, DMSO-d$^6$, 300° K):

δ (ppm) 1.24 (3H, s, CH$_3$ Aib), 1.27 (3H, s, CH$_3$ Aib), 2.83 (4H, s, CH$_2$—CH$_2$-phenyl), 3.32 (2H, m, CH$_2$ βTrp), 3.61 (6H, s, OCH$_3$), 5.02 (2H, m, CH$_2$-m-dimethoxybenzyl), 5.18 (1H, m, CH αTrp), 6.07 (2H, d, J$_m$=2 Hz, H$_2$ and H$_6$ m-dimethoxybenzyl), 6.42 (1H, brs, H$_4$ m-dimethoxybenzyl), 6.83 (1H, t, J$_o$=7 Hz, H$_5$ Trp), 6.99 (1H, t, J$_o$=8 Hz, H$_6$ Trp), 7.08 (1H, d, J=2 Hz, H$_2$ Trp), 7.13 (3H, t, J$_o$=8 Hz, H$_3$, H$_4$ and H$_5$ phenyl), 7.20 (3H, d, J$_o$=7 Hz, H$_2$ and H$_6$ phenyl, H$_4$ Trp), 7.28 (1H, d, J$_o$=8 Hz, H$_7$ Trp), 7.99 (3H, brs, NH$_2$ Aib), 8.92 (1H, d, J=8 Hz, NH amide), 10.77 (1H, s, NH indole).

$^{13}$C NMR (75 MHz, DMSO-d$^6$, 300° K):

δ (ppm) 23.5 (CH$_3$ Aib), 23.8 (CH$_3$ Aib), 26.5 (CH$_2$—CH$_2$-phenyl), 29.2 (CH$_2$ βTrp), 32.7 (CH$_2$—CH$_2$-phenyl), 45.6 (CH αTrp), 45.8 (CH$_2$-m-dimethoxybenzyl), 55.6 (OCH$_3$), 56.8 (Cq Aib), 99.6 (C$_4$ m-dimethoxybenzyl), 104.6 (C$_2$ and C$_6$ m-dimethoxybenzyl), 109.9 (C$_3$ Trp), 111.8 (C$_7$ Trp), 118.2 (C$_4$ Trp), 118.7 (C$_5$ Trp), 121.3 (C$_6$ Trp), 124.8 (C$_2$ Trp), 126.5 (C$_4$ phenyl), 127.3 (C$_9$ Trp), 128.7 (O$_2$, C$_3$, C$_5$ and C$_6$ phenyl), 136.4 (C$_8$ Trp), 138.6 (C$_4$ m-dimethoxybenzyl), 140.9 (C$_1$ phenyl), 154.6 (Cq triazole), 154.8 (Cq triazole), 161.4 (C$_3$ and C$_5$ m-dimethoxybenzyl), 171.8 (CO amide).

(R)—N-(1-(4-(4-bromobenzyl)-5-benzyl-4H-1,2,4-thiazol-3-yl)-2-(1H-indol-3-yl)ethyl)-2-amino-2-methylpropanamide (Compound 114)

$^1$H NMR (300 MHz, DMSO-d$^6$, 300° K):

δ (ppm) 1.23 (3H, s, CH$_3$ Aib), 1.25 (3H, s, CH$_3$ Aib), 3.26 (1H, dd, $^3$J=14 Hz and 6 Hz, CH$_2$ Trp), 3.34 (1H, dd, $^3$J=14 Hz and 9 Hz, CH$_2$ βTrp), 4.01 (2H, m, CH$_2$-benzyl), 5.01 (1H, m, CH αTrp), 5.08 (2H, s, CH$_2$-p-bromobenzyl), 6.59 (2H, d, J$_o$=8 Hz, H$_2$ and H$_6$ p-bromobenzyl), 6.81 (1H, t, J$_o$=7 Hz, H$_5$ Trp), 6.94 (1H, s, H$_2$ Trp), 6.98 (1H, t, J$_o$=7 Hz, H$_6$ Trp), 7.06 (2H, m, H$_2$ and H$_6$ benzyl), 7.12 (1H, d, J$_o$=7 Hz, H$_4$ Trp), 7.16-7.20 (3H, m, H$_3$, H$_4$ and H$_5$ benzyl), 7.26 (1H, d, J$_o$=8 Hz, H$_7$ Trp), 7.29 (2H, d, J$_o$=8 Hz, H$_3$ and H$_5$ benzyl), 8.00 (3H, brs, NH$_2$ Aib), 8.92 (1H, d, J=8 Hz, NH amide), 10.78 (1H, s, NH indole Trp).

$^{13}$C NMR (75 MHz, DMSO-d$^6$, 300° K):

δ (ppm) 23.5 (CH$_3$ Aib), 23.8 (CH$_3$ Aib), 29.0 (CH$_2$ βTrp), 30.5 (CH$_2$-benzyl), 45.6 (CH$_1$-p-bromobenzyl), 45.7 (CH α Trp), 56.7 (Cq Aib), 109.7 (C$_3$ Trp), 111.8 (C$_7$ Trp), 118.2 (C$_4$ tryptophane), 118.7 (C$_5$ Trp), 121.2 (C$_4$ p-bromobenzyl), 121.3 (C$_6$ Trp), 124.9 (C$_2$ tryptophane), 127.0 (C$_2$ and C$_6$ benzyl), 127.2 (C$_9$ Trp), 128.4 (C$_2$ and C$_6$ p-bromobenzyl), 128.9 (C$_3$, C$_4$ and C$_5$ benzyl), 131.9 (C$_3$ and C$_5$ p-bromobenzyl), 135.2 (C$_1$ p-bromobenzyl), 136.2 (C$_8$ Trp), 136.4 (C$_1$ benzyl), 153.9 (Cq triazole), 155.3 (Cq triazole), 171.9 (CO Aib).

(R)—N-(1-(4-(2-methoxybenzyl)-5-benzyl-4H-1,2,4-triazol-3-yl)-2-(1H-indol-3-yl)ethyl)-2-amino-2-methylpropanamide (Compound 115)

$^1$H NMR (300 MHz, DMSO-d$^6$, 300° K):

δ (ppm) 1.24 (3H, s, CH$_3$ Aib), 1.27 (3H, s, CH$_3$ Aib), 3.20 (1H, dd, J=14 Hz and 5 Hz, CH$_2$ βTrp), 3.33 (1H, dd, J=14 Hz and 9 Hz, CH$_2$ βTrp), 3.68 (3H, s, OCH$_3$), 4.00 (2H, s, CH$_2$-phenyl), 4.95 (1H, d, J=17 Hz, CH$_2$—O-methoxybenzyl), 5.07 (1H, m, CH αTrp), 5.18 (1H, d, J=17 Hz, CH$_2$—O-methoxybenzyl), 6.27 (1H, d, J$_o$=8 Hz, H$_3$ o-methoxybenzyl), 6.67 (1H, t, J$_o$=7 Hz, H$_5$ Trp), 6.77 (1H, t, J$_o$=6 Hz, H$_6$ Trp), 6.92-7.05 (6H, m, H$_2$ Trp, H$_2$ and H$_6$ phenyl, H$_4$, H$_5$ and H$_6$ o-methoxybenzyl), 7.14-7.26 (5H, m, H$_4$ and H$_7$ Trp, H$_3$, H$_4$ and H$_5$ phenyl), 8.03 (3H, brs, NH$_2$ Aib), 8.91 (1H, d, J=8 Hz, NH amide), 10.78 (1H, s, NH indole Trp).

$^{13}$C NMR (75 MHz, DMSO-d$^6$, 300° K):

δ (ppm) 23.5 (CH$_3$ Aib), 23.6 (CH$_3$ Aib), 29.1 (CH$_2$ β Trp), 30.5 (CH$_2$-phenyl), 42.1 (CH$_2$—O-methoxybenzyl), 45.7 (CH α Trp), 55.9 (OCH$_3$), 56.7 (Cq Aib), 109.8 (C$_3$ Trp), 111.3 (C$_3$ o-methoxybenzyl), 111.7 (C$_7$ Trp), 118.2 (C$_4$ Trp), 118.7 (C$_5$ Trp), 120.9 (C$_5$ o-methoxybenzyl), 121.2 (C$_6$ Trp), 123.3 (C$_1$ o-methoxybenzyl), 124.8 (C$_2$ Trp), 126.6 (C$_2$ and C$_6$ phenyl), 127.1 (C$_4$ o-methoxybenzyl), 127.2 (C$_9$ Trp), 128.8 (C$_3$, C$_4$ and C$_5$ phenyl), 129.5 (C$_6$ o-methoxybenzyl), 136.0 (C$_1$ phenyl), 136.4 (C$_8$ Trp), 154.0 (Cq triazole), 155.6 (Cq triazole), 156.5 (C$_2$ o-methoxybenzyl), 171.8 (CO Aib).

(S)—N-(1-(4-(2,4-dimethoxybenzyl)-5-phenethyl-4H-1,2,4-triazol-3-yl)-2-(1H-indol-3-yl)ethyl)-2-amino-2-methylpropanamide (Compound 116)

$^1$H NMR (300 MHz, DMSO-d$^6$, 300° K):

δ (ppm) 1.28 (3H, s, CH$_3$ Aib), 1.32 (3H, s, CH$_3$ Aib), 2.81 (4H, m, CH$_2$—CH$_2$-phenyl), 3.30 (2H, t, CH$_2$ βTrp), 3.61 (3H, s, OCH$_3$), 3.69 (3H, s, OCH$_3$), 4.87 (1H, d, J=17 Hz, CH$_2$-o,p-dimethoxybenzyl), 5.03 (1H, d, J=17 Hz, CH$_2$-o,p-dimethoxybenzyl), 5.20 (1H, m, CH αTrp), 6.29 (1H, dd, J$_o$=8 Hz and J$_m$=2 Hz, H$_5$ o,p-dimethoxybenzyl), 6.43 (1H, d, J$_o$=8 Hz, H$_6$ o,p-dimethoxybenzyl), 6.55 (1H, d, J$_m$=2 Hz, H$_3$ o,p-dimethoxybenzyl), 6.83 (1H, t, J$_o$=8 Hz, H$_5$ Trp), 6.99 (1H, t, J$_o$=8 Hz, H$_6$ Trp), 7.06 (1H, d, J=2 Hz, H$_2$ Trp), 7.09-7.25 (6H, m, H$_4$ Trp and CHar phenyl), 7.28 (1H, d, J$_o$=8 Hz, H$_7$ Trp), 8.04 (3H, brs, NH$_2$ Aib), 8.92 (1H, d, J=8 Hz, NH amide), 10.79 (1H, s, NH indole Trp).

$^{13}$C NMR (75 MHz, DMSO-d$^6$, 300° K):

δ (ppm) 23.6 (CH$_3$ Aib), 23.7 (CH$_3$ Aib), 26.5 (CH$_2$—CH$_2$-phenyl), 29.1 (CH$_2$ βTrp), 32.7 (CH$_2$—CH$_2$-phenyl), 41.8 (CH$_2$-o,p-dimethoxybenzyl), 45.7 (CH αTrp), 55.7 (OCH$_3$), 55.9 (OCH$_3$), 56.8 (Cq Aib), 99.1 (C$_3$ o,p-dimethoxybenzyl), 105.2 (C$_5$ o,p-dimethoxybenzyl), 109.9 (C$_3$ Trp), 111.8 (C$_7$ Trp), 115.6 (C$_1$ o,p-dimethoxybenzyl), 118.3 (C$_4$ Trp), 118.7 (C$_5$ Trp), 121.3 (C$_6$ Trp), 124.4 (C$_2$ Trp), 126.6 (C$_4$ phenyl), 127.3 (C$_6$ Trp), 128.2 (C$_6$ o,p-dimethoxybenzyl), 128.7 (C$_2$, C$_3$, C$_5$ and C$_6$ phenyl), 136.4 (C$_8$ Trp), 140.9 (C$_1$ phenyl), 154.6 (Cq triazole), 155.0 (Cq triazole), 157.8 (C$_2$ o,p-dimethoxybenzyl), 160.9 (C$_4$ o,p-dimethoxybenzyl), 171.8 (CO Aib).

(R)—N-(1-(4,5-diphenethyl-4H-1,2,4-triazol-3-yl)-2-(1H-indol-3-yl)ethyl)-2-amino-2-methylpropanamide (Compound 117)

$^1$H NMR (300 MHz, DMSO-d$^6$, 300° K):

δ (ppm) 1.32 (3H, s, CH$_3$ Aib), 1.37 (3H, s, CH$_3$ Aib), 2.59 (4H, m, C—CH$_2$—CH$_2$-phenyl), 2.83 (2H, t, J=8 Hz, N—CH$_2$—CH$_2$-phenyl), 3.38 (2H, m, N—CH$_2$—CH$_2$-phenyl), 3.84 (1H, m, CH$_2$ βTrp), 3.94 (1H, m, CH$_2$ βTrp), 5.23 (1H, m, CH αTrp), 6.84 (2H, m, H$_4$ phenyl from C—CH$_2$—CH$_2$-phenyl and H$_4$ phenyl from N—CH$_2$—CH$_2$-phenyl), 6.93 (1H, t, J$_o$=8 Hz, H$_5$ Trp), 7.00 (1H, t, J$_o$=8 Hz, H$_6$ Trp), 7.07 (1H, d, J=2 Hz, H$_2$ Trp), 7.11-7.27 (9H, m, H$_2$, H$_3$, H$_5$ and H$_6$ phenyl from C—CH$_2$—CH$_2$-phenyl, H$_2$, H$_3$, H$_5$ and H$_6$ phenyl from N—CH$_2$—CH$_2$-phenyl and H$_4$ Trp), 7.50 (1H, d, J$_o$=8 Hz, H$_7$ Trp), 8.07 (3H, brs, NH$_2$ Aib), 9.04 (1H, d, J=8 Hz, NH amide), 10.85 (1H, s, NH indole Trp).

$^{13}$C NMR (75 MHz, DMSO-d$^6$, 300° K):

δ (ppm) 23.5 (CH$_3$ Aib), 23.8 (CH$_3$ Aib), 25.9 (C—CH$_2$—CH$_2$-phenyl), 29.5 (CH$_2$ βTrp), 32.4 (C—CH$_2$—CH$_2$-phenyl), 35.8 (N—CH$_2$—CH$_2$-phenyl), 44.2 (N—CH$_2$—CH$_2$-phenyl), 45.9 (CH αTrp), 56.8 (Cq Aib), 109.7 (C$_3$ Trp), 111.9 (C$_7$ Trp), 118.4 (C$_4$ Trp), 118.9 (C$_5$ Trp), 121.4 (C$_6$ Trp), 124.8 (C$_2$ Trp), 126.6 (C$_4$ phenyl from C—CH$_2$—CH$_2$-phenyl), 127.2 (C$_4$ phenyl from N—CH$_2$—CH$_2$-phenyl), 127.4 (C$_9$ Trp), 128.7 (C$_2$ and C$_6$ phenyl from C—CH$_2$—CH$_2$-phenyl, C$_2$ and C$_6$ phenyl from N—CH$_2$—CH$_2$-phenyl), 128.8 (C$_3$ and C$_5$ phenyl from C—CH$_2$—CH$_2$-phenyl, C$_3$ and C$_5$ phenyl from N—CH$_2$—CH$_2$-phenyl), 136.5 (C$_1$ phenyl from N—CH$_2$—CH$_2$-phenyl), 137.5 (C$_1$ phenyl from C—CH$_2$—CH$_2$-phenyl), 140.8 (C$_8$ Trp), 154.1 (Cq triazole), 154.7 (Cq triazole), 171.9 (CO Aib).

(R)—N-(1-(4-(3,4-dichlorobenzyl)-5-benzyl-4H-1,2,4-triazol-3-yl)-2-(1H-indol-3-yl)ethyl)-2-amino-2-methylpropanamide (Compound 118)

$^1$H NMR (300 MHz, DMSO-d$^6$, 300° K):

δ (ppm) 1.24 (3H, s, CH$_3$ Aib), 1.25 (3H, s, CH$_3$ Aib), 3.33 (2H, m, CH$_2$ βTrp), 4.04 (2H, s, CH$_2$-benzyl), -benzyl), 5.05 (1H, m, CH αTrp), 5.12 (2H, s, CH$_2$-m,p-dichlorobenzyl), 6.49 (1H, dd, J$_o$=8 Hz and J$_m$=2 Hz, H$_6$ m,p-dichlorobenzyl), 6.80 (1H, t, J$_o$=8 Hz, H$_5$ Trp), 6.87 (1H, d, J$_m$=2 Hz, H$_2$ Trp), 6.98 (1H, t, J$_o$=7 Hz, H$_6$ Trp), 7.02-7.10 (3H, m, H$_2$ and H$_6$ benzyl, H$_5$ m,p-dichlorobenzyl), 7.18 (3H, m, H$_3$, H$_4$ and H$_5$ benzyl), 7.26 (2H, m, H$_4$ and H$_7$ Trp), 8.04 (3H, brs, NH$_2$ Aib), 8.94 (1H, d, J=9 Hz, NH amide), 10.81 (1H, s, NH indole Trp).

$^{13}$C NMR (75 MHz, DMSO-d$^6$, 300° K):

δ (ppm) 23.4 (CH$_3$ Aib), 23.8 (CH$_3$ Aib), 29.0 (CH$_2$ βTrp), 30.4 (CH$_2$-benzyl), 45.1 (CH$_2$-m,p-dichlorobenzyl), 45.6 (CH αTrp), 56.7 (Cq Aib), 109.6 (C$_3$ Trp), 111.8 (C$_7$ Trp), 118.1 (C$_4$ Trp), 118.6 (C$_5$ Trp), 121.3 (C$_6$ Trp), 124.9 (C$_2$ Trp), 126.4 (C$_6$ m,p-dichlorobenzyl), 127.0 (C$_2$ m,p-dichlorobenzyl), 127.2 (C$_9$ Trp), 128.4 (O$_2$ and C$_6$ benzyl), 130.7 (C$_4$ and C$_5$ m,p-dichlorobenzyl), 131.8 (C$_3$ m,p-dichlorobenzyl), 136.0 (C$_1$ benzyl), 136.4 (C$_8$ Trp), 136.7 (C$_1$ m,p-dichlorobenzyl), 154.1 (Cq triazole), 155.2 (Cq triazole), 172.0 (CO Aib).

(R)—N-(1-(4-(4-methoxybenzyl)-5-benzyl-4H-1,2,4-triazol-3-yl)-2-phenylethyl)-2-amino-2-methylpropanamide (Compound 120)

$^1$H NMR (300 MHz, DMSO-d$^6$, 300° K):

δ (ppm) 1.18 (3H, s, CH$_3$ Aib), 1.26 (3H, s, CH$_3$ Aib), 3.09 (1H, dd, J=14 Hz and 6 Hz, CH$_2$ βPhe), 3.18 (1H, dd, J=14 Hz and 9 Hz, CH$_2$ βPhe), 3.99 (2H, d, J=4 Hz, CH$_2$-phenyl), 4.95 (1H, d, J=16 Hz, CH$_2$-p-methoxybenzyl), 5.06 (1H, d, J=16 Hz, CH$_2$-p-methoxybenzyl), 5.13 (1H, m, CH αPhe), 6.78 (4H, s, CHar p-methoxybenzyl), 7.02-7.08 (4H, m, H$_2$ and H$_6$ phenyl, H$_2$ and H$_6$ Phe), 7.12-7.25 (6H, m, H$_3$, H$_4$ and H$_5$ phenyl, H$_3$, H$_4$ and H$_5$ Phe), 7.99 (3H, brs, NH$_2$ Aib), 8.92 (1H, d, J=8 Hz, NH amide).

$^{13}$C NMR (75 MHz, DMSO-d$^6$, 300° K):

δ (ppm) 23.4 (CH$_3$ Aib), 23.8 (CH$_3$ Aib), 30.7 (CH$_2$-phenyl), 38.7 (CH$_2$ βPhe), 45.9 (CH$_2$-p-methoxybenzyl), 46.4 (CH αPhe), 55.6 (OCH$_3$), 56.7 (Cq Aib), 114.6 (C$_3$ and C$_5$ p-methoxybenzyl), 126.9 and 127.1 (C$_4$ phenyl and C$_4$ Phe), 127.7 (C$_1$ p-methoxybenzyl), 128.2 (C$_2$ and C$_6$ Phe), 128.5 (C$_3$ and C$_5$ Phe), 128.9 (O$_2$, C$_3$, C$_5$ and C$_6$ phenyl), 129.7 (C$_2$ and C$_6$ p-methoxybenzyl), 136.3 (C$_1$ phenyl), 137.6 (C$_1$ Phe), 154.0 (Cq triazole), 154.9 (Cq triazole), 159.2 (C$_4$ p-methoxybenzyl), 171.7 (CO amide).

(R)—N-(1-(4-(4-fluorobenzyl)-5-phenethyl-4H-1,2,4-triazol-3-yl)-2-(1H-indol-3-yl)ethyl)-2-amino-2-methylpropanamide (Compound 121)

$^1$H NMR (300 MHz, DMSO-d$^6$, 300° K):

δ (ppm) 1.27 (3H, s, CH$_3$ Aib), 1.28 (3H, s, CH$_3$ Aib), 2.82 (4H, m, CH$_2$—CH$_2$-phenyl), 3.34 (2H, m, CH$_2$ βTrp), 5.06 (2H, s, CH$_2$-p-fluorobenzyl), 5.16 (1H, m, CH αTrp), 6.85 (3H, m, H$_5$ Trp, H$_3$ and H$_5$ p-fluorobenzyl), 6.98-7.04 (4H, m, H$_2$ and H$_6$ Trp, H$_2$ and H$_6$ phenyl), 7.09-7.11 (2H, m, H$_2$ and H$_6$ p-fluorobenzyl), 7.15 (1H, d, J$_o$=6 Hz, H$_4$ Trp), 7.19 (3H, t, J$_o$=8 Hz, H$_3$, H$_4$ and H$_5$ phenyl), 7.29 (1H, d, J$_o$=8 Hz, H$_7$ Trp), 8.01 (3H, brs, NH$_2$ Aib), 8.94 (1H, d, J=8 Hz, NH amide), 10.78 (1H, s, NH indole Trp).

$^{13}$C NMR (75 MHz, DMSO-d$^6$, 300° K):

δ (ppm) 23.5 (CH$_3$ Aib), 23.8 (CH$_3$ Aib), 26.5 (CH$_2$—CH$_2$-phenyl), 29.2 (CH$_2$ βTrp), 32.7 (CH$_2$—CH$_2$-phenyl), 45.4 (CH$_2$-p-fluorobenzyl), 45.7 (CH αTrp), 56.8 (Cq Aib), 109.8 (C$_3$ Trp), 111.8 (C$_7$ Trp), 115.9 and 116.2 (C$_3$ and C$_5$ p-fluorobenzyl), 118.3 (C$_4$ Trp), 118.7 (C$_6$ Trp), 121.3 (C$_6$ Trp), 124.8 (C$_2$ Trp), 126.5 (C$_4$ phenyl), 127.3 (C$_9$ Trp), 128.5 (O$_2$ and C$_6$ p-fluorobenzyl), 128.7 (O$_2$, C$_3$, C$_5$ and C$_6$ phenyl), 132.2 (C$_2$ p-fluorobenzyl), 136.4 (C$_8$ Trp), 140.9 (C$_1$ phenyl), 154.5 (Cq triazole), 154.7 (Cq triazole), 160.3 (C$_4$ p-fluorobenzyl), 171.9 (CO amide).

NMR$^{19}$F. (282 MHz, DMSO-d$^6$, 300° K):

δ (ppm)-114.9 (1F, m, p-fluorobenzyl).

(R)—N-(1-(4-(3,4-dichlorobenzyl)-5-phenethyl-4H-1,2,4-triazol-3-yl)-2-(1H-indol-3-yl)ethyl)-2-amino-2-methylpropanamide (Compound 122)

$^1$H NMR (300 MHz, DMSO-d$^6$, 300° K):

δ (ppm) 1.25 (3H, s, CH$_3$ Aib), 1.26 (3H, s, CH$_3$ Aib), 2.84 (4H, m, CH$_2$—CH$_2$-phenyl), 3.34 (2H, d, J=7 Hz, CH$_2$ βTrp), 5.11 (3H, m, CH αTrp and CH$_2$-m,p-dichlorobenzyl), 6.63 (1H, dd, J$_o$=8 Hz and J$_m$=2 Hz, H$_6$ m,p-dichlorobenzyl), 6.83 (1H, t, J$_o$=8 Hz, H$_5$ Trp), 6.99 (1H, t, J$_o$=8 Hz, H$_6$ Trp), 7.05 (1H, d, J=2 Hz, H$_2$ Trp), 7.12 (5H, m, CHar phenyl), 7.17 (1H, d, J$_o$=8 Hz, H$_4$ Trp), 7.21 (1H, s, H$_2$ m,p-dichlorobenzyl), 7.27 (1H, d, J$_o$=8 Hz, H$_5$ m,p-dichlorobenzyl), 7.39 (1H, d, J$_o$=8 Hz, H$_7$ Trp), 8.02 (3H, brs, NH$_2$ Aib), 8.94 (1H, d, J=8 Hz, NH amide), 10.78 (1H, s, NH indole Trp).

$^{13}$C NMR (75 MHz, DMSO-d$^6$, 300° K):

δ (ppm) 23.5 (CH$_3$ Aib), 23.8 (CH$_3$ Aib), 26.4 (CH$_2$—CH$_2$-phenyl), 29.1 (CH$_2$ βTrp), 32.6 (CH$_2$—CH$_2$-phenyl), 44.7 (CH$_2$-m,p-dichlorobenzyl), 45.6 (CH α Trp), 56.7 (Cq Aib), 109.7 (C$_3$ Trp), 111.8 (C$_7$ Trp), 118.1 (C$_4$ Trp), 118.7 (C$_5$ Trp), 121.3 (C$_6$ Trp), 124.9 (C$_2$ Trp), 126.5 (C$_4$ phenyl and C$_6$ m,p-dichlorobenzyl), 127.2 (C$_9$ Trp), 128.7 (C$_2$, C$_3$, C$_5$ and C$_6$ phenyl, C$_2$ m,p-dichlorobenzyl), 130.9 (C$_4$ m,p-dichlorobenzyl), 131.4 (C$_5$ m,p-dichlorobenzyl), 132.0 (C$_3$ m,p-dichlorobenzyl), 136.4 (C$_8$ Trp), 137.2 (C$_1$ m,p-dichlorobenzyl), 140.8 (C$_1$ phenyl), 154.5 (Cq triazole), 154.7 (Cq triazole), 171.9 (CO amide).

(R)—N-(1-(4-(4-methylbenzyl)-5-benzyl-4H-1,2,4-triazol-3-yl)-2-(1H-indol-3-yl)ethyl)-2-amino-2-methylpropanamide (Compound 124)

$^1$H NMR (300 MHz, DMSO-d$^6$, 300° K):

δ (ppm) 1.22 (3H, s, CH$_3$ Aib), 1.27 (3H, s, CH$_3$ Aib), 2.22 (3H, s, CH$_3$ p-methylbenzyl), 3.22 (1H, dd, J=14 Hz and 6 Hz, CH$_2$ βTrp), 3.33 (1H, dd, J=14 Hz and 9 Hz, CH$_2$ βTrp), 3.99 (2H, s, CH$_2$-benzyl), 5.04 (2H, s, CH$_2$-p-methylbenzyl), 5.09 (1H, m, CH αTrp), 6.64 (2H, d, J$_o$=8 Hz, H$_3$ and H$_5$ p-methylbenzyl), 6.78 (1H, t, J$_o$=7 Hz, H$_5$ Trp), 6.98 (4H, t, J$_o$=7 Hz, H$_6$ Trp, H$_3$, H$_4$ and H$_5$ benzyl), 7.01 (1H, d, J=2 Hz, H$_2$ Trp), 7.07 (2H, d, J$_o$=7 Hz, H$_2$ and H$_6$ p-methylbenzyl), 7.20 (3H, m, H$_4$ Trp, H$_2$ and H$_6$ benzyl), 7.26 (1H, d, J$_o$=8 Hz, H$_7$ Trp), 7.98 (3H, brs, NH$_2$ Aib), 8.89 (1H, d, J=8 Hz, NH amide), 10.74 (1H, s, NH indole Trp).

$^{13}$C NMR (75 MHz, DMSO-d$^6$, 300° K):

δ (ppm) 21.0 (CH$_3$ p-methylbenzyl), 23.5 (CH$_3$ Aib), 23.7 (CH$_3$ Aib), 29.1 (CH$_2$(Trp), 30.6 (CH$_2$-benzyl), 45.7 (CH αTrp), 46.0 (CH$_2$-p-methylbenzyl), 56.7 (Cq Aib), 109.8 (C$_3$ Trp), 111.7 (C$_7$ Trp), 118.3 (C$_4$ Trp), 118.6 (C$_5$ Trp), 121.2 (C$_6$ Trp), 124.8 (C$_2$ Trp), 126.3 (C$_3$ and C$_5$ p-methylbenzyl), 127.0 (C$_4$ benzyl), 127.2 (C$_9$ Trp), 128.9 (O$_2$, C$_3$, C$_5$ and C$_6$ benzyl), 129.7 (C$_2$ and C$_6$ p-methylbenzyl), 132.9 (C$_1$ p-methylbenzyl), 136.3 (C$_4$ p-methylbenzyl), 136.4 (C$_8$ Trp), 137.4 (C$_1$ benzyl), 153.9 (Cq triazole), 155.3 (Cq triazole), 171.8 (CO amide).

(S)—N-(1-(4-(4-methoxybenzyl)-5-(3-phenylpropyl)-4H-1,2,4-triazol-3-yl)-2-(1H-indol-3-yl)ethyl)-2-amino-2-methylpropanamide (Compound 125)

$^1$H NMR (300 MHz, DMSO-d$^6$, 300° K):

δ (ppm) 1.27 (3H, s, CH$_3$ Aib), 1.31 (3H, s, CH$_3$ Aib), 1.74 (2H, m, (CH$_2$—CH$_2$—CH$_2$-phenyl), 2.52 (4H, t, J=7 Hz, CH$_2$—CH$_2$—CH$_2$-phenyl), 3.35 (2H, d, J=7 Hz, CH$_2$ βTrp, 3.68 (3H, s, OCH$_3$), 4.98 (2H, s, CH$_2$-p-methoxybenzyl), 5.20 (1H, m, CH αTrp), 6.75 (4H, s, CHar p-methoxybenzyl), 6.83 (1H, t, J$_o$=8 Hz, H$_5$ Trp), 6.99 (1H, t, J$_o$=7 Hz, H$_6$ Trp), 7.06 (3H, m, H$_2$ and H$_6$ phenyl, H$_2$ Trp), 7.14 (1H, d, J$_o$=7 Hz, H$_4$ Trp), 7.19 (3H, t, J$_o$=8 Hz, H$_3$, H$_4$ and H$_5$ phenyl), 7.29 (1H, d, J$_o$=8 Hz, H$_7$ Trp), 8.01 (3H, brs, NH$_2$ Aib), 8.94 (1H, d, J=8 Hz, NH amide), 10.79 (1H, d, J=2 Hz, NH indole Trp).

$^{13}$C NMR (75 MHz, DMSO-d$^6$, 300° K):

δ (ppm) 23.6 (CH$_3$ Aib), 23.8 (CH$_3$ Aib), 24.1 (CH$_2$—CH$_2$—CH$_2$-phenyl), 28.5 (CH$_2$—CH$_2$—CH$_2$-phenyl), 29.2 (CH$_2$ βTrp), 34.7 (CH$_2$—CH$_2$—CH$_2$-phenyl), 45.5 (CH$_2$-p-methoxybenzyl), 45.8 (CH αTrp), 55.5 (OCH$_3$), 56.8 (Cq Aib), 109.8 (C$_3$ Trp), 111.8 (C$_7$ Trp), 114.6 (C$_3$ and C$_5$ p-methoxybenzyl), 118.3 (C$_4$ Trp), 118.7 (C$_5$ Trp), 121.3 (C$_6$ Trp), 124.9 (C$_2$ Trp), 126.2 (C$_4$ phenyl), 127.3 (C$_9$ Trp), 127.8 (C$_1$ p-methoxybenzyl), 127.9 (C$_3$, C$_4$ and C$_5$ phenyl), 128.7 (C$_2$ and C$_6$ p-methoxybenzyl), 136.4 (C$_8$ Trp), 141.7 (C$_1$ phenyl), 154.7 (Cq triazole), 154.8 (Cq triazole), 159.2 (C$_1$ p-methoxybenzyl), 171.9 (CO amide).

(S)—N-(1-(4-(4-methoxybenzyl)-5-benzyl-4H-1,2,4-triazol-3-yl)-2-(1H-indol-3-yl)ethyl)-2-amino-2-methylpropanamide (Compound 126)

$^1$H NMR (300 MHz, DMSO-d$^6$, 300° K):

δ (ppm) 1.25 (3H, s, CH$_3$ Aib), 1.28 (3H, s, CH$_3$ Aib), 3.26 (1H, dd, J=14 Hz and 6 Hz, CH$_2$ βTrp), 3.34 (1H, dd, J=14 Hz and 8 Hz, CH$_2$ βTrp), 3.99 (2H, s, CH$_2$-phenyl), 4.98 (2H, s, CH$_2$-p-methoxybenzyl), 5.13 (1H, m, CH αTrp), 6.68 (4H, s, CHar p-methoxybenzyl), 6.80 (1H, t, J$_o$=8 Hz, H$_5$ Trp), 6.99 (1H, t, J$_o$=8 Hz, H$_6$ Trp), 7.02-7.06 (4H, m, H$_2$ and H$_4$ Trp, H$_2$ and H$_6$ phenyl), 7.20 (3H, m, H$_3$, H$_4$ and H$_5$ phenyl), 7.27 (1H, d, J$_o$=8 Hz, H$_7$ Trp), 8.00 (3H, s, NH$_2$ Aib), 8.91 (1H, d, J=8 Hz, NH amide), 10.76 (1H, s, NH indole Trp).

$^{13}$C NMR (75 MHz, DMSO-d$^6$, 300° K):

δ (ppm) 23.5 (CH$_3$ Aib), 23.7 (CH$_3$ Aib), 29.1 (CH$_2$ βTrp), 30.6 (CH$_2$-phenyl), 45.7 (CH αTrp and CH$_2$-p-methoxybenzyl), 55.5 (OCH$_3$), 56.7 (Cq Aib), 109.8 (C$_3$ Trp), 111.7 (C$_7$ Trp), 114.5 (C$_3$ and C$_5$ p-methoxybenzyl), 118.3 (C$_4$ Trp), 118.7 (C$_5$ Trp), 121.3 (C$_6$ Trp), 124.8 (C$_2$ Trp), 127.1 (C$_4$ phenyl), 127.3 (C$_9$ Trp), 127.6 (C$_1$ p-methoxybenzyl), 127.8 (C$_2$ and C$_6$ p-methoxybenzyl), 128.8 (C$_2$ and C$_6$ phenyl), 128.9 (C$_3$ and C$_5$ phenyl), 136.3 (C$_8$ Trp), 136.4 (C$_1$ phenyl), 153.8 (Cq triazole), 155.2 (Cq triazole), 159.2 (C$_4$ p-methoxybenzyl), 171.9 (CO amide).

N—((R)-1-(4-(4-nitrobenzyl)-5-phenethyl-4H-1,2,4-triazol-3-yl)-2-(1H-indol-3-yl)ethyl)-2-amino-2-methylpropanamide (Compound 128)

$^1$H NMR (300 MHz, DMSO-d$^6$, 300° K):

δ (ppm) 1.28 (3H, s, CH$_3$ Aib), 1.29 (3H, s, CH$_3$ Aib), 2.77-2.94 (4H, m, CH$_2$—CH$_2$-phenyl), 3.28 (1H, dd, $^3$J=14 Hz and 8 Hz, CH$_2$ βTrp), 3.43 (1H, dd, $^3$J=14 Hz and 7 Hz, CH$_2$ βTrp), 5.05 (1H, m, CH αTrp), 5.25 (2H, d, J=7 Hz, CH$_2$-p-nitrobenzyl), 6.72 (1H, t, J$_o$=7 Hz, H$_5$ Trp), 6.89 (2H, d, J$_o$=9 Hz, H$_2$ and H$_6$ p-nitrobenzyl), 6.92 (1H, t, J$_o$=7 Hz, H$_6$ Trp), 7.00 (1H, d, J$_m$=2 Hz, H$_2$ Trp), 7.08-7.15 (4H, m, H$_4$ and H$_7$ Trp, H$_2$ and H$_6$ phenyl), 7.17 (2H, J$_o$=7 hz, H$_3$ and H$_5$ phenyl), 7.24 (1H, t, J$_o$=8 Hz, H$_4$ phenyl), 7.92 (2H, d, J$_o$=9 Hz, H$_3$ and H$_5$ p-nitrobenzyl), 8.06 (3H, brs, NH$_2$ Aib), 8.98 (1H, d, 8 Hz, NH amide), 10.79 (1H, s, NH indole Trp).

$^{13}$C NMR (75 MHz, DMSO-d$^6$, 300° K):

δ (ppm) 23.5 (CH$_3$ Aib), 23.8 (CH$_3$ Aib), 26.4 (CH$_2$—CH$_2$-phenyl), 29.1 (CH$_2$ βTrp), 32.6 (CH$_2$—CH$_2$-phenyl), 45.3 (CH$_2$-p-nitrobenzyl), 45.7 (CH αTrp), 56.8 (Cq Aib), 109.6 (C$_3$ Trp), 111.8 (C$_7$ Trp), 118.1 (C$_4$ Trp), 118.5 (C$_5$ Trp), 121.2 (C$_6$ Trp), 124.1 (C$_2$ and C$_5$ p-nitrobenzyl), 124.8 (C$_2$ Trp), 126.5 (C$_2$ and C$_5$ phenyl), 127.2 (C$_9$ Trp, C$_1$ and C$_6$ p-nitrobenzyl), 128.7 (C$_3$, C$_4$ and C$_5$ phenyl), 136.4 (C$_8$ Trp), 140.8 (C$_1$ phenyl), 143.5 (C$_1$ p-nitrobenzyl), 154.5 (Cq triazole), 154.8 (Cq triazole), 172.0 (CO Aib).

(S)—N-(1-(4-(4-methoxybenzyl)-5-phenethyl-4H-1,2,4-triazol-3-yl)-2-(1H-indol-3-yl)ethyl)-2-amino-2-methylpropanamide (Compound 129)

$^1$H NMR (300 MHz, DMSO-d$^6$, 300° K):

δ (ppm) 1.27 (3H, s, CH$_3$ Aib), 1.30 (3H, s, CH$_3$ Aib), 2.81 (4H, m, CH$_2$—CH$_2$-phenyl), 3.34 (2H, d, J=7 Hz, CH$_2$ βTrp), 3.68 (3H, s, OCH$_3$), 4.99 (2H, s, CH$_2$-p-methoxybenzyl), 5.20 (1H, m, CH αTrp), 6.75 (4H, m, CHar p-methoxybenzyl), 6.83 (1H, t, J$_o$=7 Hz, H$_5$ Trp), 7.03 (1H, t, J$_o$=8 Hz, H$_6$ Trp), 7.04 (1H, d, J=2 Hz, H$_2$ Trp), 7.10 (2H, d, J$_o$=7 Hz, H$_2$ and H$_6$ phenyl), 7.13 (1H, d, J$_o$=8 Hz, H$_4$ Trp), 7.19 (3H, t, J$_o$=7 Hz, H$_3$, H$_4$ and H$_5$ phenyl), 7.29 (1H, d, J$_o$=8 Hz, H$_7$ Trp), 8.01 (3H, brs, NH$_2$ Aib), 8.94 (1H, d, J=8 Hz, NH amide), 10.78 (1H, d, J=2 Hz, NH indole Trp).

$^{13}$C NMR (75 MHz, DMSO-d$^6$, 300° K):

δ (ppm) 23.6 (CH$_3$ Aib), 23.8 (CH$_3$ Aib), 26.6 (CH$_2$—CH$_2$-phenyl), 29.2 (CH$_2$ βTrp), 32.7 (CH$_2$—CH$_2$-phenyl), 45.3 (CH$_2$-p-methoxybenzyl), 45.7 (CH αTrp), 55.5 (OCH$_3$), 56.8 (Cq Aib), 109.9 (C$_3$ Trp), 111.8 (C$_7$ Trp), 114.6 (C$_3$ and C$_5$ p-methoxybenzyl), 118.3 (C$_4$ Trp), 118.7 (C$_5$ Trp), 121.3 (C$_6$ Trp), 124.8 (C$_2$ Trp), 126.5 (C$_4$ phenyl), 127.3 (C$_9$ Trp and C$_1$ p-methoxybenzyl), 127.9 (C$_2$ and C$_6$ p-methoxybenzyl), 128.7 (C$_2$, C$_3$, C$_5$ and C$_6$ p-methoxybenzyl), 136.5 (C$_8$ Trp), 140.9 (C$_1$ phenyl), 154.4 (Cq triazole), 154.7 (Cq triazole), 159.2 (C$_4$ p-methoxybenzyl), 171.9 (CO amide).

(R)—N-(1-(4-(4-methoxyphenethyl)-5-phenethyl-4H-1,2,4-triazol-3-yl)-2-(1H-indol-3-yl)ethyl)-2-amino-2-methylpropanamide (Compound 130)

$^1$H NMR (300 MHz, DMSO-d$^6$, 300° K):

δ (ppm) 1.30 (3H, s, CH$_3$ Aib), 1.35 (3H, s, CH$_3$ Aib), 2.55 (4H, m, CH$_2$—CH$_2$-phenyl and CH$_2$—CH$_2$-p-methoxybenzyl), 2.83 (2H, t, J=8 Hz, CH$_2$—CH$_2$-phenyl), 3.37 (2H, m, CH$_2$-p-methoxybenzyl), 3.65 (3H, s, OCH$_3$), 3.77 (1H, m, CH$_2$ β Trp), 3.89 (1H, m, CH$_2$ βTrp), 5.20 (1H, m, CH αTrp), 6.72 (4H, s, CHar p-methoxybenzyl), 6.94 (1H, t, J$_o$=7 Hz, H$_5$ Trp), 7.02 (1H, t, J$_o$=8 Hz, H$_6$ Trp), 7.05 (1H, d, J=2 Hz, H$_2$ Trp), 7.11 (2H, d, J$_o$=7 Hz, H$_2$ and H$_6$ phenyl), 7.16 (1H, d, J$_o$=7 Hz, H$_4$ Trp), 7.25 (3H m, H$_3$, H$_4$, H$_5$ phenyl), 7.50 (1H, d, J$_o$=8 Hz, H$_7$ Trp), 8.05 (3H, brs, NH$_2$ Aib), 9.02 (1H, d, J=8 hz, NH amide), 10.83 (1H, d, J=2 Hz, NH indole Trp).

$^{13}$C NMR (75 MHz, DMSO-d$^6$, 300° K):

δ (ppm) 23.5 (CH$_3$ Aib), 23.8 (CH$_3$ Aib), 26.0 (CH$_2$—CH$_2$-phenyl), 29.5 (CH$_2$ βTrp), 32.5 (CH$_2$—CH$_2$-phenyl), 35.0 (CH$_2$—CH$_2$-p-methoxybenzyl), 44.4 (CH$_2$—CH$_2$-p-methoxybenzyl), 45.8 (CH αTrp), 55.4 (OCH$_3$), 56.8 (Cq Aib), 109.9 (C$_3$ Trp), 111.9 (C$_7$ Trp), 114.2 (C$_3$ and C$_5$ p-methoxybenzyl), 118.4 (C$_4$ Trp), 118.9 (C$_5$ Trp), 121.4 (C$_6$ Trp), 124.7 (C$_2$ Trp), 126.5 (C$_4$ phenyl), 127.4 (C$_9$ Trp), 128.7 (O$_2$, C$_3$, C$_5$ and C$_6$ phenyl), 129.4 (C$_1$ p-methoxybenzyl), 130.3 (C$_2$ and C$_6$ p-methoxybenzyl), 136.5 (C$_8$ Trp), 141.0 (C$_1$ phenyl), 154.0 (Cq triazole), 154.5 (Cq triazole), 158.6 (C$_4$ p-methoxybenzyl), 171.8 (CO amide).

(R)—N-(2-(1H-indol-3-yl)-1-(5-phenethyl-4-(pyridin-2-ylmethyl)-4H-1,2,4-triazol-3-yl)ethyl)-2-amino-2-methylpropanamide (Compound 132)

$^1$H NMR (300 MHz, DMSO-d$^6$, 300° K):

δ (ppm) 1.26 (3H, s, CH$_3$ Aib), 1.29 (3H, s, CH$_3$ Aib), 2.95 (4H, m, CH$_2$—CH$_2$-phenyl), 3.40 (2H, m, CH$_2$ βTrp), 5.26 (1H, m, CH αTrp), 5.37 (2H, s, CH$_2$-o-pyridyl), 6.83 (1H, t, J$_o$=7 Hz, H$_5$ Trp), 6.98 (1H, t, J$_o$=8 Hz, H$_6$ Trp), 7.11-7.30 (10H, m, H$_2$, H$_4$ and H$_7$ Trp, CHar phenyl, H$_3$ and H$_5$ o-pyridyl), 7.71 (1H, t, J$_o$=7 Hz, H$_4$ o-pyridyl), 8.22 (3H, brs, NH$_2$ Aib), 8.42 (1H, d, J$_o$=4 Hz, H$_6$ o-pyridyl), 9.05 (1H, d, J=8 Hz, NH amide), 10.87 (1H, s, NH indole Trp).

$^{13}$C NMR (75 MHz, DMSO-d$^6$, 300° K):

δ (ppm) 23.4 (CH$_3$ Aib), 23.7 (CH$_3$ Aib), 26.4 (CH$_2$—CH$_2$-phenyl), 28.6 (CH$_2$ βTrp), 32.5 (CH$_2$—CH$_2$-phenyl), 45.7 (CH αTrp), 47.6 (CH$_2$ o-pyridyl), 56.8 (Cq Aib), 109.8 (C$_3$ Trp), 111.8 (C$_7$ Trp), 118.3 (C$_4$ Trp), 118.6 (C$_5$ Trp), 121.2 (C$_6$ Trp), 122.0 (C$_3$ o-pyridyl), 123.6 (C$_5$ o-pyridyl), 126.3 (C$_2$ Trp), 126.6 (C$_4$ phenyl), 127.3 (C$_9$ Trp), 128.7 (O$_2$, C$_3$, C$_5$ and C$_6$ phenyl), 136.4 (C$_8$ tryptophane), 137.7 (C$_4$ o-pyridyl), 140.7 (C$_1$ phenyl), 150.1 (C$_6$ o-pyridyl), 154.9 (Cq triazole), 155.2 (Cq triazole), 158.7 (C$_2$ o-pyridyl), 172.0 (CO amide).

N—((R)-1-(4-(2,4-dimethoxybenzyl)-5-phenethyl-4H-1,2,4-triazol-3-yl)-2-(1H-indol-3-yl)ethyl)-2-amino-2-methylpropanamide (Compound 179)

$^1$H NMR (300 MHz, DMSO d$^6$, 300° K):

δ (ppm) 1.26 (s, 3H, CH$_3$ Aib), 1.30 (s, 3H, CH$_3$ Aib), 2.82 (m, 4H, CH$_2$—CH$_2$-phenyl), 3.29 (t, 2H, J=8 Hz, CH$_2$ βTrp), 3.61 (s, 3H, OCH$_3$), 3.68 (s, 3H, OCH$_3$), 4.85 (d, 1H, J=17 Hz, CH$_2$-o,p-dimethoxybenzyl), 5.02 (d, 1H, J=17 Hz, CH$_2$-o,p-dimethoxybenzyl), 5.18 (m, 1H, CH αTrp), 6.29 (dd, 1H, J$_o$=8 Hz and J$_m$=2 Hz, H$_5$ o,p-dimethoxybenzyl), 6.40 (d, 1H, J$_o$=8 Hz, H$_6$ o,p-dimethoxybenzyl), 6.55 (d, 1H, J$_m$=2 Hz, H$_3$ o,p-dimethoxybenzyl), 6.82 (t, 1H, J$_o$=8 Hz, H$_5$ Trp), 6.99 (t, 1H, J$_o$=8 Hz, H$_6$ Trp), 7.05 (s, 1H, H$_2$ Trp), 7.09-7.24 (m, 6H, H$_4$ Trp and CHar phenyl), 7.27 (d, 1H, J$_o$=8 Hz, H$_7$ Trp), 7.99 (s, 3H, large, NH$_2$ Aib TFA salt), 8.89 (d, 1H, J=8 Hz, NH amide), 10.77 (s, 1H, NH indole Trp).

$^{13}$C NMR (75 MHz, DMSO-d$^6$, 300° K):

δ (ppm) 23.6 (CH$_3$ Aib), 23.7 (CH$_3$ Aib), 26.5 (CH$_2$—CH$_2$-phenyl), 29.2 (CH$_2$ βTrp), 32.7 (CH$_2$—CH$_2$-phenyl), 41.6 (CH$_2$-o,p-dimethoxybenzyl), 45.7 (CH αTrp), 55.7 (OCH$_3$), 55.9 (OCH$_3$), 56.7 (Cq Aib), 99.1 (C$_3$ o,p-dimethoxybenzyl), 105.2 (C$_5$ o,p-dimethoxybenzyl), 110.0 (C$_3$ Trp), 111.8 (C$_7$ Trp), 115.7 (C$_1$ o,p-dimethoxybenzyl), 118.3 (C$_4$ Trp), 118.7 (C$_5$ Trp), 121.3 (C$_6$ Trp), 126.5 (C$_2$ Trp and C$_6$ o,p-dimethoxybenzyl), 127.3 (C$_9$ Trp), 128.1 (C$_4$ phenyl), 128.7 (O$_2$, C$_3$, C$_5$ and C$_6$ phenyl), 136.4 (C$_8$ Trp), 140.9 (C$_1$ phenyl), 154.5 (Cq triazole), 155.0 (Cq triazole), 157.8 (C$_2$ o,p-dimethoxybenzyl), 160.9 (C$_4$ o,p-dimethoxybenzyl), 171.7 (CO amide).

N—((R)-1-(4-(4-methoxybenzyl)-5-phenethyl-4H-1,2,4-triazol-3-yl)-2-(1H-indol-3-yl)ethyl)-tetrahydro-2H-pyran-4-carboxamide (Compound 184)

$^1$H NMR (300 MHz, DMSO d$^6$, 300° K):

δ (ppm) 1.20 (m, 1H, H$_5$ tetrahydropyrane), 1.30 (m, 3H, H$_3$ and H$_5$ tetrahydropyrane), 2.17 (m, 1H, H$_4$ tetrahydropyrane), 2.82 (m, 4H, CH$_2$—CH$_2$-phenyl), 3.16 (m, 2H, H$_2$ and H$_6$ tetrahydropyrane), 3.31 (dd, 1H, J=14 Hz and 8 Hz, CH$_2$ βTrp), 3.35 (dd, 1H, J=14 Hz and 7 Hz, CH$_2$ βTrp), 3.66 (s, 3H, OCH$_3$), 3.72 (m, 2H, H$_2$ and H$_6$ tetrahydropyrane), 5.08 (m, 2H, CH$_2$-p-methoxybenzyl), 5.26 (m, 1H, CH αTrp), 6.73 (s, 4H, CHar p-methoxybenzyl), 6.87 (t, 1H, J$_o$=8 Hz, H$_5$ Trp), 7.02 (m, 2H, H$_2$ and H$_6$ Trp), 7.07 (d, 2H, J$_o$=7 Hz, H$_2$ and H$_6$ phenyl), 7.18 (m, 3H, H$_3$, H$_4$ and H$_5$ phenyl), 7.30 (m, 2H, H$_4$ and H$_7$ Trp), 8.52 (d, 1H, J=8 Hz, NH amide), 10.77 (s, 1H, NH indole Trp).

$^{13}$C NMR (75 MHz, DMSO d$^6$, 300° K):

δ (ppm) 26.3 (CH$_2$—CH$_2$-phenyl), 28.8 (C$_3$ and C$_5$ tetrahydropyrane), 29.2 (CH$_2$ βTrp), 32.2 (CH$_2$—CH$_2$-phenyl), 40.7 (C$_4$ tetrahydropyrane), 44.8 (CH αTrp), 45.9 (CH$_2$-p-methoxybenzyl), 55.5 (OCH$_3$), 66.6 (C$_2$ and C$_6$ tetrahydropyrane), 109.8 ($C_3$ Trp), 111.7 ($C_7$ Trp), 114.5 ($C_3$ and $C_5$ p-methoxybenzyl), 118.4 ($C_4$ Trp), 118.7 ($C_5$ Trp), 121.3 ($C_6$ Trp), 124.5 ($C_2$ Trp), 126.7 ($C_4$ phenyl), 127.2 ($C_9$ Trp), 127.5 ($C_1$ p-methoxybenzyl), 128.8 ($C_2$ and $C_6$ phenyl), 128.7 ($C_3$ and $C_5$ phenyl), 127.9 ($C_2$ and $C_6$ p-methoxybenzyl), 136.4 ($C_8$ Trp), 140.4 ($C_1$ phenyl), 154.7 (Cq triazole), 155.7 (Cq triazole), 159.2 ($C_4$ p-methoxybenzyl), 174.2 (CO amide).

N—((R)-1-(5-((1H-indol-3-yl)methyl)-4-(3-methoxybenzyl)-4H-1,2,4-triazol-3-yl)-2-(1H-indol-3-yl)ethyl)-2-amino-2-methylpropanamide (Compound 185)

$^1$H NMR (300 MHz, DMSO $d^6$, 300° K):

δ (ppm) 1.19 (s, 3H, $CH_3$ Aib), 1.23 (s, 3H, $CH_3$ Aib), 3.14 (dd, 1H, J=14 Hz and 5 Hz, $CH_2$ βTrp), 3.34 (dd, 1H, J=14 Hz and 9 Hz, $CH_2$ β Trp), 3.46 (s, 3H, $OCH_3$), 3.72 (m, 2H, $CH_2$-indole), 5.06 (m, 1H, CH αTrp), 5.14 (m, 2H, $CH_2$-m-methoxybenzyl), 6.31 (s, 1H, $H_2$ m-methoxybenzyl), 6.32 (d, 1H, $J_o$=7 Hz, $H_6$ m-methoxybenzyl), 6.77 (m, 3H, $H_5$ indole, $H_5$ Trp and $H_4$ m-methoxybenzyl), 6.92 (m, 2H, $H_6$ indole and $H_6$ Trp), 7.02 (m, 2H, $H_2$ indole and $H_2$ Trp), 7.26-7.30 (m, 3H, $H_5$ m-methoxybenzyl, $H_4$ and $H_7$ indole, $H_4$ Trp), 7.41 (d, 1H, $J_o$=8 Hz, $H_7$ Trp), 7.94 (brs, 3H, $NH_2$ Aib TFA salt), 8.87 (d, 1H, J=8 Hz, NH amide), 10.73 (d, 1H, J=2 Hz, NH indole), 10.85 (s, 1H, NH indole Trp).

$^{13}$C NMR (75 MHz, DMSO $d^6$, 300° K):

δ (ppm) 21.7 ($CH_2$-indole), 23.5 ($CH_3$ Aib), 23.7 ($CH_3$ Aib), 28.9 ($CH_2$ βTrp), 45.5 (CH αTrp), 46.2 ($CH_2$-m-methoxybenzyl), 55.2 ($OCH_3$), 56.7 (Cq Aib), 108.2 ($C_3$ indole), 109.8 ($C_3$ Trp), 111.7 ($C_7$ Trp), 111.9 ($C_7$ indole and $C_2$ m-methoxybenzyl), 113.7 ($C_4$ m-methoxybenzyl), 118.2 ($C_6$ m-methoxybenzyl), 118.4 ($C_4$ Trp), 118.6 ($C_4$ indole), 118.9 ($C_6$ indole and $C_5$ Trp), 121.2 ($C_6$ indole), 121.6 ($C_6$ Trp), 127.1 ($C_9$ indole), 127.2 ($C_9$ Trp), 136.4 ($C_8$ Trp), 136.7 ($C_8$ indole), 137.5 ($C_1$ m-methoxybenzyl), 154.2 (Cq triazole), 155.3 (Cq triazole), 160.0 ($C_3$ m-methoxybenzyl), 171.8 (CO amide).

TABLE 1

Further exemplary embodiments with synthetic sequence and MS data (compounds no. 2, 3, 14, 16, 17, 19-22, 24, 26-35, 36-122, 124-126, 128-150, 152-190):

| No. | Chemical name (Chem Draw Ultra 8) | ESI-MS (calculated) | ESI-MS [found (M+H)+] |
|---|---|---|---|
| 2 | (R)—N-(1-(5-(2-(1H-indol-3-yl)ethyl)-4-phenethyl-4H-1,2,4-triazol-3-yl)-2-(1H-indol-3-yl)ethyl)-2-amino-2-methylpropanamide | 559.3 | 560.4 |
| 3 | (R)—N-(1-(5-(3-(1H-indol-3-yl)propyl)-4-phenethyl-4H-1,2,4-triazol-3-yl)-2-(1H-indol-3-yl)ethyl)-2-amino-2-methylpropanamide | 573.3 | 574.3 |
| 14 | (R)—N-(1-(5-(3-(1H-indol-3-yl)propyl)-4-(4-bromobenzyl)-4H-1,2,4-triazol-3-yl)-2-(1H-indol-3-yl)ethyl)-2-amino-2-methylpropanamide | 637.2 | 638.1 |
| 16 | (R)—N-(1-(5-(3-(1H-indol-3-yl)propyl)-4-hexyl-4H-1,2,4-triazol-3-yl)-2-(1H-indol-3-yl)ethyl)-2-amino-2-methylpropanamide | 553.3 | 554.4 |
| 17 | (R)—N-(1-(4,5-bis(2-(1H-indol-3-yl)ethyl)-4H-1,2,4-triazol-3-yl)-2-(1H-indol-3-yl)ethyl)-2-amino-2-methylpropanamide | 598.3 | 599.2 |
| 19 | (R)—N-(1-(4-(3-methoxybenzyl)-5-phenethyl-4H-1,2,4-triazol-3-yl)-2-(1H-indol-3-yl)ethyl)-2-amino-2-methylpropanamide | 536.3 | 537.1 |
| 20 | (R)—N-(1-(4-(4-methoxybenzyl)-5-phenethyl-4H-1,2,4-triazol-3-yl)-2-(1H-indol-3-yl)ethyl)-2-amino-2-methylpropanamide | 536.3 | 537.3 |
| 21 | (R)—N-(1-(5-(2-(1H-indol-3-yl)ethyl)-4-(3,5-dimethoxybenzyl)-4H-1,2,4-triazol-3-yl)-2-(1H-indol-3-yl)ethyl)-2-amino-2-methylpropanamide | 605.3 | 606.4 |
| 22 | (R)—N-(1-(4-(4-methoxybenzyl)-5-(3-phenylpropyl)-4H-1,2,4-triazol-3-yl)-2-(1H-indol-3-yl)ethyl)-2-amino-2-methylpropanamide | 550.3 | 551.3 |
| 24 | (R)—N-(1-(4-(2-(1H-indol-3-yl)ethyl)-5-(3-(1H-indol-3-yl)propyl)-4H-1,2,4-triazol-3-yl)-2-(1H-indol-3-yl)ethyl)-2-amino-2-methylpropanamide | 612.3 | 612.8 |
| 26 | (R)—N-(1-(4-(2-methoxybenzyl)-5-phenethyl-4H-1,2,4-triazol-3-yl)-2-(1H-indol-3-yl)ethyl)-2-amino-2-methylpropanamide | 536.3 | 537.1 |
| 27 | (R)—N-(2-(1H-indol-3-yl)-1-(4-(naphthalen-1-ylmethyl)-5-phenethyl-4H-1,2,4-triazol-3-yl)ethyl)-2-amino-2-methylpropanamide | 556.3 | 557.2 |
| 28 | (R)—N-(1-(5-(2-(1H-indol-3-yl)ethyl)-4-(3,4-dichlorobenzyl)-4H-1,2,4-triazol-3-yl)-2-(1H-indol-3-yl)ethyl)-2-amino-2-methylpropanamide | 613.2 | 614.2 |
| 29 | (R)—N-(1-(5-(2-(1H-indol-3-yl)ethyl)-4-(4-fluorobenzyl)-4H-1,2,4-triazol-3-yl)-2-(1H-indol-3-yl)ethyl)-2-amino-2-methylpropanamide | 563.3 | 564.1 |
| 30 | (R)—N-(1-(4-(4-fluorobenzyl)-5-benzyl-4H-1,2,4-triazol-3-yl)-2-(1H-indol-3-yl)ethyl)-2-amino-2-methylpropanamide | 510.3 | 511.0 |
| 31 | (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)piperidine-4-carboxamide | 631.3 | 632.0 |
| 32 | (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)piperidine-3-carboxamide | 631.3 | 631.8 |
| 33 | (R)—N-(1-(4-(4-methylbenzyl)-5-(3-phenylpropyl)-4H-1,2,4-triazol-3-yl)-2-(1H-indol-3-yl)ethyl)-2-amino-2-methylpropanamide | 534.3 | 535.4 |
| 34 | (R)—N-(1-(5-(2-(1H-indol-3-yl)ethyl)-4-(4-methylbenzyl)-4H-1,2,4-triazol-3-yl)-2-(1H-indol-3-yl)ethyl)-2-amino-2-methylpropanamide | 559.7 | 559.9 |
| 36 | (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)piperidine-2-carboxamide | 631.3 | 631.8 |
| 37 | (R)—N-(1-(4-(4-methylbenzyl)-5-phenethyl-4H-1,2,4-triazol-3-yl)-2-(1H-indol-3-yl)ethyl)-2-amino-2-methylpropanamide | 520.3 | 521.0 |
| 38 | (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-aminobenzamide | 639.3 | 639.8 |
| 39 | (R)—N-(1-(5-benzyl-4-(pyridin-2-ylmethyl)-4H-1,2,4-triazol-3-yl)-2-(1H-indol-3-yl)ethyl)-2-amino-2-methylpropanamide | 493.3 | 493.9 |
| 40 | (2S,4R)—N—((R)-1-(4-(4-methoxybenzyl)-5-phenethyl-4H-1,2,4-triazol-3-yl)-2-(1H-indol-3-yl)ethyl)-4-hydroxypyrrolidine-2-carboxamide | 564.3 | 565.0 |
| 41 | (S)—N—((R)-1-(4-(4-methoxybenzyl)-5-phenethyl-4H-1,2,4-triazol-3-yl)-2-(1H-indol-3-yl)ethyl)piperidine-3-carboxamide | 562.3 | 563.0 |
| 42 | (R)—N—((R)-1-(4-(4-methoxybenzyl)-5-phenethyl-4H-1,2,4-triazol-3-yl)-2-(1H-indol-3-yl)ethyl)piperidine-3-carboxamide | 562.3 | 562.9 |

TABLE 1-continued

Further exemplary embodiments with synthetic sequence and MS data (compounds no. 2, 3, 14, 16, 17, 19-22, 24, 26-35, 36-122, 124-126, 128-150, 152-190):

| No. | Chemical name (Chem Draw Ultra 8) | ESI-MS (calculated) | ESI-MS [found (M+H)+] |
|---|---|---|---|
| 43 | (R)—N-(1-(4-(4-ethylbenzyl)-5-phenethyl-4H-1,2,4-triazol-3-yl)-2-(1H-indol-3-yl)ethyl)-2-amino-2-methylpropanamide | 534.3 | 535.0 |
| 44 | (R)-N-(1-(4-(4-methoxybenzyl)-5-phenethyl-4H-1,2,4-triazol-3-yl)-2-(1H-indol-3-yl)ethyl)piperidine-4-carboxamide | 562.3 | 563.0 |
| 45 | (R)—N-1-(4-(5-(2-(1H-indol-3-yl)ethyl)-4-(4-methoxybenzyl)-4H-1,2,4-triazol-3-yl)-2-(1H-indol-3-yl)ethyl)piperidine-4-carboxamide | 601.3 | 602.0 |
| 46 | (S)—N—((R)-1-(4-(4-methoxybenzyl)-5-phenethyl-4H-1,2,4-triazol-3-yl)-2-(1H-indol-3-yl)ethyl)pyrrolidine-2-carboxamide | 548.3 | 548.9 |
| 47 | (R)—N—((R)-1-(4-(4-methoxybenzyl)-5-phenethyl-4H-1,2,4-triazol-3-yl)-2-(1H-indol-3-yl)ethyl)pyrrolidine-2-carboxamide | 548.3 | 548.9 |
| 48 | (S)—N—((R)-1-(4-(4-methoxybenzyl)-5-phenethyl-4H-1,2,4-triazol-3-yl)-2-(1H-indol-3-yl)ethyl)piperidine-2-carboxamide | 562.3 | 563.0 |
| 49 | (R)—N—(1-(4-(4-methoxybenzyl)-5-phenethyl-4H-1,2,4-triazol-3-yl)-2-(1H-indol-3-yl)ethyl)piperidine-2-carboxamide | 562.3 | 562.9 |
| 50 | (R)-N-(1-(4-(4-methoxybenzyl)-5-phenethyl-4H-1,2,4-triazol-3-yl)-2-(1H-indol-3-yl)ethyl)-2-aminoacetamide | 508.3 | 508.9 |
| 51 | (R)-N-(1-(4-(4-methoxybenzyl)-5-phenethyl-4H-1,2,4-triazol-3-yl)-2-(1H-indol-3-yl)ethyl)-2-(pyridin-2-yl)acetamide | 570.3 | 571.2 |
| 52 | N—((R)-1-(4-(4-methoxybenzyl)-5-phenethyl-4H-1,2,4-triazol-3-yl)-2-(1H-indol-3-yl)ethyl)-2-(pyridin-4-yl)acetamide | 570.3 | 570.9 |
| 53 | (R)—N-(1-(4-(4-methoxybenzyl)-5-phenethyl-4H-1,2,4-triazol-3-yl)-2-(1H-indol-3-yl)ethyl)cyclohexanecarboxamide | 561.3 | 562.4 |
| 54 | (R)—N-(1-(5-(2-(1H-indol-3-yl)ethyl)-4-benzyl-4H-1,2,4-triazol-3-yl)-2-(1H-indol-3-yl)ethyl)piperidine-4-carboxamide | 571.3 | 572.5 |
| 55 | (R)—N-(1-(5-(2-(1H-indol-3-yl)ethyl)-4-benzyl-4H-1,2,4-triazol-3-yl)-2-(1H-indol-3-yl)ethyl)piperidine-3-carboxamide | 571.3 | 572.4 |
| 56 | (R)-N-(1-(4-(4-methoxybenzyl)-5-phenethyl-4H-1,2,4-triazol-3-yl)-2-(1H-indol-3-yl)ethyl)-3-aminopropanamide | 522.3 | 523.3 |
| 57 | (S)—N—((R)-1-(4-(4-methoxybenzyl)-5-phenethyl-4H-1,2,4-triazol-3-yl)-2-(1H-indol-3-yl)ethyl)-2-aminopropanamide | 522.3 | 523.3 |
| 58 | (R)-N-(1-(4-(4-methoxybenzyl)-5-phenethyl-4H-1,2,4-triazol-3-yl)-2-(1H-indol-3-yl)ethyl)-2-(pyridin-3-yl)acetamide | 570.3 | 571.2 |
| 59 | (R)-N-(1-(4-(4-methoxybenzyl)-5-phenethyl-4H-1,2,4-triazol-3-yl)-2-(1H-indol-3-yl)ethyl)-3-(pyridin-3-yl)propanamide | 584.3 | 585.3 |
| 60 | (R)—N-(1-(5-(2-(1H-indol-3-yl)ethyl)-4-benzyl-4H-1,2,4-triazol-3-yl)-2-(1H-indol-3-yl)ethyl)-2-(pyridin-2-yl)acetamide | 579.3 | 580.2 |
| 61 | (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-(pyridin-2-yl)acetamide | 639.3 | 640.5 |
| 62 | (R)-N-(1-(4-(2,4-dimethoxybenzyl)-5-phenethyl-4H-1,2,4-triazol-3-yl)-2-(1H-indol-3-yl)ethyl)piperidine-4-carboxamide | 592.3 | 593.3 |
| 63 | (R)—N—((R)-1-(4-(2,4-dimethoxybenzyl)-5-phenethyl-4H-1,2,4-triazol-3-yl)-2-(1H-indol-3-yl)ethyl)piperidine-2-carboxamide | 592.3 | 593.3 |
| 64 | (R)-N-(1-(4-(2,4-dimethoxybenzyl)-5-phenethyl-4H-1,2,4-triazol-3-yl)-2-(1H-indol-3-yl)ethyl)picolinamide | 586.3 | 587.2 |
| 65 | (R)-N-(1-(4-(2,4-dimethoxybenzyl)-5-phenethyl-4H-1,2,4-triazol-3-yl)-2-(1H-indol-3-yl)ethyl)isonicotinamide | 586.3 | 587.2 |
| 66 | (R)—N-(1-(4-(2,4-dimethoxybenzyl)-5-phenethyl-4H-1,2,4-triazol-3-yl)-2-(1H-indol-3-yl)ethyl)pyrazine-2-carboxamide | 587.3 | 588.2 |
| 67 | (R)—N-1-(4-(2,4-dimethoxybenzyl)-5-phenethyl-4H-1,2,4-triazol-3-yl)-2-(1H-indol-3-yl)ethyl)piperazine-2-carboxamide | 593.3 | 594.2 |
| 68 | (S)—N-1-(4-(2,4-dimethoxybenzyl)-5-phenethyl-4H-1,2,4-triazol-3-yl)-2-(1H-indol-3-yl)ethyl)pyrrolidine-2-carboxamide | 578.3 | 579.4 |
| 69 | (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-aminoacetamide | 577.3 | 578.0 |
| 70 | (S)—N—((R)-1-(5-(2-(1H-indol-3-yl)ethyl)-4-(2,4-dimethoxybenzyl)-4H-1,2,4-triazol-3-yl)-2-(1H-indol-3-yl)ethyl)pyrrolidine-2-carboxamide | 617.3 | 618.0 |
| 71 | (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)pyrazine-2-carboxamide | 626.3 | 627.2 |
| 72 | (R)—N-1-(5-(2-(1H-indol-3-yl)ethyl)-4-(2,4-dimethoxybenzyl)-4H-1,2,4-triazol-3-yl)-2-(1H-indol-3-yl)ethyl)piperazine-2-carboxamide | 632.3 | 633.2 |
| 73 | (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)picolinamide | 625.3 | 626.3 |
| 74 | (R)—1-(5-(2-(1H-indol-3-yl)ethyl)-4-(2,4-dimethoxybenzyl)-4H-1,2,4-triazol-3-yl)-2-(1H-indol-3-yl)ethanamine | 520.3 | 520.8 |
| 75 | (R)—N-(1-(4-(2,4-dimethoxybenzyl)-5-phenethyl-4H-1,2,4-triazol-3-yl)-2-(1H-indol-3-yl)ethyl)-2-aminoacetamide | 538.3 | 539.3 |
| 76 | (R)—N-(1-(4-(4-methoxybenzyl)-5-phenethyl-4H-1,2,4-triazol-3-yl)-2-(1H-indol-3-yl)ethyl)pyrazine-2-carboxamide | 557.3 | 558.0 |
| 77 | (R)—N-(1-(4-(4-methoxybenzyl)-5-phenethyl-4H-1,2,4-triazol-3-yl)-2-(1H-indol-3-yl)ethyl)isonicotinamide | 556.3 | 556.9 |
| 78 | (R)—N-1-(4-(4-methoxybenzyl)-5-phenethyl-4H-1,2,4-triazol-3-yl)-2-(1H-indol-3-yl)ethyl)piperazine-2-carboxamide | 563.3 | 564.0 |
| 79 | (R)—N-(1-(4-(4-methoxybenzyl)-5-phenethyl-4H-1,2,4-triazol-3-yl)-2-(1H-indol-3-yl)ethyl)picolinamide | 556.3 | 557.3 |
| 80 | (R)—N-(1-(5-(2-(1H-indol-3-yl)ethyl)-4-(4-methoxybenzyl)-4H-1,2,4-triazol-3-yl)-2-(1H-indol-3-yl)ethyl)picolinamide | 595.3 | 596.2 |
| 81 | (R)—N-1-(5-(2-(1H-indol-3-yl)ethyl)-4-(4-methoxybenzyl)-4H-1,2,4-triazol-3-yl)-2-(1H-indol-3-yl)ethyl)piperazine-2-carboxamide | 602.3 | 603.3 |
| 82 | (R)—N-(1-(4-(4-ethylbenzyl)-5-phenethyl-4H-1,2,4-triazol-3-yl)-2-(1H-indol-3-yl)ethyl)-2-(pyridin-2-yl)acetamide | 568.3 | 569.3 |
| 83 | (R)—N-(1-(4-(4-ethylbenzyl)-5-phenethyl-4H-1,2,4-triazol-3-yl)-2-(1H-indol-3-yl)ethyl)piperidine-4-carboxamide | 560.3 | 561.3 |
| 84 | (R)—N-1-(4-(4-ethylbenzyl)-5-phenethyl-4H-1,2,4-triazol-3-yl)-2-(1H-indol-3-yl)ethyl)piperazine-2-carboxamide | 561.3 | 562.2 |
| 85 | (R)—N-(1-(4-(4-ethylbenzyl)-5-phenethyl-4H-1,2,4-triazol-3-yl)-2-(1H-indol-3-yl)ethyl)pyrazine-2-carboxamide | 555.3 | 556.2 |
| 86 | (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-cis-aminocyclohexanecarboxamide | 645.3 | 646.2 |
| 87 | (S)—N—((R)-1-(5-(2-(1H-indol-3-yl)ethyl)-4-(4-methoxybenzyl)-4H-1,2,4-triazol-3-yl)-2-(1H-indol-3-yl)ethyl)piperidine-3-carboxamide | 601.3 | 601.9 |

TABLE 1-continued

Further exemplary embodiments with synthetic sequence and MS data (compounds no. 2, 3, 14, 16, 17, 19-22, 24, 26-35, 36-122, 124-126, 128-150, 152-190):

| No. | Chemical name (Chem Draw Ultra 8) | ESI-MS (calculated) | ESI-MS [found (M + H)+] |
|---|---|---|---|
| 88 | (R)—N—((R)-1-(5-(2-(1H-indol-3-yl)ethyl)-4-(4-methoxybenzyl)-4H-1,2,4-triazol-3-yl)-2-(1H-indol-3-yl)ethyl)piperidine-2-carboxamide | 601.3 | 602.2 |
| 89 | (S)—N—((R)-1-(5-(2-(1H-indol-3-yl)ethyl)-4-(4-methoxybenzyl)-4H-1,2,4-triazol-3-yl)-2-(1H-indol-3-yl)ethyl)pyrrolidine-2-carboxamide | 587.3 | 588.2 |
| 90 | (R)—N—((R)-1-(5-(2-(1H-indol-3-yl)ethyl)-4-(4-methoxybenzyl)-4H-1,2,4-triazol-3-yl)-2-(1H-indol-3-yl)ethyl)pyrrolidine-2-carboxamide | 587.3 | 588.0 |
| 91 | (R)—N-(1-(5-(2-(1H-indol-3-yl)ethyl)-4-(4-methoxybenzyl)-4H-1,2,4-triazol-3-yl)-2-(1H-indol-3-yl)ethyl)-2-(pyridin-2-yl)acetamide | 609.3 | 610.0 |
| 92 | (R)—N-(1-(5-(2-(1H-indol-3-yl)ethyl)-4-(4-bromobenzyl)-4H-1,2,4-triazol-3-yl)-2-(1H-indol-3-yl)ethyl)-2-amino-2-methylpropanamide | 623.2 | 624.1 |
| 93 | (R)—N-(1-(5-(2-(1H-indol-3-yl)ethyl)-4-(4-methoxybenzyl)-4H-1,2,4-triazol-3-yl)-2-phenylethyl)-2-amino-2-methylpropanamide | 536.3 | 536.9 |
| 94 | (R)—N-(2-(1H-indol-3-yl)-1-(5-phenethyl-4-(thiophen-2-ylmethyl)-4H-1,2,4-triazol-3-yl)ethyl)piperidine-4-carboxamide | 538.3 | 538.8 |
| 95 | (R)—N-(1-(4-(2-(1H-indol-3-yl)ethyl)-4H-1,2,4-triazol-3-yl)-2-(1H-indol-3-yl)ethyl)-2-amino-2-methylpropanamide | 455.2 | 456.2 |
| 96 | (R)—N-(1-(5-((1H-indol-3-yl)methyl)-4-methyl-4H-1,2,4-triazol-3-yl)-2-(1H-indol-3-yl)ethyl)-2-amino-2-methylpropanamide | 455.2 | 456.4 |
| 97 | (R)—N-(1-(5-(2-(1H-indol-3-yl)ethyl)-4-methyl-4H-1,2,4-triazol-3-yl)-2-(1H-indol-3-yl)ethyl)-2-amino-2-methylpropanamide | 469.3 | 470.2 |
| 98 | (R)—N-(1-(5-((1H-indol-3-yl)methyl)-4H-1,2,4-triazol-3-yl)-2-(1H-indol-3-yl)ethyl)-2-amino-2-methylpropanamide | 441.3 | 442.1 |
| 99 | (R)—N-(1-(5-((1H-indol-3-yl)methyl)-4-(2,4-dimethoxybenzyl)-4H-1,2,4-triazol-3-yl)-2-(1H-indol-3-yl)ethyl)-2-amino-2-methylpropanamide | 591.3 | 592.1 |
| 100 | (R)—N-(1-(4-(2,4-dimethoxybenzyl)-5-methyl-4H-1,2,4-triazol-3-yl)-2-(1H-indol-3-yl)ethyl)-2-amino-2-methylpropanamide | 476.3 | 477.4 |
| 101 | (R)—N-(1-(5-((1H-indol-3-yl)methyl)-4-(4-methoxybenzyl)-4H-1,2,4-triazol-3-yl)-2-(1H-indol-3-yl)ethyl)-2-amino-2-methylpropanamide | 561.3 | 562.3 |
| 102 | (R)—N-(1-(4-(2,4-dimethoxybenzyl)-5-benzyl-4H-1,2,4-triazol-3-yl)-2-(1H-indol-3-yl)ethyl)-2-amino-2-methylpropanamide | 552.3 | 553.2 |
| 103 | (R)—N-(1-(5-(3-(1H-indol-3-yl)propyl)-4-(2,4-dimethoxybenzyl)-4H-1,2,4-triazol-3-yl)-2-(1H-indol-3-yl)ethyl)-2-amino-2-methylpropanamide | 619.3 | 620.2 |
| 104 | (R)—N-(1-(5-((1H-indol-3-yl)methyl)-4-phenethyl-4H-1,2,4-triazol-3-yl)-2-(1H-indol-3-yl)ethyl)-2-amino-2-methylpropanamide | 545.3 | 546.4 |
| 105 | (R)—N-(1-(5-benzyl-4-phenethyl-4H-1,2,4-triazol-3-yl)-2-(1H-indol-3-yl)ethyl)-2-amino-2-methylpropanamide | 506.3 | 507.4 |
| 106 | (R)—N-(1-(5-benzyl-4-(2,2-diphenylethyl)-4H-1,2,4-triazol-3-yl)-2-(1H-indol-3-yl)ethyl)-2-amino-2-methylpropanamide | 582.3 | 583.3 |
| 107 | (R)—N-(1-(5-(2-(1H-indol-3-yl)ethyl)-4-(2,2-diphenylethyl)-4H-1,2,4-triazol-3-yl)-2-(1H-indol-3-yl)ethyl)-2-amino-2-methylpropanamide | 635.3 | 636.4 |
| 108 | (R)—N-(1-(4-(3,5-dimethoxybenzyl)-5-benzyl-4H-1,2,4-triazol-3-yl)-2-(1H-indol-3-yl)ethyl)-2-amino-2-methylpropanamide | 552.3 | 553.3 |
| 109 | (R)—N-(1-(4,5-dibenzyl-4H-1,2,4-triazol-3-yl)-2-(1H-indol-3-yl)ethyl)-2-amino-2-methylpropanamide | 492.3 | 493.3 |
| 110 | (R)—N-(1-(5-benzyl-4-hexyl-4H-1,2,4-triazol-3-yl)-2-(1H-indol-3-yl)ethyl)-2-amino-2-methylpropanamide | 486.3 | 487.4 |
| 111 | (R)—N-(1-(4-(2-(1H-indol-3-yl)ethyl)-5-benzyl-4H-1,2,4-triazol-3-yl)-2-(1H-indol-3-yl)ethyl)-2-amino-2-methylpropanamide | 545.3 | 546.2 |
| 112 | (S)—N-(1-(4-(2,4-dimethoxybenzyl)-5-benzyl-4H-1,2,4-triazol-3-yl)-2-(1H-indol-3-yl)ethyl)-2-amino-2-methylpropanamide | 552.3 | 553.1 |
| 113 | (R)—N-(1-(4-(3,5-dimethoxybenzyl)-5-phenethyl-4H-1,2,4-triazol-3-yl)-2-(1H-indol-3-yl)ethyl)-2-amino-2-methylpropanamide | 566.3 | 567.3 |
| 114 | (R)—N-(1-(4-(4-bromobenzyl)-5-benzyl-4H-1,2,4-triazol-3-yl)-2-(1H-indol-3-yl)ethyl)-2-amino-2-methylpropanamide | 570.2 | 571.0 |
| 115 | (R)—N-(1-(4-(2-methoxybenzyl)-5-benzyl-4H-1,2,4-triazol-3-yl)-2-(1H-indol-3-yl)ethyl)-2-amino-2-methylpropanamide | 522.3 | 523.0 |
| 116 | (S)—N-(1-(4-(2,4-dimethoxybenzyl)-5-phenethyl-4H-1,2,4-triazol-3-yl)-2-(1H-indol-3-yl)ethyl)-2-amino-2-methylpropanamide | 566.3 | 567.0 |
| 117 | (R)—N-(1-(4,5-diphenethyl-4H-1,2,4-triazol-3-yl)-2-(1H-indol-3-yl)ethyl)-2-amino-2-methylpropanamide | 520.3 | 521.1 |
| 118 | (R)—N-(1-(4-(3,4-dichlorobenzyl)-5-benzyl-4H-1,2,4-triazol-3-yl)-2-(1H-indol-3-yl)ethyl)-2-amino-2-methylpropanamide | 560.2 | 561.3 |
| 119 | (R)-1-(5-(2-(1H-indol-3-yl)ethyl)-4-(2,4-dimethoxybenzyl)-4H-1,2,4-triazol-3-yl)-2-(1H-indol-3-yl)ethanamine | 451.3 | 452.1 |
| 120 | (R)—N-(1-(4-(4-methoxybenzyl)-5-benzyl-4H-1,2,4-triazol-3-yl)-2-phenylethyl)-2-amino-2-methylpropanamide | 483.3 | 484.0 |
| 121 | (R)—N-(1-(4-(4-fluorobenzyl)-5-phenethyl-4H-1,2,4-triazol-3-yl)-2-(1H-indol-3-yl)ethyl)-2-amino-2-methylpropanamide | 524.3 | 524.9 |
| 122 | (R)—N-(1-(4-(3,4-dichlorobenzyl)-5-phenethyl-4H-1,2,4-triazol-3-yl)-2-(1H-indol-3-yl)ethyl)-2-amino-2-methylpropanamide | 574.2 | 574.9 |
| 124 | (R)—N-(1-(4-(4-methylbenzyl)-5-benzyl-4H-1,2,4-triazol-3-yl)-2-(1H-indol-3-yl)ethyl)-2-amino-2-methylpropanamide | 506.3 | 507.3 |
| 125 | (S)—N-(1-(4-(4-methoxybenzyl)-5-(3-phenylpropyl)-4H-1,2,4-triazol-3-yl)-2-(1H-indol-3-yl)ethyl)-2-amino-2-methylpropanamide | 550.3 | 551.3 |
| 126 | (S)—N-(1-(4-(4-methoxybenzyl)-5-benzyl-1,2,4-triazol-3-yl)-2-(1H-indol-3-yl)ethyl)-2-amino-2-methylpropanamide | 522.3 | 523.4 |
| 128 | (R)—N-(1-(4-(4-nitrobenzyl)-5-phenethyl-4H-1,2,4-triazol-3-yl)-2-(1H-indol-3-yl)ethyl)-2-amino-2-methylpropanamide | 551.3 | 551.9 |
| 129 | (S)—N-(1-(4-(4-methoxybenzyl)-5-phenethyl-4H-1,2,4-triazol-3-yl)-2-(1H-indol-3-yl)ethyl)-2-amino-2-methylpropanamide | 536.3 | 537.0 |
| 130 | (R)—N-(1-(4-(4-methoxyphenethyl)-5-phenethyl-4H-1,2,4-triazol-3-yl)-2-(1H-indol-3-yl)ethyl)-2-amino-2-methylpropanamide | 550.3 | 551.0 |
| 131 | (R)—N-(2-(1H-indol-3-yl)-1-(5-phenethyl-4-(thiophen-2-ylmethyl)-4H-1,2,4-triazol-3-yl)ethyl)-2-amino-2-methylpropanamide | 512.2 | 512.8 |
| 132 | (R)—N-(2-(1H-indol-3-yl)-1-(5-phenethyl-4-(pyridin-2-ylmethyl)-4H-1,2,4-triazol-3-yl)ethyl)-2-amino-2-methylpropanamide | 507.3 | 508.4 |
| 133 | (R)—N-(-2-(1H-indol-3-yl)-1-(5-phenethyl-4-(pyridin-2-ylmethyl)-4H-1,2,4-triazol-3-yl)ethyl)piperidine-3-carboxamide | 533.3 | 534.0 |

TABLE 1-continued

Further exemplary embodiments with synthetic sequence and MS data (compounds no. 2, 3, 14, 16, 17, 19-22, 24, 26-35, 36-122, 124-126, 128-150, 152-190):

| No. | Chemical name (Chem Draw Ultra 8) | ESI-MS (calculated) | ESI-MS [found (M + H)+] |
|---|---|---|---|
| 134 | (S)—N—((R)-1-(4-(4-ethylbenzyl)-5-phenethyl-4H-1,2,4-triazol-3-yl)-2-(1H-indol-3-yl)ethyl)pyrrolidine-2-carboxamide | 546.3 | 547.3 |
| 135 | N—((R)-1-(4-(4-ethylbenzyl)-5-phenethyl-4H-1,2,4-triazol-3-yl)-2-(1H-indol-3-yl)ethyl)-2-aminoacetamide | 506.3 | 507.3 |
| 136 | N—((R)-1-(5-(2-(1H-indol-3-yl)ethyl)-4-(4-methoxybenzyl)-4H-1,2,4-triazol-3-yl)-2-(1H-indol-3-yl)ethyl)-2-(pyridin-4-yl)acetamide | 609.3 | 610.4 |
| 137 | (2R)—N—((R)-1-(4-(4-ethylbenzyl)-5-phenethyl-4H-1,2,4-triazol-3-yl)-2-(1H-indol-3-yl)ethyl)piperidine-2-carboxamide | 560.3 | 561.3 |
| 138 | N—((R)-1-(4-(4-ethylbenzyl)-5-phenethyl-4H-1,2,4-triazol-3-yl)-2-(1H-indol-3-yl)ethyl)picolinamide | 554.3 | 555.3 |
| 139 | N—((R)-1-(4-(4-ethylbenzyl)-5-phenethyl-4H-1,2,4-triazol-3-yl)-2-(1H-indol-3-yl)ethyl)-2-aminopyridine-3-carboxamide | 569.3 | 570.3 |
| 140 | (2S)—N—((R)-1-(4-(4-ethylbenzyl)-5-phenethyl-4H-1,2,4-triazol-3-yl)-2-(1H-indol-3-yl)ethyl)-2-aminopropanamide | 520.3 | 521.2 |
| 141 | N—((R)-1-(4-(4-ethylbenzyl)-5-phenethyl-4H-1,2,4-triazol-3-yl)-2-(1H-indol-3-yl)ethyl)isonicotinamide | 554.3 | 555.4 |
| 142 | N—((R)-2-(1H-indol-3-yl)-1-(5-phenethyl-4-phenyl-4H-1,2,4-triazol-3-yl)ethyl)piperidine-4-carboxamide | 518.3 | 519.3 |
| 143 | (2S)—N—((R)-2-(1H-indol-3-yl)-1-(5-phenethyl-4-phenyl-4H-1,2,4-triazol-3-yl)ethyl)pyrrolidine-2-carboxamide | 504.3 | 505.1 |
| 144 | N—((R)-2-(1H-indol-3-yl)-1-(5-phenethyl-4-phenyl-4H-1,2,4-triazol-3-yl)ethyl)-2-aminoacetamide | 464.3 | 465.1 |
| 145 | N—((R)-2-(1H-indol-3-yl)-1-(5-phenethyl-4-phenyl-4H-1,2,4-triazol-3-yl)ethyl)-2-(pyridin-2-yl)acetamide | 526.3 | 527.2 |
| 146 | N—((R)-2-(1H-indol-3-yl)-1-(5-phenethyl-4-phenyl-4H-1,2,4-triazol-3-yl)ethyl)picolinamide | 512.3 | 513.4 |
| 147 | N—((R)-1-(5-(2-(1H-indol-3-yl)ethyl)-4-(4-ethylphenyl)-4H-1,2,4-triazol-3-yl)-2-(1H-indol-3-yl)ethyl)picolinamide | 579.3 | 580.1 |
| 148 | N—((R)-1-(5-(2-(1H-indol-3-yl)ethyl)-4-(4-ethylphenyl)-4H-1,2,4-triazol-3-yl)-2-(1H-indol-3-yl)ethyl)-2-(pyridin-2-yl)acetamide | 593.3 | 594.2 |
| 149 | N—((R)-1-(5-(2-(1H-indol-3-yl)ethyl)-4-(4-ethylphenyl)-4H-1,2,4-triazol-3-yl)-2-(1H-indol-3-yl)ethyl)-2-aminoacetamide | 531.3 | 532.2 |
| 150 | (2S)—N—((R)-1-(5-(2-(1H-indol-3-yl)ethyl)-4-(4-ethylphenyl)-4H-1,2,4-triazol-3-yl)-2-(1H-indol-3-yl)ethyl)pyrrolidine-2-carboxamide | 571.3 | 572.4 |
| 152 | N—((R)-1-(5-(2-(1H-indol-3-yl)ethyl)-4-(4-methoxybenzyl)-4H-1,2,4-triazol-3-yl)-2-(1H-indol-3-yl)ethyl)-2-aminoacetamide | 547.3 | 548.0 |
| 153 | N—((R)-1-(4-(4-methoxybenzyl)-5-phenethyl-4H-1,2,4-triazol-3-yl)-2-(1H-indol-3-yl)ethyl)-2-trans-aminocyclohexanecarboxamide | 576.3 | 577.2 |
| 154 | N—((R)-1-(4-(4-ethylbenzyl)-5-phenethyl-4H-1,2,4-triazol-3-yl)-2-(1H-indol-3-yl)ethyl)-2-(pyridin-3-yl)acetamide | 568.3 | 569.3 |
| 155 | (3S)—N—((R)-1-(4-(4-ethylbenzyl)-5-phenethyl-4H-1,2,4-triazol-3-yl)-2-(1H-indol-3-yl)ethyl)piperidine-3-carboxamide | 560.3 | 561.5 |
| 156 | N—((R)-1-(4-(4-ethylbenzyl)-5-phenethyl-4H-1,2,4-triazol-3-yl)-2-(1H-indol-3-yl)ethyl)-2-aminobenzamide | 568.3 | 569.1 |
| 157 | N—((R)-1-(5-(2-(1H-indol-3-yl)ethyl)-4-phenyl-4H-1,2,4-triazol-3-yl)-2-(1H-indol-3-yl)ethyl)picolinamide | 551.3 | 552.2 |
| 158 | N—((R)-1-(5-(2-(1H-indol-3-yl)ethyl)-4-phenyl-4H-1,2,4-triazol-3-yl)-2-(1H-indol-3-yl)ethyl)piperidine-4-carboxamide | 557.3 | 558.1 |
| 159 | N—((R)-2-(1H-indol-3-yl)-1-(4-(2,4-dimethoxyphenyl)-5-phenethyl-4H-1,2,4-triazol-3-yl)ethyl)picolinamide | 572.3 | 573.4 |
| 160 | N—((R)-2-(1H-indol-3-yl)-1-(4-(2,4-dimethoxyphenyl)-5-phenethyl-4H-1,2,4-triazol-3-yl)ethyl)-2-(pyridin-2-yl)acetamide | 586.3 | 587.3 |
| 161 | N—((R)-2-(1H-indol-3-yl)-1-(4-(2,4-dimethoxyphenyl)-5-phenethyl-4H-1,2,4-triazol-3-yl)ethyl)pyrazine-2-carboxamide | 573.3 | 574.2 |
| 162 | N—((R)-2-(1H-indol-3-yl)-1-(4-(2,4-dimethoxyphenyl)-5-phenethyl-4H-1,2,4-triazol-3-yl)ethyl)-2-aminoacetamide | 524.3 | 525.3 |
| 163 | N—((R)-2-(1H-indol-3-yl)-1-(4-(2,4-dimethoxyphenyl)-5-phenethyl-4H-1,2,4-triazol-3-yl)ethyl)piperidine-4-carboxamide | 578.3 | 579.4 |
| 164 | N—((R)-1-(5-benzyl-4-((pyridin-2-yl)methyl)-4H-1,2,4-triazol-3-yl)-2-(1H-indol-3-yl)ethyl)picolinamide | 513.3 | 514.3 |
| 165 | N—((R)-1-(5-benzyl-4-((pyridin-2-yl)methyl)-4H-1,2,4-triazol-3-yl)-2-(1H-indol-3-yl)ethyl)-2-amino-acetamide | 465.3 | 466.4 |
| 166 | N—((R)-1-(5-benzyl-4-((pyridin-2-yl)methyl)-4H-1,2,4-triazol-3-yl)-2-(1H-indol-3-yl)ethyl)piperidine-4-carboxamide | 519.3 | 520.2 |
| 167 | N—((R)-1-(5-benzyl-4-((pyridin-4-yl)methyl)-4H-1,2,4-triazol-3-yl)-2-(1H-indol-3-yl)ethyl)-2-amino-2-methylpropanamide | 493.3 | 494.3 |
| 168 | N—((R)-1-(5-(4-methoxybenzyl)-4-phenethyl-4H-1,2,4-triazol-3-yl)-2-(1H-indol-3-yl)ethyl)-2-amino-2-methylpropanamide | 536.3 | 537.3 |
| 169 | N—((R)-1-(5-benzyl-4-((pyridin-4-yl)methyl)-4H-1,2,4-triazol-3-yl)-2-(1H-indol-3-yl)ethyl)picolinamide | 513.3 | 514.2 |
| 170 | N—((R)-1-(5-benzyl-4-((pyridin-4-yl)methyl)-4H-1,2,4-triazol-3-yl)-2-(1H-indol-3-yl)ethyl)2-amino-acetamide | 465.3 | 466.1 |
| 171 | (R)-benzyl-3-(2-aminoisobutyramido)-3-(5-(2-(1H-indol-3-yl)ethyl)-4-(4-methoxybenzyl)-4H-1,2,4-triazol-3-yl)-propanoate | 594.3 | 595.2 |
| 172 | N—((R)-1-(5-benzyl-4-((pyridin-3-yl)methyl)-4H-1,2,4-triazol-3-yl)-2-(1H-indol-3-yl)ethyl)-2-amino-2-methylpropanamide | 493.3 | 494.3 |
| 173 | N—((R)-1-(4-benzyl-5-phenethyl-4H-1,2,4-triazol-3-yl)-2-(1H-indol-3-yl)ethyl)-2-amino-2-methylpropanamide | 506.3 | 507.3 |
| 174 | N—((R)-2-(1H-indol-3-yl)-1-(4-methyl-5-phenethyl-4H-1,2,4-triazol-3-yl)ethyl)picolinamide | 450.3 | 451.3 |
| 175 | N—((R)-1-(5-(2-(1H-indol-3-yl)ethyl)-4-phenyl-4H-1,2,4-triazol-3-yl)-2-(1H-indol-3-yl)ethyl)-2-amino-2-methylpropanamide | 531.3 | 532.4 |
| 176 | N—((R)-1-(4-(4-methoxybenzyl)-5-phenethyl-4H-1,2,4-triazol-3-yl)-2-(1H-indol-3-yl)ethyl)benzamide | 555.3 | 556.2 |
| 177 | (R)-1-(4-(2,4-dimethoxybenzyl)-5-phenethyl-4H-1,2,4-triazol-3-yl)-2-(1H-indol-3-yl)-N-phenylmethanesulfonylamine | 635.3 | 637.0 |
| 178 | (R)-1-(4-(2,4-dimethoxybenzyl)-5-phenethyl-4H-1,2,4-triazol-3-yl)-2-(1H-indol-3-yl)-N-tosylethanamine | 635.3 | 636.3 |
| 179 | N—((R)-1-(4-(2,4-dimethoxybenzyl)-5-phenethyl-4H-1,2,4-triazol-3-yl)-2-(1H-indol-3-yl)ethyl)-2-amino-2-methylpropanamide | 566.3 | 567.2 |
| 180 | N-1-((R)-1-(4-(2,4-dimethoxybenzyl)-5-phenethyl-4H-1,2,4-triazol-3-yl)-2-(1H-indol-3-yl)ethyl)ethane-1,2-diamine | 524.3 | 525.2 |

TABLE 1-continued

Further exemplary embodiments with synthetic sequence and MS data (compounds no. 2, 3, 14, 16, 17, 19-22, 24, 26-35, 36-122, 124-126, 128-150, 152-190):

| No. | Chemical name (Chem Draw Ultra 8) | ESI-MS (calculated) | ESI-MS [found (M + H)+] |
|---|---|---|---|
| 181 | N—((R)-1-(4-((furan-2-yl)methyl)-5-phenethyl-4H-1,2,4-triazol-3-yl)-2-(1H-indol-3-yl)ethyl)-2-amino-2-methylpropanamide | 496.3 | 497.1 |
| 182 | N—((R)-1-(4-((furan-2-yl)methyl)-5-phenethyl-4H-1,2,4-triazol-3-yl)-2-(1H-indol-3-yl)ethyl)picolinamide | 516.3 | 517.1 |
| 183 | N—((R)-1-(4-((furan-2-yl)methyl)-5-phenethyl-4H-1,2,4-triazol-3-yl)-2-(1H-indol-3-yl)ethyl)piperidine-4-carboxamide | 522.3 | 523.2 |
| 184 | N—((R)-1-(4-(4-methoxybenzyl)-5-phenethyl-4H-1,2,4-triazol-3-yl)-2-(1H-indol-3-yl)ethyl)-tetrahydro-2H-pyran-4-carboxamide | 563.3 | 564.2 |
| 185 | N—((R)-1-(5-((1H-indol-3-yl)methyl)-4-(3-methoxybenzyl)-4H-1,2,4-triazol-3-yl)-2-(1H-indol-3-yl)ethyl)-2-amino-2-methylpropanamide | 561.3 | 562.2 |
| 186 | (2S)—N—((R)-1-(4-(4-methoxybenzyl)-5-phenethyl-4H-1,2,4-triazol-3-yl)-2-(1H-indol-3-yl)ethyl)-2-amino-3-phenylpropanamide | 598.3 | 599.1 |
| 187 | (R)-1-(5-(2-(1H-indol-3-yl)ethyl)-4-(2,4-dimethoxybenzyl)-4H-1,2,4-triazol-3-yl)-2-(1H-indol-3-yl)-N-tosylethanamine | 674.3 | 675.0 |
| 188 | N—((R)-1-(4-(2,4-dimethoxybenzyl)-5-phenethyl-4H-1,2,4-triazol-3-yl)-2-(1H-indol-3-yl)ethyl)-4-azidobenzamide | 626.3 | 627.3 |
| 189 | N-benzyl-(R)-1-(4-(2,4-dimethoxybenzyl)-5-phenethyl-4H-1,2,4-triazol-3-yl)-2-(1H-indol-3-yl)ethanamine | 571.3 | 572.3 |
| 190 | (2S)—N—((R)-1-(5-(2-(1H-indol-3-yl)ethyl)-4-(4-methoxybenzyl)-4H-1,2,4-triazol-3-yl)-2-(1H-indol-3-yl)ethyl)-2,5-dihydro-1H-pyrrole-2-carboxamide | 585.3 | 586.2 |

II) GHS-R 1a Receptor-Ligand Binding Assay (Membrane Preparations from Transfected LLC PK-1 Cells)

The GHS-R 1a receptor binding/affinity studies were performed according to Guerlavais et al. (J. Med. Chem. 2003, 46: 1191-1203).

Isolated plasma membranes from LLC PK-1 cells, a renal epithelial cell line originally derived from porcine kidneys (ECACC No. 86121112) (10 μg of protein), that were transiently transfected with human GHS-R 1a cDNA (Guerlavais et al., J. Med. Chem. 2003, 46: 1191-1203), were incubated in homogenization buffer HB [50 mM Tris (pH 7.3), 5 mM $MgCl_2$, 2.5 mM EDTA, and 30 μg/mL bacitracin (Sigma)] for 60 min at 25° C. (steady-state conditions) with 60 pM $^{125}$I-His$^9$-ghrelin (Amersham) in the presence or absence of competing compounds (compounds of the invention).

The binding affinity for each compound to be tested for the human GHS-R 1a was measured by displacement of the radiolabelled ghrelin with increasing concentrations of the test compound ($10^{-11}$M to $10^{-2}$M) (each experiment being performed in triplicates).

Nonspecific binding was defined using an excess ($10^{-6}$ M) of ghrelin. The binding reaction was stopped by addition of 4 mL of ice-cold HB followed by rapid filtration over Whatman GP/C filters presoaked with 0.5% polyethyleneimine to prevent excessive binding of radioligand to the filters. Filters were rinsed three times with 3 mL of ice-cold wash buffer [50 mM Tris (pH 7.3), 10 mM $MgCl_2$, 2.5 mM EDTA, and 0.015% (w/v) X-100 Triton], and the radioactivity bound to membranes was measured in a gamma-counter (Kontron Analytical Gamma Matic, Automatic gamma counting system).

The concentration of test compounds required to inhibit radiolabelled ghrelin binding by 50% ($IC_{50}$) was determined by fitting competitive binding curves using non-linear regression (PRISM 3.0, Graph Pad San Diego, USA).

In the following table 2 results obtained for selected compounds of the invention are presented in comparison to an example of the prior art. $IC_{50}$ values given are the mean of at least two independent experiments performed in triplicates.

FIGS. 1-13 show the measured competition plots of the GHS-R 1a Receptor-ligand binding assay with $^{125}$I-His$^9$-ghrelin and the selected compounds 9, 31, 39, 45, 50, 62, 64, 71, 73, 74, 79, 81 and 90.

TABLE 2

GHS-R 1a Receptor-ligand binding assay test results ($IC_{50}$ values for a number of selected exemplary compounds)

| No. | GHS-R 1a $IC_{50}$ [nM] | Chemical name |
|---|---|---|
| 1 | 160 | (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-amino-2-methylpropanamide |
| 2 | 81 | (R)—N-(1-(5-(2-(1H-indol-3-yl)ethyl)-4-phenethyl-4H-1,2,4-triazol-3-yl)-2-(1H-indol-3-yl)ethyl)-2-amino-2-methylpropanamide |
| 3 | 14 | (R)—N-(1-(5-(3-(1H-indol-3-yl)propyl)-4-phenethyl-4H-1,2,4-triazol-3-yl)-2-(1H-indol-3-yl)ethyl)-2-amino-2-methylpropanamide |
| 4 | 220 | (R)—N-(1-(5-benzyl-4-(naphthalen-1-ylmethyl)-4H-1,2,4-triazol-3-yl)-2-(1H-indol-3-yl)ethyl)-2-amino-2-methylpropanamide |
| 5 | 125 | (R)—N-(1-(5-(2-(1H-indol-3-yl)ethyl)-4-(naphthalen-1-ylmethyl)-4H-1,2,4-triazol-3-yl)-2-(1H-indol-3-yl)ethyl)-2-amino-2-methylpropanamide |
| 6 | 18 | (R)—N-(1-(5-(2-(1H-indol-3-yl)ethyl)-4-(3-methoxybenzyl)-4H-1,2,4-triazol-3-yl)-2-(1H-indol-3-yl)ethyl)-2-amino-2-methylpropanamide |

TABLE 2-continued

GHS-R 1a Receptor-ligand binding assay test results ($IC_{50}$ values for a number of selected exemplary compounds)

| No. | GHS-R 1a $IC_{50}$ [nM] | Chemical name |
|---|---|---|
| 7 | 120 | (R)—N-(1-(4-(3-methoxybenzyl)-5-benzyl-4H-1,2,4-triazol-3-yl)-2-(1H-indol-3-yl)ethyl)-2-amino-2-methylpropanamide |
| 8 | 18 | (R)—N-(1-(5-(2-(1H-indol-3-yl)ethyl)-4-benzyl-4H-1,2,4-triazol-3-yl)-2-(1H-indol-3-yl)ethyl)-2-amino-2-methylpropanamide |
| 9 | 46 | (R)—N-(1-(5-(3-(1H-indol-3-yl)propyl)-4-benzyl-4H-1,2,4-triazol-3-yl)-2-(1H-indol-3-yl)ethyl)-2-amino-2-methylpropanamide |
| 10 | 32 | (R)—N-(1-(5-(3-(1H-indol-3-yl)propyl)-4-(3-methoxybenzyl)-4H-1,2,4-triazol-3-yl)-2-(1H-indol-3-yl)ethyl)-2-amino-2-methylpropanamide |
| 11 | 137 | (R)—N-(1-(5-(3-(1H-indol-3-yl)propyl)-4-(naphthalen-1-ylmethyl)-4H-1,2,4-triazol-3-yl)-2-(1H-indol-3-yl)ethyl)-2-amino-2-methylpropanamide |
| 12 | 6 | (R)—N-(1-(5-(2-(1H-indol-3-yl)ethyl)-4-(4-methoxybenzyl)-4H-1,2,4-triazol-3-yl)-2-(1H-indol-3-yl)ethyl)-2-amino-2-methylpropanamide |
| 13 | 138 | (R)—N-(1-(4-(4-methoxybenzyl)-5-benzyl-4H-1,2,4-triazol-3-yl)-2-(1H-indol-3-yl)ethyl)-2-amino-2-methylpropanamide |
| 14 | 150 | (R)—N-(1-(5-(3-(1H-indol-3-yl)propyl)-4-(4-bromobenzyl)-4H-1,2,4-triazol-3-yl)-2-(1H-indol-3-yl)ethyl)-2-amino-2-methylpropanamide |
| 15 | 120 | (R)—N-(1-(5-(2-(1H-indol-3-yl)ethyl)-4-hexyl-4H-1,2,4-triazol-3-yl)-2-(1H-indol-3-yl)ethyl)-2-amino-2-methylpropanamide |
| 16 | 240 | (R)—N-(1-(5-(3-(1H-indol-3-yl)propyl)-4-hexyl-4H-1,2,4-triazol-3-yl)-2-(1H-indol-3-yl)ethyl)-2-amino-2-methylpropanamide |
| 17 | 156 | (R)—N-(1-(4,5-bis(2-(1H-indol-3-yl)ethyl)-4H-1,2,4-triazol-3-yl)-2-(1H-indol-3-yl)ethyl)-2-amino-2-methylpropanamide |
| 18 | 83 | (S)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-amino-2-methylpropanamide |
| 19 | 78 | (R)—N-(1-(4-(3-methoxybenzyl)-5-phenethyl-4H-1,2,4-triazol-3-yl)-2-(1H-indol-3-yl)ethyl)-2-amino-2-methylpropanamide |
| 20 | 14 | (R)—N-(1-(4-(4-methoxybenzyl)-5-phenethyl-4H-1,2,4-triazol-3-yl)-2-(1H-indol-3-yl)ethyl)-2-amino-2-methylpropanamide |
| 21 | 203 | (R)—N-(1-(5-(2-(1H-indol-3-yl)ethyl)-4-(3,5-dimethoxybenzyl)-4H-1,2,4-triazol-3-yl)-2-(1H-indol-3-yl)ethyl)-2-amino-2-methylpropanamide |
| 22 | 12 | (R)—N-(1-(4-(4-methoxybenzyl)-5-(3-phenylpropyl)-4H-1,2,4-triazol-3-yl)-2-(1H-indol-3-yl)ethyl)-2-amino-2-methylpropanamide |
| 23 | 37 | (R)—N-(1-(5-(3-(1H-indol-3-yl)propyl)-4-(4-methoxybenzyl)-4H-1,2,4-triazol-3-yl)-2-(1H-indol-3-yl)ethyl)-2-amino-2-methylpropanamide |
| 24 | 29 | (R)—N-(1-(4-(2-(1H-indol-3-yl)ethyl)-5-(3-(1H-indol-3-yl)propyl)-4H-1,2,4-triazol-3-yl)-2-(1H-indol-3-yl)ethyl)-2-amino-2-methylpropanamide |
| 25 | 96 | (R)—N-(1-(5-(2-(1H-indol-3-yl)ethyl)-4-(2-methoxy)benzyl)-4H-1,2,4-triazol-3-yl)-2-(1H-indol-3-yl)ethyl)-2-amino-2-methylpropanamide |
| 26 | 56 | (R)—N-(1-(4-(2-methoxybenzyl)-5-phenethyl-4H-1,2,4-triazol-3-yl)-2-(1H-indol-3-yl)ethyl)-2-amino-2-methylpropanamide |
| 27 | 126 | (R)—N-(2-(1H-indol-3-yl)-1-(4-(naphthalen-1-ylmethyl)-5-phenethyl-4H-1,2,4-triazol-3-yl)ethyl)-2-amino-2-methylpropanamide |
| 28 | 79 | (R)—N-(1-(5-(2-(1H-indol-3-yl)ethyl)-4-(3,4-dichlorobenzyl)-4H-1,2,4-triazol-3-yl)-2-(1H-indol-3-yl)ethyl)-2-amino-2-methylpropanamide |
| 29 | 66 | (R)—N-(1-(5-(2-(1H-indol-3-yl)ethyl)-4-(4-fluorobenzyl)-4H-1,2,4-triazol-3-yl)-2-(1H-indol-3-yl)ethyl)-2-amino-2-methylpropanamide |
| 30 | 171 | (R)—N-(1-(4-(4-fluorobenzyl)-5-benzyl-4H-1,2,4-triazol-3-yl)-2-(1H-indol-3-yl)ethyl)-2-amino-2-methylpropanamide |
| 31 | 0.5 | (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)piperidine-4-carboxamide |

TABLE 2-continued

GHS-R 1a Receptor-ligand binding assay test results (IC$_{50}$ values for a number of selected exemplary compounds)

| No. | GHS-R 1a IC$_{50}$ [nM] | Chemical name |
| --- | --- | --- |
| 32 | 10.3 | (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)piperidine-3-carboxamide |
| 33 | 30 | (R)—N-(1-(4-(4-methylbenzyl)-5-(3-phenylpropyl)-4H-1,2,4-triazol-3-yl)-2-(1H-indol-3-yl)ethyl)-2-amino-2-methylpropanamide |
| 34 | 28 | (R)—N-(1-(5-(2-(1H-indol-3-yl)ethyl)-4-(4-methylbenzyl)-4H-1,2,4-triazol-3-yl)-2-(1H-indol-3-yl)ethyl)-2-amino-2-methylpropanamide |
| 36 | 53 | (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)piperidine-2-carboxamide |
| 37 | 136 | (R)—N-(1-(4-(4-methylbenzyl)-5-phenethyl-4H-1,2,4-triazol-3-yl)-2-(1H-indol-3-yl)ethyl)-2-amino-2-methylpropanamide |
| 38 | 112 | (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-aminobenzamide |
| 40 | 249 | (2S,4R)—N-((R)-1-(4-(4-methoxybenzyl)-5-phenethyl-4H-1,2,4-triazol-3-yl)-2-(1H-indol-3-yl)ethyl)-4-hydroxypyrrolidine-2-carboxamide |
| 41 | 16 | (S)—N-((R)-1-(4-(4-methoxybenzyl)-5-phenethyl-4H-1,2,4-triazol-3-yl)-2-(1H-indol-3-yl)ethyl)piperidine-3-carboxamide |
| 42 | 7 | (R)—N-((R)-1-(4-(4-methoxybenzyl)-5-phenethyl-4H-1,2,4-triazol-3-yl)-2-(1H-indol-3-yl)ethyl)piperidine-3-carboxamide |
| 43 | 44 | (R)—N-(1-(4-(4-ethylbenzyl)-5-phenethyl-4H-1,2,4-triazol-3-yl)-2-(1H-indol-3-yl)ethyl)-2-amino-2-methylpropanamide |
| 44 | 0.6 | (R)—N-(1-(4-(4-methoxybenzyl)-5-phenethyl-4H-1,2,4-triazol-3-yl)-2-(1H-indol-3-yl)ethyl)piperidine-4-carboxamide |
| 45 | 0.3 | (R)—N-(1-(5-(2-(1H-indol-3-yl)ethyl)-4-(4-methoxybenzyl)-4H-1,2,4-triazol-3-yl)-2-(1H-indol-3-yl)ethyl)piperidine-4-carboxamide |
| 46 | 12 | (S)—N-((R)-1-(4-(4-methoxybenzyl)-5-phenethyl-4H-1,2,4-triazol-3-yl)-2-(1H-indol-3-yl)ethyl)pyrrolidine-2-carboxamide |
| 47 | 27 | (R)—N-((R)-1-(4-(4-methoxybenzyl)-5-phenethyl-4H-1,2,4-triazol-3-yl)-2-(1H-indol-3-yl)ethyl)pyrrolidine-2-carboxamide |
| 48 | 11 | (S)—N-((R)-1-(4-(4-methoxybenzyl)-5-phenethyl-4H-1,2,4-triazol-3-yl)-2-(1H-indol-3-yl)ethyl)piperidine-2-carboxamide |
| 49 | 23 | (R)—N-((R)-1-(4-(4-methoxybenzyl)-5-phenethyl-4H-1,2,4-triazol-3-yl)-2-(1H-indol-3-yl)ethyl)piperidine-2-carboxamide |
| 50 | 56 | (R)—N-(1-(4-(4-methoxybenzyl)-5-phenethyl-4H-1,2,4-triazol-3-yl)-2-(1H-indol-3-yl)ethyl)-2-aminoacetamide |
| 51 | 3 | (R)—N-(1-(4-(4-methoxybenzyl)-5-phenethyl-4H-1,2,4-triazol-3-yl)-2-(1H-indol-3-yl)ethyl)-2-(pyridin-2-yl)acetamide |
| 53 | 18 | (R)—N-(1-(4-(4-methoxybenzyl)-5-phenethyl-4H-1,2,4-triazol-3-yl)-2-(1H-indol-3-yl)ethyl)cyclohexanecarboxamide |
| 54 | 35 | (R)—N-(1-(5-(2-(1H-indol-3-yl)ethyl)-4-benzyl-4H-1,2,4-triazol-3-yl)-2-(1H-indol-3-yl)ethyl)piperidine-4-carboxamide |
| 55 | 11 | (R)—N-1-(5-(2-(1H-indol-3-yl)ethyl)-4-benzyl-4H-1,2,4-triazol-3-yl)-2-(1H-indol-3-yl)ethyl)piperidine-3-carboxamide |
| 56 | 59 | (R)—N-(1-(4-(4-methoxybenzyl)-5-phenethyl-4H-1,2,4-triazol-3-yl)-2-(1H-indol-3-yl)ethyl)-3-aminopropanamide |
| 57 | 140 | (S)—N-((R)-1-(4-(4-methoxybenzyl)-5-phenethyl-4H-1,2,4-triazol-3-yl)-2-(1H-indol-3-yl)ethyl)-2-aminopropanamide |
| 58 | 29 | (R)—N-(1-(4-(4-methoxybenzyl)-5-phenethyl-4H-1,2,4-triazol-3-yl)-2-(1H-indol-3-yl)ethyl)-2-(pyridin-3-yl)acetamide |
| 59 | 173 | (R)—N-(1-(4-(4-methoxybenzyl)-5-phenethyl-4H-1,2,4-triazol-3-yl)-2-(1H-indol-3-yl)ethyl)-3-(pyridin-3-yl)propanamide |

TABLE 2-continued

GHS-R 1a Receptor-ligand binding assay test results (IC$_{50}$ values for a number of selected exemplary compounds)

| No. | GHS-R 1a IC$_{50}$ [nM] | Chemical name |
|---|---|---|
| 60 | 61 | (R)—N-(1-(5-(2-(1H-indol-3-yl)ethyl)-4-benzyl-4H-1,2,4-triazol-3-yl)-2-(1H-indol-3-yl)ethyl)-2-(pyridin-2-yl)acetamide |
| 61 | 34 | (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-(pyridin-2-yl)acetamide |
| 62 | 0.9 | (R)—N-(1-(4-(2,4-dimethoxybenzyl)-5-phenethyl-4H-1,2,4-triazol-3-yl)-2-(1H-indol-3-yl)ethyl)piperidine-4-carboxamide |
| 63 | 210 | (R)—N-((R)-1-(4-(2,4-dimethoxybenzyl)-5-phenethyl-4H-1,2,4-triazol-3-yl)-2-(1H-indol-3-yl)ethyl)piperidine-2-carboxamide |
| 64 | 1.1 | (R)—N-(1-(4-(2,4-dimethoxybenzyl)-5-phenethyl-4H-1,2,4-triazol-3-yl)-2-(1H-indol-3-yl)ethyl)picolinamide |
| 65 | 58 | (R)—N-(1-(4-(2,4-dimethoxybenzyl)-5-phenethyl-4H-1,2,4-triazol-3-yl)-2-(1H-indol-3-yl)ethyl)isonicotinamide |
| 66 | 8 | (R)—N-(1-(4-(2,4-dimethoxybenzyl)-5-phenethyl-4H-1,2,4-triazol-3-yl)-2-(1H-indol-3-yl)ethyl)pyrazine-2-carboxamide |
| 67 | 35 | (R)—N-1-(4-(2,4-dimethoxybenzyl)-5-phenethyl-4H-1,2,4-triazol-3-yl)-2-(1H-indol-3-yl)ethyl)-piperazine-2-carboxamide |
| 68 | 44 | (S)—N-((R)-1-(4-(2,4-dimethoxybenzyl)-5-phenethyl-4H-1,2,4-triazol-3-yl)-2-(1H-indol-3-yl)ethyl)pyrrolidine-2-carboxamide |
| 69 | 38 | (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-aminoacetamide |
| 70 | 6 | (S)—N-((R)-1-(5-(2-(1H-indol-3-yl)ethyl)-4-(2,4-dimethoxybenzyl)-4H-1,2,4-triazol-3-yl)-2-(1H-indol-3-yl)ethyl)pyrrolidine-2-carboxamide |
| 71 | 19 | (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)pyrazine-2-carboxamide |
| 72 | 32 | (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)-piperazine-2-carboxamide |
| 73 | 1.8 | (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)picolinamide |
| 75 | 140 | (R)—N-(1-(4-(2,4-dimethoxybenzyl)-5-phenethyl-4H-1,2,4-triazol-3-yl)-2-(1H-indol-3-yl)ethyl)-2-aminoacetamide |
| 76 | 14 | (R)—N-(1-(4-(4-methoxybenzyl)-5-phenethyl-4H-1,2,4-triazol-3-yl)-2-(1H-indol-3-yl)ethyl)pyrazine-2-carboxamide |
| 77 | 119 | (R)—N-(1-(4-(4-methoxybenzyl)-5-phenethyl-4H-1,2,4-triazol-3-yl)-2-(1H-indol-3-yl)ethyl)isonicotinamide |
| 78 | 54 | (R)—N-(1-(4-(4-methoxybenzyl)-5-phenethyl-4H-1,2,4-triazol-3-yl)-2-(1H-indol-3-yl)ethyl)-piperazine-2-carboxamide |
| 79 | 0.7 | (R)—N-(1-(4-(4-methoxybenzyl)-5-phenethyl-4H-1,2,4-triazol-3-yl)-2-(1H-indol-3-yl)ethyl)picolinamide |
| 80 | 1.9 | (R)—N-(1-(5-(2-(1H-indol-3-yl)ethyl)-4-(4-methoxybenzyl)-4H-1,2,4-triazol-3-yl)-2-(1H-indol-3-yl)ethyl)picolinamide |
| 81 | 18 | (R)—N-(1-(5-((1H-indol-3-yl)ethyl)-4-(4-methoxybenzyl)-4H-1,2,4-triazol-3-yl)-2-(1H-indol-3-yl)ethyl)-piperazine-2-carboxamide |
| 82 | 51 | (R)—N-(1-(4-(4-ethylbenzyl)-5-phenethyl-4H-1,2,4-triazol-3-yl)-2-(1H-indol-3-yl)ethyl)-2-(pyridin-2-yl)acetamide |
| 83 | 19 | (R)—N-(1-(4-(4-ethylbenzyl)-5-phenethyl-4H-1,2,4-triazol-3-yl)-2-(1H-indol-3-yl)ethyl)piperidine-4-carboxamide |
| 84 | 247 | (R)—N-(1-(4-(4-ethylbenzyl)-5-phenethyl-4H-1,2,4-triazol-3-yl)-2-(1H-indol-3-yl)ethyl)-piperazine-2-carboxamide |
| 85 | 89 | (R)—N-(1-(4-(4-ethylbenzyl)-5-phenethyl-4H-1,2,4-triazol-3-yl)-2-(1H-indol-3-yl)ethyl)pyrazine-2-carboxamide |
| 86 | 143 | (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-cis-aminocyclohexanecarboxamide |
| 87 | 10 | (S)—N-((R)-1-(5-(2-(1H-indol-3-yl)ethyl)-4-(4-methoxybenzyl)-4H-1,2,4-triazol-3-yl)-2-(1H-indol-3-yl)ethyl)piperidine-3-carboxamide |
| 88 | 29 | (R)—N-((R)-1-(5-(2-(1H-indol-3-yl)ethyl)-4-(4-methoxybenzyl)-4H-1,2,4-triazol-3-yl)-2-(1H-indol-3-yl)ethyl)piperidine-2-carboxamide |

TABLE 2-continued

GHS-R 1a Receptor-ligand binding assay test results (IC$_{50}$ values for a number of selected exemplary compounds)

| No. | GHS-R 1a IC$_{50}$ [nM] | Chemical name |
|---|---|---|
| 89 | 9 | (S)—N-((R)-1-(5-(2-(1H-indol-3-yl)ethyl)-4-(4-methoxybenzyl)-4H-1,2,4-triazol-3-yl)-2-(1H-indol-3-yl)ethyl)pyrrolidine-2-carboxamide |
| 90 | 28 | (R)—N-((R)-1-(5-(2-(1H-indol-3-yl)ethyl)-4-(4-methoxybenzyl)-4H-1,2,4-triazol-3-yl)-2-(1H-indol-3-yl)ethyl)pyrrolidine-2-carboxamide |
| 91 | 11 | (R)—N-(1-(5-(2-(1H-indol-3-yl)ethyl)-4-(4-methoxybenzyl)-4H-1,2,4-triazol-3-yl)-2-(1H-indol-3-yl)ethyl)-2-(pyridin-2-yl)acetamide |
| 92 | 200 | (R)—N-(1-(5-(2-(1H-indol-3-yl)ethyl)-4-(4-bromobenzyl)-4H-1,2,4-triazol-3-yl)-2-(1H-indol-3-yl)ethyl)-2-amino-2-methylpropanamide |
| 94 | 255 | (R)—N-(2-(1H-indol-3-yl)-1-(5-phenethyl-4-(thiophen-2-ylmethyl)-4H-1,2,4-triazol-3-yl)ethyl)piperidine-4-carboxamide |
| 108 | 250 | (R)—N-(1-(4-(3,5-dimethoxybenzyl)-5-benzyl-4H-1,2,4-triazol-3-yl)-2-(1H-indol-3-yl)ethyl)-2-amino-2-methylpropanamide |
| 136 | 106 | (R)—N-(1-(5-(2-(1H-indol-3-yl)ethyl)-4-(4-methoxybenzyl)-4H-1,2,4-triazol-3-yl)-2-(1H-indol-3-yl)ethyl)-2-(pyridin-4-yl)acetamide |
| 138 | 44 | N-((R)-1-(4-(4-ethylbenzyl)-5-phenethyl-4H-1,2,4-triazol-3-yl)-2-(1H-indol-3-yl)ethyl)picolinamide |
| 146 | 105 | N-((R)-2-(1H-indol-3-yl)-1-(5-phenethyl-4-phenyl-4H-1,2,4-triazol-3-yl)ethyl)picolinamide |
| 147 | 49 | N-((R)-1-(5-(2-(1H-indol-3-yl)ethyl)-4-(4-ethylphenyl)-4H-1,2,4-triazol-3-yl)-2-(1H-indol-3-yl)ethyl)picolinamide |
| 148 | 96 | N-((R)-1-(5-(2-(1H-indol-3-yl)ethyl)-4-(4-ethylphenyl)-4H-1,2,4-triazol-3-yl)-2-(1H-indol-3-yl)ethyl)-2-(pyridin-2-yl)acetamide |
| 152 | 138 | N-((R)-1-(5-(2-(1H-indol-3-yl)ethyl)-4-(4-methoxybenzyl)-4H-1,2,4-triazol-3-yl)-2-(1H-indol-3-yl)ethyl)-2-aminoacetamide |
| 155 | 188 | (3S)—N-((R)-1-(4-(4-ethylbenzyl)-5-phenethyl-4H-1,2,4-triazol-3-yl)-2-(1H-indol-3-yl)ethyl)piperidine-3-carboxamide |
| 157 | 160 | N-((R)-1-(5-(2-(1H-indol-3-yl)ethyl)-4-phenyl-4H-1,2,4-triazol-3-yl)-2-(1H-indol-3-yl)ethyl)picolinamide |
| 158 | 70 | N-((R)-1-(5-(2-(1H-indol-3-yl)ethyl)-4-phenyl-4H-1,2,4-triazol-3-yl)-2-(1H-indol-3-yl)ethyl)piperidine-4-carboxamide |
| 159 | 33 | N-((R)-2-(1H-indol-3-yl)-1-(4-(2,4-dimethoxyphenyl)-5-phenethyl-4H-1,2,4-triazol-3-yl)ethyl)picolinamide |
| 160 | 121 | N-((R)-2-(1H-indol-3-yl)-1-(4-(2,4-dimethoxyphenyl)-5-phenethyl-4H-1,2,4-triazol-3-yl)ethyl)-2-(pyridin-2-yl)acetamide |
| 163 | 63 | N-((R)-2-(1H-indol-3-yl)-1-(4-(2,4-dimethoxyphenyl)-5-phenethyl-4H-1,2,4-triazol-3-yl)ethyl)piperidine-4-carboxamide |
| 164 | 207 | N-((R)-1-(5-benzyl-4-((pyridin-2-yl)methyl)-4H-1,2,4-triazol-3-yl)-2-(1H-indol-3-yl)ethyl)picolinamide |
| 173 | 114 | N-((R)-1-(4-benzyl-5-phenethyl-4H-1,2,4-triazol-3-yl)-2-(1H-indol-3-yl)ethyl)-2-amino-2-methylpropanamide |
| 175 | 140 | N-((R)-1-(5-(2-(1H-indol-3-yl)ethyl)-4-phenyl-4H-1,2,4-triazol-3-yl)-2-(1H-indol-3-yl)ethyl)-2-amino-2-methylpropanamide |
| 176 | 80 | N-((R)-1-(4-(4-methoxybenzyl)-5-phenethyl-4H-1,2,4-triazol-3-yl)-2-(1H-indol-3-yl)ethyl)benzamide |
| 179 | 62 | N-((R)-1-(4-(2,4-dimethoxybenzyl)-5-phenethyl-4H-1,2,4-triazol-3-yl)-2-(1H-indol-3-yl)ethyl)-2-amino-2-methylpropanamide |
| 180 | 189 | N-1-((R)-1-(4-(2,4-dimethoxybenzyl)-5-phenethyl-4H-1,2,4-triazol-3-yl)-2-(1H-indol-3-yl)ethyl)ethane-1,2-diamine |
| 182 | 81 | N-((R)-1-(4-((furan-2-yl)methyl)-5-phenethyl-4H-1,2,4-triazol-3-yl)-2-(1H-indol-3-yl)ethyl)picolinamide |
| 184 | 5.9 | N-((R)-1-(4-(4-methoxybenzyl)-5-phenethyl-4H-1,2,4-triazol-3-yl)-2-(1H-indol-3-yl)ethyl)-tetrahydro-2H-pyran-4-carboxamide |
| 186 | 175 | (2S)—N-((R)-1-(4-(4-methoxybenzyl)-5-phenethyl-4H-1,2,4-triazol-3-yl)-2-(1H-indol-3-yl)ethyl)-2-amino-3-phenylpropanamide |
| 187 | 66 | (R)-1-(5-(2-(1H-indol-3-yl)ethyl)-4-(2,4-dimethoxybenzyl)-4H-1,2,4-triazol-3-yl)-2-(1H-indol-3-yl)-N-tosylethanamine |

TABLE 2-continued

GHS-R 1a Receptor-ligand binding assay test results (IC$_{50}$ values for a number of selected exemplary compounds)

| No. | GHS-R 1a IC$_{50}$ [nM] | Chemical name |
|---|---|---|
| 188 | 87 | N-((R)-1-(4-(2,4-dimethoxybenzyl)-5-phenethyl-4H-1,2,4-triazol-3-yl)-2-(1H-indol-3-yl)ethyl)-4-azidobenzamide |
| 190 | 12 | (2S)—N-((R)-1-(5-(2-(1H-indol-3-yl)ethyl)-4-(4-methoxybenzyl)-4H-1,2,4-triazol-3-yl)-2-(1H-indol-3-yl)ethyl)-2,5-dihydro-1H-pyrrole-2-carboxamide |
| Example 39 from WO 00/54729 A2 | ca. 5000 | (R)—N-(1-(5-(tert-butylthio)-4-(furan-2-ylmethyl)-4H-1,2,4-triazol-3-yl)-2-(1H-indol-3-yl)ethyl)-2-amino-2-methylpropanamide |
| Example 8 from WO 00/54729 A2 | ca. 20000 | (S)—N-(1-(4-benzyl-5-(tert-butylthio)-1,2,4-triazol-3-yl)-2-(benzyloxy)ethyl)-2-amino-2-methylpropanamide |
| Example 3 from WO 00/54729 A2 | ca. 3000 | (R)—N-(1-(1-methylpropanoate-tetrazol-5-yl)-2-(1H-indol-3-yl)ethyl)-2-amino-2-methylpropanamide |
| Example from page 175, WO 00/54729 A2 | ca. 25000 | (S)—N-(1-(1-benzyl-tetrazol-5-yl)-2-(benzyloxy)ethyl)-2-amino-2-methylpropanamide |

III) In Vitro Intracellular Calcium Release Assay Using Human GHS-R 1a Transfected CHO Cells The potential of the compounds of the invention to modulate GHS receptor activity was assessed by an in vitro intracellular Calcium release assay employing CHO cells that were transfected with human GHS-R 1a.

Release of intracellular calcium or inhibition thereof was measured using the fluorescent calcium indicator assay (FLIPR) and Fluo-4 AM.

CHO cells (CHO-KI Chinese Hamster Ovary cell line, ATCC No. CCL-61) were transiently transfected with human GHS-R 1a cDNA by electroporation and plated into 96-well black bottom plates (Corning 3603) (80,000 cells/well). Transient transfections were performed using the Easyject Optima Electroporator (Equibio), according to the manufacturer's instructions.

Transfected cells were grown in Dulbecco's modified Eagle's medium without phenol red, supplemented with 10% (v/v) non-essential amino acids, 2 nM glutamine and strep-tomycin-penicillin (250 µg/ml-250 u/ml) (all purchased from Cambrex) at 37° C., 5% $CO_2$ in a humidified atmosphere for 24 hours.

After incubation, transfected cells were washed with 150 µl Buffer A [Hanks' balanced salt solution (Sigma H-6648), 0.5% (v/v) BSA (Sigma A-7906), 20 mM $CaCl_2$, 2.5 mM probenecid (pH 7.4, dissolved in 1M NaOH) (Sigma P-8761)] and were then loaded with fluorescent calcium indicator Fluo-4 AM ($10^{-6}$ M) (Interchim UP72972) prepared in Buffer A, additionally containing 0.06% pluronic acid (Molecular probes P-6867) (a mild-ionic detergent which facilitates Fluo-4AM ester loading).(Loading: 100 µl per well of Buffer A containing 120 µl/ml Pluronic Acid and 1 µM Fluo-4AM was added to the cells).

After loading with Fluo-4 AM, transfected cells were incubated for 1 hour in the dark at 37° C.

Compounds to be tested were dissolved in Buffer A in triplicates at a concentration of $10^{-6}$ M and distributed into another 96-well plate (Fisher Labosi A1210500).

Following incubation, excess Fluo-4AM was removed, 100 µl of Buffer A was added to each well at room temperature and immediately removed by aspiration. This was then repeated, before adding 50 µl Buffer A to each well.

Transfected cells were further incubated room temperature for 30 min to allow complete de-esterification of intracellular Fluo-4AM esters.

Subsequently, both plates, the black-bottom plate containing transfected cells and the microtiter plate containing the compounds to be tested, were then placed into a temperature-regulated (25° C.) FlexStation machine (benchtop scanning fluorometer Flex Station II, Molecular Devices, Sunnyvale, Calif., USA) for fluorescence output measurements.

Since Fluo-4AM exhibits a large fluorescence intensity increase upon binding of calcium, fluorescence output can be used directly as a proportional measure of intracellular calcium release.

Basal fluorescence output from the transfected cells was measured for 15 sec and then 50 µl of the compounds to be tested were automatically distributed into the wells containing the transfected cells. The fluorescence output was then recorded for a further 45 sec.

Excitation and emission wavelengths were 485 nm and 525 nm, respectively. Basal fluorescence intensity of Fluo-4AM-loaded transfected cells without compounds to be tested varied between 800-1200 arbitrary units, whereas maximal fluorescence output of dye-loaded transfected cells upon incubation with the compounds to be tested varied between 5000-7000 arbitrary units and was equivalent to that achieved by stimulation of dye-loaded transfected cells with $10^{-6}$ M ghrelin.

For each compound to be tested change in fluorescence output upon addition of the respective compound was compared with the basal fluorescence output measured with a negative control, i.e. addition 50 µl of buffer A to transfected cells only.

The ability and extent to which each compound to be tested caused calcium release was determined relative to the basal level (0%) and the maximum level (100%) achieved with 1 µM ghrelin.

For the compounds to be tested that were identified as GHS receptor agonists, $EC_{50}$ and KI values were determined using a dose-response curve.

As for the compounds to be tested that were identified as GHS receptor antagonists, $IC_{50}$ and Kb (antagonist dissociation constant) values were determined using antagonist inhibition curves in the presence of $10^{-7}$ M ghrelin (submaximal concentration). $IC_{50}$ values were calculated as the molar concentration of GHS receptor antagonist that reduced the maximal response of ghrelin by 50%. Kb values were estimated using the Cheng-Prusoff Equation (Lazareno S and Birdsall N J, Trends Pharmacol Sci. 1993, 14(6):237-239).

FIGS. 14-40 show the calculated dose-response plots of the in vitro intracellular Calcium release assay with human GHS-R 1a transfected CHO cells of the selected compounds 1, 9, 12, 20, 22, 31, 39, 41, 42, 45, 46, 47, 48, 49, 50, 51, 55, 62, 64, 67, 71, 73, 74, 79, 81, 90 and ghrelin as well as individual $EC_{50}$ and KI values for agonistic compounds and $IC_{50}$ and Kb values for antagonistic compounds.

IV) Assaying In Vivo GH Concentration in the Plasma of Male Rat Pups

GH plasma concentrations of male rat pubs were assayed to characterize the modulation effect (antagonistic or agonistic) of the compounds of the invention being GHS receptor analogue ligands.

In principle, assaying in vivo GH concentration in rat plasma was performed according to Torsello et al. (Eur. J. Pharmacol. 1998, 360: 123-129).

Male Sprague-Dawley rat pups (Charles River, Calco, Italy) were separated on postnatal day seven from their mothers and randomly redistributed to the dams, so that each one nurtured ten to twelve pups. On postnatal day ten, the pups were again separated from their mothers.

The compounds to be tested were dissolved in solvent [DMSO (0.4% of total volume), distilled water (4% of total volume), brought to the final volume with physiological saline].

One hour after separation from their mothers, the pups were given isovolumetric amounts of the compounds to be tested (160 μg/kg body weight s.c.) at time −10 min and then administered with hexarelin (80 μg/kg body weight s.c.) or solvent at time 0 min before being killed 15 min later by decapitation. Trunk blood was collected, immediately centrifuged and plasma samples were stored at −20° C. until assayed for the determination of GH concentrations.

Plasma GH concentrations were measured using a rat growth hormone enzyme immunoassay kit (SPIbio, France, cat. no. 589601) according to the manufacturer's instructions. Values are expressed in terms of NIDDK rat-GH-RP2 standard (potency 2 IU/mg) as ng/mL of plasma The limit of detection calculated as the concentration producing 15% displacement of initial tracer was 0.5 ng/ml; intra-assay and inter-assay coefficient of variation are 4% (n=24) and 14% (n=9).

In the following table 3 results obtained for selected compounds of the invention are presented.

TABLE 3

Relative GH concentration in rat plasma after treatment with selected compounds of the invention (160 μg/kg body weight s.c.) and/or hexarelin (80 μg/kg body weight s.c.) and/or solvent

| Treatment | GH concentration (ng/mL) |
| --- | --- |
| solvent | 4.008 ± 0.469 |
| hexarelin | 162.839 ± 21.095 |
| compound 1 | n.d. |
| compound 1 + hexarelin | 80.22 ± 18.66 |
| compound 12 | 4.0 ± 0.12 |
| compound 12 + hexarelin | 200.0 ± 19.7 |
| compound 20 | 5.27 ± 0.59 |
| compound 20 + hexarelin | 220.51 ± 15.52 |
| compound 22 | 4.88 ± 0.33 |
| compound 22 + hexarelin | 239.91 ± 19.75 |
| compound 47 | 5.658 ± 1.192 |
| compound 47 + hexarelin | 160.857 ± 13.52 |
| compound 39 | 5.509 ± 1.950 |
| compound 39 + hexarelin | 82.481 ± 11.530 |
| compound 31 | 119.937 ± 33.054 |
| compound 31 + hexarelin | 103.528 ± 14.094 |
| compound 48 | 6.096 ± 2.091 |
| compound 48 + hexarelin | 145.946 ± 12.159 |
| compound 44 | 87.520 ± 15.066 |
| compound 44 + hexarelin | 100.52 ± 12.112 |
| solvent | 2.237 ± 0.073 |
| hexarelin | 170.101 ± 13.226 |
| compound 9 | 13.016 ± 1.960 |
| compound 9 + hexarelin | 183.562 ± 16.729 |
| compound 39 | 5.509 ± 1.95 |
| compound 39 + hexarelin | 82.481 ± 11.53 |
| compound 50 | 9.852 ± 1.040 |
| compound 50 + hexarelin | 164.459 ± 4.443 |
| compound 64 | 13.056 ± 2.169 |
| compound 64 + hexarelin | 138.394 ± 14.580 |
| solvent | 10.729 ± 2.027 |
| hexarelin | 253.820 ± 12.268 |
| compound 71 | 15.326 ± 1.355 |
| compound 71 + hexarelin | 173.611 ± 18.444 |
| compound 74 | 10.571 ± 0.791 |
| compound 74 + hexarelin | 194.564 ± 7.658 |
| compound 81 | 18.634 ± 2.933 |
| compound 81 + hexarelin | 216.575 ± 19.734 |
| compound 90 | 16.857 ± 2.152 |
| compound 90 + hexarelin | 218.844 ± 19.723 |

V) Assaying the Feeding Behavior (Food Intake) of Young-Adult Male Rats

The impact of compounds of the invention being GHS receptor analogue ligands on the feeding behaviour, i.e. food intake, of young-adult male rats was assayed.

In principle, assaying the feeding behavior (food intake) of young-adult male rats was performed according to Torsello et al. (Eur. J. Pharmacol. 1998, 360: 123-129).

For the assay, young-adult male Sprague-Dawley rats (Charles River, Calco, Italy), weighing 200-250 g, were used.

Rats had 1 week of acclimation in individual home cages, and animal room conditions (22±2° C., 65% humidity, artificial light from 08.00 to 20.00 h). The following week, they were daily trained to mimic the experimental procedure. Rats maintained free access to dry pellets and tap water throughout the whole experimental period. At the end of training, rats were administered (around 10.00-11.00 a.m.) subcutaneously with the compounds to be tested (160 μg/kg body weight) and/or hexarelin (80 μg/kg body weight) and/or solvent [DMSO (0.4% of total volume), distilled water (4% of total volume), brought to the final volume with physiological saline].

Hexarelin was used to study the effects of the compounds to be tested on stimulated feeding behavior. Immediately after the injections, the animals were returned to their home cages, which contained a known amount of standard rat chow and ad libitum water. Every hour for the following 6 hours, the remaining food was carefully collected and weighed to the nearest 0.1 g. Food intake was normalized for the body weight of the rats and expressed as grams of food eaten per 100 g body weight of rats.

In the following table 4 results obtained for selected compounds of the invention are presented.

TABLE 4

Cumulative food intake (g food/100 g body weight) of young-adult rats after 2 hours and 6 hours and after treatment with selected compounds of the invention (160 µg/kg body weight s.c.) and/or hexarelin (80 µg/kg body weight s.c.) and/or solvent

| Treatment | Cumulative food intake (after 2 hours) | Cumulative food intake (after 6 hours) |
|---|---|---|
| solvent | 0.003 ± 0.0015 | 0.017 ± 0.0026 |
| hexarelin | 0.533 ± 0.194 | 1.0014 ± 0.1973 |
| compound 1 | 0.02 ± 0.002 | 0.06 ± 0.03 |
| compound 1 + hexarelin | 0.06 ± 0.02 | 0.33 ± 0.21 |
| compound 12 | 0.034 ± 0.011 | 0.06 ± 0.019 |
| compound 12 + hexarelin | 0.13 ± 0.07 | 0.48 ± 0.22 |
| compound 20 | 0.01 | 0.2 ± 0.19 |
| compound 20 + hexarelin | 0.53 ± 0.21 | 0.63 ± 0.19 |
| compound 22 | 0.01 | 0.44 ± 0.2 |
| compound 22 + hexarelin | 0.67 ± 0.12 | 0.86 ± 0.18 |
| compound 47 | 0.006 ± 0.002 | 0.02 ± 0 |
| compound 47 + hexarelin | 0.35 ± 0.201 | 0.47 ± 0.1943 |
| compound 44 | 0.43 ± 0.0721 | 0.7075 ± 0.1471 |
| compound 44 + hexarelin | 1.2667 ± 0.1319 | 1.4033 ± 0.1177 |
| solvent | 0.184 ± 0.111 | 0.497 ± 0.183 |
| hexarelin | 0.536 ± 0.176 | 0.594 ± 0.169 |
| compound 9 | 0.01 ± 0 | 0.01 ± 0 |
| compound 9 + hexarelin | 0.0104 ± 0.0032 | 0.0231 ± 0.0032 |
| solvent | 0.184 ± 0.111 | 0.497 ± 0.183 |
| hexarelin | 1.060 ± 0.143 | 1.138 ± 0.114 |
| compound 13 | 0.057 ± 0.057 | 0.167 ± 0.167 |
| compound 13 + hexarelin | 0.731 ± 0.318 | 0.792 ± 0.337 |
| solvent | 0.184 ± 0.111 | 0.497 ± 0.183 |
| hexarelin | 1.060 ± 0.143 | 1.138 ± 0.114 |
| compound 17 | 0.001 ± 0.001 | 0.2661 ± 0.166 |
| compound 17 + hexarelin | 0.0501 ± 0.049 | 0.846 ± 0.411 |
| solvent | 0.184 ± 0.111 | 0.497 ± 0.183 |
| hexarelin | 0.428 ± 0.192 | 0.588 ± 0.303 |
| compound 24 | 0.008 ± 0.008 | 0.215 ± 0.200 |
| compound 24 + hexarelin | 0.586 ± 0.252 | 0.912 ± 0.359 |
| solvent | 0.184 ± 0.111 | 0.497 ± 0.183 |
| hexarelin | 0.627 ± 0.211 | 0.778 ± 0.218 |
| compound 30 | 0.264 ± 0.244 | 0.277 ± 0.246 |
| compound 30 + hexarelin | 1.350 ± 0.177 | 1.449 ± 0.213 |
| solvent | 0.184 ± 0.018 | 0.399 ± 0.201 |
| hexarelin | 0.278 ± 0.078 | 0.883 ± 0.259 |
| compound 38 | 0.001 ± 0 | 0.076 ± 0.096 |
| compound 38 + hexarelin | 0.002 ± 0.002 | 0.478 ± 0.141 |
| solvent | 0.184 ± 0.111 | 0.497 ± 0.183 |
| hexarelin | 0.260 ± 0.13 | 0.78 ± 0.25 |
| compound 49 | 0.004 ± 0.004 | 0.004 ± 0.004 |
| compound 49 + hexarelin | 0.057 ± 0.037 | 0.558 ± 0.212 |
| solvent | 0.184 ± 0.111 | 0.497 ± 0.183 |
| hexarelin | 0.536 ± 0.176 | 0.594 ± 0.169 |
| compound 50 | 0.012 ± 0.008 | 0.039 ± 0.011 |
| compound 50 + hexarelin | 0.003 ± 0.002 | 0.017 ± 0.001 |
| solvent | 0.184 ± 0.111 | 0.497 ± 0.183 |
| hexarelin | 0.427 ± 0.16 | 0.688 ± 0.203 |
| compound 64 | 0.012 ± 0.008 | 0.039 ± 0.011 |
| compound 64 + hexarelin | 0.012 ± 0.004 | 0.021 ± 0.007 |
| solvent | 0.184 ± 0.111 | 0.497 ± 0.183 |
| hexarelin | 0.696 ± 0.267 | 0.74 ± 0.27 |
| compound 71 | 0.522 ± 0.283 | 0.53 ± 0.28 |
| compound 71 + hexarelin | 0.117 ± 0.074 | 0.20 ± 0.01 |
| solvent | 0.184 ± 0.111 | 0.497 ± 0.183 |
| hexarelin | 0.70 ± 0.116 | 1.221 ± 0.06 |
| compound 72 | 0.008 ± 0.003 | 0.011 ± 0 |
| compound 72 + hexarelin | 0.634 ± 0.33 | 0.746 ± 0.31 |
| solvent | 0.184 ± 0.111 | 0.497 ± 0.183 |
| hexarelin | 1.031 ± 0.219 | 1.455 ± 0.192 |
| compound 80 | 0.145 ± 0.143 | 0.346 ± 0.159 |
| compound 80 + hexarelin | 0.475 ± 0.196 | 0.733 ± 0.238 |
| solvent | 0.184 ± 0.111 | 0.497 ± 0.183 |

TABLE 4-continued

Cumulative food intake (g food/100 g body weight) of young-adult rats after 2 hours and 6 hours and after treatment with selected compounds of the invention (160 µg/kg body weight s.c.) and/or hexarelin (80 µg/kg body weight s.c.) and/or solvent

| Treatment | Cumulative food intake (after 2 hours) | Cumulative food intake (after 6 hours) |
|---|---|---|
| hexarelin | 0.696 ± 0.267 | 0.74 ± 0.27 |
| compound 81 | 0.017 ± 0.004 | 0.03 ± 0 |
| compound 81 + hexarelin | 0.024 ± 0.0101 | 0.116 ± 0.077 |
| solvent | 0.184 ± 0.111 | 0.497 ± 0.183 |
| hexarelin | 0.323 ± 0.131 | 0.45 ± 0.17 |
| compound 90 | 0.014 ± 0.001 | 0.035 ± 0.003 |
| compound 90 + hexarelin | 0.054 ± 0.041 | 0.069 ± 0.041 |

VI) Motilin Receptor-Ligand Binding Assay (Using Human Recombinant HEK-293 Cells)

Motilin Receptor binding/affinity studies were performed as described by Feighner S D et al. (Science 1999, 284: 2184-2188). The assays were run under the following conditions:

| Source: | Human recombinant HEK-293 cells [Motilin-Receptor 1a (MTL-R1a)] |
|---|---|
| Ligand: | 0.1 nM [$^{125}$I] Motilin (human, porcine) |
| Vehicle: | 1% DMSO |
| Incubation Time/Temperature: | 2.5 hours at 25° C. |
| Incubation Buffer: | 50 mM Tris, pH 7.4, 10 mM MgCl$_2$, 0.5% BSA |
| Non-Specific Ligand: | 1 µM Motilin (human, porcine) |

Compounds of the invention were tested in concentrations comprising 0.01 µM, 0.1 µM, 1 µM and 10 µM.

IC$_{50}$ values were determined by a non-linear, least square regression analysis using Data Analysis Toolbox (MDL Information Systems, USA).

In the following table 5 results obtained for selected compounds of the invention are presented.

TABLE 5

Motilin Receptor-ligand binding assay test results (IC$_{50}$ values for a number of selected exemplary compounds)

| No. | MTL-R 1a IC$_{50}$ [µM] | Chemical name |
|---|---|---|
| 44 | 1.61 | (R)—N-(1-(4-(4-methoxybenzyl)-5-phenethyl-4H-1,2,4-triazol-3-yl)-2-(1H-indol-3-yl)ethyl)piperidine-4-carboxamide, |
| 64 | 1.39 | (R)—N-(1-(4-(2,4-dimethoxybenzyl)-5-phenethyl-4H-1,2,4-triazol-3-yl)-2-(1H-indol-3-yl)ethyl)picolinamide, |

VII) Study of Anti-Cachectic Effects in an Adjuvant-Induced Arthritis Model System The effectiveness of compounds of the invention in the treatment of cachexia was investigated according to Ibanez de Caceres I et al. (J Endocrinol. 2000, 165(3): 537-544) using a cachexia model system (Roubenoff R et al., Arthritis Rheum. 1997, 40(3): 534-539).

Table 6 shows the anti-cachetic effect of compound 44 (0.1 µg/kg/day s.c. injection) in arthritic rats in comparison to adjuvant induced arthritis without medical treatment.

TABLE 6

Body weight change in gram (mean of 6 animals per group)

|  | Day 3 | Day 6 | Day 10 | Day 13 | Day 15 | Day 17 |
|---|---|---|---|---|---|---|
| Rats with adjuvant induced arthritis + vehicle | −3.02 | 2.95 | 11.97 | 9.32 | −2.78 | −8.27 |
| Arthritic rats + treatment with compound 44 (0.1 µg/kg/day s.c.) | −5.32 | 2.98 | 14.92 | 19.08 | 7.05 | 1.47 |

VIII) Study of Anti-Inhibitory Effects of Isoproterol-Induced Lipolysis in Adipocyte Models The effectiveness of compounds of the invention in the inhibition of the unacylated ghrelin-induced inhibition of isoproterol-induced lipolysis was investigated using adipocyte models.

Isolation of Primary Mouse Adipocytes

Mice were fed with high fat diet induce obesity (60% of lipids) starting at 4 weeks of age for 12 and 18 weeks.

White adipose tissue from epididymal fat was minced and digested in Krebs-Ringer-Bicarbonate-Hepes (KRBH) buffer (20 mM Hepes pH 7.4, 120 mM NaCl, 4.7 mM KCl, 1.2 mM $K_2HPO_4$, 2.5 mM $CaCl_2$, 1.2 mM $MgSO_4$, 24 mM $NaHCO_3$) saturated with $CO_2$ containing glucose (1 mg/mL), 1% BSA and collagenase (2 mg/g tissue). The digestion was made under constant shaking (250 rpm) at 37° C. for 45 minutes.

The cell suspension was filtered through a nylon mesh to separate the adipocytes from tissue fragments, and washed three times in 3 mL of warm KRBH 1% BSA.

The cells was resuspended in KRBH 1% BSA and incubated in shaker (75 rpm) at 37° C. for 30 minutes.

Lipolysis Assay

Lipolysis in primary adipocytes cells was induced with 30 nM of isoproterenol in KRBH 4% BSA for 90 minutes with constant (125 rpm) shaking at 37° C.

Lipolysis in differentiated cells was induced with 30 nM of isoproterenol in DMEM FBS free for 90 minutes at 37° C. with shaking every 15 minutes.

The inhibitory effect of unacylated ghrelin (UAG) on isoproterenol induced lipolysis was documented with increasing concentration of UAG from $10^{-11}$ M to $10^{-6}$ M in presence or in absence of selected compounds of the invention at $10^{-7}$ M.

The lipolysis index was assessed by measuring glycerol release following triglyceride hydrolysis.

The antagonistic effect was determined as follows:

$$pA2 = -\log\frac{[\text{concentration of competitor (M)}]}{\text{Ratio} - 1}$$

with $$\text{Ratio} = \frac{EC50 \text{ in presence of competitor (M)}}{EC50 \text{ in absence of competitor (M)}}$$

FIGS. 41-46 show the effects of selected compounds 9, 38, 50, 64, 74, 81 on the isoprorerenol-induced lipolysis inhibition curve of unacylated ghrelin (UAG) in primary adipocytes from mice under diet-induced obesity.

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials. Terms such as "contain(s)" and the like as used herein are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention method, compounds and compositions are preferably used by subjects desirous of the benefits noted herein, subjects "in need of" these benefits. Such subjects are typically suffering from physiological and/or pathophysiological conditions such as those selected from the group consisting of acute fatigue syndrome and muscle loss following election surgery, adipogenesis, adiposity, age-related decline of thymic function, age-related functional decline (ARFD) in the elderly, aging disorder in companion animals, Alzheimer's disease, anorexia; anxiety, blood pressure (lowering), body weight gain/reduction, bone fracture repair (acceleration), bone remodeling stimulation, cachexia and protein loss reduction due to chronic illness such as cancer or AIDS, cardiac dysfunctions, cardiomyopathy, cartilage growth stimulation, catabolic disorders in connection with pulmonary dysfunction and ventilator dependency, catabolic side effects of glucocorticoids, catabolic state of aging, central nervous system disorders (in combination with antidepressants), chronic dialysis, chronic fatigue syndrome (CFS), cognitive function improvement, complicated fractures, complications associated with transplantation, congestive heart failure (alone/in combination with corticotropin releasing factor antagonists), Crohn's disease and ulcerative colits, Cushing's syndrome, dementia, depressions, short-, medium- and/or long-term regulation of energy balance, short-, medium- and/or long-term regulation of food intake (stimulation and/or inhibition), fraility, gastrectomy (ghrelin replacement therapy), gastric postoperative ileus, glycemic control improvement, growth hormone release stimulation in the elderly, growth hormone replacement in stressed patients, growth promotion in livestock, growth retardation associated with the Prader-Willi syndrome and Turner's syndrome, growth retardation in connection with Crohn's disease, growth retardation, hair/nail growth maintenance, hip fractures, hunger, hypercortisolism, hyperinsulinemia including nesidioblastosis, hypothermia, immune deficiency in individuals with a depressed T4/T8 cell ratio, immune response improvement to vaccination, immune system stimulation in companion animals, immune system stimulation, immunosuppression in immunosuppressed patients, inflammation or inflammatory effects, inflammatory bowel disease, insulin resistance in the heart, insulin resistance in type 2 diabetic patients, insulin resistance including NIDDM, diabetes, diabetes type I, diabetes type II, intrauterine growth retardation, irritable bowel syndrome, lipodystrophy, metabolic homeostasis maintenance, milk production increase in livestock, muscle mass/strength increase, muscle mobility improvement, muscle strength improvement, muscle strength/function maintenance in elderly humans, muscular atrophy, musculoskeletal impairment (e.g. in elderly), Noonan's syndrome, obesity and growth retardation associated with obesity, osteoblast stimulation, osteochondrodysplasias, osteoporosis, ovulation induction (adjuvant treatment), physiological short stature including growth hormone deficient children, postoperative ileus, protein catabolic response attenuation after major surgery/trauma, protein kinase B activity enhancement, psychosocial deprivation, pulmonary dysfunction and ventilator dependency, pulmonary function improvement, pulsatile growth hormone release induction, recovery of burn patients and reducing hospitalization of burn patients (acceleration), renal failure or insufficiency resulting from growth retardation, renal homeostasis maintenance in the frail elderly, sarcopenia, schizophrenia, sensory function maintenance, short bowel syndrome, short stature associated with chronic illness, skeletal dysplasia, skin thickness maintenance, sleep disorders, sleep quality improvement, thrombocytopenia, thymic development stimulation, tooth repair or growth, tumor cell proliferation, ventricular dysfunction or reperfusion events, wasting in connection with AIDS, wasting in connection with chronic liver disease, wasting in connection with chronic obstructive pulmonary disease (COPD), wasting in connection with multiple sclerosis or other neurodegenerative disorders, wasting secondary to fractures, wool growth stimulation in sheep, wound healing (acceleration) and/or wound healing delay, such as by self diagnosis or medical diagnosis, or are at recognized and appreciated risk of developing such conditions and who use the invention methods and compositions to combat these effects. Naturally, one using the invention as disclosed will use an amount of the invention compounds and compositions effective to obtain the desired results. Such amount is inclusive of the amounts described herein.

The invention claimed is:

1. A method for increasing or decreasing growth hormone levels in a mammal or for increasing or decreasing food intake of a mammal comprising:
administering to a mammal in need of treatment at least one compound according to formula (I):

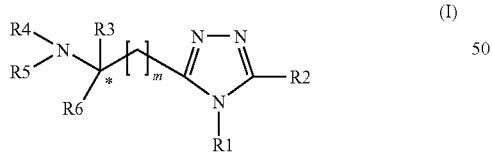

(I)

wherein:
R1 and R2 are independently of one another a hydrogen atom or are selected from the group of radicals consisting of alkyl, alkenyl, alkynyl, cycloalkyl, cycloalkylalkyl, aryl, heteroaryl, arylalkyl, heteroarylalkyl, heterocyclyl, heterocyclylalkyl, alkylsulfonyl, arylsulfonyl, and arylalkylsulfonyl;
wherein said radicals at R1 or R2 are optionally substituted in an alkyl, cycloalkyl, cycloalkylalkyl, aryl, heteroaryl, arylalkyl, heteroarylalkyl, heterocyclyl and/or heterocyclylalkyl group by up to 3 substituents independently selected from the group consisting of halogen, —F,
—Cl, —Br, —I, —N$_3$, —CN, —NR7R8, —OH, —NO$_2$, alkyl, aryl, arylalkyl, —O-alkyl, —O-aryl, and —O-arylalkyl;
R3 is selected from the group of radicals consisting of alkyl, aryl, heteroaryl, arylalkyl, heteroarylalkyl, heterocyclyl, heterocyclylalkyl, -alkyl-O-aryl, -alkyl-O-arylalkyl, -alkyl-O-heteroaryl, -alkyl-O-heteroarylalkyl, -alkyl-O-heterocyclyl, alkyl-O-heterocyclylalkyl, -alkyl-CO-aryl, -alkyl-CO-arylalkyl, -alkyl-CO-heteroaryl, -alkyl-CO-heteroarylalkyl, -alkyl-CO-heterocyclyl, -alkyl-CO-heterocyclylalkyl, -alkyl-C(O)O-aryl, -alkyl-C(O)O-arylalkyl, -alkyl-C(O)O-heteroaryl, -alkyl-C(O)O-heteroarylalkyl, -alkyl-C(O)O-heterocyclyl, -alkyl-C(O)O-heterocyclylalkyl, -alkyl-CO—NH$_2$, -alkyl-CO—OH, -alkyl-NH$_2$, -alkyl-NH—C(NH)—NH$_2$, alkyl-S-alkyl, and alkyl-S—H;
wherein said radicals are optionally substituted in the aryl, heteroaryl, arylalkyl, heteroarylalkyl, heterocyclyl and/or heterocyclylalkyl group by up to 3 substituents independently selected from the group consisting of halogen, —F, —Cl, —Br, —I, —N$_3$, —CN, —NR7R8, —OH, —NO$_2$, alkyl, aryl, arylalkyl, —O-alkyl, —O-aryl, and —O-arylalkyl;
R4 is hydrogen;
R5 is a radical
a) selected from the group consisting of alkyl, cycloalkyl, cycloalkylalkyl, aryl, heteroaryl, arylalkyl, heteroarylalkyl, heterocyclyl, heterocyclylalkyl, —CO-alkyl, —CO-cycloalkyl, —CO-cycloalkylalkyl, —CO-aryl, and —CO-arylalkyl, wherein said radical from (a) is optionally substituted by up to 3 substituents independently selected from the group consisting of halogen, —F, —Cl, —Br, —I, —N$_3$, —CN, —OH, —NO$_2$, alkyl, aryl, arylalkyl, —O-alkyl, —O-aryl, and —O-arylalkyl; or
b) selected from the group consisting of —CO-heteroaryl, —CO-heteroarylalkyl, —CO-heterocyclyl, —CO-heterocyclylalkyl, wherein said radical from (b) is optionally substituted by up to 3 substituents independently selected from the group consisting of halogen, —F, —Cl, —Br, —I, —N$_3$, —CN, —NR7R8, —OH, —NO$_2$, alkyl, aryl, arylalkyl, —O-alkyl, —O-aryl, and —O-arylalkyl;
R6 is hydrogen;
R7 and R8 are independently of one another selected from the group consisting of a hydrogen atom, alkyl, cycloalkyl, and cycloalkylalkyl; and
m is 0;
wherein * designates a carbon atom of R or S configuration when chiral.

2. The method of claim 1, where R3 is selected from the group consisting of -alkyl-CO-aryl, -alkyl-CO-arylalkyl, -alkyl-CO-heteroaryl, -alkyl-CO-heteroarylalkyl, -alkyl-CO-heterocyclyl, alkyl-CO-heterocyclylalkyl, -alkyl-C(O)O-aryl, -alkyl-C(O)O-arylalkyl, -alkyl-C(O)O-heteroaryl, -alkyl-C(O)O-heteroarylalkyl, -alkyl-C(O)O-heterocyclyl, -alkyl-C(O)O-heterocyclylalkyl, -alkyl-CO—NH$_2$, -alkyl-CO—OH, -alkyl-NH—C(NH)—NH$_2$, alkyl-S-alkyl, and alkyl-S—H.

3. The method of claim 1, wherein
R5 is selected from the group consisting of —CO-heteroaryl, —CO-heteroarylalkyl, —CO-heterocyclyl, and —CO-heterocyclylalkyl;
with the proviso that if R5 is —CO-heteroarylalkyl, then heteroaryl is not imidazole; and with the proviso that if R5 is —CO-heterocyclyl and heterocyclyl contains only nitrogen atoms as heteroatoms, that at least two nitrogen atoms are contained in heterocyclyl; and with the proviso that if R5 is —CO-heterocyclylalkyl and heterocyclyl contains only nitrogen atoms as heteroatoms that in the case that one or two nitrogen atoms are contained in heterocyclyl then no nitrogen atom is positioned at position 1 of heterocyclyl that is the atom directly linking heterocyclyl to the carbonyl group —CO—;

wherein —CO-heteroaryl, —CO-heteroarylalkyl, —CO-heterocyclyl, and/or —CO-heterocyclylalkyl are optionally substituted by up to 3 substituents independently selected from the group consisting of halogen, —F, —Cl, —Br, —I, —$N_3$, —CN, —NR7R8, —OH, —$NO_2$, alkyl, aryl, arylalkyl, —O-alkyl, —O-aryl, and —O-arylalkyl.

4. The method of claim 1, where
R1 is selected from the group consisting of hydrogen, methyl, (2-methoxyphenyl)-methyl, (3-methoxyphenyl)-methyl, (4-methoxyphenyl)-methyl, (3-methoxyphenyl)-ethyl, (4-methoxyphenyl)-ethyl, phenyl, phenyl-methyl, phenyl-ethyl, (4-ethylphenyl)-methyl, (4-methylphenyl)-methyl, (4-fluorophenyl)-methyl, (4-bromophenyl)-methyl, (2,4-dimethoxyphenyl)-methyl, (3,5-dimethoxyphenyl)-methyl, 2,2-diphenyl-ethyl, naphthaline-1-yl-methyl, 1H-indole-3-yl-methyl, 2-(1H-indole-3-yl)-ethyl, 3-(1H-indole-3-yl)-propyl, 4-methyl-phenyl, 4-ethyl-phenyl, n-hexyl, (3,4-dichlorophenyl)-methyl, (4-nitro-phenyl)-methyl, (pyridine-2-yl)-methyl, (pyridine-3-yl)-methyl, (pyridine-4-yl)-methyl, (thiophene-2-yl)-methyl, (thiophene-3-yl)-methyl, (furan-2-yl)-methyl, (furan-3-yl)-methyl; and R2 is selected from the group consisting of methyl, 1H-indole-3-yl-methyl, 2-(1H-indole-3-yl)-ethyl, 3-(1H-indole-3-yl)-propyl, 2-phenyl-ethyl, 3-phenyl-propyl, 4-phenyl-butyl, 2-methoxy-phenylmethyl, 3-methoxy-phenylmethyl, 4-methoxy-phenylmethyl, 2-methoxy-phenylethyl, 3-methoxy-phenylethyl, and 4-methoxy-phenylethyl;

R3 is selected from the group consisting of methyl, propan-2-yl, 2-methyl-propan-1-yl, butan-2-yl, butan-1-yl, —$CH_2$—SH, —$(CH_2)_2$—S—$CH_3$, 1H-indole-3-yl-methyl, phenyl-methyl, 2-phenyl-ethyl, —$CH_2$—O—$CH_2$-phenyl, —$CH_2$—CO—$CH_2$-phenyl, —$(CH_2)_2$—CO—$CH_2$-phenyl, —$CH_2$—C(O)O-phenyl, —$(CH_2)_2$—C(O)O-phenyl, hydroxy-methyl, 1-hydroxy-ethan-1-yl, —$CH_2$—CO—$NH_2$, —$(CH_2)_2$—CO—$NH_2$, (1-hydroxy-benzene-4-yl)-methyl, —$CH_2$—CO—OH, —$(CH_2)_2$—CO—OH, —$(CH_2)_4$—$NH_2$, (1H-imidazol-5-yl)-methyl, —$(CH_2)_3$—NH—C(NH)—$NH_2$, —$(CH_2)_3$—$NH_2$, and —$(CH_2)_3$—NH—CO—$NH_2$;

R5 is selected from the group consisting of —CO-(pyrrolidine-2-yl), 4-carbonyl-1H-piperidine, 3-carbonyl-1H-piperidine, R-(3-carbonyl-1H-piperidine), S-(3-carbonyl-1H-piperidine), 2-carbonyl-1H-piperidine, R-(2-carbonyl-1H-piperidine), S-(2-carbonyl-1H-piperidine), 2-acetyl-pyridine, 3-acetyl-pyridine, 4-acetyl-pyridine, 2-propionyl-pyridine, 3-propionyl-pyridine, 4-propionyl-pyridine, 2-carbonyl-1H-imidazole, 2-carbonyl-pyridine, 3-carbonyl-pyridine, 4-carbonyl-pyridine, 2-amino-3-carbonyl-pyridine, 2-carbonyl-pyrazine, 2-carbonyl-4-hydroxy-1H-pyrrolidine, 4-carbonyl-1H,3H-diazacyclohexane, 2-carbonyl-2,5-dihydro-1H-pyrrole, 2-carbonyl-piperazine, 2-carbonyl-1H-pyrrolidine, 2-carbonyl-pyrazine, 3-carbonyl-pyrazine, and 4-carbonyl-oxacyclohexane.

5. The method of claim 4, where R3 is selected from the group consisting of —$CH_2$—CO—$CH_2$-phenyl, —$(CH_2)_2$—CO—$CH_2$-phenyl, —$CH_2$—CO—$NH_2$, —$(CH_2)_2$—CO—$NH_2$, —$CH_2$—CO—OH, —$(CH_2)_2$—CO—OH, —$(CH_2)_3$—NH—C(NH)—$NH_2$, —$CH_2$—SH, and —$(CH_2)_2$—S—$CH_3$.

6. The method of claim 4, where R5 is selected from the group consisting of 2-carbonyl-pyridine, 3-carbonyl-pyridine, 4-carbonyl-pyridine, 2-acetyl-pyridine, 3-acetyl-pyridine, 4-acetyl-pyridine, 2-propionyl-pyridine, 3-propionyl-pyridine, 4-propionyl-pyridine, 2-amino-3-carbonyl-pyridine, 2-carbonyl-1H-imidazole, 2-carbonyl-pyrazine, and 4-carbonyl-1H,3H-diazacyclohexane.

7. The method of claim 1, wherein the compound according to formula (I) that increases or decreases growth hormone level and is selected from the group consisting of Compound 31: (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)piperidine-4-carboxamide, Compound 44: (R)—N-(1-(4-(4-methoxybenzyl)-5-phenethyl-4H-1,2,4-triazol-3-yl)-2-(1H-indol-3-yl)ethyl)piperidine-4-carboxamide, Compound 64: (R)—N-(1-(4-(2,4-dimethoxybenzyl)-5-phenethyl-4H-1,2,4-triazol-3-yl)-2-(1H-indol-3-yl)ethyl)picolinamide, Compound 71: (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)pyrazine-2-carboxamide, Compound 90: (R)—N—((R)-1-(5-(2-(1H-indol-3-yl)ethyl)-4-(4-methoxybenzyl)-4H-1,2,4-triazol-3-yl)-2-(1H-indol-3-yl)ethyl)pyrrolidine-2-carboxamide.

8. The method of claim 1, wherein the compound according to formula (I) decreases food intake and is selected from the group consisting of Compound 38: (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-aminobenzamide, Compound 47: (R)—N—((R)-1-(4-(4-methoxybenzyl)-5-phenethyl-4H-1,2,4-triazol-3-yl)-2-(1H-indol-3-yl)ethyl)pyrrolidine-2-carboxamide, Compound 49: (R)—N—((R)-1-(4-(4-methoxybenzyl)-5-phenethyl-4H-1,2,4-triazol-3-yl)-2-(1H-indol-3-yl)ethyl)piperidine-2-carboxamide, Compound 64: (R)—N-(1-(4-(2,4-dimethoxybenzyl)-5-phenethyl-4H-1,2,4-triazol-3-yl)-2-(1H-indol-3-yl)ethyl)picolinamide, Compound 71: (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)pyrazine-2-carboxamide, Compound 72: (R)—N-1-(5-(2-(1H-indol-3-yl)ethyl)-4-(2,4-dimethoxybenzyl)-4H-1,2,4-triazol-3-yl)-2-(1H-indol-3-yl)ethyl)piperazine-2-carboxamide, Compound 80: (R)—N-(1-(5-(2-(1H-indol-3-yl)ethyl)-4-(4-methoxybenzyl)-4H-1,2,4-triazol-3-yl)-2-(1H-indol-3-yl)ethyl)picolinamide, Compound 81: (R)—N-1-(5-(2-(1H-indol-3-yl)ethyl)-4-(4-methoxybenzyl)-4H-1,2,4-triazol-3-yl)-2-(1H-indol-3-yl)ethyl)piperazine-2-carboxamide, and Compound 90: (R)—N—((R)-1-(5-(2-(1H-indol-3-yl)ethyl)-4-(4-methoxybenzyl)-4H-1,2,4-triazol-3-yl)-2-(1H-indol-3-yl)ethyl)pyrrolidine-2-carboxamide.

9. The method of claim 8, wherein the mammal is a human and is in need of treatment for adiposity, for obesity, or for body weight gain.

10. The method of claim 1, comprising administering a compound according to formula (I) that increases food intake selected from the group consisting of
Compound 44: (R)—N-(1-(4-(4-methoxybenzyl)-5-phenethyl-4H-1,2,4-triazol-3-yl)-2-(1H-indol-3-yl)ethyl)piperidine-4-carboxamide, and
Compound 83: (R)—N-1-(5-(2-(1H-indol-3-yl)ethyl)-4-(4-methoxybenzyl)-4H-1,2,4-triazol-3-yl)-2-(1H-indol-3-yl)ethyl)piperazine-2-carboxamide.

11. The method of claim 10, wherein the subject is in need of treatment for anorexia.

12. The method of claim 1, wherein the compound according to formula (I) is (R)—N-(1-(4-(4-methoxybenzyl)-5-phenethyl-4H-1,2,4-triazol-3-yl)-2-(1H-indol-3-yl)ethyl)piperidine-4-carboxamide (compound 44) that increases food intake and binds to the Motilin Receptor.

13. The method of claim 12, wherein the subject is in need of treatment for cachexia.

14. The method of claim 1, further comprising administering at least one other pharmacologically active substance.

15. The method of claim 1, wherein the compound of formula (I) is administered before, during or after administration of the at least one other pharmacologically active substance.

16. A method for increasing or decreasing growth hormone-levels in a mammal comprising administering to a mammal in need of treatment a compound selected from the group consisting of:
Compound 1: (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-amino-2-methylpropanamide,
Compound 9: (R)—N-(1-(5-(3-(1H-indol-3-yl)propyl)-4-benzyl-4H-1,2,4-triazol-3-yl)-2-(1H-indol-3-yl)ethyl)-2-amino-2-methylpropanamide,
Compound 12: (R)—N-(1-(5-(2-(1H-indol-3-yl)ethyl)-4-(4-methoxybenzyl)-4H-1,2,4-triazol-3-yl)-2-(1H-indol-3-yl)ethyl)-2-amino-2-methylpropanamide,
Compound 20: (R)—N-(1-(4-(4-methoxybenzyl)-5-phenethyl-4H-1,2,4-triazol-3-yl)-2-(1H-indol-3-yl)ethyl)-2-amino-2-methylpropanamide,
Compound 22: (R)—N-(1-(4-(4-methoxybenzyl)-5-(3-phenylpropyl)-4H-1,2,4-triazol-3-yl)-2-(1H-indol-3-yl)ethyl)-2-amino-2-methylpropanamide,
Compound 39: (R)—N-(1-(5-benzyl-4-(pyridin-2-ylmethyl)-4H-1,2,4-triazol-3-yl)-2-(1H-indol-3-yl)ethyl)-2-amino-2-methylpropanamide,
Compound 50: (R)—N-(1-(4-(4-methoxybenzyl)-5-phenethyl-4H-1,2,4-triazol-3-yl)-2-(1H-indol-3-yl)ethyl)-2-aminoacetamide, and
Compound 74: (R)-1-(5-(2-(1H-indol-3-yl)ethyl)-4-(2,4-dimethoxybenzyl)-4H-1,2,4-triazol-3-yl)-2-(1H-indol-3-yl)ethanamine.

17. A method for decreasing food intake in a mammal comprising:
administering to a mammal in need of treatment a compound selected from the group consisting of:
Compound 9: (R)—N-(1-(5-(3-(1H-indol-3-yl)propyl)-4-benzyl-4H-1,2,4-triazol-3-yl)-2-(1H-indol-3-yl)ethyl)-2-amino-2-methylpropanamide,
Compound 13: (R)—N-(1-(4-(4-methoxybenzyl)-5-benzyl-4H-1,2,4-triazol-3-yl)-2-(1H-indol-3-yl)ethyl)-2-amino-2-methylpropanamide,
Compound 17: (R)—N-(1-(4,5-bis(2-(1H-indol-3-yl)ethyl)-4H-1,2,4-triazol-3-yl)-2-(1H-indol-3-yl)ethyl)-2-amino-2-methylpropanamide,
Compound 24: (R)—N-(1-(4-(2-(1H-indol-3-yl)ethyl)-5-(3-(1H-indol-3-yl)propyl)-4H-1,2,4-triazol-3-yl)-2-(1H-indol-3-yl)ethyl)-2-amino-2-methylpropanamide,
Compound 30: (R)—N-(1-(4-(4-fluorobenzyl)-5-benzyl-4H-1,2,4-triazol-3-yl)-2-(1H-indol-3-yl)ethyl)-2-amino-2-methylpropanamide, and
Compound 50: (R)—N-(1-(4-(4-methoxybenzyl)-5-phenethyl-4H-1,2,4-triazol-3-yl)-2-(1H-indol-3-yl)ethyl)-2-aminoacetamide.

18. The method of claim 17, wherein the mammal is a human and is in need of treatment for adiposity, for obesity, or for body weight gain.

19. A method for decreasing food intake in a mammal receiving hexarelin comprising:
administering to a mammal in need of treatment a compound selected from the group consisting of:
Compound 1: (R)—N-(1-(5-(2-(1H-indol-3-yl)ethyl)-4-(2,4-dimethoxybenzyl)-4H-1,2,4-triazol-3-yl)-2-(1H-indol-3-yl)ethyl)-2-amino-2-methylpropanamide
Compound 12: (R)—N-(1-(5-(2-(1H-indol-3-yl)ethyl)-4-(4-methoxybenzyl)-4H-1,2,4-triazol-3-yl)-2-(1H-indol-3-yl)ethyl)-2-amino-2-methylpropanamide
Compound 20: (R)—N-(1-(4-(4-methoxybenzyl)-5-phenethyl-4H-1,2,4-triazol-3-yl)-2-(1H-indol-3-yl)ethyl)-2-amino-2-methylpropanamide, and
Compound 22: (R)—N-(1-(4-(4-methoxybenzyl)-5-(3-phenylpropyl)-4H-1,2,4-triazol-3-yl)-2-(1H-indol-3-yl)ethyl)-2-amino-2-methylpropanamide.

20. The method of claim 17, wherein the subject is in need of treatment of obesity or growth retardation associated with obesity, wherein the compound of formula (I) is (R)—N-(1-(4-(4-methoxybenzyl)-5-phenethyl-4H-1,2,4-triazol-3-yl)-2-(1H-indol-3-yl)ethyl)-2-aminoacetamide (compound 50).

* * * * *